(12) United States Patent
Chang et al.

(10) Patent No.: US 8,883,160 B2
(45) Date of Patent: *Nov. 11, 2014

(54) DOCK-AND-LOCK (DNL) COMPLEXES FOR THERAPEUTIC AND DIAGNOSTIC USE

(75) Inventors: Chien-Hsing Chang, Downingtown, PA (US); David M. Goldenberg, Mendham, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 211 days.

This patent is subject to a terminal disclaimer.

(21) Appl. No.: 13/036,820

(22) Filed: Feb. 28, 2011

(65) Prior Publication Data
US 2011/0158905 A1 Jun. 30, 2011

Related U.S. Application Data

(60) Continuation-in-part of application No. 13/004,349, filed on Jan. 11, 2011, now abandoned, and a continuation-in-part of application No. 12/968,936, filed on Dec. 15, 2010, which is a division of application No. 12/396,965, filed on Mar. 3, 2009, now Pat. No. 7,871,622, which is a division of application No. 11/391,584, filed on Mar. 28, 2006, now Pat. No. 7,521,056, application No. 13/036,820, which is a continuation-in-part of application No. 12/964,021, filed on Dec. 9, 2010, now Pat. No. 8,491,914, application No. 13/036,820, which is a continuation-in-part of application No. 12/949,536, filed on Nov. 18, 2010, now Pat. No. 8,211,440, which is a division of application No. 12/396,605, filed on Mar. 3, 2009, now Pat. No. 7,858,070, which is a division of application No. 11/633,729, filed on Dec. 5, 2006, now Pat. No. 7,527,787, application No. 13/036,820, which is a continuation-in-part of application No. 12/915,515, filed on Oct. 29, 2010, now abandoned, application No. 13/036,820, which is (Continued)

(51) Int. Cl.
| C07K 16/28 | (2006.01) |
| A61K 47/48 | (2006.01) |
| A61K 51/08 | (2006.01) |
| A61K 51/10 | (2006.01) |
| C12N 9/12 | (2006.01) |
| C07K 14/47 | (2006.01) |

(52) U.S. Cl.
CPC ............ *A61K 51/08* (2013.01); *C07K 2317/732* (2013.01); *A61K 47/48415* (2013.01); *A61K 47/48561* (2013.01); *C07K 2317/734* (2013.01); *A61K 51/1045* (2013.01); *C07K 2317/31* (2013.01); *C12N 9/12* (2013.01); *C07K 14/47* (2013.01); *A61K 47/48569* (2013.01); *A61K 51/1027* (2013.01); *C07K 2317/55* (2013.01); *C07K 2319/70* (2013.01)

USPC .................. 424/178.1; 424/134.1; 424/143.1; 424/185.1; 424/192.1; 424/193.1; 530/387.3; 530/388.22; 530/391.1

(58) Field of Classification Search
None
See application file for complete search history.

(56) References Cited

U.S. PATENT DOCUMENTS

| 4,036,945 A | 7/1977 | Haber |
| 4,046,722 A | 9/1977 | Rowland |

(Continued)

FOREIGN PATENT DOCUMENTS

| EP | 0332865 | 9/1989 |
| EP | 0510949 | 10/1992 |

(Continued)

OTHER PUBLICATIONS

Stryer et al, in Biochemistry, Third edition, W H Freeman Company, New York, pp. 31-33, 1998.*

(Continued)

*Primary Examiner* — Phuong Huynh
(74) *Attorney, Agent, or Firm* — Richard A. Nakashima

(57) ABSTRACT

The prediction of protein function as well as the reconstruction of evolutionary genesis employing sequence comparison at large is still the most powerful tool in sequence analysis. Due to the exponential growth of the number of known protein sequences and the subsequent quadratic growth of the similarity matrix, the computation of the Similarity Matrix of Proteins (SIMAP) becomes a computational intensive task. The SIMAP database provides a comprehensive and up-to-date pre-calculation of the protein sequence similarity matrix, sequence-based features and sequence clusters. As of September 2009, SIMAP covers 48 million proteins and more than 23 million non-redundant sequences. Novel features of SIMAP include the expansion of the sequence space by including databases such as ENSEMBL as well as the integration of metagenomes based on their consistent processing and annotation. Furthermore, protein function predictions by Blast2GO are pre-calculated for all sequences in SIMAP and the data access and query functions have been improved. SIMAP assists biologists to query the up-to-date sequence space systematically and facilitates large-scale downstream projects in computational biology. Access to SIMAP is freely provided through the web portal for individuals (http://mips.gsf.de/simap/) and for programmatic access through DAS (http://webclu.bio.wzw.tum.de/das/) and Web-Service (http://mips.gsf.de/webservices/services/SimapService2.0?wsdl).

3 Claims, 31 Drawing Sheets

Related U.S. Application Data a continuation-in-part of application No. 12/871,345, filed on Aug. 30, 2010, now Pat. No. 8,551,480, application No. 13/036,820, which is a continuation-in-part of application No. 12/869,823, filed on Aug. 27, 2010, application No. 13/036,820, which is a continuation-in-part of application No. 12/754,140, filed on Apr. 5, 2010, now Pat. No. 8,722,047, application No. 13/036,820, which is a continuation-in-part of application No. 12/754,740, filed on Apr. 6, 2010, now Pat. No. 8,562,988, application No. 13/036,820, which is a continuation-in-part of application No. 12/752,649, filed on Apr. 1, 2010, now Pat. No. 8,034,352, application No. 13/036,820, which is a continuation-in-part of application No. 12/731,781, filed on Mar. 25, 2010, now Pat. No. 8,003,111, application No. 13/036,820, which is a continuation-in-part of application No. 12/644,146, filed on Dec. 22, 2009, now Pat. No. 7,981,398, which is a division of application No. 11/925,408, filed on Oct. 26, 2007, now Pat. No. 7,666,400, application No. 13/036,820, which is a continuation-in-part of application No. 12/544,476, filed on Aug. 20, 2009, now Pat. No. 7,901,680, application No. 13/036,820, which is a continuation-in-part of application No. 12/468,589, filed on May 19, 2009, now Pat. No. 8,163,291, which is a division of application No. 11/389,358, filed on Mar. 24, 2006, now Pat. No. 7,550,143, application No. 13/036,820, which is a continuation-in-part of application No. 12/418,877, filed on Apr. 6, 2009, now Pat. No. 7,906,118, application No. 13/036,820, which is a continuation-in-part of application No. 12/417,917, filed on Apr. 3, 2009, now Pat. No. 7,906,121, which is a division of application No. 11/478,021, filed on Jun. 29, 2006, now Pat. No. 7,534,866, application No. 13/036,820, which is a continuation-in-part of application No. 11/056,182, filed on Feb. 14, 2005, now Pat. No. 7,544,487.

(60) Provisional application No. 61/293,846, filed on Jan. 11, 2010, provisional application No. 61/323,001, filed on Apr. 12, 2010, provisional application No. 61/374,449, filed on Aug. 17, 2010, provisional application No. 60/668,603, filed on Apr. 6, 2005, provisional application No. 60/728,292, filed on Oct. 19, 2005, provisional application No. 60/751,196, filed on Dec. 16, 2005, provisional application No. 60/782,332, filed on Mar. 14, 2006, provisional application No. 61/267,877, filed on Dec. 9, 2009, provisional application No. 61/302,682, filed on Feb. 9, 2010, provisional application No. 61/414,592, filed on Nov. 17, 2010, provisional application No. 60/864,530, filed on Nov. 6, 2006, provisional application No. 61/258,369, filed on Nov. 5, 2009, provisional application No. 61/258,729, filed on Nov. 6, 2009, provisional application No. 61/378,059, filed on Aug. 30, 2010, provisional application No. 61/238,473, filed on Aug. 31, 2009, provisional application No. 61/266,305, filed on Dec. 3, 2009, provisional application No. 61/316,996, filed on Mar. 24, 2010, provisional application No. 61/323,960, filed on Apr. 14, 2010, provisional application No. 61/238,424, filed on Aug. 31, 2009, provisional application No. 61/166,809, filed on Apr. 6, 2009, provisional application No. 61/168,715, filed on Apr. 13, 2009, provisional application No. 61/168,290, filed on Apr. 10, 2009, provisional application No. 61/168,657, filed on Apr. 13, 2009, provisional application No. 61/168,668, filed on Apr. 13, 2009, provisional application No. 61/163,666, filed on Mar. 26, 2009, provisional application No. 61/090,487, filed on Aug. 20, 2008, provisional application No. 61/043,932, filed on Apr. 10, 2008, provisional application No. 61/104,916, filed on Oct. 13, 2008, provisional application No. 61/119,542, filed on Dec. 3, 2008, provisional application No. 60/544,227, filed on Feb. 13, 2004.

(56) References Cited

U.S. PATENT DOCUMENTS

| | | |
|---|---|---|
| 4,331,647 A | 5/1982 | Goldenberg |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Hawthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,530,101 A | 6/1996 | Queen et al. |
| 5,565,215 A | 10/1996 | Gref et al. |
| 5,567,610 A | 10/1996 | Borrebaeck et al. |
| 5,585,089 A | 12/1996 | Queen et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,716,595 A | 2/1998 | Goldenberg |
| 5,736,119 A | 4/1998 | Goldenberg et al. |
| 5,776,456 A | 7/1998 | Anderson et al. |
| 5,789,554 A | 8/1998 | Leung et al. |
| 5,792,845 A | 8/1998 | O'Reilly et al. |
| 5,795,967 A | 8/1998 | Aggarwal et al. |
| 5,798,554 A | 8/1998 | Grimaldi et al. |
| 5,859,205 A | 1/1999 | Adair et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,077,499 A | 6/2000 | Griffiths et al. |
| 6,096,289 A | 8/2000 | Goldenberg |
| 6,165,440 A | 12/2000 | Esenaliev |
| 6,180,370 B1 | 1/2001 | Queen et al. |
| 6,180,377 B1 | 1/2001 | Morgan et al. |
| 6,183,744 B1 | 2/2001 | Goldenberg |
| 6,187,287 B1 | 2/2001 | Leung et al. |
| 6,254,868 B1 | 7/2001 | Leung et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |

(56) References Cited

U.S. PATENT DOCUMENTS

| | | | |
|---|---|---|---|
| 6,530,944 | B2 | 3/2003 | West et al. |
| 6,562,318 | B1 | 5/2003 | Filler |
| 6,653,104 | B2 | 11/2003 | Goldenberg |
| 6,730,300 | B2 | 5/2004 | Leung et al. |
| 7,022,500 | B1 | 4/2006 | Queen et al. |
| 7,074,403 | B1 | 7/2006 | Goldenberg et al. |
| 7,312,318 | B2 | 12/2007 | Hansen et al. |
| 7,387,779 | B2 | 6/2008 | Kalluri |
| 7,521,056 | B2* | 4/2009 | Chang et al. ............... 424/192.1 |
| 7,527,787 | B2* | 5/2009 | Chang et al. ............... 424/133.1 |
| 7,534,866 | B2* | 5/2009 | Chang et al. ................. 530/350 |
| 7,550,143 | B2* | 6/2009 | Chang et al. ............... 424/134.1 |
| 7,612,180 | B2 | 11/2009 | Goldenberg et al. |
| 7,666,400 | B2* | 2/2010 | Chang et al. ................. 424/85.1 |
| 7,772,373 | B2 | 8/2010 | Hansen et al. |
| 7,863,432 | B2* | 1/2011 | Klussmann et al. ......... 536/23.5 |
| 7,901,680 | B2* | 3/2011 | Chang et al. ............... 424/134.1 |
| 7,906,118 | B2* | 3/2011 | Chang et al. ............... 424/134.1 |
| 7,906,121 | B2* | 3/2011 | Chang et al. ............... 424/178.1 |
| 7,919,087 | B2 | 4/2011 | Hansen et al. |
| 7,931,903 | B2 | 4/2011 | Hansen et al. |
| 2002/0018749 | A1 | 2/2002 | Hudson et al. |
| 2003/0103979 | A1 | 6/2003 | Leung et al. |
| 2003/0198956 | A1* | 10/2003 | Makowski et al. ............... 435/6 |
| 2003/0232420 | A1* | 12/2003 | Braun et al. .................. 435/194 |
| 2004/0001825 | A1* | 1/2004 | Govindan et al. .......... 424/141.1 |
| 2004/0076683 | A1 | 4/2004 | Hoarau et al. |
| 2007/0140966 | A1* | 6/2007 | Chang et al. ................. 424/1.49 |
| 2011/0070156 | A1* | 3/2011 | Govindan et al. ............ 424/1.49 |
| 2011/0112851 | A1* | 5/2011 | Poley ................................ 705/2 |
| 2011/0143417 | A1* | 6/2011 | Chang et al. .................. 435/188 |
| 2011/0243841 | A1* | 10/2011 | Chang et al. ................. 424/1.49 |
| 2011/0256053 | A1* | 10/2011 | Chang et al. ................. 424/1.11 |

FOREIGN PATENT DOCUMENTS

| | | | |
|---|---|---|---|
| WO | 91/13974 | | 9/1991 |
| WO | 94/27638 | | 12/1994 |
| WO | 9509917 | | 4/1995 |
| WO | 96/04925 | | 2/1996 |
| WO | 98/42378 | | 10/1998 |
| WO | 98/50435 | | 11/1998 |
| WO | 99/02567 | | 1/1999 |
| WO | 99/54440 | | 10/1999 |
| WO | 00/29584 | | 5/2000 |
| WO | 00/67795 | | 11/2000 |
| WO | 00/74718 | | 12/2000 |
| WO | WO 2004 022591 | * | 3/2004 |
| WO | WO2006/107786 | * | 10/2006 |

OTHER PUBLICATIONS

Ngo et al, The Protein Folding Problem and Tertiary Structure Prediction, pp. 492-495, 1994.*
Zhu et al, Investigational New Drugs 17: 195-212, 1999.*
Henry et al, Cancer Res. 64: 7995-8001, Nov. 1, 2004.*
Stancovski et al, Proceedings of the National Academy of Science USA 88: 8691-8695, 1991.*
Riemer et al, Mol. Immunol. 42: 1121-1124, 2005.*
Tol et al, N Engl J Med. 360(6):563-72, Feb. 5, 2009.*
Banky et al, J Biol Chem 273(52): 35048-35055, 1998.*
Skolnick et al., Trends in Biotechnology, 18: 34-39, 2000.*
Jones et al., Pharmacogenomics Journal, 1:126-134, 2001.*
Tosatto et al., Current Pharmaceutical Design, 12:2067-2086, 2006.*
Jubala et al., Vet Pathol 42: 468-476, 2005.*
US 6,558,648, 5/2003, Griffiths et al. (withdrawn).
Bagshawe et al., "Developments with targeted enzymes in cancer therapy", Curr. Opin. Immunol. 11(5):579-83 (1999).
Bally et al. (Eds.), "Controlling the Drug Delivery Attributes of Lipid-Based Drug Formulations", Journal of Liposome Research, 1998, vol. 8, No. 3, pp. 299-335.
Beers et al., The Merck Manual of Diagnosis and Therapy, Ch. 180, p. 1474-1476; 17th Ed., Whitehouse Station, NJ, Merck Research Labs (1999).
Bendas et al., "Immunoliposomes: a promising approach to targeting cancer therapy", BioDrugs 15(4):215-24 (2001).
Bendig, M., "Humanization of Rodent Monoclonal Antibodies by CDR Grafting", Academic Press Inc., New York, NY, vol. 8, (1995), pp. 83-93.
Bird et al., "Single chain antibody variable regions", Trends Biotechnol. 9(4):132-7 (1991).
Bom et al., "The highly lipophilic DNA topoisomerase I inhibitor DB-67 displays elevated lactone levels in human blood and potent anticancer activity", J. Control Release 74(1-3):325-33 (2001).
Breen et al., "Non-Hodgkin's B cell lymphoma in persons with acquired immunodeficiency syndrome is associated with increased serum levels of IL10, or the IL10 promoter –592 C/C genotype", Clin. Immunol. 109(2):119-29 (2003).
Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol. 111:2129-2138 (1990).
Carter et al., "Humanization of an anti-p185HER2 antibody for human cancer therapy", Proc. Natl. Acad. Sci. USA 89(10):4285-9 (1992).
Chen et al., "Differential Effects of Milatuzumab on Human Antigen-Presenting Cells in Comparison to Malignant B Cells", 2009 ASH Annual Meeting Abstracts, vol. 114(22):1073; Abstr #2744 (Nov. 20, 2009).
Cochlovius et al., "Cure of Burkitt's lymphoma in severe combined immunodeficiency mice by T cells, tetravalent CD3 x CD19 tandem diabody, and CD28 costimulation", Cancer Res. 60(16):4336-41 (2000).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Colman, P., "Effects of amino acid sequence changes on antibody-antigen interactions", Res. Immunol. 1994, 145:33-36.
Coloma et al., "Design and production of novel tetravalent bispecific antibodies", Nat. Biotechnol. 15(2):159-63 (1997).
Constantinides et al., "Formulation development and antitumor activity of a filter-sterilizable emulsion of paclitaxel", Pharm. Res. 17(2):175-82 (2000).
Courtenay-Luck, N. S., "Genetic manipulation of monoclonal antibodies", Monoclonal Antibodies: Production, Engineering and Clinical Application, p. 166-179, Ritter et al. (Eds.), Cambridge University Press (1995).
Fitzgerald et al., "Improved tumour targeting by disulphide stabilized diabodies expressed in *Pichia pastoris*", Protein Eng. 10(10):1221-5 (1997).
Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).
Freedman et al., "Non-Hodgkin's Lymphomas", Cancer Medicine, 3rd Ed., vol. 2, p. 2028-2068, Holland et al., (Eds.), Lea & Febiger (1993).
French et al., "Response of B-cell lymphoma to a combination of bispecific antibodies and saporin", Leuk. Res. 20 (7):607-17 (1996).
Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Gold et al., "Expression of CD74 in pancreatic and colorectal carcinomas as a basis for milatuzumab immunotherapy", Abstract #5485; Proceeding of the American Association for Cancer Research, vol. 50, p. 1322-1323; Apr. 2009.
Goldenberg, D. M. "Radiolabeled antibodies", Science & Medicine, 1(1):64 (Apr. 1994).
Goldenberg, D. M. "Future role of radiolabeled monoclonal antibodies in oncological diagnosis and therapy", Semin. Nucl. Med. 19(4):332-9 (1989).
Goldenberg, D. M. "New Developments in Monoclonal Antibodies for Cancer Detection and Therapy", CA Cancer J. Clin. 44(1):43-64 (1994).

(56) References Cited

OTHER PUBLICATIONS

Gondo et al., "HLA class II antigen associated invariant chain gene expression in malignant lymphoma", Br. J. Haematol. 67(4):413-7 (1987).
Goto et al. "A novel membrane antigen selectively expressed on terminally differentiated human B cells", Blood 84 (6):1922-30 (1994).
Green et al., "Antigen-specific human monoclonal antibodies from mice engineered with human Ig heavy and light chain YACs", Nature Genetics 7:13-21 (1994).
Greenwood et al., "Effector functions of matched sets of recombinant human IgG subclass antibodies", Protein Engineering of Antibody Molecules for Prophylactic and Therapeutic Applications in Man, Clark (Ed.), p. 89; p. 97; Academic Titles (1993).
Griffiths et al., "Cure of SCID Mice Bearing Human B-Lymphoma Xenografts by an Anti-CD74 Antibody-Anthracycline Drug Conjugate", vol. 9, 6567-6571, Dec. 15, 2003.
Hansen et al., "Internalization and catabolism of radiolabelled antibodies to the MHC class-II invariant chain by B-cell lymphomas", Biochem. J. 1996, 320:293-300.
Hasan et al., "Laser-induced selective cytotoxicity using monoclonal antibody-chromophore conjugates", Prog. Clin. Biol. Res. 288:471-7 (1989).
Hekman et al., "Initial experience with treatment of human B cell lymphoma with anti-CD19 monoclonal antibody", Cancer Immunol. Immunother. 1991;32(6):364-72.
Hertlein et al., "Immunoliposomes Incorporated with Humanized Monoclonal Antibody, Milatuzumab, Induce Cell Death in CLL by Retention of the CD74 Receptor on the Surface of B Cells" 2009 ASH Annual Meeting Abstracts, vol. 114(22):301; Abstr # 721 (Nov. 20, 2009).
Hertlein et al., "Milatuzumab immunoliposomes induce cell death in CLL by promoting accumulation of CD74 on the surface of B cells", Blood. Jun. 23, 2010. [Epub ahead of print].
Hess et al., "Specificity of effector T lymphocytes in autologous graft-versus-host disease: role of the major histocompatibility complex class II invariant chain peptide", Blood 89(6):2203-9 (1997).
Hong et al., "pH-sensitive, serum-stable and long-circulating liposomes as a new drug delivery system", J. Pharm. Pharmacol. 54(1):51-8 (2002).
Hua et al., "Immunoreactivity for LN2 and LN3 distinguishes small cell carcinomas from non-small cell carcinomas in the lung", Hum. Pathol. 29(12):1441-6 (1998).
Huse et al., "Generation of a Large Combinatorial Library of the Immunoglobulin Repertoire in Phage Lambda", Science 246:1275-1281 (1989).
Ibragimova et al., "Stability of the beta-sheet of the WW domain: A molecular dynamics simulation study", Biophys. J. 77(4):2191-8 (1999).
Johnson et al., "Human antibody engineering", Current Opin. Struct. Biol. 3:564-571 (1993).
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiesel et al., "Removal of cells from a malignant B-cell line from bone marrow with immunomagnetic beads and with complement and immunoglobulin switch variant mediated cytolysis", Leuk. Res. 11(12):1119-25 (1987).
Kirpotin et al., "Sterically stabilized anti-HER2 immunoliposomes: design and targeting to human breast cancer cells in vitro", Biochemistry 36(1):66-75 (1997).
Kohler et al., "Continuous cultures of fused cells secreting antibody of predefined specificity", Nature 256:495-7 (1975).
Kolata, G., "Clinical promise with new hormones", Science 236:517-519 (1987).
Koning et al., "Selective transfer of a lipophilic prodrug of 5-fluorodeoxyuridine from immunoliposomes to colon cancer cells", Biochim. Biophys. Acta. 1420(1-2):153-67 (1999).
Kratz et al., "Drug-polymer conjugates containing acid-cleavable bonds", Crit. Rev. Ther. Drug Carrier Syst. 16 (3):245-88 (1999).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Larrick et al., "PCR Amplification of Antibody Genes", Methods: A Companion to methods in Enzymology 2 (2):106-110 (1991).
Lazar et al.,"Transforming growth factor alpha: mutation of aspartic acid 47 and leucine 48 results in different biological activities", Mol. Cell. Biol. 8(3):1247-1252 (1988).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).
Leung et al., "Chimerization of LL2, a Rapidly Internalizing Antibody Specific for B Cell Lymphoma", Hybridoma 13 (6):469-476 (1994).
Leung et al., "Engineering a Unique Glycosylation Site for Site-Specific Conjugation of Haptens to Antibody Fragments", J. Immunol. 154:5919-5926 (1995).
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52 (8):1701-4 (1999).
Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L. "Immunotherapy for non-Hodgkin's lymphoma", Curr. Opin. Oncol. 8(5):353-9 (1996).
Lopez De Menezes et al., "In vitro and in vivo targeting of immunoliposomal doxorubicin to human B-cell lymphoma", Cancer Res. 58(15):3320-30 (1998).
Lopez De Menezes et al., "Cellular Trafficking and Cytotoxicity of Anti-Cd19-Targeted Liposomal Doxorubicin in B Lymphoma Cells", J. Liposome Research 1999, vol. 9, No. 2, pp. 199-228.
Lundberg, B. "Preparation of drug-carrier emulsions stabilized with phosphatidylcholine-surfactant mixtures", J. Pharm. Sci. 83(1):72-5 (1994).
Lundberg, B. "The solubilization of lipophilic derivatives of podophyllotoxins in sub-micron sized lipid emulsions and their cytotoxic activity against cancer cells in culture", Int. J. Pharm. 109:73-81 (1994).
Lundberg et al., "Submicron lipid emulsions containing amphipathic polyethylene glycol for use as drug-carriers with prolonged circulation time", Int. J. Pharm. 134:119-127 (1996).
Lundberg et al., A submicron lipid emulsion coated with amphipathic polyethylene glycol for parenteral administration of paclitaxel (Taxol), J Pharm Pharmacol. 49:16-21 (1997).
Lundberg et al., "Biologically active camptothecin derivatives for incorporation into liposome bilayers and lipid emulsions", Anticancer Drug Des. 13(5):453-61 (1998).
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Lundberg et al., "Specific binding of sterically stabilized anti-B-cell immunoliposomes and cytotoxicity of entrapped doxorubicin", Int. J. Pharm. 205(1-2):101-8 (2000).
Lundberg et al., "Cellular association and cytotoxicity of anti-CD74-targeted lipid drug-carriers in B lymphoma cells", J. Control. Release 94(1):155-61 (2004).

(56) References Cited

OTHER PUBLICATIONS

Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maranhao et al., "Association of carmustine with a lipid emulsion: in vitro, in vivo and preliminary studies in cancer patients", Cancer Chemother. Pharmacol. 49(6):487-98 (2002).
McCafferty et al., "Phage antibodies: filamentous phage displaying antibody variable domains", Nature 348:552-553 (1990).
Mendez et al., "Functional transplant of megabase human immunoglobulin loci recapitulates human antibody response in mice", Nature Genetics 15:146-156 (1997).
Mew et al., "Photoimmunotherapy: treatment of animal tumors with tumor-specific monoclonal antibody-hematoporphyrin conjugates", J. Immunol. 130(3):1473-7 (1983).
Mew et al., "Ability of Specific Monoclonal Antibodies and Conventional Antisera Conjugated to Hematoporphyrin to Label and Kill Selected Cell Lines Subsequent to Light Activation", Cancer Res. 45:4380-4386 (1985).
Moase et al., "Anti-MUC-1 immunoliposomal doxorubicin in the treatment of murine models of metastatic breast cancer", Biochim. Biophys. Acta. 1510(1-2):43-55 (2001).
Moller et al., "CD74", J. Biol. Regul. Homeost. Agents 14(4):299-301 (2000).
Mosmann, T., "Rapid colorimetric assay for cellular growth and survival: application to proliferation and cytotoxicity assays", J. Immunol. Methods 65(1-2):55-63 (1983).
Nagel et al., "HLXB9 activates IL6 in Hodgkin lymphoma cell lines and is regulated by PI3K signalling involving E2F3", Leukemia 19(5):841-6 (2005).
Nakagawa et al., "Clinical trial of intrathecal administration of 5-fluoro-2'-deoxyuridine for treatment of meningeal dissemination of malignant tumors", J. Neurooncol. 45(2):175-83 (1999).
Nisonoff et al., "Separation of Univalent Fragments from the Bivalent Rabbit Antibody Molecule by Reduction of Disulfide Bonds", Arch. Biochem. Biophys. 89:230-244 (1960).
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Oseroff et al., "Antibody-targeted photolysis: Selective photodestruction of human T-cell leukemia cells using monoclonal antibody-chlorin e6 conjugates", Proc. Natl. Acad. Sci. USA 83:8744-8748 (1986).
Oseroff et al., "Strategies for selective cancer photochemotherapy: antibody-targeted and selective carcinoma cell photolysis", Photochem. Potobiol. 46(1):83-96 (1987).
Oster et al., "Erythropoietin for the Treatment of Anemia of Malignancy Associated with Neoplastic Bone Marrow Infiltration", J. Clin. Oncol. 8(6):956-962 (1990).
Pastan et al., "Immunotoxins", Cell 47:641-648 (1986).
Patti et al., "High-dose cyclophosphamide, etoposide and BCNU (CVB) with autologous stem cell rescue in malignant lymphomas", Eur. J. Haematol. 51(1):18-24 (1993).
Pawlak-Byczkowska et al., "Two new monoclonal antibodies, EPB-1 and EPB-2, reactive with human lymphoma", Cancer Res. 49(16):4568-77 (1989).
Pelegrin et al., "Antibody-Fluorescein Conjugates for Photoimmunodiagnosis of Human Colon Carcinoma in Nude Mice", Cancer 67:2529-2537 (1991).
Perkins et al., "Novel therapeutic nano-particles (lipocores): trapping poorly water soluble compounds", Int. J. Pharm. 200(1):27-39 (2000).
Pirker et al., "Characterization of immunotoxins active against ovarian cancer cell lines", J. Clin. Invest. 76(3):1261-7 (1985).
Porter et al., "The Hydrolysis of Rabbit γ-Globulin and Antibodies with Crystalline Papain", Biochem. J. 73 (1):119-127 (1959).
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates", Cancer J. Sci. Am. 4(Suppl 2):S19-26 (1998).
Price, K. M., "Production and characterization of synthetic peptide-derived antibodies", Monoclonal Antibodies: Production, Engineering and Clinical Application, Ritter et al., (Eds.), pp. 60-84, Cambridge University Press (1995).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).
Qu et al., "Internalization and cytotoxic effects of a humanized anti-CD74 antibody, LL1", Proc Am Assoc Cancer Res 2002;43:255, Abstract # 1269.
Raag et al., "Single-chain Fvs", FASEB J. 9(1):73-80 (1995).
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79 (6):1979-83 (1982).
Ryser et al., "Conjugation of methotrexate to poly(L-lysine) increases drug transport and overcomes drug resistance in cultured cells", Proc. Natl. Acad. Sci. USA 75(8):3867-70 (1978).
Saltzman et al., "Transport rates of proteins in porous materials with known microgeometry", Biophys. J. 55 (1):163-71 (1989).
Sandhu, J. S., "Protein engineering of antibodies", Crit. Rev. Biotechnol. 12(5-6):437-62 (1992).
Schlom, J., "Monoclonal Antibodies: They're More and Less Than You Think", Molecular Foundations of Oncology, Broader, S. (Ed.), pp. 95-134 (1991).
Sherwood et al., "Controlled antibody delivery systems", Biotechnology 10(11):1446-9 (1992).
Shih et al., "Site-specific linkage of methotrexate to monoclonal antibodies using an intermediate carrier", Int J Cancer 41(6):832-9 (1988).
Shih et al., "A fluorouridine-anti-CEA immunoconjugate is therapeutically effective in a human colonic cancer xenograft model", Int. J. Cancer 46(6):1101-6 (1990).
Shih et al., "Internalization and intracellular processing of an anti-B-cell lymphoma monoclonal antibody, LL2", Int J Cancer 56(4):538-45 (1994).
Shih et al., "Localization of an antibody to CD74 (MHC class II invariant chain) to human B cell lymphoma xenografts in nude mice", Cancer Immunol. Immunother. 49(4-5):208-16 (2000).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Straubinger et al., "Endocytosis and intracellular fate of liposomes using pyranine as a probe", Biochemistry 29 (20):4929-39 (1990).

(56) References Cited

OTHER PUBLICATIONS

Tatsuta et al., "Diagnosis of gastric cancers with fluorescein-labeled monoclonal antibodies to carcinoembryonic antigen", Lasers Surg. Med. 9(4):422-6 (1989).
Taylor et al., "A transgenic mouse that expresses a diversity of human sequence heavy and light chain immunoglobulins", Nucleic Acids Res. 20(23):6287-95 (1992).
Tempest et al., "Reshaping a human monoclonal antibody to inhibit human respiratory syncytial virus infection in vivo", Biotechnology 9(3):266-71 (1991).
Theocharis et al., "Characterization of in vivo mutated T cell clones from patients with systemic lupus erythematosus", Clin. Immunol. Immunopathol. 74(2):135-42 (1995).
Thorpe et al., "Monoclonal antibodies: clinical and regulatory issues", Trends Biotechnol. 11(2):40-2 (1993).
Torchilin et al., "The antibody-linked chelating polymers for nuclear therapy and diagnostics", Crit. Rev. Ther. Drug Carrier Syst. 7(4):275-308 (1991).
Torchilin et al., "Immunomicelles: targeted pharmaceutical carriers for poorly soluble drugs", Proc. Natl. Acad. Sci. USA 100(10):6039-44 (2003).
Upeslacis et al., "Modification of Antibodies by Chemical Methods," Monoclonal Antibodies: Principles and Applications, Birch et al. (eds.), pp. 187-230 (Wiley-Liss, Inc., 1995).
Van Den Bergh, H., "Light and porphyrins in cancer therapy", Chem. Britain 22:430 (1986).
Vaughan et al., "Human antibodies with sub-nanomolar affinities isolated from a large non-immunized phage display library", Nat. Biotechnol. 14(3):309-14 (1996).
Verhoeyen et al., "Reshaping human antibodies: grafting an antilysozyme activity", Science 239(4847):1534-6 (1988).
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Ward et al., "Genetic Manipulation and Expression of Antibodies," Monoclonal Antibodies: Principles and Applications, Birch et al., (eds.), pp. 137-185 (Wiley-Liss, Inc. 1995).
West et al., "Applications of nanotechnology to biotechnology commentary", Curr Opin Biotechnol. 11(2):215-7 (2000).
Wong, S., Chemistry of Protein Conjugation and Cross-Linking, CRC Press, Inc. (1991).
Wraight et al., "Human major histocompatibility complex class II invariant chain is expressed on the cell surface", J Biol Chem. Apr. 5, 1990;265(10):5787-92.
Wrobel et al., "Fusion of cationic liposomes with mammalian cells occurs after endocytosis", Biochim. Biophys. Acta. 1235(2):296-304 (1995).
Xu et al., "Systemic tumor-targeted gene delivery by anti-transferrin receptor scFv-immunoliposomes", Mol. Cancer Ther. 1(5):337-46 (2002).
Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells", Int. J. Cancer 56(2):244-8 (1994).
Zwart et al., "The invariant chain transports TNF family member CD70 to MHC class II compartments in dendritic cells", J Cell Sci. Nov. 1, 2010;123(Pt 21):3817-27.
Alinari et al., "Combination Anti-CD74 (Milatuzumab) and Anti-CD20 (Rituximab) Monoclonal Antibody Therapy Has in Vitro and in Vivo Activity in Mantle Cell Lymphoma", 2008 ASH Annual Meeting Abstracts, Blood 112(11):327 (2008).
Altomonte et al., "Targeting of HLA-DR molecules transduces agonistic functional signals in cutaneous melanoma", J Cell Physiol. 2004;200:272-276.
Aoudjit et al., "HLA-DR signaling inhibits Fas-mediated apoptosis in A375 melanoma cells", Exp Cell Res. 2004;299: 79-90.
Banapour et al., "Characterization and epitope mapping of a human monoclonal antibody reactive with the envelope glycoprotein of human immunodeficiency virus", J. Immunol. 139(12):4027-33 (1987).
Berkova et al., "Milatuzumab—a promising new immunotherapeutic agent", Expert Opin Investig Drugs. Jan. 2010;19 (1):141-9.
Beswick et al., "CD74 in antigen presentation, inflammation, and cancers of the gastrointestinal tract", World J Gastroenterol. Jun. 21, 2009;15(23):2855-61.
Binsky et al., "IL-8 secreted in a macrophage migration-inhibitory factor- and CD74-dependent manner regulates B cell chronic lymphocytic leukemia survival", Proc Natl Acad Sci U S A. Aug. 14, 2007;104(33):13408-13. Epub Aug. 8, 2007.
Binsky et al., "TAp63 regulates VLA-4 expression and chronic lymphocytic leukemia cell migration to the bone marrow in a CD74-dependent manner", J Immunol. May 1, 2010;184(9):4761-9. Epub Mar. 31, 2010.
Blancheteau et al., "HLA class II signals sensitize B lymphocytes to apoptosis via Fas/CD95 by increasing FADD recruitment to activated Fas and activation of caspases", Hum Immunol. 2002;63:375-383.
Bridges et al., "Selective in vivo antitumor effects of monoclonal anti-I-A antibody on a B lymphoma", J Immunol. 1987;139:4242-4249.
Brozek et al., "Anti-DR antibodies inhibit in vitro production of human rheumatoid factor", J Clin Lab Immunol. 1990;31:105-109.
Burton et al., "CD74 is expressed by multiple myeloma and is a promising target for therapy", Clin Cancer Res. Oct. 1, 2004;10(19):6606-11.
Chang et al., "Effective therapy of human lymphoma xenografts with a novel recombinant ribonuclease/anti-CD74 humanized IgG4 antibody immunotoxin", Blood. Dec. 15, 2005;106(13):4308-14. Epub Aug. 18, 2005.
Dechant et al., "HLA class II antibodies in the treatment of hematologic malignancies", Semin Oncol. Aug. 2003;30 (4):465-75.
Elsasser et al., "HLA class II as potential target antigen on malignant B cells for therapy with bispecific antibodies in combination with granulocyte colony-stimulating factor", Blood 1996;87:3803-3812.
Fu et al., "HLA-DR alpha chain residues located on the outer loops are involved in non-polymorphic and polymorphic antibody-binding epitopes", Hum Immunol. 1994; 39:253-260.
Govindan et al., "Radionuclides linked to a CD74 antibody as therapeutic agents for B-cell lymphoma: comparison of Auger electron emitters with beta-particle emitters", J Nucl Med. Dec. 2000;41(12):2089-97.
Griffiths et al., "Cytotoxicity with Auger electron-emitting radionuclides delivered by antibodies", Int J Cancer. Jun. 11, 1999;81(6):985-92.
Gussow et al., "Humanization of monoclonal antibodies", Method Enzymol. 203:99-121, (1991).
Hertlein et al., "HLA-DR meets ERK", Blood. Jun. 24, 2010;115(25):5126-7.
Jongbloed et al., "Plasmacytoid dendritic cells regulate breach of self-tolerance in autoimmune arthritis", J Immunol. Jan. 15, 2009;182(2):963-8.
Kabelitz et al., "Growth inhibition of Epstein-Barr virus-transformed B cells by anti-HLA-DR antibody L243: possible relationship to L243-induced down-regulation of CD23 antigen expression", Cell Immunol. 1989;120:21-30.
Kopper et al., "Genomics of renal cell cancer—does it provide breakthrough?", Pathol Oncol Res. 2006;12(1):5-11. Epub Mar. 23, 2006.
Lampson et al., "Two populations of Ia-like molecules on a human B cell line", J. Immunol. (1980) 125:293-299.
Landsverk et al., "MHC II and the endocytic pathway: regulation by invariant chain", Scand J Immunol. Sep. 2009;70 (3):184-93.
Lantner et al., "CD74 induces TAp63 expression leading to B-cell survival", Blood. Dec. 15, 2007;110(13):4303-11. Epub Sep. 10, 2007.
Lapter et al., A role for the B-cell CD74/macrophage migration inhibitory factor pathway in the immunomodulation of systemic lupus erythematosus by a therapeutic tolerogenic peptide, Immunology. Jan. 2011;132(1):87-95. doi: 10.1111/j.1365-2567.2010.03342. x. Epub Aug. 25, 2010.

(56) References Cited

OTHER PUBLICATIONS

Leng et al., "MIF signal transduction initiated by binding to CD74", J Exp Med. Jun. 2, 2003;197(11):1467-76.

Liu et al., "Up-regulation of vascular endothelial growth factor-D expression in clear cell renal cell carcinoma by CD74: a critical role in cancer cell tumorigenesis", J Immunol. Nov. 1, 2008;181(9):6584-94.

Lund et al., "Expression and characterization of truncated forms of humanized L243 IgG1. Architectural features can influence synthesis of its oligosaccharide chains and affect superoxide production triggered through human Fcgamma receptor I", Eur. J. Biochem. Dec. 2000. vol. 267, No. 24, pp. 7246-7257.

Mark et al., "Milatuzumab: a promising new agent for the treatment of lymphoid malignancies", Expert Opin Investig Drugs. Jan. 2009;18(1):99-104.

McClelland et al., Expression of CD74, the receptor for macrophage migration inhibitory factor, in non-small cell lung cancer, Am J Pathol. Feb. 2009;174(2):638-46. Epub Jan. 8, 2009.

Meyer-Siegler et al., "Further evidence for increased macrophage migration inhibitory factor expression in prostate cancer", BMC Cancer. Jul. 6, 2005;5:73.

Meyer-Siegler et al., "Inhibition of macrophage migration inhibitory factor or its receptor (CD74) attenuates growth and invasion of DU-145 prostate cancer cells", J Immunol. Dec. 15, 2006;177(12):8730-9.

Nagy et al., "Fully human, HLA-DR-specific monoclonal antibodies efficiently induce programmed death of malignant lymphoid cells", Nat Med. 2002;8:801-807.

Nagy et al., A novel, alternative pathway of apoptosis triggered through class II major histocompatibility complex molecules, J Mol Med. Dec. 2003;81(12):757-65. Epub Oct. 9, 2003.

Ong et al., "Cell surface expression and metabolism of major histocompatibility complex class II invariant chain (CD74) by diverse cell lines", Immunology. Oct. 1999;98(2):296-302.

Rossi et al., "A bispecific antibody-IFNalpha2b immunocytokine targeting CD20 and HLA-DR is highly toxic to human lymphoma and multiple myeloma cells", Cancer Res. Oct. 1, 2010;70(19):7600-9. Epub Sep. 28, 2010.

Sapra et al., "Anti-CD74 antibody-doxorubicin conjugate, IMMU-110, in a human multiple myeloma xenograft and in monkeys", Clin Cancer Res. Jul. 15, 2005;11(14):5257-64.

Stein et al., "Antiproliferative activity of a humanized anti-CD74 monoclonal antibody, hLL1, on B-cell malignancies", Blood. Dec. 1, 2004;104(12):3705-11. Epub Aug. 5, 2004.

Stein et al., "Characterization of a humanized IgG4 anti-HLA-DR monoclonal antibody that lacks effector cell functions but retains direct antilymphoma activity and increases the potency of rituximab", Blood 2006;108:2736-44.

Stein et al., "CD74: a new candidate target for the immunotherapy of B-cell neoplasms", Clin Cancer Res. Sep. 15, 2007;13(18 Pt 2):5556s-5563s.

Stein et al., "Combining milatuzumab with bortezomib, doxorubicin, or dexamethasone improves responses in multiple myeloma cell lines", Clin Cancer Res. Apr. 15, 2009;15(8):2808-17. Epub Apr. 7, 2009.

Stein et al., "Therapy of B-cell malignancies by anti-HLA-DR humanized monoclonal antibody, IMMU-114, is mediated through hyperactivation of ERK and JNK MAP kinase signaling pathways", Blood. Jun. 24, 2010;115 (25):5180-90. Epub Jan. 25, 2010.

Stein et al., "Evaluation of anti-human leukocyte antigen-DR monoclonal antibody therapy in spontaneous canine lymphoma", Leuk Lymphoma. Feb. 2011;52(2):273-84. Epub Dec. 6, 2010.

Takahashi et al., "Macrophage CD74 contributes to MIF-induced pulmonary inflammation", Respir Res. May 4, 2009;10:33.

Tutt et al., "Monoclonal antibody therapy of B cell lymphoma: signaling activity on tumor cells appears more important than recruitment of effectors", J Immunol. Sep. 15, 1998;161(6):3176-85.

Vaswani et al., "Humanized antibodies as potential therapeutic drugs", Ann. Allergy Asthma Immunol. 1998; 81:105-119.

\* cited by examiner

Pharmacokinetics of Various Interferon-α2b Conjugates in Male Swiss-Webster Mice

| | %ID/g<br>[F-18]-FDG | | %ID/g<br>pretargeted<br>Al[F-18]<br>IMP 449 | | %ID/g<br>Al[F-18]<br>IMP 449<br>alone |
|---|---|---|---|---|---|
| Tumor<br>(weight (g) | 7.91<br>(0.056) | | 3.01<br>(0.021) | | 0.09<br>(0.082) |
| Liver | 1.03 | | 0.08 | | 0.13 |
| Spleen | 3.05 | | 0.05 | | 0.06 |
| Kidneys | 1.62 | | 2.01 | | 2.67 |
| Lungs | 4.98 | | 0.06 | | 0.13 |
| Blood | 0.80 | | 0.01 | | 0.03 |
| Stomach | 2.09 | | 0.04 | | 0.21 |
| Sm Intestine | 2.56 | | 0.03 | | 0.08 |
| Muscle | 1.73 | | 0.02 | | 0.02 |
| Femur | 2.49 | | 0.04 | | 0.07 |
| Tumor/blood | 10:1 | | 249:1 | | 3:1 |

FIG. 18

| Cell line | | 20-C2-2b | | | 20-2b-2b | | | 734-2b-2b | | hL243γ4P | | v-mab + hL243γ4P + 734-2b-2b | |
|---|---|---|---|---|---|---|---|---|---|---|---|---|---|
| | | I-EC₅₀, nM | TI, fold | I_max, % | I-EC₅₀, nM | TI, fold | I_max, % | I-EC₅₀, nM | I_max, % | EC₅₀,* nM | I_max, % | I-EC₅₀, nM | I_max, % |
| NHL | Daudi | 8×10⁻⁵ | 125 | 95 | 4×10⁻⁴ | 25 | 95 | 0.01 | 95 | 5.13 | 67 | 0.01 | 95 |
| | Raji | 0.30 | 118 | 70 | 15.56 | 2 | 60 | 32.52 | 62 | ND | 45 | 2.25 | 70 |
| | Ramos | 2.04 | >40 | 82 | 31.04 | >2.5 | 70 | ND | 35 | ND | 25 | ND | 43 |
| | Jeko-1 | 0.34 | >200 | 90 | 4.40 | >20 | 59 | ND | 21 | 0.40* | 98 | 0.72 | 90 |
| Myeloma | CAG | 0.01 | 55 | 95 | 0.53 | 1 | 85 | 0.66 | 85 | 20* | 52 | 0.31† | 98 |
| | NCI-H929 | 0.61 | 1 | 98 | 0.56 | 1 | 98 | 0.44 | 98 | ND | 0 | 0.46† | 98 |
| | KMS11 | 34.12 | >2 | 52 | ND | 1 | 21 | ND | 24 | 2.19* | 62 | 6.88† | 66 |
| | KMS12-PE | 1.56 | 10 | 83 | 13.12 | 1 | 72 | 15.60 | 68 | ND | 27 | 3.88† | 76 |
| | KMS12-BM | 0.20 | >500 | 99 | 31.28 | >3 | 55 | ND | 22 | 3.47* | 59 | 2.44 | 73 |
| | MM1R | 0.01 | 10 | 95 | 0.19 | 0.5 | 95 | 0.10 | 97 | ND | 10 | 0.11† | 98 |
| | OPM6 | 0.02 | 2 | 99 | 0.03 | 1 | 99 | 0.03 | 99 | ND | 6 | 0.03† | 99 |
| | U266 | 0.01 | 7 | 92 | 0.09 | 1 | 93 | 0.07 | 92 | ND | 10 | 0.03† | 91 |

A (A)

(B)

(A)

(B)

DOCK-AND-LOCK (DNL) COMPLEXES FOR THERAPEUTIC AND DIAGNOSTIC USE

CROSS-REFERENCE TO RELATED APPLICATIONS

This application is a continuation-in-part of U.S. patent application Ser. No. 13/004,349, filed Jan. 11, 2011; Ser. No. 12/968,936, filed Dec. 15, 2010, (which was a divisional of Ser. No. 12/396,965, filed Mar. 3, 2009, which was a divisional of U.S. Pat. No. 7,521,056); Ser. No. 12/964,021, filed Dec. 9, 2010; Ser. No. 12/949,536, filed Nov. 18, 2010, (which was a divisional of Ser. No. 12/396,605, filed Mar. 3, 2009, which was a divisional of U.S. Pat. No. 7,527,787); Ser. No. 12/915,515, filed Oct. 29, 2010; Ser. No. 12/871,345, filed Aug. 30, 2010; Ser. No. 12/869,823, filed Aug. 27, 2010; Ser. No. 12/754,140, filed Apr. 5, 2010; Ser. No. 12/754,740, filed Apr. 6, 2010; Ser. No. 12/752,649, filed Apr. 1, 2010; Ser. No. 12/731,781, filed Mar. 25, 2010; Ser. No. 12/644,146 (which was a divisional of U.S. Pat. No. 7,666,400), filed Dec. 22, 2009; Ser. No. 12/544,476, filed Aug. 20, 2009; Ser. No. 12/468,589 (which was a divisional of U.S. Pat. No. 7,550,143), filed May 19, 2009; Ser. No. 12/418,877, filed Apr. 6, 2009; and Ser. No. 12/417,917 (which was a divisional of U.S. Pat. No. 7,534,866), filed Apr. 3, 2009; Ser. No. 11/056,182 (now U.S. Pat. No. 7,544,487), filed Feb. 14, 2005. Those applications claimed the benefit under 35 U.S.C. 119(e) of provisional U.S. Patent Application 61/414,592, filed Nov. 17, 2010; 61/378,059, filed Aug. 30, 2010; 61/374,449, filed Aug. 17, 2010; 61/323,960, filed Apr. 14, 2010; 61/323,001, filed Apr. 12, 2010; 61/316,996, filed Mar. 24, 2010; 61/302,682, filed Feb. 9, 2010; 61/293,846, filed Jan. 11, 2010; 61/267,877, filed Dec. 9, 2009; 61/266,305, filed Dec. 3, 2009; 61/258,729, filed Nov. 6, 2009; 61/258,369, filed Nov. 5, 2009; 61/238,424, filed Aug. 31, 2009; 61/238,473, filed Aug. 31, 2009; 61/168,715, filed Apr. 13, 2009; 61/168,668, filed Apr. 13, 2009; 61/168,657, filed Apr. 13, 2009; 61/168,290, filed Apr. 10, 2009; 61/166,809, filed Apr. 6, 2009; 61/163,666, filed Mar. 26, 2009; 61/119,542, filed Dec. 3, 2008; 61/104,916, filed Oct. 13, 2008; 61/090,487, filed Aug. 20, 2008; 61/043,932, filed Apr. 10, 2008; 60/864,530, filed Nov. 6, 2006; 60/782,332, filed Mar. 14, 2006; 60/751,196, filed Dec. 16, 2005; 60/728,292, filed Oct. 19, 2005; 60/668,603, filed Apr. 6, 2005; and 60/544,227, filed Feb. 13, 2004.

SEQUENCE LISTING

The instant application contains a Sequence Listing which has been submitted in ASCII format via EFS-Web and is hereby incorporated by reference in its entirety. Said ASCII copy, created on Feb. 18, 2011, is named IBC131US.txt and is 69,147 bytes in size.

FIELD OF THE INVENTION

The present invention concerns compositions and methods of use of dock-and-lock (DNL) complexes, comprising at least two copies of a dimerization and docking domain (DDD) moiety and at least one copy of an anchoring domain (AD) moiety. In preferred embodiments, the DDD moiety comprises the amino acid sequence of a dimerization and docking domain from a human protein kinase A regulatory subunit protein, while the AD moiety comprises the amino acid sequence of an anchoring domain from an AKAP (A-kinase anchoring protein). Many such proteins with different DDD or AD sequences are known and any such known amino acid sequence may be utilized. More preferably, the DNL complexes comprise fusion proteins in which the AD and DDD moieties are incorporated into the fusion proteins, although alternatively the AD and/or DDD moieties may be attached to effector moieties by other methods, such as chemical coupling. Effectors incorporated into the DNL complex may include, but are not limited to, proteins, peptides, antibodies, antibody fragments, immunomodulators, cytokines, interleukins, interferons, binding proteins, peptide ligands, carrier proteins, toxins, ribonucleases such as ONCONASE® (ranpirnase), inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule known to produce physiological effects. The subject DNL complexes may be comprised of dimers, trimers, tetramers, pentamers, hexamers or other multimers. The skilled artisan will realize that the DNL technology allows the efficient and reproducible formation of multimeric complexes comprising virtually any combination of effector subunits.

BACKGROUND

Existing technologies for the production of antibody-based agents having multiple functions or binding specificities suffer a number of limitations. For agents generated by recombinant engineering, such limitations may include high manufacturing cost, low expression yields, instability in serum, instability in solution resulting in formation of aggregates or dissociated subunits, undefined batch composition due to the presence of multiple product forms, contaminating side-products, reduced functional activities or binding affinity/avidity attributed to steric factors or altered conformations, etc. For agents generated by various methods of chemical cross-linking, high manufacturing cost and heterogeneity of the purified product are two major limitations.

In recent years there has been an increased interest in antibodies or other binding moieties that can bind to more than one antigenic determinant (also referred to as epitopes). Generally, naturally occurring antibodies and monoclonal antibodies have two antigen binding sites that recognize the same epitope. In contrast, bifunctional or bispecific antibodies (hereafter, only the term bispecific antibodies will be used throughout) are synthetically or genetically engineered structures that can bind to two distinct epitopes. Thus, the ability to bind to two different antigenic determinants resides in the same molecular construct.

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. Lancet. 1990; 355:368-371).

Numerous methods to produce bispecific antibodies are known. Methods for construction and use of bispecific and multi-specific antibodies are disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello. Nature. 1983; 305:537-540). The fused hybridomas are capable of synthesizing two different heavy chains and two different light chains, which can associate randomly to give a heterogeneous population of 10 different antibody structures of which only one of them, amounting to ⅛ of the total antibody molecules, will be bispecific, and therefore must be further purified from the other forms, which even if feasible will not be cost effective. Furthermore, fused hybridomas are often less stable cytogenically than the parent hybridomas, making the generation of a production cell line more problematic.

Another method for producing bispecific antibodies uses heterobifunctional cross-linkers to chemically tether two different monoclonal antibodies, so that the resulting hybrid conjugate will bind to two different targets (Staerz, et al. Nature. 1985; 314:628-631; Perez, et al. Nature. 1985; 316: 354-356). Bispecific antibodies generated by this approach are essentially heteroconjugates of two IgG molecules, which diffuse slowly into tissues and are rapidly removed from the circulation. Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). An alternative approach involves chemically cross-linking two or three separately purified Fab' fragments using appropriate linkers. For example, European Patent Application 0453082 (now withdrawn) disclosed the application of a tri-maleimide compound to the production of bi- or tri-specific antibody-like structures. A method for preparing tri- and tetra-valent monospecific antigen-binding proteins by covalently linking three or four Fab fragments to each other via a connecting structure is provided in U.S. Pat. No. 6,511,663. All these chemical methods are undesirable for commercial development due to high manufacturing cost, laborious production process, extensive purification steps, low yields (<20%), and heterogeneous products.

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody. These methods also face the inevitable purification problems discussed above.

A method to produce a recombinant bispecific antibody composed of Fab fragments from the same or different antibodies that are brought into association by complementary interactive domains inserted into a region of the antibody heavy chain constant region was disclosed in U.S. Pat. No. 5,582,996. The complementary interactive domains are selected from reciprocal leucine zippers or a pair of peptide segments, one containing a series of positively charged amino acid residues and the other containing a series of negatively charged amino acid residues. One limitation of such a method is that the individual Fab subunits containing the fused complementary interactive domains appear to have much reduced affinity for their target antigens unless both subunits are combined.

Discrete $V_H$ and $V_L$ domains of antibodies produced by recombinant DNA technology may pair with each other to form a dimer (recombinant Fv fragment) with binding capability (U.S. Pat. No. 4,642,334). However, such non-covalently associated molecules are not sufficiently stable under physiological conditions to have any practical use. Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946,778 and U.S. Pat. No. 5,132,405. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

Monospecific diabodies, triabodies, and tetrabodies with multiple valencies have been obtained using peptide linkers consisting of 5 amino acid residues or less. Bispecific diabodies, which are heterodimers of two different scFvs, each scFv consisting of the $V_H$ domain from one antibody connected by a short peptide linker to the $V_L$ domain of another antibody, have also been made using a dicistronic expression vector that contains in one cistron a recombinant gene construct comprising $V_H1$-linker-$V_L2$ and in the other cistron a second recombinant gene construct comprising $V_H2$-linker-$V_L1$ (Holliger, et al. Proc Natl Acad Sci USA. 1993; 90: 6444-6448; Atwell, et al. Mol Immunol. 1996; 33:1301-1302; Holliger, et al. Nature Biotechnol. 1997; 15: 632-631; Helfrich, et al. Int. J. Cancer. 1998; 76: 232-239; Kipriyanov, et al. Int J. Cancer. 1998; 77: 763-772; Holliger, et al. Cancer Res. 1999; 59: 2909-2916).

A tetravalent tandem diabody (termed tandab) with dual specificity has also been reported (Cochlovius, et al. Cancer Res. 2000; 60: 4336-4341). The bispecific tandab is a dimer of two identical polypeptides, each containing four variable domains of two different antibodies ($V_H1$, $V_L1$, $V_H2$, $V_L2$) linked in an orientation to facilitate the formation of two potential binding sites for each of the two different specificities upon self-association.

To date, the construction of a vector that expresses bispecific or trispecific triabodies has not been achieved. However, polypeptides comprising a collectin neck region are reported to trimerize (Hoppe, et al. FEBS Letters. 1994; 344: 191-195). The production of homotrimers or heterotrimers from fusion proteins containing a neck region of a collectin is disclosed in U.S. Pat. No. 6,190,886.

Methods of manufacturing scFv-based agents of multivalency and multispecificity by varying the linker length were disclosed in U.S. Pat. No. 5,844,094, U.S. Pat. No. 5,837,242 and WO 98/44001. Methods of manufacturing scFv-based agents of multivalency and multispecificity by constructing two polypeptide chains, one comprising of the $V_H$ domains from at least two antibodies and the other the corresponding $V_L$ domains were disclosed in U.S. Pat. No. 5,989,830 and U.S. Pat. No. 6,239,259. Common problems that have been frequently associated with generating scFv-based agents of multivalency and multispecificity by prior art are low expression levels, heterogeneous products, instability in solution leading to aggregates, instability in serum, and impaired affinity.

A recombinantly produced bispecific or trispecific antibody in which the C-termini of $C_H1$ and $C_L$ of a Fab are each fused to a scFv derived from the same or different monoclonal antibodies was disclosed in U.S. Pat. No. 6,809,185. Major deficiencies of this "Tribody" technology include impaired binding affinity of the appended scFvs, heterogeneity of product forms, and instability in solution leading to aggregates.

Thus, there remains a need in the art for a method of making multimeric structures of multiple specificities or functionalities in general, and bispecific antibodies in particular, which are of defined composition, homogeneous purity, and unaltered affinity, and can be produced in high yields without the requirement of extensive purification steps. Furthermore, such structures must also be sufficiently stable in serum to allow in vivo applications. A need exists for stable, multimeric structures of multiple specificities or functionalities that are easy to construct and/or obtain in relatively purified form. Although the discussion above is primarily focused on antibody-containing complexes, the skilled artisan will realize that similar considerations apply to multimeric complexes comprising other types of effector moieties.

SUMMARY

The present invention concerns improved compositions and methods of use of complexes comprising multiple effector moieties, referred to as dock-and-lock (DNL) complexes. The DNL complexes may comprise two, three, four, five, six or more subunits. In preferred embodiments, the individual subunits are fusion proteins, each fusion protein comprising an AD moiety or a DDD moiety attached to an effector moiety. However, in alternative embodiments the subunits may comprise AD or DDD moieties attached to effector moieties by other methods, such as chemical cross-linking, click chemistry conjugation, etc. Most preferably, the DDD moiety comprises the amino acid sequence of a dimerization and docking domain from a human protein kinase A regulatory subunit protein, while the AD moiety comprises the amino acid sequence of an anchoring domain from an AKAP (A-kinase anchoring protein).

A particular embodiment concerns fusion proteins, each fusion protein comprising an AD moiety or a DDD moiety attached to a protein or peptide effector moiety. The effector moieties found in the subject fusion proteins may comprise any known protein or peptide, including but not limited to antibodies, antibody fragments, hormones, enzymes, carrier proteins, histones, serum albumin, antigens, xenoantigens, polymeric amino acids, cytotoxins, anti-angiogenic agents, pro-apoptotic agents, binding proteins, peptide ligands, agonists or antagonists, immunomodulators, cytokines, interleukins, interferons, ribonucleases, therapeutic agents, diagnostic agents, cytotoxic agents, or any other known protein or peptide that may be incorporated into a multimeric complex. Where the subunit is not a fusion protein, the effector moiety may also comprise a non-peptide molecule or aggregate, such as a nanoparticle, a micelle, a liposome, a polymer such as PEG, an inhibitory oligonucleotide such as siRNA, a synthetic gene, therapeutic agents, diagnostic agents, non-peptide hormones, cytotoxic agents, non-peptide anti-angiogenic agents, non-peptide pro-apoptotic agents or any other effector moiety known in the art. A given DNL complex may comprise multiple copies of the same effector moiety or may comprise two or more different effector moieties.

Where the subject DNL complex comprises one or more antibodies and/or antibody fragments, these may be incorporated as naked antibodies, alone or in combination with one or more therapeutic agents. Alternatively, the antibodies or fragments may be utilized as immunoconjugates, attached to one or more therapeutic agents. (For methods of making immunoconjugates, see, e.g., U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.) Therapeutic agents may be selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide molecule (e.g., an antisense molecule or a gene) or a second antibody or fragment thereof.

In certain embodiments, a therapeutic and/or diagnostic agent may be administered to a subject after a DNL complex, for example in pre-targeting strategies discussed below. A DNL complex comprising a first antibody against a targeted cell antigen and a second antibody against a hapten may be administered to the subject and allowed to localize in, for example, a diseased tissue such as a tumor. A targetable construct comprising one or more copies of the hapten, along with at least one diagnostic and/or therapeutic agent is subsequently administered and binds to the DNL complex. Where the targetable construct is conjugated to a toxic moiety, such as a radionuclide, this pretargeting method reduces the systemic exposure of the subject to toxicity, allowing a proportionately greater delivery of toxic agent to the targeted tissue.

In some embodiments, the antibody or fragment thereof may be a human, chimeric, or humanized antibody or fragment thereof. A humanized antibody or fragment thereof may comprise the complementarity-determining regions (CDRs) of a murine antibody and the constant and framework (FR) region sequences of a human antibody, which may be substituted with at least one amino acid from corresponding FRs of a murine antibody. A chimeric antibody or fragment thereof may include the light and heavy chain variable regions of a murine antibody, attached to human antibody constant regions. The antibody or fragment thereof may include human constant regions of IgG1, IgG2a, IgG3, or IgG4. Human antibodies may be made by methods known in the art, as discussed below. Exemplary known antibodies of use include, but are not limited to, hR1 (anti-IGF-1R), hPAM4 (anti-mucin), hA20 (anti-CD20), hA19 (anti-CD19), hIMMU31 (anti-AFP), hLL1 (anti-CD74), hLL2 (anti-CD22), hMu-9 (anti-CSAp), hL243 (anti-HLA-DR), hMN-14 (anti-CEACAM5), hMN-15 (anti-CEACAM6), 29H2 (anti-CEACAM1, ABCAM®), hRS7 (anti-EGP-1) and hMN-3 (anti-CEACAM6).

Also disclosed is a method for treating and/or diagnosing a disease or disorder that includes administering to a patient a DNL complex that is attached to or binds to at least one therapeutic and/or diagnostic agent. In preferred embodiments, the disease or disorder may be cancer, hyperplasia, an immune dysregulation disease, an autoimmune disease, organ-graft rejection, graft-versus-host disease, a solid tumor, non-Hodgkin's lymphoma, Hodgkin's lymphoma, multiple myeloma, a B-cell malignancy, a T-cell malignancy, a neurodegenerative disease such as Alzheimer's disease, a metabolic disease such as amyloidosis, diabetes, vasculitis, sepsis, viral infection, fungal infection, bacterial infection, diabetic retinopathy, macular degeneration, asthma, edema, pulmonary hypertension, juvenile diabetes, psoriasis, a cardiovascular disease such as myocardial angiogenesis, plaque neovascularization, restenosis, neointima formation after vascular trauma, angiofibroma, fibrosis associated with chronic inflammation, lung fibrosis, deep venous thrombosis or wound granulation.

A B-cell malignancy may include indolent forms of B-cell lymphomas, aggressive forms of B-cell lymphomas, chronic lymphatic leukemias, acute lymphatic leukemias, and/or multiple myeloma. Solid tumors may include melanomas, carcinomas, sarcomas, and/or gliomas. A carcinoma may include renal carcinoma, lung carcinoma, intestinal carcinoma, stomach carcinoma, breast carcinoma, prostate cancer, ovarian cancer, endometrial cancer, cervical cancer, bladder cancer, liver cancer, pancreatic cancer and/or melanoma.

Antigens that may be targeted by an antibody-based DNL complex include, but are not limited to, carbonic anhydrase IX, alpha-fetoprotein, α-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CDC27, CDK-4/m, CDKN2A, CXCR4, colon-specific antigen-p (CSAp), CEA (CEACAM5), CEACAM1, CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-13, IL-2, IL-4R, IL-6R, IL-13R, IL-15R, IL-17R, IL-18R, IL-6, IL-8, IL-12, IL-15, IL-17, IL-18, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, antigen specific for PAM-4 antibody, placental growth factor, p53, PLAGL2, prostatic acid phosphatase, PSA, PRAME, PSMA, PlGF, IGF, IGF-1R, IL-6, IL-25, RS5, RANTES, T101, SAGE, 5100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207). Reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63).

Other embodiments may concern methods for treating a lymphoma, leukemia, or autoimmune disorder in a subject, by administering to the subject one or more dosages of a DNL complex, where the binding site of the second effector binds to a lymphocyte antigen, and where the binding site of the first effector binds to the same or a different lymphocyte antigen. The binding site or sites may bind a distinct epitope, or epitopes of an antigen selected from the group consisting of CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, CD154, B7, MUC1, Ia, 11, HM1.24, HLA-DR, tenascin, VEGF, P1GF, ED-B fibronectin, an oncogene, an oncogene product, NCA 66a-d, necrosis antigens, IL-2, T101, TAG, IL-6, MIF, TRAIL-R1 (DR4) and TRAIL-R2 (DR5). The composition may be parenterally administered in a dosage of 20 to 500 milligrams protein per dose, 20 to 100 milligrams protein per dose, or 20 to 1500 milligrams protein per dose, for example.

Exemplary autoimmune diseases include acute idiopathic thrombocytopenic purpura, chronic idiopathic thrombocytopenic purpura, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

In still other embodiments, the DNL complexes may be of use to treat subjects infected with pathogenic organisms, such as bacteria, viruses or fungi. Exemplary fungi that may be treated include *Microsporum, Trichophyton, Epidermophyton, Sporothrix schenckii, Cryptococcus neoformans, Coccidioides immitis, Histoplasma capsulatum, Blastomyces dermatitidis* or *Candida albicans*. Exemplary viruses include human immunodeficiency virus (HIV), herpes virus, cytomegalovirus, rabies virus, influenza virus, human papilloma virus, hepatitis B virus, hepatitis C virus, Sendai virus, feline leukemia virus, Reo virus, polio virus, human serum parvo-like virus, simian virus 40, respiratory syncytial virus, mouse mammary tumor virus, Varicella-Zoster virus, Dengue virus, rubella virus, measles virus, adenovirus, human T-cell leukemia viruses, Epstein-Barr virus, murine leukemia virus, mumps virus, vesicular stomatitis virus, Sindbis virus, lymphocytic choriomeningitis virus or blue tongue virus. Exemplary bacteria include *Bacillus anthracis, Streptococcus agalactiae, Legionella pneumophila, Streptococcus pyogenes, Escherichia coli, Neisseria gonorrhoeae, Neisseria meningitidis, Pneumococcus* spp., *Hemophilus influenzae* B, *Treponema pallidum*, Lyme disease spirochetes, *Pseudomonas aeruginosa, Mycobacterium leprae, Brucella abortus, Mycobacterium tuberculosis* or a *Mycoplasma*. Such DNL complexes may comprise, for example, binding sites for one or more antigenic determinant on a pathogen, and may be conjugated or attached to a therapeutic agent for the pathogen, for example an anti-viral, antibiotic or anti-fungal agent. Alternatively, a DNL complex may comprise a first binding site for a pathogen antigen and a second binding site for a hapten or carrier that is attached to one or more therapeutic agents.

Various embodiments may concern methods of treating inflammatory and immune-dysregulatory diseases, infectious diseases, pathologic angiogenesis or cancer. The DNL complexes may bind to two different targets selected from the group consisting of (A) proinflammatory effectors of the innate immune system, (B) coagulation factors, (C) complement factors and complement regulatory proteins, and (D) targets specifically associated with an inflammatory or immune-dysregulatory disorder or with a pathologic angiogenesis or cancer, wherein the latter target is not (A), (B), or (C). At least one of the targets is (A), (B) or (C). Suitable combinations of targets are described in U.S. patent application Ser. No. 11/296,432, filed Dec. 8, 2005, the Examples section of which is incorporated herein in their entirety.

The proinflammatory effector of the innate immune system to which the DNL complex may bind may be a proinflammatory effector cytokine, a proinflammatory effector chemokine or a proinflammatory effector receptor. Suitable proinflammatory effector cytokines include MIF, HMGB-1 (high mobility group box protein 1), TNF-a, IL-1, IL-4, IL-5, IL-6, IL-8, IL-12, IL-15, and IL-18. Examples of proinflammatory effector chemokines include CCL19, CCL21, IL-8, MCP-1, RANTES, MIP-1A, MIP-1B, ENA-78, MCP-1, IP-10, GROB, and Eotaxin. Proinflammatory effector receptors include IL-4R (interleukin-4 receptor), IL-6R (interleukin-6 receptor), IL-13R (interleukin-13 receptor), IL-15R (interleukin-15 receptor) and IL-18R (interleukin-18 receptor).

The DNL complex also may react specifically with at least one coagulation factor, particularly tissue factor (TF) or thrombin. In other embodiments, the DNL complex reacts specifically with at least one complement factor or complement regulatory protein. In preferred embodiments, the complement factor is selected from the group consisting of C3, C5, C3a, C3b, and C5a. When the DNL complex reacts specifically with a complement regulatory protein, the complement regulatory protein preferably is selected from the group consisting of CD46, CD55, CD59 and mCRP.

Also described herein are nucleic acids comprising DNA sequences encoding a fusion protein or other DNL subunit, as described herein. Other embodiments concern expression vectors and/or host cells comprising the encoding DNA sequences. In certain preferred embodiments, the host cell may be an Sp2/0 cell line transformed with a mutant Bcl-2 gene, for example with a triple mutant Bcl-2 gene (T69E, S70E, S87E), that has been adapted to cell transformation and growth in serum free medium. (See, e.g., U.S. Pat. Nos. 7,531,327; 7,537,930; and 7,608,425, the Examples section of each of which is incorporated herein by reference.) The host cell transfected with expression vector(s) encoding a DNL complex, or a subunit of a DNL complex, may be cultured by standard techniques for production of the encoded protein or complex. Advantageously, the host cell is adapted for growth and protein production under serum-free conditions.

Another embodiment concerns methods of delivering a diagnostic or therapeutic agent, or a combination thereof, to a target comprising (i) providing a composition that comprises a DNL complex conjugated to at least one diagnostic and/or therapeutic agent and (ii) administering to a subject in need thereof the conjugated DNL complex, wherein the DNL complex comprises at least one antibody or antigen-binding fragment thereof that binds to a targeted cell antigen.

Also contemplated is a method of delivering a diagnostic agent, a therapeutic agent, or a combination thereof to a target, comprising: (a) administering to a subject a DNL complex having an affinity toward a targeted cell antigen and a second affinity toward one or more haptens; (b) waiting a sufficient amount of time for DNL complex that does not bind to the target cell to clear the subject's blood stream; and (c) administering to said subject a carrier molecule comprising a diagnostic agent, a therapeutic agent, or a combination thereof, that binds to the DNL complex.

Further contemplated is a method of imaging a diseased tissue or organ, such as a tumor, by administering a DNL complex to a subject. The DNL complex contains at least one effector, such as an antibody, that binds to a targeted antigen on a cell, tissue or organ to be imaged. The DNL complex may be directly conjugated to one or more imaging agents, or may bind to a targetable construct that is attached to one or more imaging agents. In preferred embodiments the imaging agent is $^{18}$F, although any other imaging agent known in the art may be used.

An alternative embodiment concerns DNL complexes for PEGylation of a therapeutic agent. The complex may comprise one or more copies of a therapeutic agent, such as MIF, HMGB-1 (high mobility group box protein 1), TNF-α, IL-1, IL-2, IL-3, IL-4, IL-5, IL-6, IL-7, IL-8, IL-9, IL-10, IL-11, IL-12, IL-13, IL-15, IL-16, IL-17, IL-18, IL-19, IL-23, IL-24, CCL19, CCL21, IL-8, MCP-1, RANTES, MIP-IA, MIP-1B, ENA-78, MCP-1, IP-10, Gro-β, Eotaxin, interferon-α, interferon-β, interferon-γ, interferon-λ, G-CSF, GM-CSF, SCF, PDGF, MSF, Flt-3 ligand, erythropoietin, thrombopoietin, hGH, CNTF, leptin, oncostatin M, VEGF, EGF, FGF, PlGF, insulin, hGH, calcitonin, Factor VIII, IGF, somatostatin, tissue plasminogen activator, and LIF. The DNL complex further comprises at least one PEG moiety. Preferably, the DNL complex comprising PEGylated therapeutic agent exhibits improved efficacy and pharmacokinetic properties compared to the therapeutic agent alone or to other PEGylated forms of the therapeutic agent.

Another alternative embodiment concerns DNL complexes comprising multiple copies of a cytokine, attached to an antibody or fragment thereof. In preferred embodiments, the complexes comprise tetrameric copies of a cytokine, preferably selected from the group consisting of interferon (IFN)-α2b, G-CSF and erythropoietin. However, the skilled artisan will realize that many protein or peptide cytokines are known in the art, and any such cytokine may be incorporated into the subject DNL complexes. More preferably, the cytokine-antibody DNL complex exhibits a greater in vivo efficacy against lymphoma cells than the cytokine moiety alone, the antibody moiety alone, the combination of unconjugated cytokine moiety with unconjugated antibody moiety and a PEGylated form of the cytokine moiety. In a most preferred embodiment, the antibody moiety is hA20 IgG antibody and the cytokine moiety is human IFNα2b.

In certain embodiments, the DNL complexes are of use for inducing or enhancing an immune response and may comprise an antigen or xenoantigen and one or more antibodies or fragments thereof that direct the antigen to a target immune cell. In a non-limiting example, the antibody may bind to a dendritic cell or antigen-presenting cell (APC) antigen, such as CD209 (DC-SIGN), CD34, CD74, CD205, TLR 2 (toll-like receptor 2), TLR 4, TLR 7, TLR 9, BDCA-2, BDCA-3, BDCA-4 or HLA-DR. Preferably, the xenoantigen is a non-human homologue of an antigen expressed on a disease-associated cell, such as a tumor-associated antigen. The skilled artisan will realize that the subject DNL complexes may be of use for production of vaccines against a wide range of target cells, tissues or pathogens. In another non-limiting example, the DNL complex comprises at least one antigenic peptide from a poxvirus protein, such as viral IL-18 binding protein (vIL18BP), or a viral envelope protein such as L1R, A27L or D8L, attached to an antibody or fragment thereof that binds to an APC. Any antigen expressed by a virus, bacterium, mycoplasma, or other pathogenic agent may be incorporated into a subject DNL complex for inducing an immune response against the pathogen.

In still other embodiments, the DNL complex may comprise three or more different effector moieties, such as a first antibody or fragment thereof, a second antibody or fragment thereof, and a cytokine. Preferably, the first and second antibodies bind to two different antigens on a target cell, although in alternative embodiments the two antibodies may bind to antigens expressed by two different cell types. In an exemplary embodiment, the first antibody or antibody fragment is veltuzumab, the second antibody or antibody fragment is hL243, and the cytokine is human interferon-α2b. The combination of antibodies targeting two different antigens in the same DNL complex may provide even greater efficacy against and/or affinity for target cells than DNL complexes comprising multiple copies of an antibody against a single target antigen.

Another preferred embodiments concerns DNL complexes comprising an antibody or antigen-binding fragment thereof attached to multiple copies of a toxin, such as a bacterial toxin, a plant toxin, ricin, abrin, alpha toxin, saporin, ribonuclease (RNase), DNase I, Staphylococcal enterotoxin-A, pokeweed antiviral protein, gelonin, diphtheria toxin, *Pseudomonas* exotoxin, *Pseudomonas* endotoxin, ranpirnase (Rap) or Rap (N69Q). More preferably, the toxin is ranpirnase and the antibody is an anti-EGP-1 (anti-Trop-2), anti-CD74, anti-CD22 or anti-CD20 antibody. Most preferably, the DNL conjugated toxin is cytotoxic at nanomolar or lower concentrations.

Yet another embodiment relates to DNL complexes for delivery of therapeutic nucleic acid species, such as artificial genes or siRNA. In such embodiments, the DNL complex may comprise an antibody or fragment thereof attached to one or more copies of a nucleic acid carrier, such as a dendrimer, a protamine, a histone, histidine-containing reducible polycation, cationic comb-type copolymer, chitosan-thiamine pyrophosphate, polyethyleneimine or polylysine. Many examples of nucleic acid binding polymers are known in the art, such as PAMAM, polylysine, polypropyleneimine, polyethyleneimine, polyethyleneglycol or carbosilane. Generally, the carrier molecule is polycationic and binds to nucleic acids by electrostatic interaction. As discussed below, many examples of siRNA or other therapeutic nucleic acids are known in the art and any such known species may be delivered to a target cell, tissue, organ or pathogen using the DNL complexes described herein.

The skilled artisan will realize that the DNL complexes and uses thereof disclosed above are exemplary only and that many other different types of DNL complexes, for either therapeutic or diagnostic use, are included within the scope of the present invention.

Serum elimination curves are shown. Serum half-life ($T_{1/2}$) elimination rates and mean residence times (MRT) are summarized in the inserted table.

Figure 10:
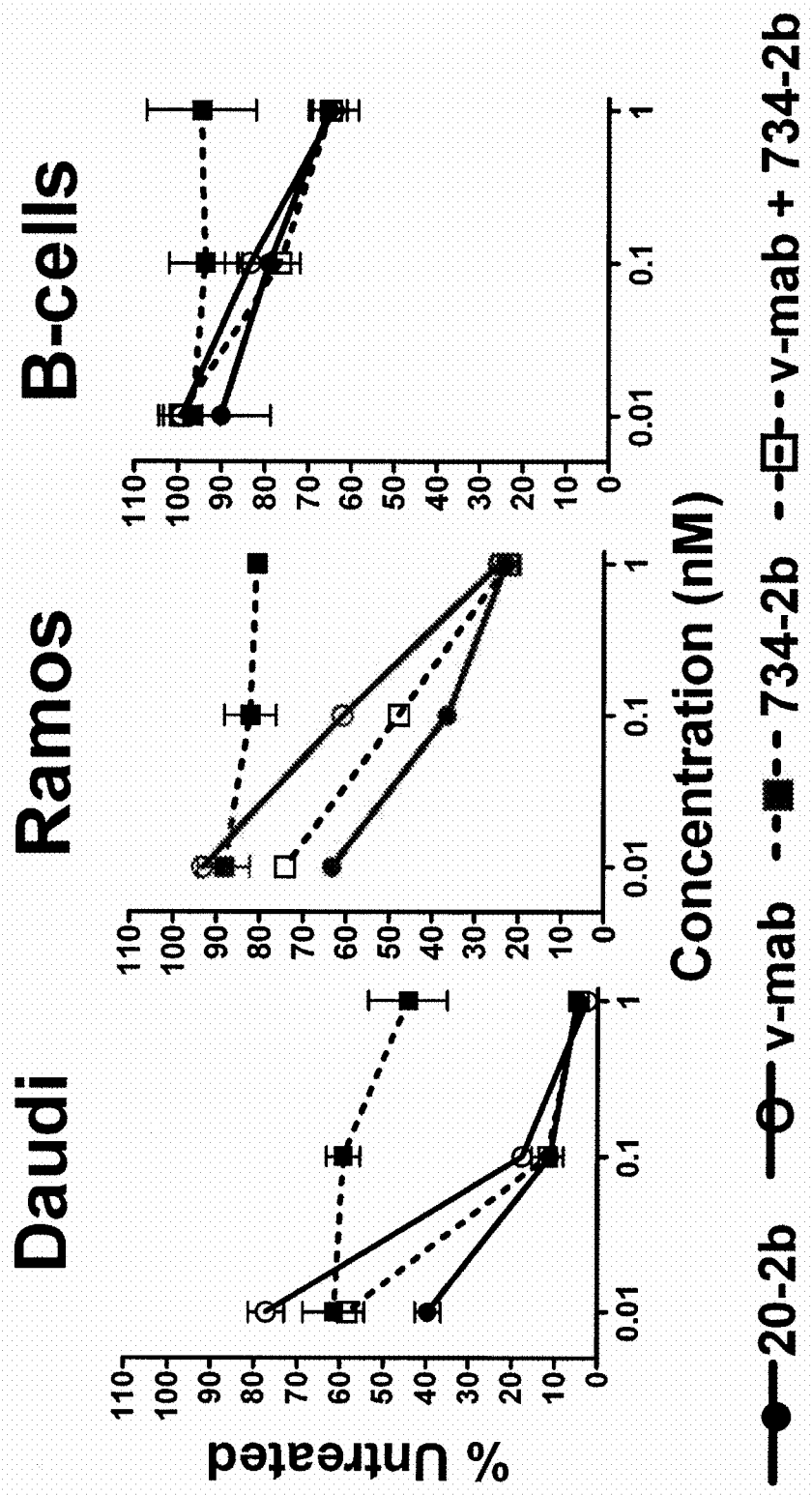

FIG. 10. Enhanced depletion of NHL cells from whole blood by 20-2b. Fresh heparinized human blood was mixed with either Daudi or Ramos and incubated with 20-2b (●), v-MAb (○), 734-2b (■) or v-MAb+734-2b (□) at 0.01, 0.1 or 1 nM for two days. The effect of the indicated treatments on lymphoma and peripheral blood lymphocytes was evaluated using flow cytometry. Error bars, SD.

Figure 11:
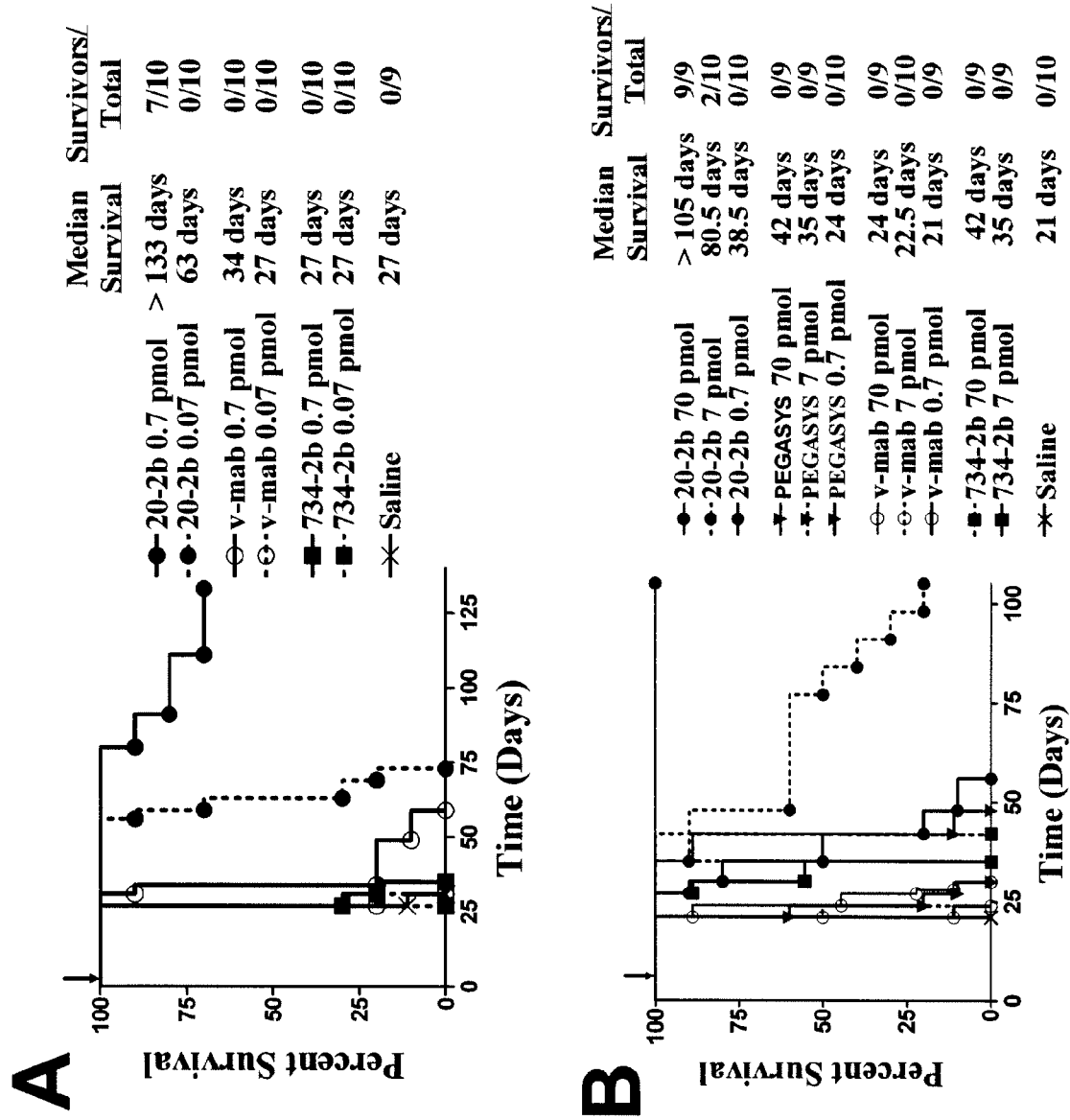

FIG. 11. (A) Survival curves showing therapeutic efficacy of 20-2b in a disseminated Burkitt's lymphoma (Daudi) xenograft model. Female C.B. 17 SCID mice were administered Daudi cells i.v. on day 0. Treatments consisted of 20-2b (●), 734-2b (■), v-MAb (○), PEGASYS® (▼) or saline (X) given as a single s.c. doses. Days of treatment are indicated with arrows. Survival curves were analyzed using Prism software. In an Early Daudi model. Groups of 10 mice were given a single dose of 0.7 pmol (solid line) or 0.07 pmol (dashed line) on day 1. (B) A similar study to FIG. 11(A), but in an Advanced Daudi model. Groups of 10 mice were given a single dose of 0.7 pmol (solid line), 7 pmol (dashed line) or 70 pmol (gray line) on day 7.

Figure 12:
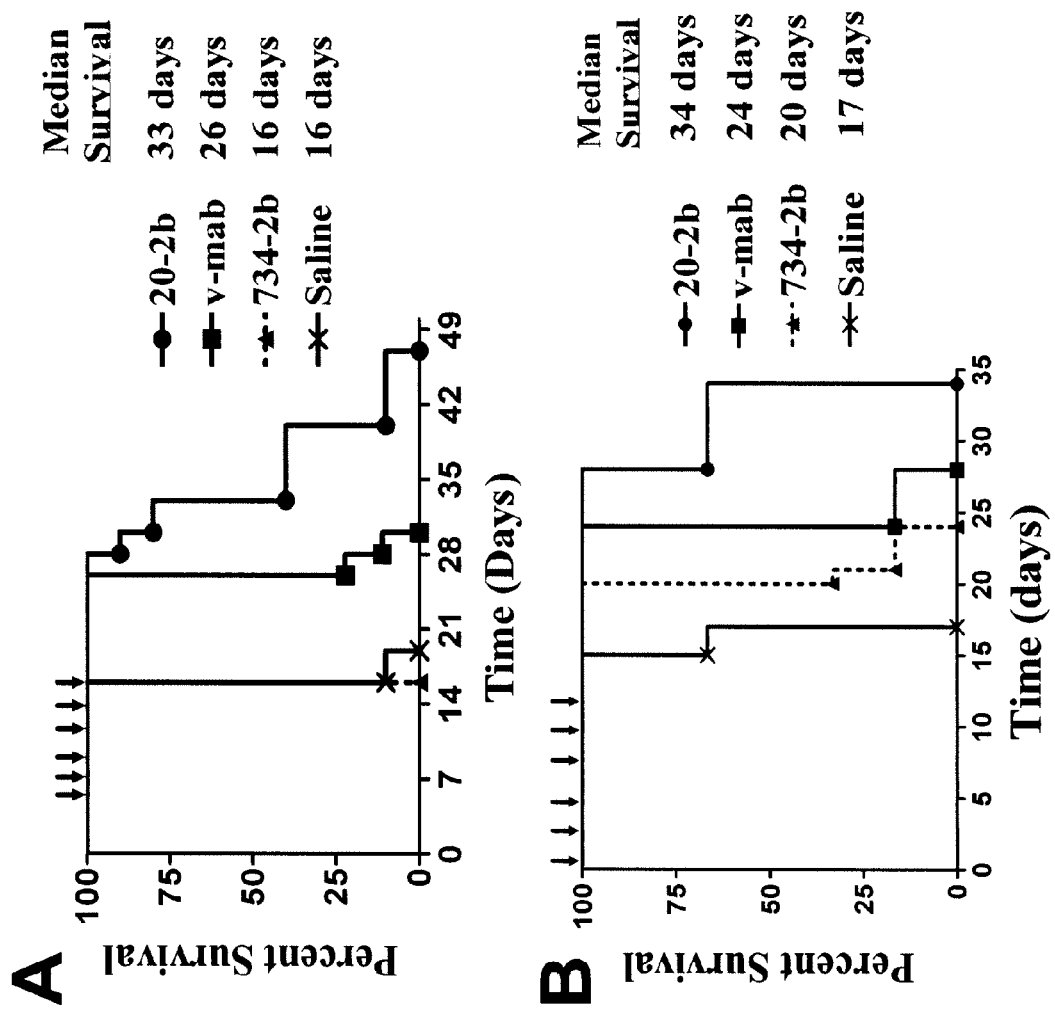

FIG. 12. (A) Survival curves showing therapeutic efficacy of 20-2b in disseminated Burkitt's lymphoma (Raji and NAMALWA) xenograft models. Female C.B. 17 SCID mice were administered NHL cells i.v. on day 0. Treatments consisted of 20-2b (●), 734-2b (■), v-MAb (○) or saline (X) given as s.c. doses. Days of treatment are indicated with arrows. Survival curves were analyzed using Prism software. In an Advanced Raji model, groups of 10 received 250 pmol doses on days 5, 7, 9, 12, 14 and 16. (B) A similar study to FIG. 12(A), but in an Early NAMALWA model. Groups of 6 received 250 pmol doses of 20-2b or 734-2b on days 1, 3, 5, 8, 10 and 12 or 3.5 nmol doses of v-MAb on days 1, 5, 9, 13, 17, 21 and 25.

Figure 13:
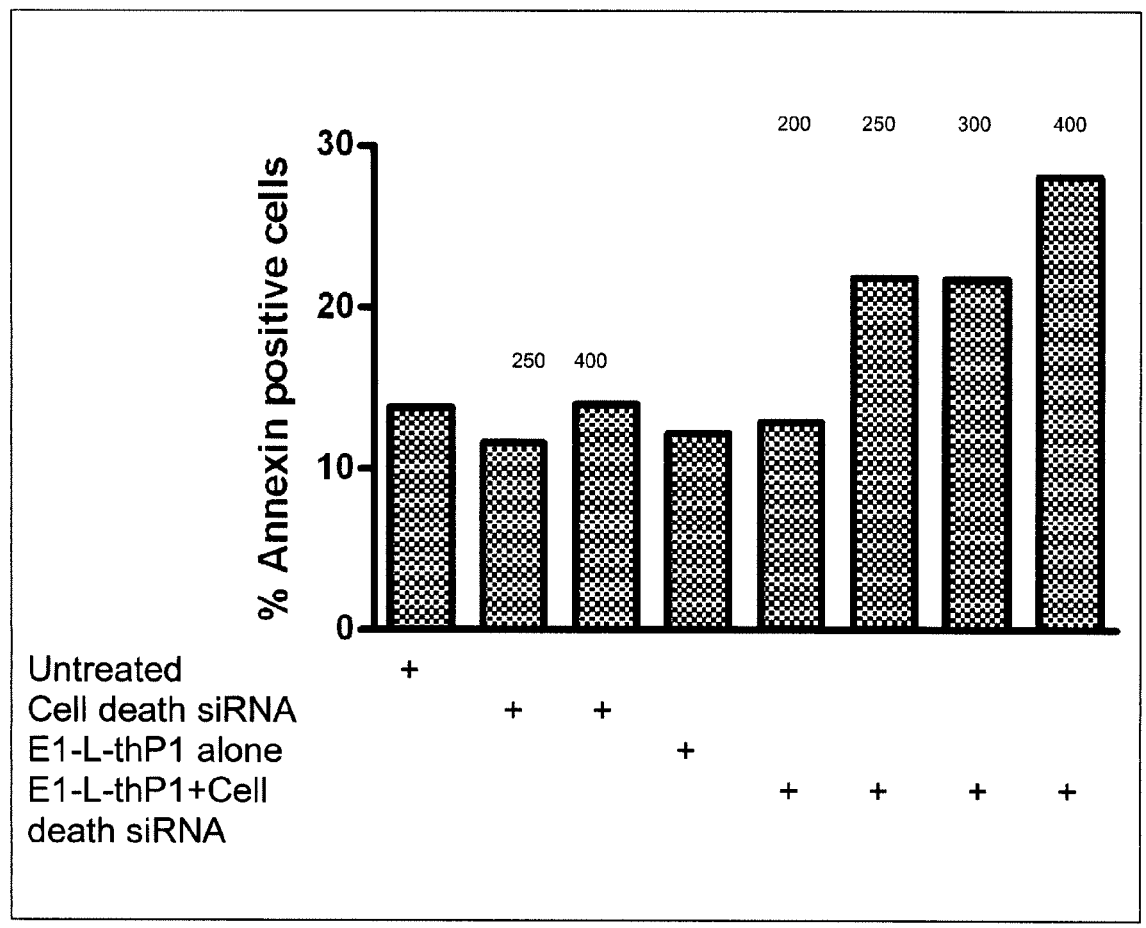

FIG. 13. Apoptosis of ME180 induced by E1-L-thP1 internalization of cell death siRNA.

Figure 14:
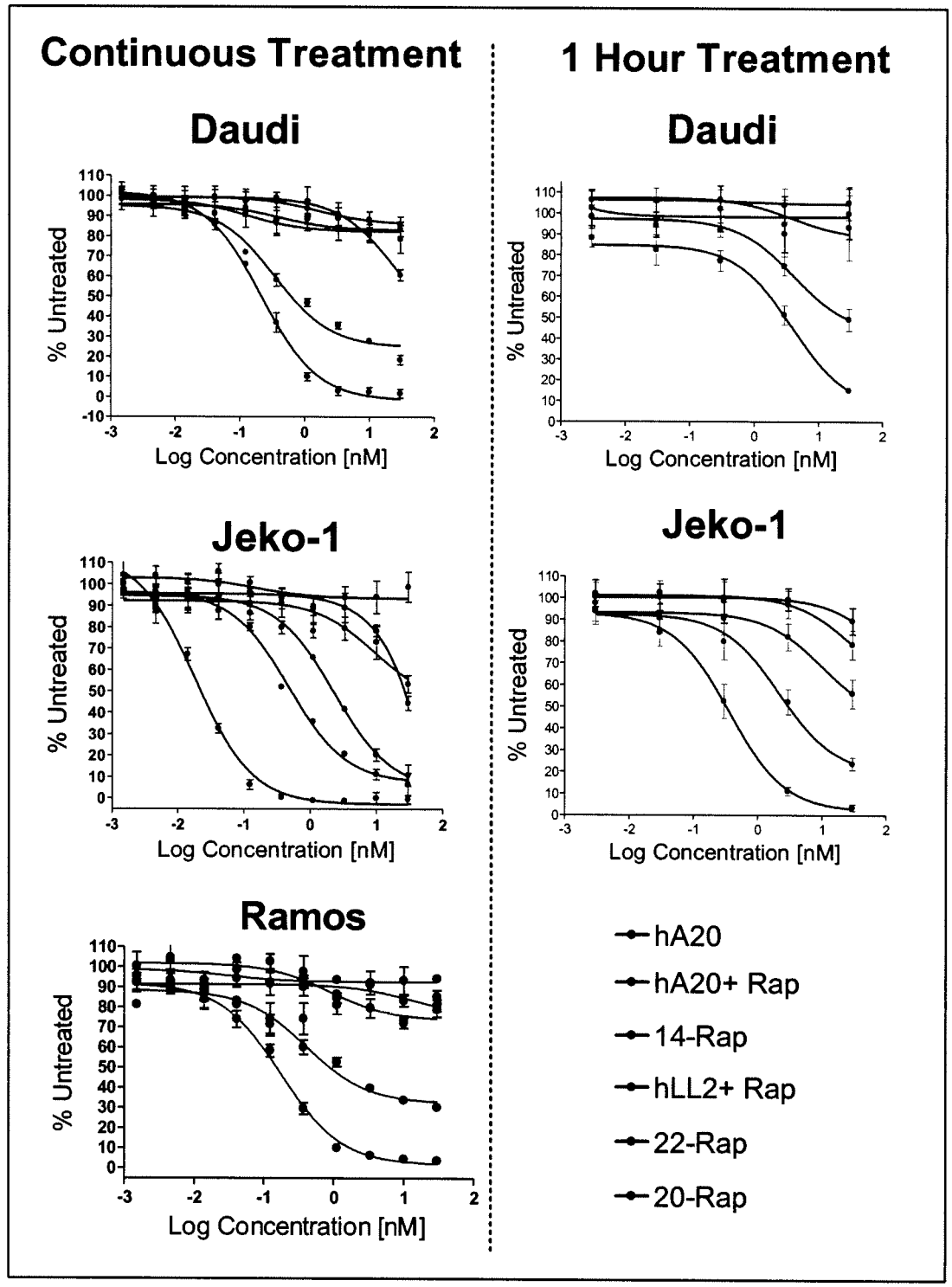

FIG. 14. In vitro cytotoxicity of DNL-Rap immunotoxin constructs either treated continuously with immunotoxin or with washing after a 1 hour treatment.

Figure 15:
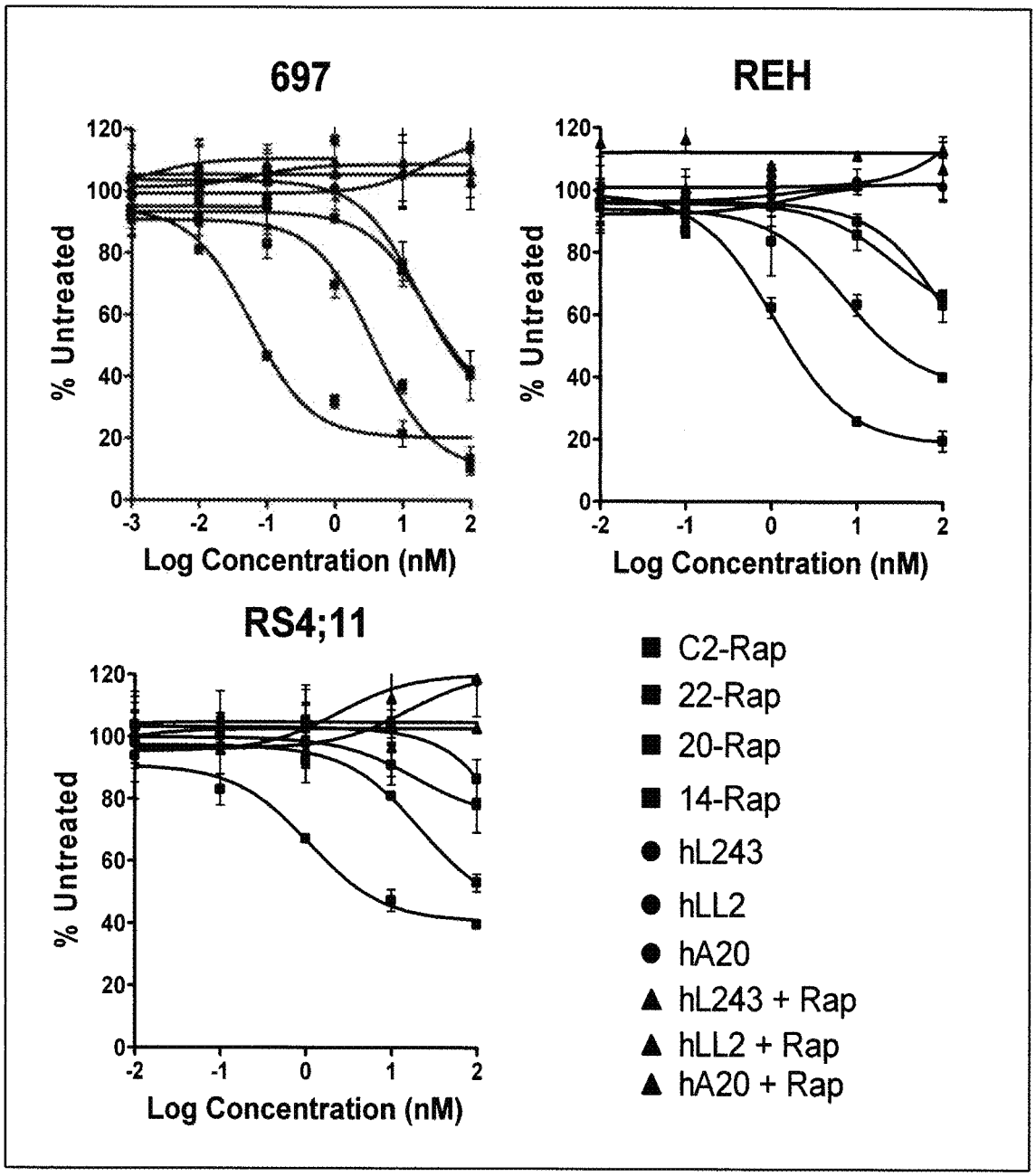

FIG. 15. In vitro cytotoxicity of DNL-Rap immunotoxin constructs in ALL cell lines.

Figure 16:
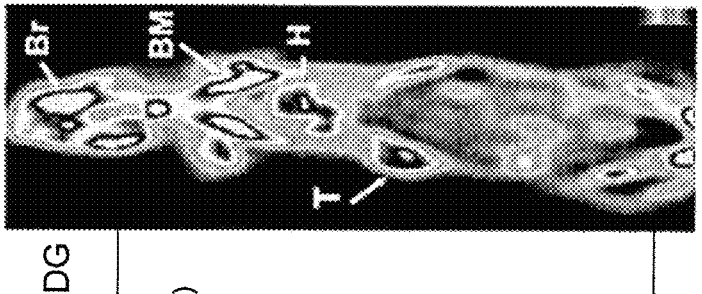
Figure 16:
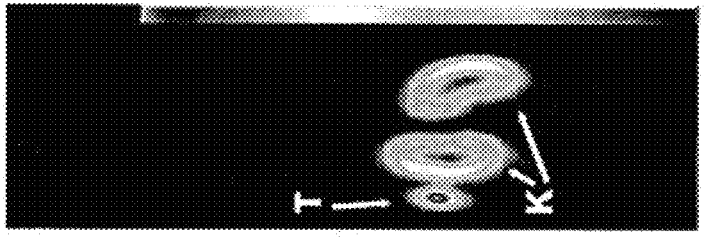
Figure 16:
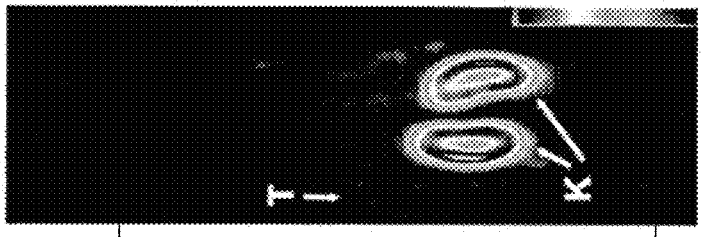

FIG. 16. Biodistribution of $^{18}$F-labeled agents in tumor-bearing nude mice by microPET imaging. Coronal slices of 3 nude mice bearing a small, subcutaneous LS174T tumor on each left flank after being injected with either (A) [$^{18}$F]FDG, (B) Al[$^{18}$F] IMP 449 pretargeted with the anti-CEA× anti-HSG bsMAb, (C) Al[$^{18}$F] IMP 449 alone (not pretargeted with the bsMAb). Biodistribution data expressed as percent-injected dose per gram (% ID/g) are given for the tissues removed from the animals at the conclusion of the imaging session. Abbreviations: B, bone marrow; H, heart; K, kidney; T, tumor.

Figure 17:
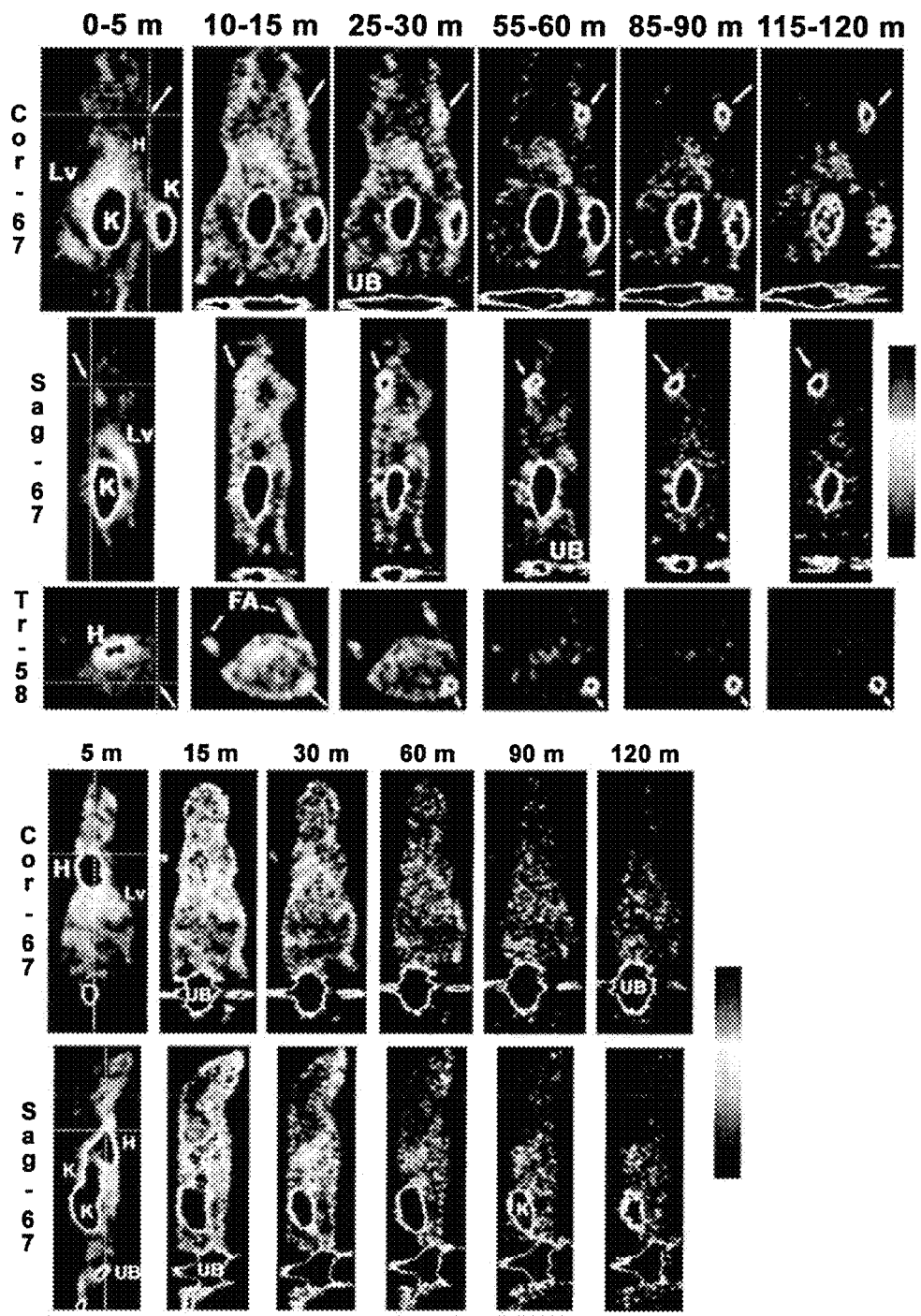

FIG. 17. Dynamic imaging study of pretargeted Al [$^{18}$F] IMP 449 given to a nude mouse bearing a 35-mg LS174T human colorectal cancer xenograft in the upper flank. The top 3 panels show coronal, sagittal, and transverse sections, respectively, taken of a region of the body centering on the tumor's peripheral location at 6 different 5-min intervals over the 120-min imaging session. The first image on the left in each sectional view shows the positioning of the tumor at the intersection of the crosshairs, which is highlighted by arrows. The animal was partially tilted to its right side during the imaging session. The bottom 2 panels show additional coronal and sagittal sections that focus on a more anterior plane in the coronal section to highlight distribution in the liver and intestines, while the sagittal view crosses more centrally in the body. Abbreviations: Cor, coronal; FA, forearms; H, heart; K, kidney; Lv, liver; Sag, sagittal; Tr, transverse; UB, urinary bladder.

FIG. 18. In vitro cytotoxicity of MAb-IFNα on NHL and MM cell lines. I-$EC_{50}$=Total IFNα concentration (nM) resulting in 50% growth inhibition compared to untreated cells. ND, treatment failed to reach 50% inhibition; *$EC_{50}$ for hL243γ4p IgG; †v-mab excluded. TI, targeting index=fold reduction in $EC_{50}$ compared to non targeted IFNα (734-2b-2b). $I_{max}$≤maximal % decrease in viable cells compared to untreated cells.

Figure 19:
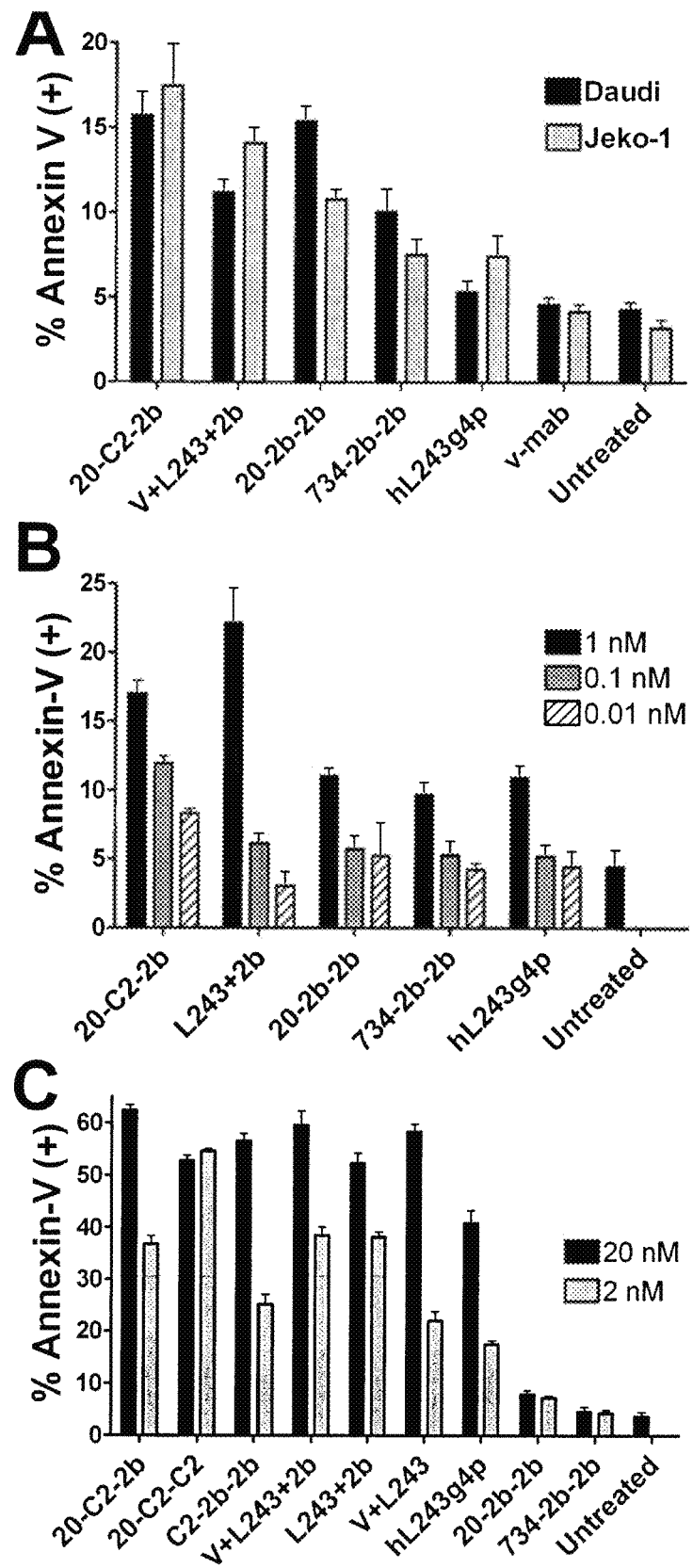

FIG. 19. Apoptosis in NHL and MM cells. Cells were treated for 48 h before quantification of the % annexin-V-positive cells by flow cytometry. (A) For Daudi: v-mab and hL243γ4p were 10 pM; 20-C2-2b, 20-2b-2b and V+L243+2b (a mixture of v-mab, hL243γ4p and 734-2b-2b) were 1 pM. For Jeko-1, all treatments were at 0.5 nM. (B) CAG was treated at 1, 0.1 and 0.01 nM. (C) KMS12-BM was treated at 20 and 2 nM. V+L243, mixture of v-mab and hL243γ4p; L243+2b, mixture of hL243γ4p and 734-2b-2b.

Figure 20:
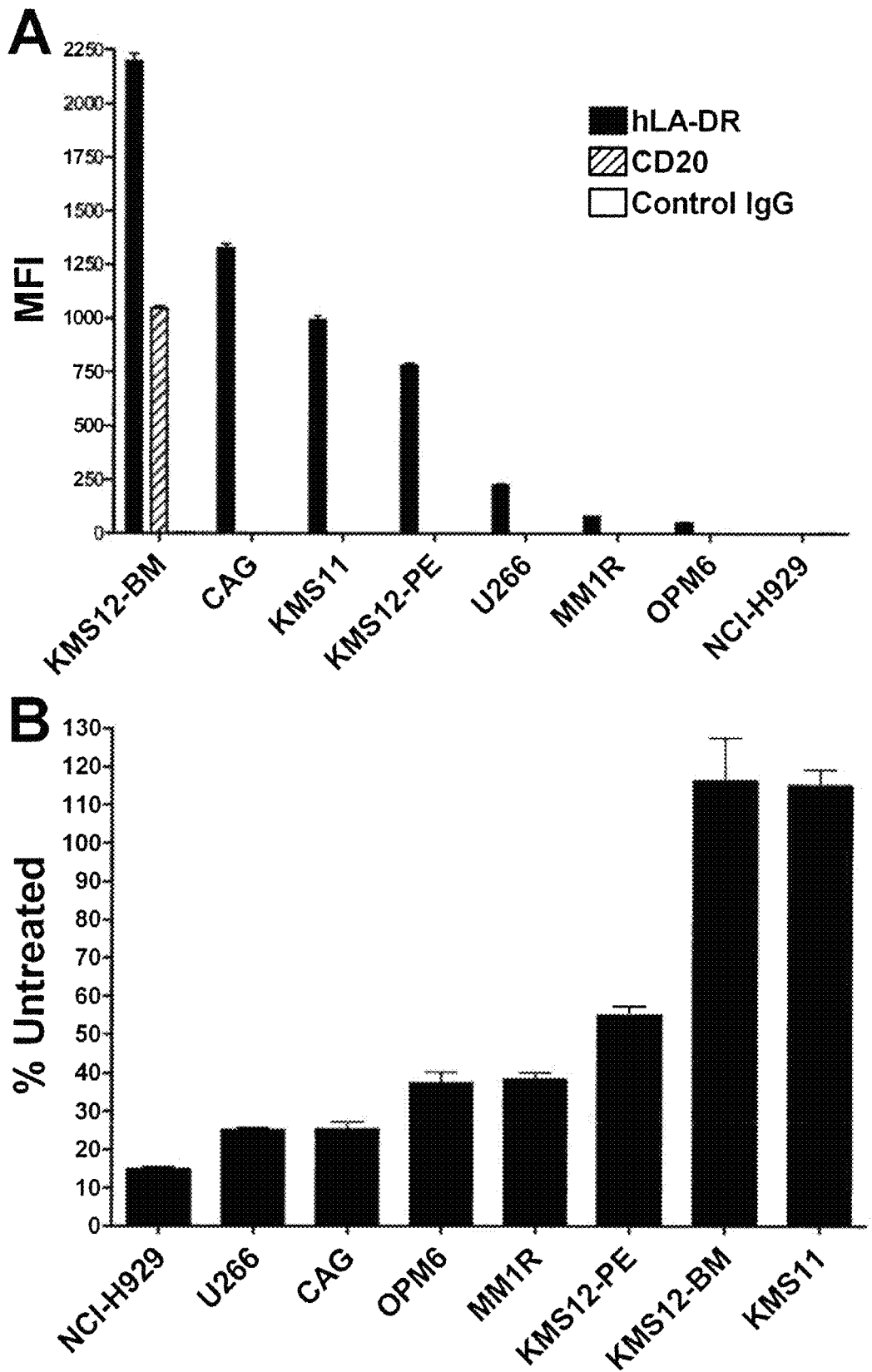

FIG. 20. Characterization of multiple myeloma cell lines. (A) Antigen densities of HLA-DR and CD20 on selected myeloma lines. After 30 min incubation with hL243γ4p, v-mab or hMN-14 (isotype control MAb), cells were probed with PE-Goat anti-human IgG (Fab) and analyzed by flow cytometry. (B) Relative sensitivity of myeloma lines to IFNα2. Cells were incubated in the presence or absence of 3 nM peginterferon alfa-2b for 4 days prior to quantification of viable cells with MTS.

Figure 21:
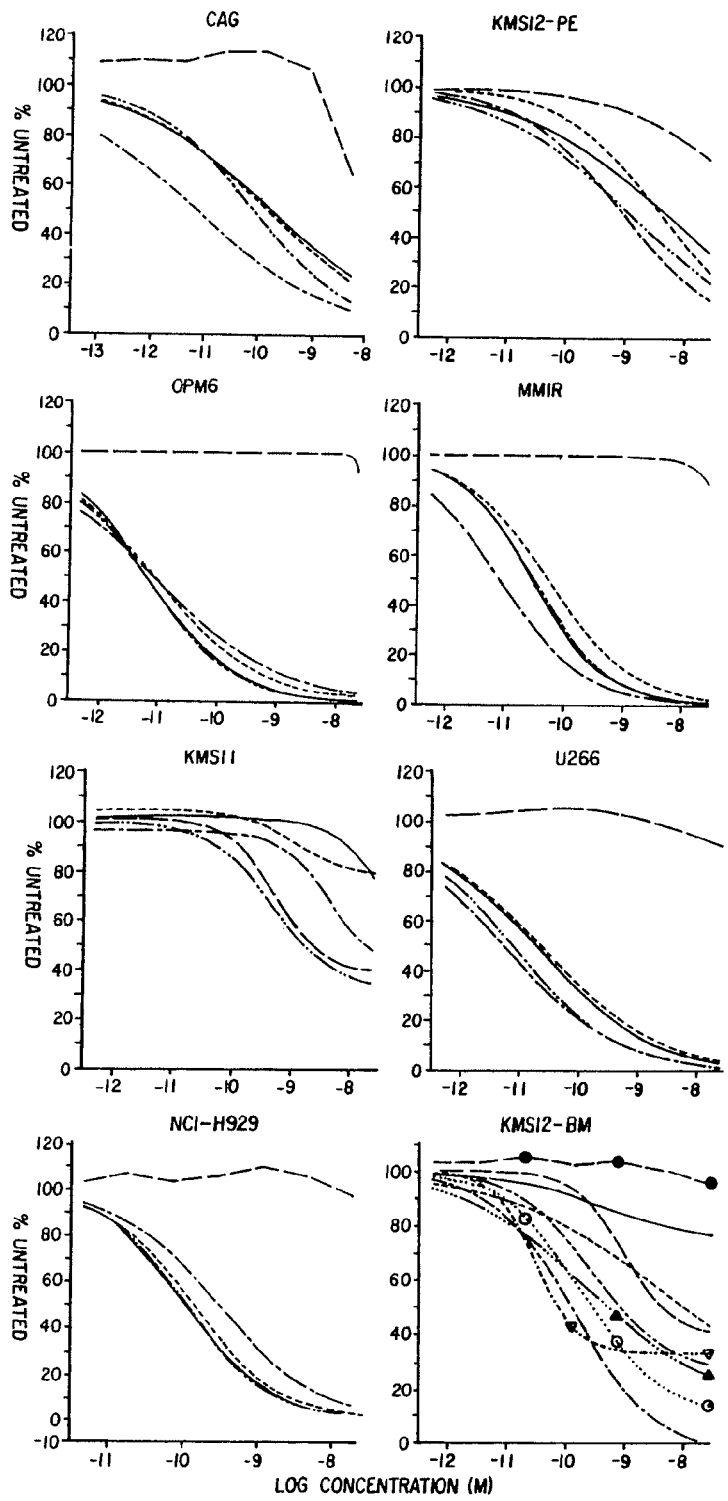

FIG. 21. In vitro cytotoxicity of multiple myeloma. Indicated cell lines were cultured in the presence of increasing concentrations of the indicated constructs or combinations and the relative viable cell densities were measured with MTS. The % of the signal obtained from untreated cells was plotted vs. the log of the molar concentration. Dose-response curves and $EC_{50}$ values were generated using Prism software. Error bars, SD.

Figure 22:
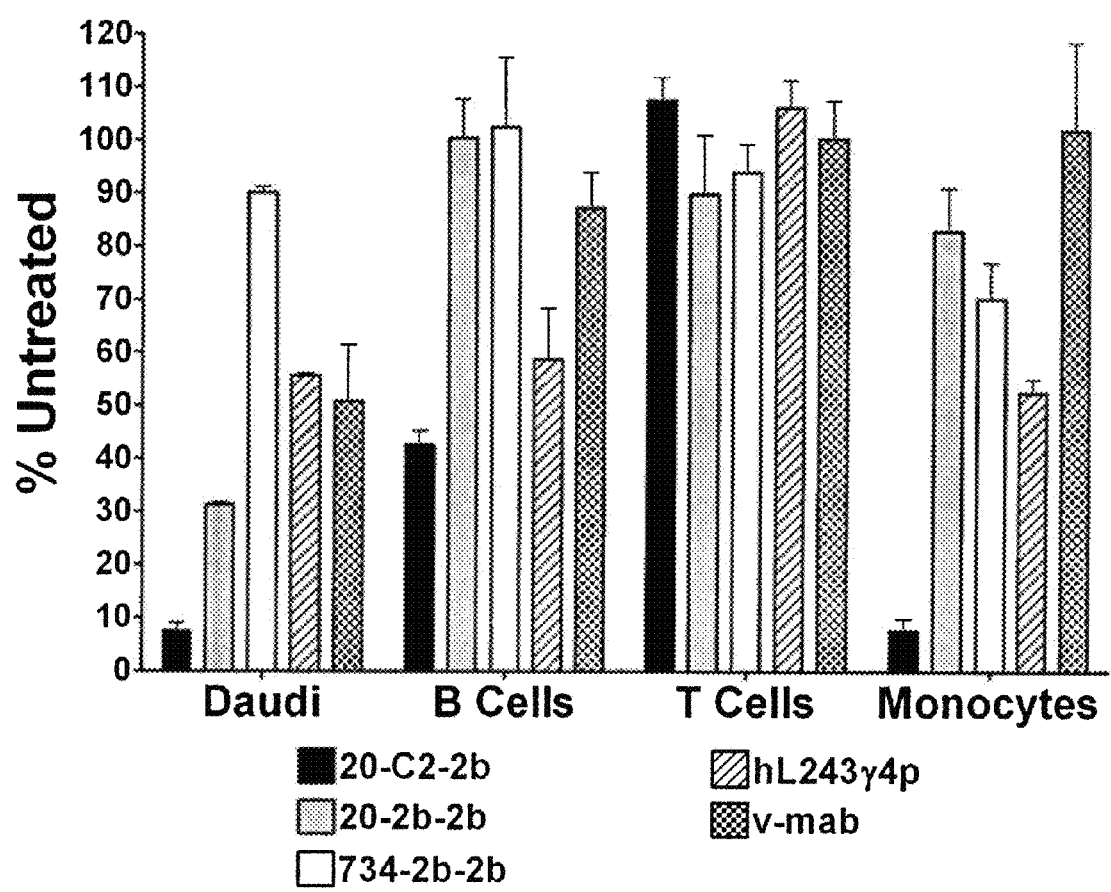

FIG. 22. Enhanced depletion of NHL cells from whole blood. Fresh heparinized human blood was mixed with Daudi and incubated with 1 nM of the indicated Mab-IFNα or MAb for two days. The effect on Daudi, B cells, T cells, and monocytes was evaluated by flow cytometry. Error bars, SD.

Figure 23:
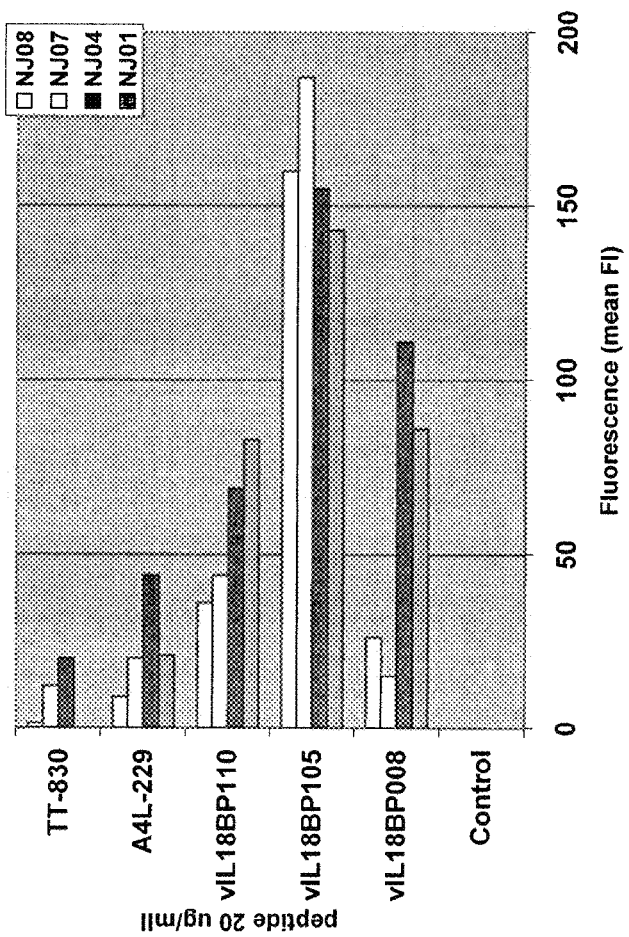
Figure 23:
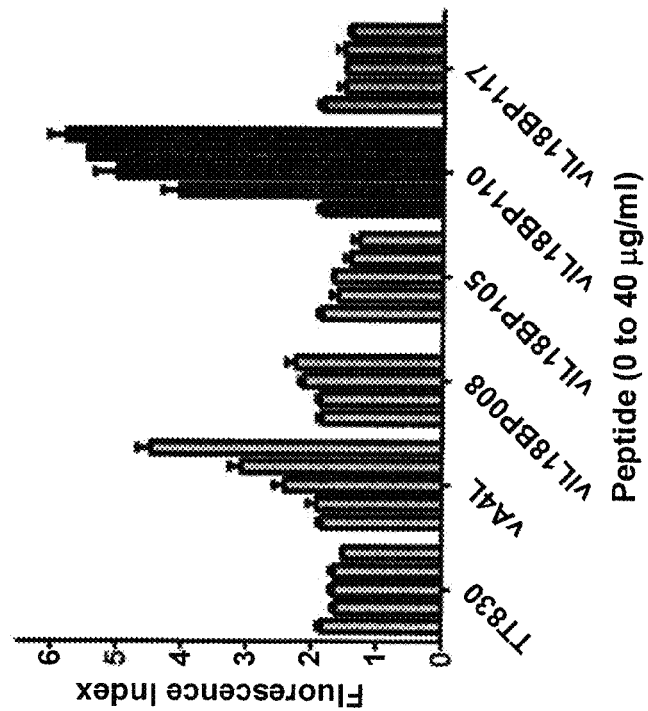

FIG. 23. Binding and uptake of peptides derived from vIL18BP sequence (SEQ ID NO:159). (A) vIL18BP110 (SEQ ID NO:146) bound to T2 cells. Indicated peptides (TT830, SEQ ID NO:149; vA4L229, SEQ ID NO:148; vIL18BP008, SEQ ID NO:143; vIL18BP105, SEQ ID NO:145; vIL18BP110, SEQ ID NO:146; vIL18BP117, SEQ ID NO:147) were incubated with T2 cells for 24 h. Relative abundance of HLA-A02 on T2 cells is shown. Each bar, left to right, represents increasing concentrations of peptide from 0 to 40 μg/mL in 10-μg/mL increments. (B) vIL18BP105 (SEQ ID NO:145) demonstrated the highest uptake by donor PBMCs. Duplicate samples were evaluated after incubation with the indicated biotinylated peptides for 24 h. NJ01, NJ04, NJ07 and NJ08. Results were analyzed by flow cytometry after addition of an avidin-FITC conjugate. Fluorescence value for each peptide equals fluorescence value of peptide-treated cells minus the fluorescence value of untreated cells in the same experiment. Peptide concentration was 20 μg/mL.

Figure 24:
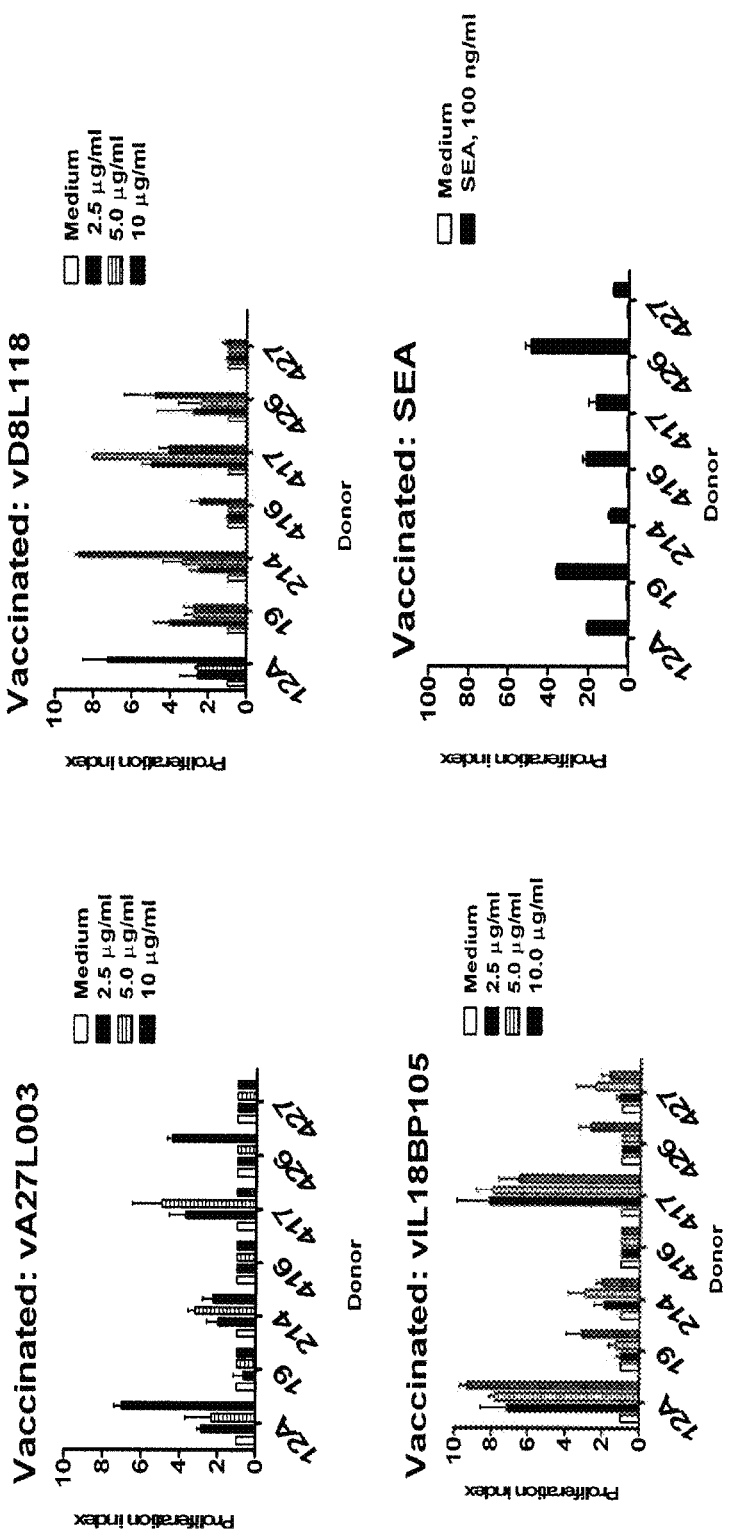
Figure 24:
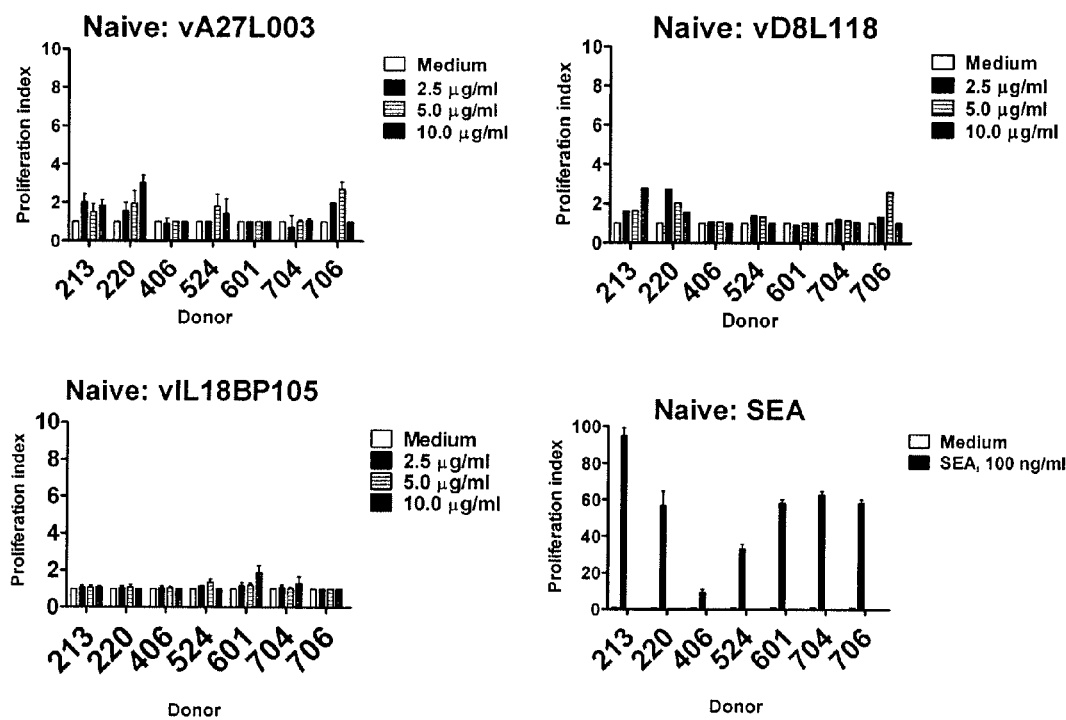

FIG. 24. PBMCs from vaccinated donors proliferate when incubated with viral peptides. CFSE-loaded PBMCs from vaccinated (A) and unvaccinated (B) human donors were incubated with 10 μg/mL of the designated peptide (vA27L003-027, SEQ ID NO:150; vD8L118, SEQ ID NO:154; vIL18BP105, SEQ ID NO:145 or control) for 5 days. Cells were harvested and analyzed by flow cytometry (means±SD). Bars shown in order: open bars, medium control; solid black bars, 2.5 mg/mL peptide (or SEA); horizontal-hatch light-grey bars, 5.0 mg/mL peptide; vertical-hatch dark-grey bars, 10.0 mg/mL peptide. (C) Results from separate experiments where cells from the designated samples were incubated with vD8L118 (SEQ ID NO:154) to determine intracellular cytokine and activation marker expression. The results are shown in the embedded table (C) (DBL, vD8L118 peptide, SEQ ID NO:154). * Group average P<0.05 vs. medium controls (t-test).

Figure 25:
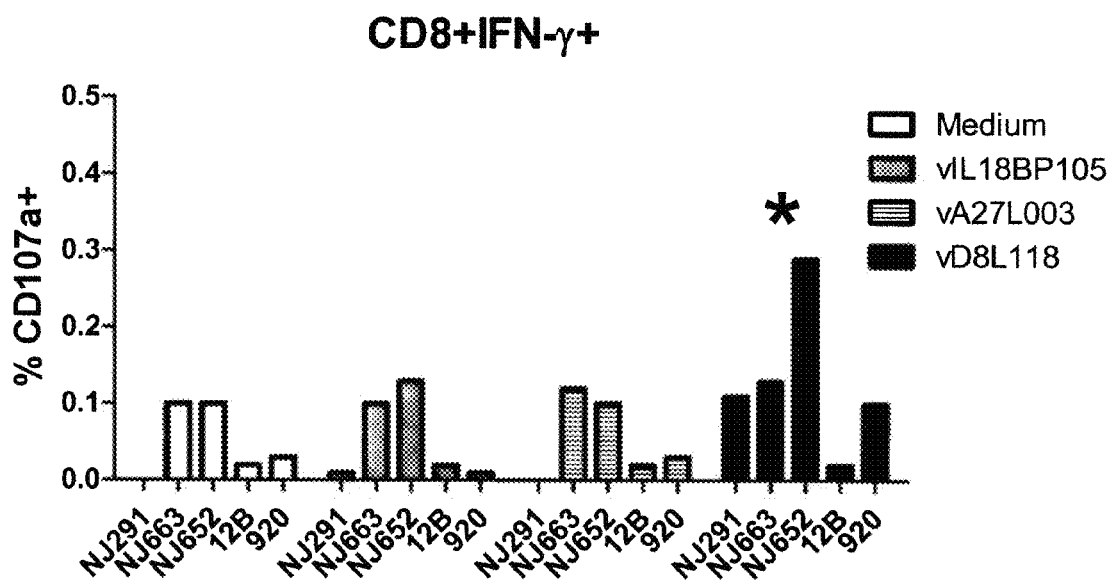
Figure 25:
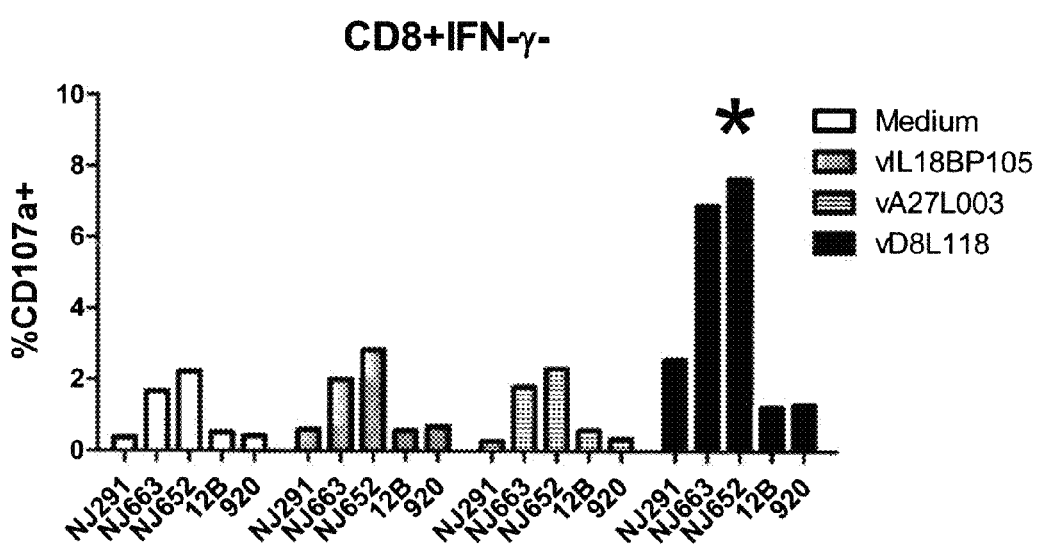
Figure 25:
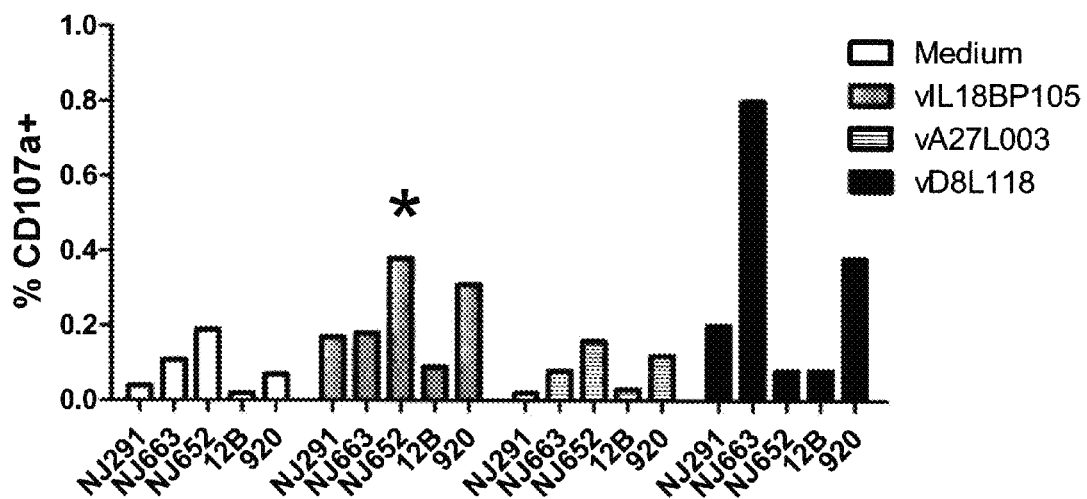

FIG. 25. CD107a expression by CD8+ cells. CD8+ cell population was assessed for IFN-γ, IL-2 vs. degranulation potential marker CD 107a. Numbers and bar values represent percentage of gated cells for (A) CD8+IFN-γ+ cells, (B) CD8+IFN-γ– cells, and (C) CD8+IL-2+ cells. * group average P<0.04 vs. medium control (t-test).

Figure 26:
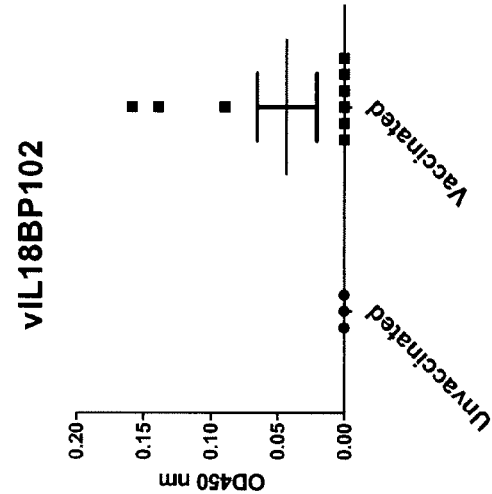
Figure 26:
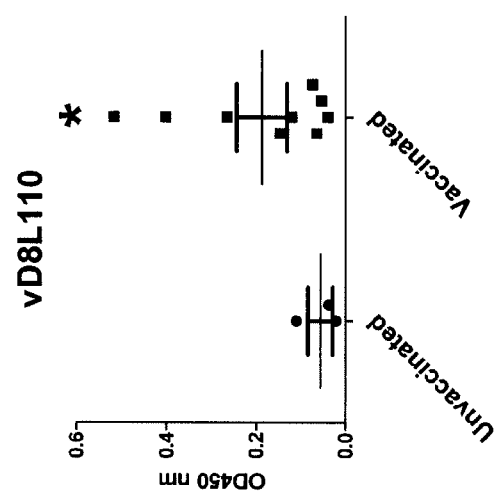
Figure 26:
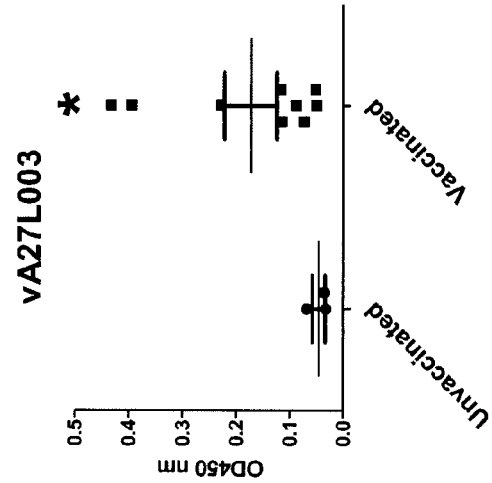

FIG. 26. Antibody to peptides is present in serum from vaccinated donors. Serum from unvaccinated or vaccinated donors was diluted 1:200 and incubated with peptide immobilized on 96-well plates in a modified ELISA for (A) peptide vA27L003 (SEQ ID NO:150), (B) peptide vD8L110 (SEQ ID NO:153), and (C) peptide vIL18BP102 (SEQ ID NO:144). Dots represent the A450 for each donor. * P<0.03 vs. unvaccinated (ANOVA). Unvaccinated donors: 213, 704, 220; vaccinated donors: 05, 12A, 12B, 19, 26, 720, 308, 416, and 920. Peptides vD8L110 (SEQ ID NO:153) and vIL18BP102 (SEQ ID NO:144) were 25-mers which included the full sequences of vD8L118 (SEQ ID NO:154) and vIL18BP105 (SEQ ID NO:145).

Figure 27:
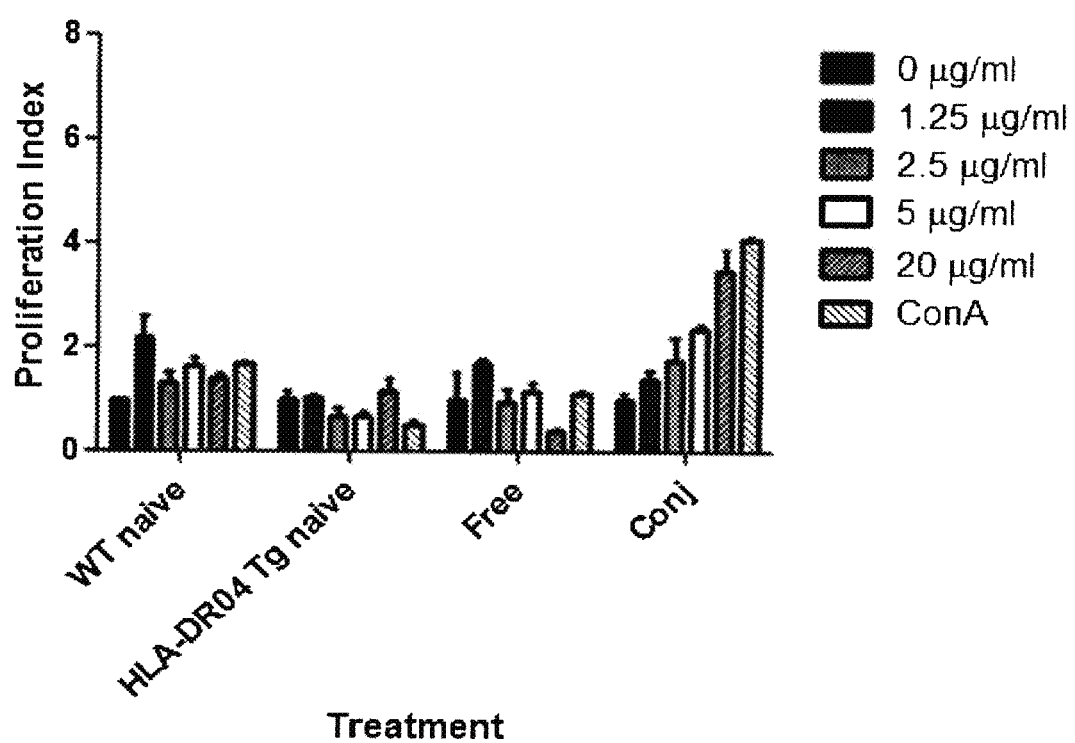

FIG. 27. HLA-DR04 μg splenocyte proliferation to vIL18BP105. HLA-DR04 μg mice were immunized with vIL18BP105-L243 conjugate (conj) or free vIL18BP105 (SEQ ID NO:145) (Free), naïve HLA-DR04 μg mice (HLA-DR04 μg naïve) and wild type C57BL/6J (WT naive) (n=3 mice/group). Assays were performed in triplicate with CFSE-labeled splenocytes incubated with varied concentrations of peptides. Results are typical of 3 separate experiments (n=3, means±SD).

Figure 28:
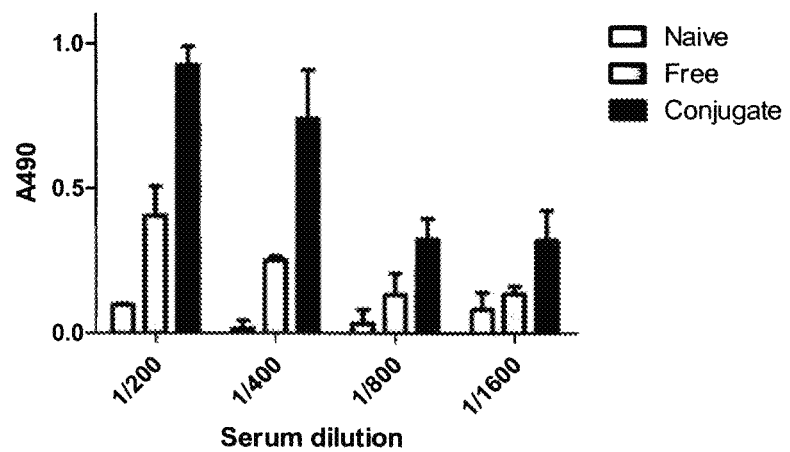
Figure 28:
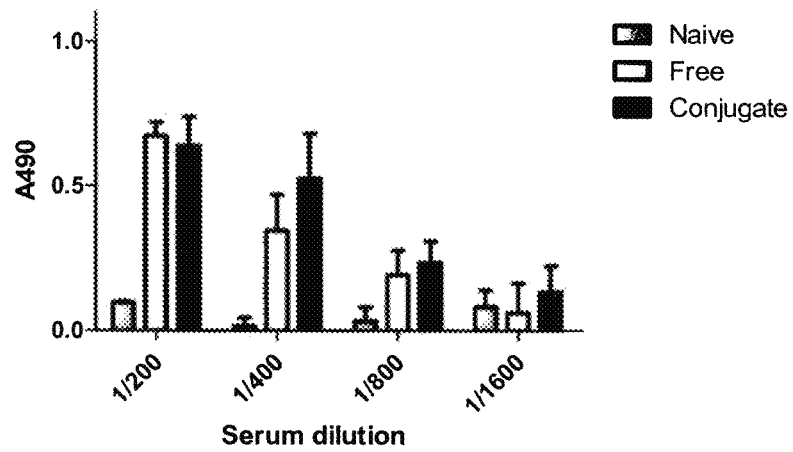

FIG. 28. Peptide-specific serum antibody production in HLA-DR04 μg mice immunized with CIL18BP105 (Conjugate) and IL18BP105 (SEQ ID NO:145) (Free) 7 and 14 days following the first boost. Naïve HLA-DR04 μg mouse serum was used as control (Naïve). Experiments were performed in triplicate with pooled sera (n=3, means±SD).

Figure 29:
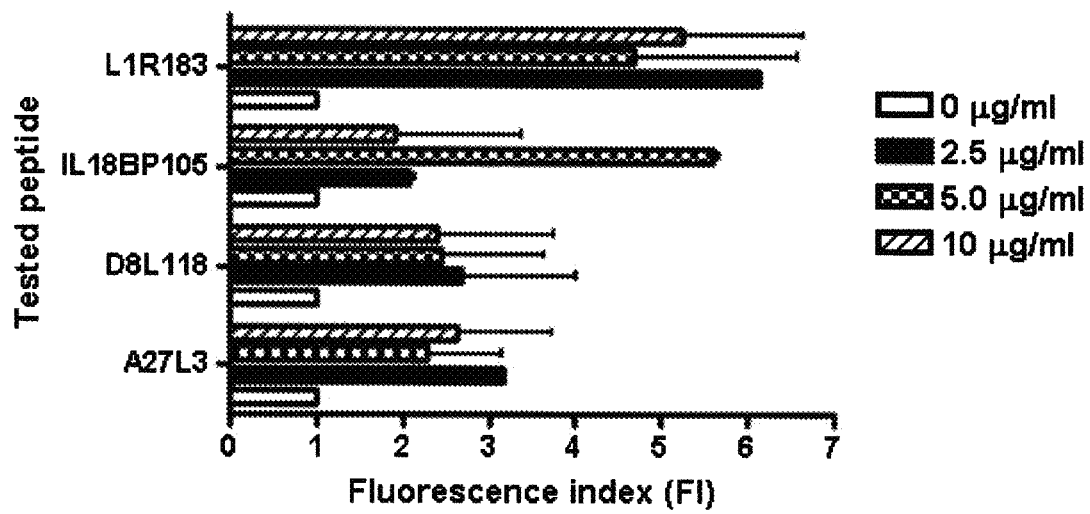
Figure 29:
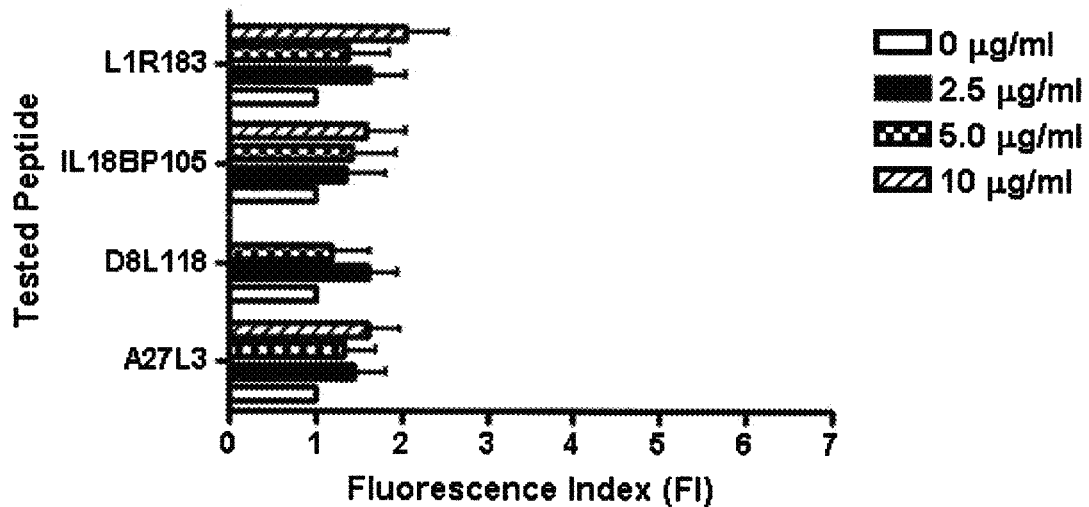

FIG. 29. Liposome based immunoconjugate for subunit vaccine. (A) Liposome-displayed peptide-L243 antibody conjugate. (B) Liposome-displayed bare peptide without antibody.

DETAILED DESCRIPTION

Definitions

As used herein, the terms "a", "an" and "the" may refer to either the singular or plural, unless the context otherwise makes clear that only the singular is meant.

An "antibody" refers to a full-length (i.e., naturally occurring or formed by normal immunoglobulin gene fragment recombinatorial processes) immunoglobulin molecule (e.g., an IgG antibody) or an immunologically active (i.e., antigen-binding) portion of an immunoglobulin molecule, like an antibody fragment.

An "antibody fragment" is a portion of an antibody such as F(ab')$_2$, F(ab)$_2$, Fab', Fab, Fv, scFv, single domain antibodies (DABs or VHHs) and the like, including half-molecules of IgG4 (van der Neut Kolfschoten et al. (Science 2007; 317(14 September):1554-1557). Regardless of structure, an antibody fragment binds with the same antigen that is recognized by the intact antibody. The term "antibody fragment" also includes isolated fragments consisting of the variable regions, such as the "Fv" fragments consisting of the variable regions of the heavy and light chains and recombinant single chain polypeptide molecules in which light and heavy chain variable regions are connected by a peptide linker ("scFv proteins").

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains. Additional FR amino acid substitutions from the parent, e.g. murine, antibody may be made. The constant domains of the antibody molecule are derived from those of a human antibody.

A "human antibody" is an antibody obtained from transgenic mice that have been genetically engineered to produce human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229,275).

A "therapeutic agent" is an atom, molecule, or compound that is useful in the treatment of a disease. Examples of therapeutic agents include but are not limited to antibodies, antibody fragments, drugs, toxins, enzymes, nucleases, hormones, immunomodulators, antisense oligonucleotides, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds.

As used herein, the term "antibody fusion protein" is a recombinantly produced antigen-binding molecule in which an antibody or antibody fragment is linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

Dock-and-Lock (DNL)

In preferred embodiments, the multimeric complex is formed by a technique known as dock-and-lock (DNL) (see, e.g., U.S. Pat. Nos. 7,521,056; 7,527,787; 7,534,866; 7,550,143 and 7,666,400, the Examples section of each of which is incorporated herein by reference.) Generally, the DNL technique takes advantage of the specific and high-affinity binding interaction between a dimerization and docking domain (DDD) sequence derived from cAMP-dependent protein kinase and an anchor domain (AD) sequence derived from any of a variety of AKAP proteins. The DDD and AD peptides may be attached to any protein, peptide or other molecule. Because the DDD sequences spontaneously dimerize and bind to the AD sequence, the DNL technique allows the formation of complexes between any selected molecules that may be attached to DDD or AD sequences. Although the standard DNL complex comprises a trimer with two DDD-linked molecules attached to one AD-linked molecule, variations in complex structure allow the formation of dimers, trimers, tetramers, pentamers, hexamers and other multimers. In some embodiments, the DNL complex may comprise two or more antibodies, antibody fragments or fusion proteins which bind to the same antigenic determinant or to two or more different antigens. The DNL complex may also comprise one or more other effectors, such as proteins, peptides, immunomodulators, cytokines, interleukins, interferons, binding proteins, peptide ligands, carrier proteins, toxins, ribonucleases such as ONCONASE® (ranpirnase), inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

In certain preferred embodiments, bispecific or multispecific antibodies may be produced using the dock-and-lock (DNL) technology (see, e.g., U.S. Pat. Nos. 7,521,056; 7,550,143; 7,534,866; 7,527,787 and 7,666,400; the Examples section of each of which is incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell. Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has $\alpha$ and $\beta$ isoforms (Scott, Pharmacol. Ther. 1991; 50:123). Thus, the four isoforms of PKA regulatory subunits are RI$\alpha$, RII$\alpha$ and RII$\beta$. The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561)

Since the first AKAP, microtubule-associated protein-2, was characterized in 1984 (Lohmann et al., Proc. Natl. Acad. Sci. USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell. Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RII$\alpha$, the AD binds to a hydrophobic surface formed by the 23 amino-terminal residues (Colledge and Scott, Trends Cell Biol. 1999; 6:216). Thus, the dimerization domain and AKAP binding domain of human RII$\alpha$ are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human RII$\alpha$ and the AD of AKAP as an excellent pair of linker modules for docking any two entities, referred to hereafter as A and B, into a noncovalent complex, which could be further locked into a DNL complex through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Structure-Function Relationships in AD and DDD Moieties

For different types of DNL constructs, different AD or DDD sequences may be utilized. Exemplary DDD and AD sequences are provided below.

```
                                       (SEQ ID NO: 1)
DDD1 SHIQIPPGLTELLQGYTVEVLRQQPPDLVEFAVEYFTRLREARA (SEQ ID NO: 2)
DDD2 CGHIQIPPGLTELLQGYTVEVLRQQPPDLVEFAVEYFTRLREARA (SEQ ID NO: 3)
AD1  QIEYLAKQIVDNAIQQA (SEQ ID NO: 4)
AD2  CGQIEYLAKQIVDNAIQQAGC
```

The skilled artisan will realize that DDDI and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                       (SEQ ID NO: 5)
SLRECELYVQKHNIQALLKDSIVQLCTARPERPMAFLREYFERLEKEEA
K

DDD3C
                                       (SEQ ID NO: 6)
MSCGGSLRECELYVQKHNIQALLKDSIVQLCTARPERPMAFLREYFERL
EKEEAK

AD3
                                       (SEQ ID NO: 7)
CGFEELAWKIAKMIWSDVFQQGC
```

In other alternative embodiments, other sequence variants of AD and/or DDD moieties may be utilized in construction of the DNL complexes. For example, there are only four variants of human PKA DDD sequences, corresponding to the DDD moieties of PKA RIα, RIIα, RIβ and RIIβ. The RIIα DDD sequence is the basis of DDD 1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                       (SEQ ID NO: 8)
SLRECELYVQKHNIQALLKDVSIVQLCTARPERPMAFLREYFEKLEKEE
AK

PKA RIβ
                                       (SEQ ID NO: 9)
SLKGCELYVQLHGIQQVLKDCIVHLCISKPERPMKFLREHFEKLEKEEN
RQILA

PKA RIIα
                                       (SEQ ID NO: 10)
SHIQIPPGLTELLQGYTVEVGQQPPDLVDFAVEYFTRLREARRQ

PKA RIIβ
                                       (SEQ ID NO: 11)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Can et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

Figure 1:
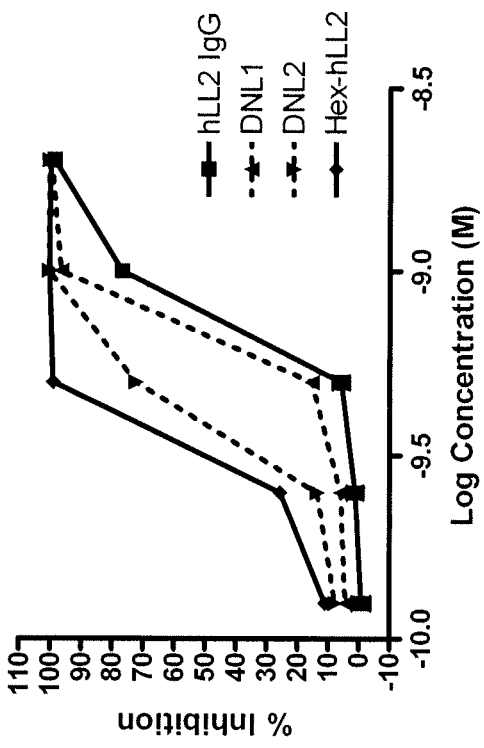
FIG. 1. Competitive ELISA experiments to compare the relative hA20/hLL2 binding avidities of DNL 1, DNL2, Hex-hA20 and Hex-hLL2 with the parental IgGs. Microtiter plates were coated with hA20 or hLL2 IgG at 5 µg/ml. Dilution series of the HIDS were mixed with anti-Ids specific to hA20 or hLL2 IgG, which was maintained at a constant concentration (2 nM). The level of binding of the anti-Ids to the coated wells was detected using peroxidase-conjugated-Goat anti-Rat IgG and OPD substrate solution. The results are plotted as % inhibition (of anti-Id binding to coated wells) vs. concentration of HIDS. $EC_{50}$ (the effective concentration resulting in 50% inhibition) values were derived using Prism software. The HIDS were used to compete for binding to (A) WI2 (hA20 Rat anti-Id) in hA20-coated wells or (B) WN (hLL2 Rat anti-Id) in hLL2-coated wells.
Figure 1:
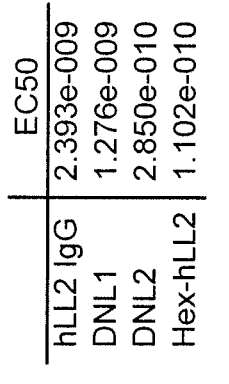
Figure 1:
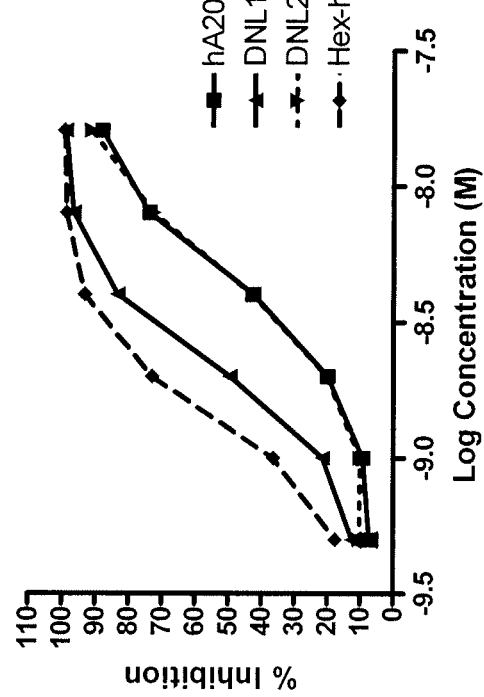

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                       (SEQ ID NO: 1)
SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 1. In devising Table 1, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. Even with such conservative substitutions, there are over twenty million possible alternative sequences for the 44 residue peptide (2×3×2×2× 2×2×2×2×2×2×2×2×2×2×4×2×2×2×2×2×4×2×4). A limited number of such potential alternative DDD moiety sequences are shown in SEQ ID NO:12 to SEQ ID NO:31 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

AKAP-IS (AD1, SEQ ID NO:3), similar to that shown for DDD1 (SEQ ID NO:1) in Table 1 above.

Even with such conservative substitutions, there are over thirty-five thousand possible alternative sequences for the 17 residue AD1 (SEQ ID NO:3) peptide sequence (2×3×2×4×3×2×2×2×2×2×2×4). A limited number of such potential alternative AD moiety sequences are shown in SEQ ID NO:32

TABLE 1

Conservative Amino Acid Substitutions in DDD1 (SEQ ID NO: 1).
Consensus sequence disclosed as SEQ ID NO: 171.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K |   | N |   |   |   | A |   | S | D |   |   |   | N | A | S |   | D |   |   | K |
|   | R |   |   |   |   |   |   |   |   |   |   |   |   |   |   |   |   |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E |   |   | D |   | D |   | D |   |   | S | K |   | K | D | L | K | L |
|   |   |   |   |   |   |   |   |   | L |   |   |   |   |   |   |   |   |   | I |   | I |
|   |   |   |   |   |   |   |   |   | V |   |   |   |   |   |   |   |   |   | V |   | V |

| Sequence | |
|---|---|
| THIQIPPGLTELLQGYTVEVLRQQPPDLVEFAVEYFTRLREARA | (SEQ ID NO: 12) |
| SKIQIPPGLTELLQGYTVEVLRQQPPDLVEFAVEYFTRLREARA | (SEQ ID NO: 13) |
| SRIQIPPGLTELLQGYTVEVLRQQPPDLVEFAVEYFTRLREARA | (SEQ ID NO: 14) |
| SHINIPPGLTELLQGYTVEVLRQQPPDLVEFAVEYFTRLREARA | (SEQ ID NO: 15) |
| SHIQIPPALTELLQGYTVEVLRQQPPDLVEFAVEYFTRLREARA | (SEQ ID NO: 16) |
| SHIQIPPGLSELLQGYTVEVLRQQPPDLVEFAVEYFTRLREARA | (SEQ ID NO: 17) |
| SHIQIPPGLTDLLQGYTVEVLRQQPPDLVEFAVEYFTRLREARA | (SEQ ID NO: 18) |
| SHIQIPPGLTELLNGYTVEVLRQQPPDLVEFAVEYFTRLREARA | (SEQ ID NO: 19) |
| SHIQIPPGLTELLQAYTVEVLRQQPPDLVEFAVEYFTRLREARA | (SEQ ID NO: 20) |
| SHIQIPPGLTELLQGYSVEVLRQQPPDLVEFAVEYFTRLREARA | (SEQ ID NO: 21) |
| SHIQIPPGLTELLQGYTVDVLRQQPPDLVEFAVEYFTRLREARA | (SEQ ID NO: 22) |
| SHIQIPPGLTELLQGYTVEVLKQQPPDLVEFAVEYFTRLREARA | (SEQ ID NO: 23) |
| SHIQIPPGLTELLQGYTVEVLRNQPPDLVEFAVEYFTRLREARA | (SEQ ID NO: 24) |
| SHIQIPPGLTELLQGYTVEVLRQNPPDLVEFAVEYFTRLREARA | (SEQ ID NO: 25) |
| SHIQIPPGLTELLQGYTVEVLRQQPPELVEFAVEYFTRLREARA | (SEQ ID NO: 26) |
| SHIQIPPGLTELLQGYTVEVLRQQPPDLVDFAVEYFTRLREARA | (SEQ ID NO: 27) |
| SHIQIPPGLTELLQGYTVEVLRQQPPDLVEFLVEYFTRLREARA | (SEQ ID NO: 28) |
| SHIQIPPGLTELLQGYTVEVLRQQPPDLVEFIVEYFTRLREARA | (SEQ ID NO: 29) |
| SHIQIPPGLTELLQGYTVEVLRQQPPDLVEFVVEYFTRLREARA | (SEQ ID NO: 30) |
| SHIQIPPGLTELLQGYTVEVLRQQPPDLVEFAVDYFTRLREARA | (SEQ ID NO: 31) |

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 2 shows potential conservative amino acid substitutions in the sequence of to SEQ ID NO:49 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

AKAP-IS

QIEYLAKQIVDNAIQQA    (SEQ ID NO: 3)

TABLE 2

Conservative Amino Acid Substitutions in AD1 (SEQ ID NO: 3).
Consensus sequence disclosed as SEQ ID NO: 172.

| Q | I | E | Y | L | A | K | Q | I | V | D | N | A | I | Q | Q | A |
|---|---|---|---|---|---|---|---|---|---|---|---|---|---|---|---|---|
| N | L | D | F | I |   | R | N |   |   | E | Q |   |   | N | N | L |
|   | V |   | T | V |   |   |   |   |   |   |   |   |   |   |   | I |
|   |   |   | S |   |   |   |   |   |   |   |   |   |   |   |   | V |

| NIEYLAKQIVDNAIQQA | (SEQ ID NO: 32) |
| QLEYLAKQIVDNAIQQA | (SEQ ID NO: 33) |
| QVEYLAKQIVDNAIQQA | (SEQ ID NO: 34) |
| QIDYLAKQIVDNAIQQA | (SEQ ID NO: 35) |
| QIEFLAKQIVDNAIQQA | (SEQ ID NO: 36) |
| QIETLAKQIVDNAIQQA | (SEQ ID NO: 37) |
| QIESLAKQIVDNAIQQA | (SEQ ID NO: 38) |
| QIEYIAKQIVDNAIQQA | (SEQ ID NO: 39) |
| QIEYVAKQIVDNAIQQA | (SEQ ID NO: 40) |
| QIEYLARQIVDNAIQQA | (SEQ ID NO: 41) |
| QIEYLAKNIVDNAIQQA | (SEQ ID NO: 42) |
| QIEYLAKQIVENAIQQA | (SEQ ID NO: 43) |
| QIEYLAKQIVDQAIQQA | (SEQ ID NO: 44) |
| QIEYLAKQIVDNAINQA | (SEQ ID NO: 45) |
| QIEYLAKQIVDNAIQNA | (SEQ ID NO: 46) |
| QIEYLAKQIVDNAIQQL | (SEQ ID NO: 47) |
| QIEYLAKQIVDNAIQQI | (SEQ ID NO: 48) |
| QIEYLAKQIVDNAIQQV | (SEQ ID NO: 49) |

Gold et al. (2006, Mol Cell 24:383-95) utilized crystallography and peptide screening to develop a SuperAKAP-IS sequence (SEQ ID NO:50), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

```
SuperAKAP-IS
QIEYVAKQIVDYAIHQA       (SEQ ID NO: 50)

Alternative AKAP sequences
QIEYKAKQIVDHAIHQA       (SEQ ID NO: 51)
```

-continued

```
QIEYHAKQIVDHAIHQA       (SEQ ID NO: 52)

QIEYVAKQIVDHAIHQA       (SEQ ID NO: 53)
```

Figure 2:
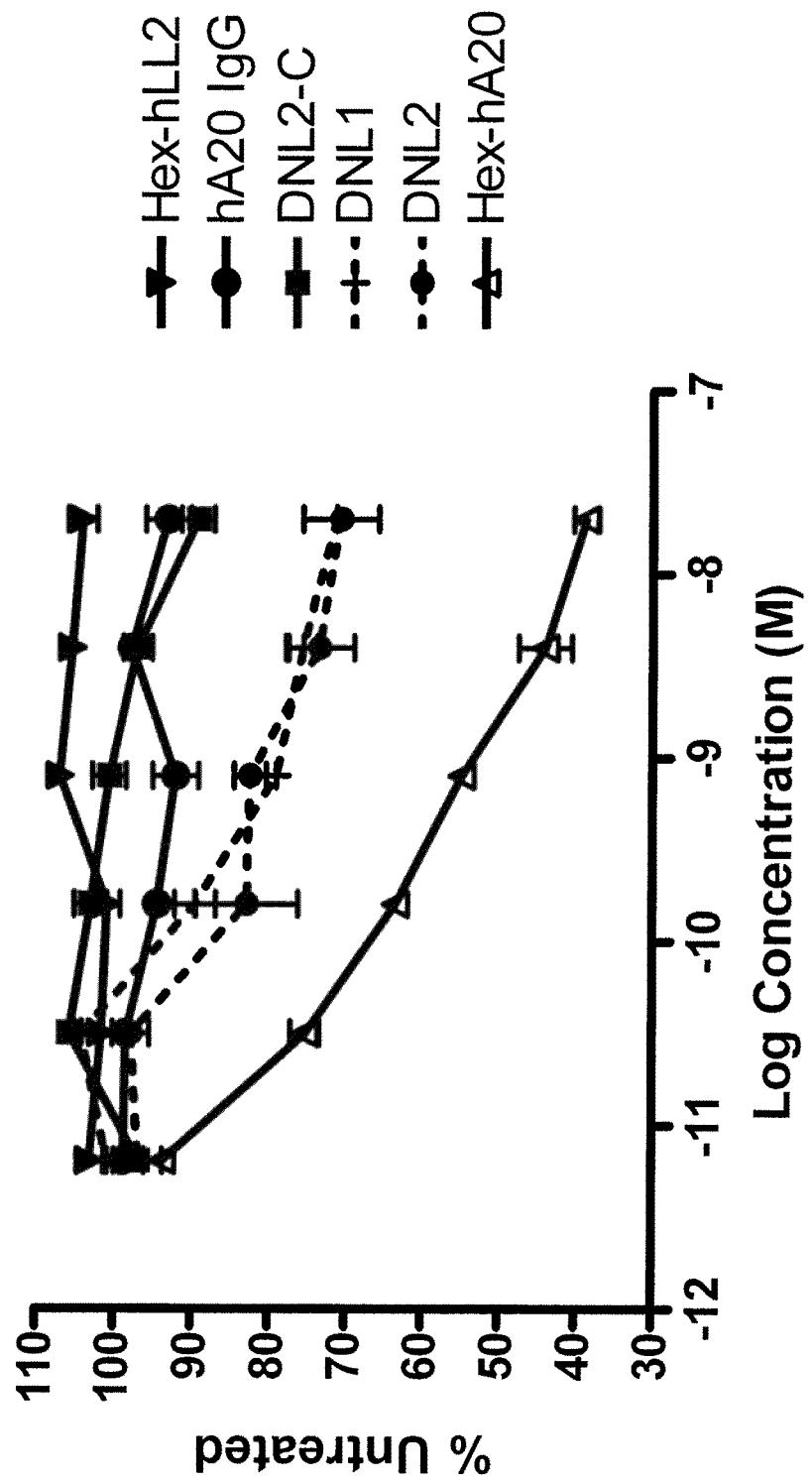
FIG. 2. Dose-response experiment for treatment of Daudi cells with various HIDS. Cells were plated in 96-well plates at 5,000 cells/well in RPMI 1640 media. Five-fold serial dilutions were performed in triplicate from concentrations of $2 \times 10^{-8}$ down to $6.4 \times 10^{-12}$ M. The plates were incubated for four days, after which MTS reagent was added and the incubation was continued for an additional four hours before reading the plates at 490 nm. The results are given as percent of the $OD_{490}$ for untreated wells vs. the log of the molar concentration of HIDS. $EC_{40}$ (the effective concentration resulting in 40% growth inhibition) values were measured for each dose-response curve.

FIG. 2 of Gold et al. disclosed additional DDD-binding sequences from a variety of AKAP proteins, shown below.

```
RII-Specific AKAPs
AKAP-KL
PLEYQAGLLVQNAIQQAI      (SEQ ID NO: 54)

AKAP79
LLIETASSLVKNAIQLSI      (SEQ ID NO: 55)

AKAP-Lbc
LIEEAASRIVDAVIEQVK      (SEQ ID NO: 56)

RI-Specific AKAPs
AKAPce
ALYQFADRFSELVISEAL      (SEQ ID NO: 57)

RIAD
LEQVANQLADQIIKEAT       (SEQ ID NO: 58)

PV38
FEELAWKIAKMIWSDVF       (SEQ ID NO: 59)

Dual-Specificity AKAPs
AKAP7
ELVRLSKRLVENAVLKAV      (SEQ ID NO: 60)
```

```
MAP2D
TAEEVSARIVQVVTAEAV        (SEQ ID NO: 61)

DAKAP1
QIKQAAFQLISQVILEAT        (SEQ ID NO: 62)

DAKAP2
LAWKIAKMIVSDVMQQ          (SEQ ID NO: 63)
```

Stokka et al. (2006, Biochem J 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

```
Ht31
DLIEEAASRIVDAVIEQVKAAGAY  (SEQ ID NO: 64)

RIAD
LEQYANQLADQIIKEATE        (SEQ ID NO: 65)

PV-38
FEELAWKIAKMIWSDVFQQC      (SEQ ID NO: 66)
```

Hundsrucker et al. (2006, Biochem J 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 3 below. AKAPIS represents a synthetic RII subunit-binding peptide. All other peptides are derived from the RII-binding domains of the indicated AKAPs.

TABLE 3

AKAP Peptide sequences

| | Peptide Sequence |
|---|---|
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |

TABLE 3-continued

AKAP Peptide sequences

| | Peptide Sequence |
|---|---|
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Figure 4:
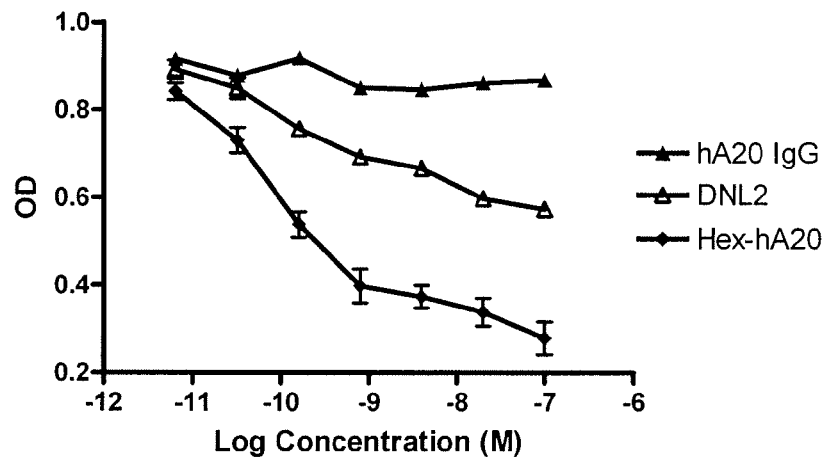
FIG. 4. Relative dose-response curves generated using an MTS proliferation assay for Daudi cells, Raji cells and Ramos cells treated with a bispecific HID (DNL2-four hLL2 Fab fragments tethered to an hA20 IgG) and a monospecific HID (Hex-hA20), compared with an hA20 IgG control. In Daudi cells (top panel), DNL2 showed >100-fold and Hex-hA20 showed >10,000 fold more potent antiproliferative activity than hA20 IgG. In Raji cells (middle panel), Hex-hA20 displayed potent anti-proliferative activity, while DNL2 showed only minimal activity, compared to hA20 IgG. In Ramos cells (bottom panel), both DNLs and Hex-hA20 displayed potent anti-proliferative activity compared to hA20 IgG.
Figure 4:
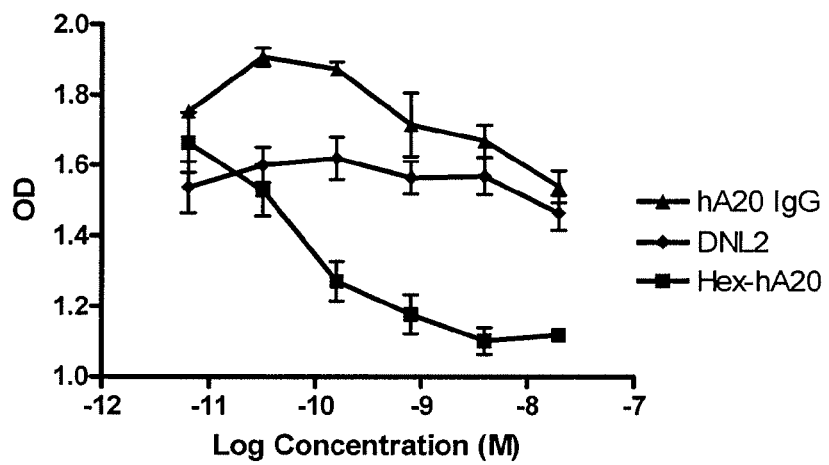
Figure 4:
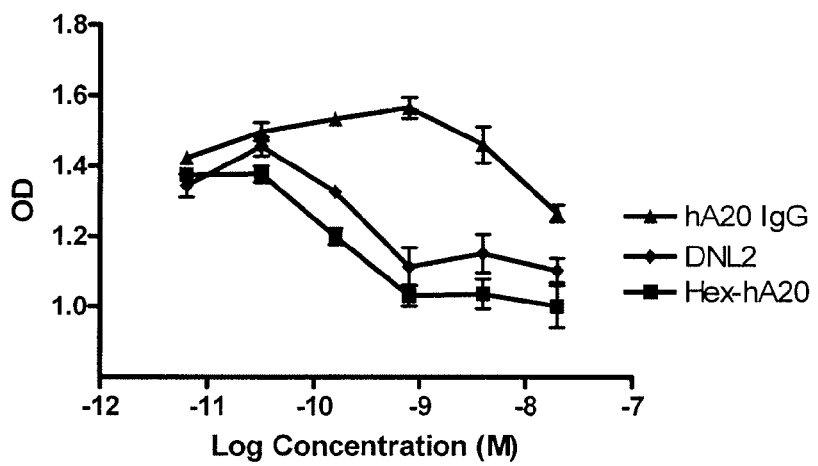

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
AKAP-IS
QIEYLAKQIVDNAIQQA         (SEQ ID NO: 3)
```

Carr et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
                                          (SEQ ID NO: 1)
SHIQIPPGLTELLQGYTVEVLRQQPPDLVEFAVEYFTRLREARA
```

A modified set of conservative amino acid substitutions for the DDD1 (SEQ ID NO:1) sequence, based on the data of Can et al. (2001) is shown in Table 4. Even with this reduced set of substituted sequences, there are over 65,000 possible alternative DDD moiety sequences that may be produced, tested and used by the skilled artisan without undue experimentation.

TABLE 4

Conservative Amino Acid Substitutions
in DDD1 (SEQ ID NO: 1).
Consensus sequence disclosed as SEQ ID NO: 173.

```
S  H  I  Q  I  P  P  G  L  T  E  L  L  Q  G  Y  T  V  E  V  L  R
T           N              S                          I
                                                      L
                                                      A

Q  Q  P  P  D  L  V  E  F  A  V  E  Y  F  T  R  L  R  E  A  R  A
N                                I  D           S  K     K  L     L
                                 L                          I     I
                                 A                          V     V
```

The skilled artisan could readily derive such alternative DDD amino acid sequences as disclosed above for Table 1 and Table 2.

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In alternative embodiments, the disclosed methods and compositions may involve production and use of proteins or peptides with one or more substituted amino acid residues. For example, the DDD and/or AD sequences used to make DNL constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (O) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Preparation of Antibodies

The DNL complexes described herein may comprise one or more monoclonal antibodies or fragments thereof. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)).

General techniques for cloning murine immunoglobulin variable domains have been disclosed, for example, by the publication of Orlandi et al., Proc. Nat'l Acad. Sci. USA 86: 3833 (1989). Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and $IgG_1$ constant region domains. This publication also provides the nucleotide sequences of the LL2 light and heavy chain variable regions, $V_k$ and $V_H$, respectively. Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)).

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Pharmacol. 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, Genet. Mol. Res. 4:126-40, incorporated herein by reference). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XENOMOUSE® (e.g., Green et al., 1999, *J. Immunol. Methods* 231:11-23) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Known Antibodies

In various embodiments, the DNL constructs may comprise any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312,318; 7,282,567; 7,151, 164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,15; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206' 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Particular antibodies that may be of use for therapy of cancer or autoimmune disease within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA or CEACAM5, also known as CD66e)), Mu-9 (anti-colon-specific antigen-p), Immu-31 (an anti-alpha-fetoprotein), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), hL243 (anti-HLA-DR), R1 (anti-IGF-1R), A20 (anti-CD20), A19 (anti-CD19), MN-3 or MN-15 (anti-CEACAM6). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 7,074,403), hMu-9 (U.S. Pat. No. 7,387, 773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/689,336), hRS7 (U.S. Pat. No. 7,238,785), hMN-3 (U.S. Pat. No. 7,541,440), AB-PG1-XG1-026 (U.S. patent application Ser. No. 11/983, 372, deposited as ATCC PTA-4405 and PTA-4406), 29H2 (ABCAM®, Cambridge, Mass.) and D2/B (WO 2009/ 130575) the text of each recited patent or application is incorporated herein by reference with respect to the Figures and Examples sections.

Other antibodies are known for therapy of diseases other than cancer or autoimmune disease. For example, bapineuzumab is in clinical trials for Alzheimer's disease therapy. Other antibodies proposed for therapy of Alzheimer's disease include Alz 50 (Ksiezak-Reding et al., 1987, J Biol Chem 263:7943-47), gantenerumab, and solanezumab. Infliximab, an anti-TNF-α antibody, has been reported to reduce amyloid plaques and improve cognition. Anti-CD3 antibodies have been proposed for therapy of type 1 diabetes (Cernea et al., 2010, Diabetes Metab Rev 26:602-05). Antibodies to fibrin (e.g., scFv(59D8); T2G1s; MH1) are known and in clinical trials as imaging agents for disclosing fibrin clots and pulmonary emboli, while anti-granulocyte antibodies, such as MN-3, MN-15, anti-NCA95, and anti-CD15 antibodies, can target myocardial infarcts and myocardial ischemia. (See, e.g., U.S. Pat. Nos. 5,487,892; 5,632,968; 6,294,173; 7,541, 440, the Examples section of each incorporated herein by reference) Anti-macrophage, anti-low-density lipoprotein (LDL) and anti-CD74 (e.g., hLL1) antibodies can be used to target atherosclerotic plaques. Abciximab (anti-glycoprotein IIb/IIIa) has been approved for adjuvant use for prevention of restenosis in percutaneous coronary interventions and the treatment of unstable angina (Waldmann et al., 2000, Hematol 1:394-408). Anti-CD3 antibodies have been reported to reduce development and progression of atherosclerosis (Steffens et al., 2006, Circulation 114:1977-84). Antibodies against oxidized LDL induced a regression of established atherosclerosis in a mouse model (Ginsberg, 2007, J Am Coll Cardiol 52:2319-21). Anti-ICAM-1 antibody was shown to reduce ischemic cell damage after cerebral artery occlusion in rats (Zhang et al., 1994, Neurology 44:1747-51). Commercially available monoclonal antibodies to leukocyte antigens are represented by: OKT anti-T cell monoclonal antibodies (available from Ortho Pharmaceutical Company) which bind to normal T-lymphocytes; the monoclonal antibodies produced by the hybridomas having the ATCC accession numbers HB44, HB55, HB12, HB78 and HB2; G7E11, W8E7, NKP15 and GO22 (Becton Dickinson); NEN9.4 (New England Nuclear); and FMC11 (Sera Labs). A description of antibodies against fibrin and platelet antigens is contained in Knight, Semin. Nucl. Med., 20:52-67 (1990).

Other Disease-Associated Target Antigens

In one embodiment, a target may be an antigen or receptor of the adaptive immune system. In other embodiments, the target of the DNL complex may occur on cells of the innate immune system, such as granulocytes, monocytes, macrophages, dendritic cells, and NK-cells. Other targets include platelets and endothelial cells. Yet another group of targets is the group consisting of C5a, LPS, IFNγ and B7. A further group of suitable targets include CD2, CD3, CD4, CD14, CD18, CD11a, CD20, CD22, CD23, CD25, CD29, CD38, CD40L, CD52, CD64, CD83, CD147, and CD154. The CDs are targets on immune cells, which can be blocked to prevent an immune cell response. CD83 is particularly useful as a marker of activated dendritic cells (Cao et al., *Biochem J., Aug.* 23, 2004 (Epub ahead of print); Zinser et al., *J. Exp Med.* 200(3):345-51 (2004)).

Certain targets are of particular interest, such as MIF, HMGB-1, TNF-α, the complement factors and complement regulatory proteins, and the coagulation factors. MIF is a pivotal cytokine of the innate immune system and plays an important part in the control of inflammatory responses. MIF is released from macrophages and T lymphocytes that have been stimulated by glucocorticoids. Once released, MIF overcomes the inhibitory effects of glucocorticoids on TNF-α, IL-1 beta, IL-6, and IL-8 production by LPS-stimulated monocytes in vitro and suppresses the protective effects of steroids against lethal endotoxemia in vivo. MIF also antagonizes glucocorticoid inhibition of T-cell proliferation in vitro by restoring IL-2 and IFN-gamma production. MIF is the first mediator to be identified that can counter-regulate the inhibitory effects of glucocorticoids and thus plays a critical role in the host control of inflammation and immunity. MIF is particularly useful in treating cancer, pathological angiogenesis, and sepsis or septic shock.

HMGB-1, a DNA binding nuclear and cytosolic protein, is a proinflammatory cytokine released by monocytes and macrophages that have been activated by IL-1β, TNF, or LPS. Via its B box domain, it induces phenotypic maturation of DCs. It also causes increased secretion of the proinflammatory cytokines IL-1 alpha, IL-6, IL-8, IL-12, TNF-α and RANTES. HMGB-1 released by necrotic cells may be a signal of tissue or cellular injury that, when sensed by DCs, induces and/or enhances an immune reaction. Palumbo et al. report that HMBG1 induces mesoangioblast migration and proliferation (*J Cell Biol*, 164:441-449 (2004)).

HMGB-1 is a late mediator of endotoxin-induced lethality that exhibits significantly delayed kinetics relate to TNF and IL-1beta. Experimental therapeutics that target specific early inflammatory mediators such as TNF and IL-1beta alone have not proven efficacious in the clinic, but DNL complexes can improve response by targeting both early and late inflammatory inflammatory mediators.

DNL complexes that target HMBG-1 are especially useful in treating arthritis, particularly collagen-induced arthritis. DNL complexes comprising HMBG-1 also are useful in treating sepsis and/or septic shock. Yang et al., *PNAS USA* 101: 296-301 (2004); Kokkola et al., *Arthritis Rheum,* 48:2052-8 (2003); Czura et al., *J Infect Dis,* 187 Suppl 2:S391-6 (2003); Treutiger et al., *J Intern Med,* 254:375-85 (2003).

TNF-α is an important cytokine involved in systemic inflammation and the acute phase response. TNF-α is released by stimulated monocytes, fibroblasts, and endothelial cells. Macrophages, T-cells and B-lymphocytes, granulocytes, smooth muscle cells, eosinophils, chondrocytes, osteoblasts, mast cells, glial cells, and keratinocytes also produce TNF-α after stimulation. Its release is stimulated by several other mediators, such as interleukin-1 and bacterial endotoxin, in the course of damage, e.g., by infection. It has a number of actions on various organ systems, generally together with interleukins-1 and -6. One of the actions of TNF-α is appetite suppression; hence DNL complexes for treating cachexia preferably target TNF-α. It also stimulates the acute phase response of the liver, leading to an increase in C-reactive protein and a number of other mediators. It also is a useful target when treating sepsis or septic shock.

The complement system is a complex cascade involving proteolytic cleavage of serum glycoproteins often activated by cell receptors. The "complement cascade" is constitutive and non-specific but it must be activated in order to function. Complement activation results in a unidirectional sequence of enzymatic and biochemical reactions. In this cascade, a specific complement protein, C5, forms two highly active, inflammatory byproducts, C5a and C5b, which jointly activate white blood cells. This in turn evokes a number of other inflammatory byproducts, including injurious cytokines, inflammatory enzymes, and cell adhesion molecules. Together, these byproducts can lead to the destruction of tissue seen in many inflammatory diseases. This cascade ultimately results in induction of the inflammatory response, phagocyte chemotaxis and opsonization, and cell lysis.

The complement system can be activated via two distinct pathways, the classical pathway and the alternate pathway. Most of the complement components are numbered (e.g., C1, C2, C3, etc.) but some are referred to as "Factors." Some of the components must be enzymatically cleaved to activate their function; others simply combine to form complexes that are active. Active components of the classical pathway include C1q, C1r, C1s, C2a, C2b, C3a, C3b, C4a, and C4b. Active components of the alternate pathway include C3a, C3b, Factor B, Factor Ba, Factor Bb, Factor D, and Properdin. The last stage of each pathway is the same, and involves component assembly into a membrane attack complex. Active components of the membrane attack complex include C5a, C5b, C6, C7, C8, and C9n.

While any of these components of the complement system can be targeted by a DNL complex, certain of the complement components are preferred. C3a, C4a and C5a cause mast cells to release chemotactic factors such as histamine and serotonin, which attract phagocytes, antibodies and complement, etc. These form one group of preferred targets. Another group of preferred targets includes C3b, C4b and C5b, which enhance phagocytosis of foreign cells. Another preferred group of targets are the predecessor components for these two groups, i.e., C3, C4 and C5. C5b, C6, C7, C8 and C9 induce lysis of foreign cells (membrane attack complex) and form yet another preferred group of targets.

Complement C5a, like C3a, is an anaphylatoxin. It mediates inflammation and is a chemotactic attractant for induction of neutrophilic release of antimicrobial proteases and oxygen radicals. Therefore, C5a and its predecessor C5 are particularly preferred targets. By targeting C5, not only is C5a affected, but also C5b, which initiates assembly of the membrane-attack complex. Thus, C5 is another preferred target. C3b, and its predecessor C3, also are preferred targets, as both the classical and alternate complement pathways depend upon C3b. Three proteins affect the levels of this factor, C1 inhibitor, protein H and Factor I, and these are also preferred targets according to the invention. Complement regulatory proteins, such as CD46, CD55, and CD59, may be targets to which the DNL complexes bind.

Coagulation factors also are preferred targets, particularly tissue factor (TF) and thrombin. TF is also known also as tissue thromboplastin, CD142, coagulation factor III, or factor III. TF is an integral membrane receptor glycoprotein and a member of the cytokine receptor superfamily. The ligand binding extracellular domain of TF consists of two structural modules with features that are consistent with the classification of TF as a member of type-2 cytokine receptors. TF is involved in the blood coagulation protease cascade and initiates both the extrinsic and intrinsic blood coagulation cascades by forming high affinity complexes between the extracellular domain of TF and the circulating blood coagulation factors, serine proteases factor VII or factor VIIa. These enzymatically active complexes then activate factor IX and factor X, leading to thrombin generation and clot formation.

TF is expressed by various cell types, including monocytes, macrophages and vascular endothelial cells, and is induced by IL-1, TNF-α or bacterial lipopolysaccharides. Protein kinase C is involved in cytokine activation of endothelial cell TF expression. Induction of TF by endotoxin and cytokines is an important mechanism for initiation of disseminated intravascular coagulation seen in patients with Gram-negative sepsis. TF also appears to be involved in a variety of non-hemostatic functions including inflammation, cancer, brain function, immune response, and tumor-associated angiogenesis. Thus, DNL complexes that target TF are useful not only in the treatment of coagulopathies, but also in the treatment of sepsis, cancer, pathologic angiogenesis, and other immune and inflammatory dysregulatory diseases according to the invention. A complex interaction between the coagulation pathway and the cytokine network is suggested by the ability of several cytokines to influence TF expression in a variety of cells and by the effects of ligand binding to the receptor. Ligand binding (factor VIIa) has been reported to give an intracellular calcium signal, thus indicating that TF is a true receptor.

Thrombin is the activated form of coagulation factor II (prothrombin); it converts fibrinogen to fibrin. Thrombin is a potent chemotaxin for macrophages, and can alter their production of cytokines and arachidonic acid metabolites. It is of particular importance in the coagulopathies that accompany sepsis. Numerous studies have documented the activation of the coagulation system either in septic patients or following LPS administration in animal models. Despite more than thirty years of research, the mechanisms of LPS-induced liver toxicity remain poorly understood. It is now clear that they involve a complex and sequential series of interactions between cellular and humoral mediators. In the same period of time, gram-negative systemic sepsis and its sequalae have become a major health concern, attempts to use monoclonal antibodies directed against LPS or various inflammatory mediators have yielded only therapeutic failures. DNL complexes that target both thrombin and at least one other target address the clinical failures in sepsis treatment.

In other embodiments, the DNL complexes bind to a MHC class I, MHC class II or accessory molecule, such as CD40, CD54, CD80 or CD86. The DNL complex also may bind to a T-cell activation cytokine, or to a cytokine mediator, such as NF-κB.

In certain embodiments, one of the two different targets may be a cancer cell receptor or cancer-associated antigen, particularly one that is selected from the group consisting of B-cell lineage antigens (CD19, CD20, CD21, CD22, CD23, etc.), VEGFR, EGFR, carcinoembryonic antigen (CEA), placental growth factor (PlGF), tenascin, HER-2/neu, EGP-1, EGP-2, CD25, CD30, CD33, CD38, CD40, CD45, CD52, CD74, CD80, CD138, NCA66, CEACAM1, CEACAM6 (carcinoembryonic antigen-related cellular adhesion molecule 6), MUC1, MUC2, MUC3, MUC4, MUC16, IL-6, α-fetoprotein (AFP), A3, CA125, colon-specific antigen-p (CSAp), folate receptor, HLA-DR, human chorionic gonadotropin (HCG), Ia, EL-2, insulin-like growth factor (ILGF) and ILGF receptor, KS-1, Le(y), MAGE, necrosis antigens, PAM-4, prostatic acid phosphatase (PAP), Pr1, prostate specific antigen (PSA), prostate specific membrane antigen (PSMA), S100, T101, TAC, TAG72, TRAIL receptors, and carbonic anhydrase IX.

Targets associated with sepsis and immune dysregulation and other immune disorders include MIF, IL-1, IL-6, IL-8, CD74, CD83, and C5aR. Antibodies and inhibitors against C5aR have been found to improve survival in rodents with sepsis (Huber-Lang et al., *FASEB J* 2002; 16:1567-1574; Riedemann et al., *J Clin Invest* 2002; 110:101-108) and septic shock and adult respiratory distress syndrome in monkeys (Hangen et al., *J Surg Res* 1989; 46:195-199; Stevens et al., *J Clin Invest* 1986; 77:1812-1816). Thus, for sepsis, one of the two different targets preferably is a target that is associated with infection, such as LPS/C5a. Other preferred targets include HMGB-1, TF, CD14, VEGF, and IL-6, each of which is associated with septicemia or septic shock. Preferred DNL complexes are those that target two or more targets from HMGB-1, TF and MIF, such as MIF/TF, and HMGB-1/TF.

In still other embodiments, one of the two different targets may be a target that is associated with graft versus host disease or transplant rejection, such as MIF (Lo et al., *Bone Marrow Transplant*, 30(6):375-80 (2002)). One of the two different targets also may be one that associated with acute respiratory distress syndrome, such as IL-8 (Bouros et al., *PMC Pulm Med*, 4(1):6 (2004), atherosclerosis or restenosis, such as MIF (Chen et al., *Arterioscler Thromb Vasc Biol*, 24(4):709-14 (2004), asthma, such as IL-18 (Hata et al., *Int Immunol*, Oct. 11, 2004 Epub ahead of print), a granulomatous disease, such as TNF-α (Ulbricht et al., *Arthritis Rheum*, 50(8):2717-8 (2004), a neuropathy, such as carbamylated EPO (erythropoietin) (Leist et al., *Science* 305(5681):164-5 (2004), or cachexia, such as IL-6 and TNF-α.

Other targets include C5a, LPS, IFN-gamma, B7; CD2, CD4, CD14, CD18, CD11a, CD11b, CD11c, CD14, CD18, CD27, CD29, CD38, CD40L, CD52, CD64, CD83, CD147, CD154. Activation of mononuclear cells by certain microbial antigens, including LPS, can be inhibited to some extent by antibodies to CD18, CD11b, or CD11c, which thus implicate β2-integrins (Cuzzola et al., *J Immunol* 2000; 164:5871-5876; Medvedev et al., *J Immunol* 1998; 160: 4535-4542). CD83 has been found to play a role in giant cell arteritis (GCA), which is a systemic vasculitis that affects medium- and large-size arteries, predominately the extracranial branches of the aortic arch and of the aorta itself, resulting in vascular stenosis and subsequent tissue ischemia, and the severe complications of blindness, stroke and aortic arch syndrome (Weyand and Goronzy, *N Engl J Med* 2003; 349: 160-169; Hunder and Valente, In: Inflammatory Diseases of Blood Vessels. G. S. Hoffman and C. M. Weyand, eds, Marcel Dekker, New York, 2002; 255-265). Antibodies to CD83 were found to abrogate vasculitis in a SCID mouse model of human GCA (Ma-Krupa et al., *J Exp Med* 2004; 199:173-183), suggesting to these investigators that dendritic cells, which express CD83 when activated, are critical antigen-processing cells in GCA. In these studies, they used a mouse anti-CD83 MAb (IgG1 clone HB15e from Research Diagnostics). CD154, a member of the TNF family, is expressed on the surface of CD4-positive T-lymphocytes, and it has been reported that a humanized monoclonal antibody to CD154 produced significant clinical benefit in patients with active systemic lupus erythematosus (SLE) (Grammar et al., *J Clin Invest* 2003; 112:1506-1520). It also suggests that this antibody might be useful in other autoimmune diseases (Kelsoe, *J Clin Invest* 2003; 112:1480-1482). Indeed, this antibody was also reported as effective in patients with refractory immune thrombocytopenic purpura (Kuwana et al., *Blood* 2004; 103:1229-1236).

In rheumatoid arthritis, a recombinant interleukin-1 receptor antagonist, IL-1Ra or anakinra, has shown activity (Cohen et al., *Ann Rheum Dis* 2004; 63:1062-8; Cohen, *Rheum Dis*

*Clin North Am* 2004; 30:365-80). An improvement in treatment of these patients, which hitherto required concomitant treatment with methotrexate, is to combine anakinra with one or more of the anti-proinflammatory effector cytokines or anti-proinflammatory effector chemokines (as listed above). Indeed, in a review of antibody therapy for rheumatoid arthritis, Taylor (*Curr Opin Pharmacol* 2003; 3:323-328) suggests that in addition to TNF, other antibodies to such cytokines as IL-1, IL-6, IL-8, IL-15, IL-17 and IL-18, are useful.

Some of the more preferred target combinations are shown in Table 5. This is a list of examples of preferred combinations, but is not intended to be exhaustive.

TABLE 5

Potential Combinations of Target Antigens for DNL Complexes

| First target | Second target |
|---|---|
| MIF | A second proinflammatory effector cytokine, especially HMGB-1, TNF-α, IL-1, or IL-6 |
| MIF | Proinflammatory effector chemokine, especially MCP-1, RANTES, MIP-1A, or MIP-1B |
| MIF | Proinflammatory effector receptor, especially IL-6R IL-13R, and IL-15R |
| MIF | Coagulation factor, especially TF or thrombin |
| MIF | Complement factor, especially C3, C5, C3a, or C5a |
| MIF | Complement regulatory protein, especially CD46, CD55, CD59, and mCRP |
| MIF | Cancer associated antigen or receptor |
| HMGB-1 | A second proinflammatory effector cytokine, especially MIF, TNF-α, IL-1, or IL-6 |
| HMGB-1 | Proinflammatory effector chemokine, especially MCP-1, RANTES, MIP-1A, or MIP-1B |
| HMGB-1 | Proinflammatory effector receptor especially MCP-1, RANTES, MIP-1A, or MIP-1B |
| HMGB-1 | Coagulation factor, especially TF or thrombin |
| HMGB-1 | Complement factor, especially C3, C5, C3a, or C5a |
| HMGB-1 | Complement regulatory protein, especially CD46, CD55, CD59, and mCRP |
| HMGB-1 | Cancer associated antigen or receptor |
| TNF-α | A second proinflammatory effector cytokine, especially MIF, HMGB-1, TNF-α, IL-1, or IL-6 |
| TNF-α | Proinflammatory effector chemokine, especially MCP-1, RANTES, MIP-1A, or MIP-1B |
| TNF-α | Proinflammatory effector receptor, especially IL-6R IL-13R, and IL-15R |
| TNF-α | Coagulation factor, especially TF or thrombin |
| TNF-α | Complement factor, especially C3, C5, C3a, or C5a |
| TNF-α | Complement regulatory protein, especially CD46, CD55, CD59, and mCRP |
| TNF-α | Cancer associated antigen or receptor |
| LPS | Proinflammatory effector cytokine, especially MIF, HMGB-1, TNF-α, IL-1, or IL-6 |
| LPS | Proinflammatory effector chemokine, especially MCP-1, RANTES, MIP-1A, or MIP-1B |
| LPS | Proinflammatory effector receptor, especially IL-6R IL-13R, and IL-15R |
| LPS | Coagulation factor, especially TF or thrombin |
| LPS | Complement factor, especially C3, C5, C3a, or C5a |
| LPS | Complement regulatory protein, especially CD46, CD55, CD59, and mCRP |
| TF or thrombin | Proinflammatory effector cytokine, especially MIF, HMGB-1, TNF-α, IL-1, or IL-6 |
| TF or thrombin | Proinflammatory effector chemokine, especially MCP-1, RANTES, MIP-1A, or MIP-1B |
| TF or thrombin | Proinflammatory effector receptor, especially IL-6R IL-13R, and IL-15R |
| TF or thrombin | Complement factor, especially C3, C5, C3a, or C5a |
| TF or thrombin | Complement regulatory protein, especially CD46, CD55, CD59, and mCRP |
| TF or thrombin | Cancer associated antigen or receptor |

Antibody Fragments

Antibody fragments which recognize specific epitopes can be generated by known techniques. The antibody fragments are antigen binding portions of an antibody, such as F(ab)$_2$, Fab', Fab, Fv, scFv and the like. Antibody fragments include, but are not limited to: the F(ab')$_2$ fragments which can be produced by pepsin digestion of the antibody molecule and the Fab' fragments, which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a $V_L$ domain and a $V_H$ domain. The $V_L$ and $V_H$ domains associate to form a target binding site. These two domains are further covalently linked by a peptide linker. Methods for making scFv molecules and designing suitable peptide linkers are disclosed in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991).

An antibody fragment can be prepared by known methods, for example, as disclosed by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780). Single domain antibodies may be obtained, for example, from camels, alpacas or llamas by standard immunization techniques. (See, e.g., Muyldermans et al., TIBS 26:230-235, 2001; Yau et al., J Immunol Methods 281: 161-75, 2003; Maass et al., J Immunol Methods 324:13-25, 2007). They can have potent antigen-binding capacity and can interact with novel epitopes that are inaccessible to conventional $V_H$-$V_L$ pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and single domain antibodies can be isolated that bind to and neutralize the target antigen (Maass et al., 2007). PCR primers that amplify virtually all alpaca antibody coding sequences have been identified and may be used to construct single domain phage display libraries, which can be used for antibody fragment isolation by standard biopanning techniques well known in the art (Maass et al., 2007).

In certain embodiments, the sequences of antibodies or antibody fragments, such as the Fc portions of antibodies, may be varied to optimize their physiological characteristics, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797).

Multispecific and Multivalent Antibodies

Various embodiments may concern use of multispecific and/or multivalent antibodies. For example, an anti-CD74 antibody or fragment thereof and an anti-HLA-DR antibody or fragment thereof may be joined together by the dock-and-lock technique. Other combinations of antibodies or fragments thereof may be utilized. For example, another target antigen may include a tumor marker selected from a B-cell lineage antigen, (e.g., CD19, CD20, or CD22 for the treatment of B-cell malignancies). The tumor cell marker may be a non-B-cell lineage antigen selected from the group consisting of HLA-DR, CD30, CD33, CD52 MUC1, MUCS and TAC. Other useful antigens may include carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CXCR4, CXCR7, CXCL12, HIF-1a, CEACAM1, CEACAM5, CEACAM-6, alpha-fetoprotein (AFP), VEGF (e.g. AVASTIN®, fibronectin splice variant), ED-B fibronectin (e.g., L19), EGP-1, EGP-2 (e.g., 17-1A), EGF receptor (ErbB1) (e.g., ERBITUX®), ErbB2, ErbB3, Factor H, FHL-1, Flt-3, folate receptor, Ga 733, GROB, HMGB-1, hypoxia inducible factor (HIF), HM1.24, HER-2/neu, insulin-like growth factor (IGF), IFN-γ, IFN-α, IFN-β, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5, placental growth factor (PlGF), PSA (prostate-specific antigen), PSMA, pancreatic cancer mucin, pancreatic cancer mucin, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), VEGFR, RANTES, T101, as well as cancer stem cell antigens, complement factors C3, C3a, C3b, C5a, C5, and an oncogene product. Multispecific, multivalent DNL antibody complexes may be used, for example, in pre-targeting methods as described below.

Pre-Targeting

In certain embodiments, therapeutic agents may be administered by a pretargeting method, utilizing DNL constructs comprising bispecific or multispecific antibodies. In pretargeting, the bispecific or multispecific antibody comprises at least one binding arm that binds to an antigen exhibited by a targeted cell or tissue, while at least one other binding arm binds to a hapten on a targetable construct. The targetable construct comprises one or more haptens and one or more therapeutic and/or diagnostic agents.

Pre-targeting is a multistep process originally developed to resolve the slow blood clearance of directly targeting antibodies, which contributes to undesirable toxicity to normal tissues such as bone marrow. With pre-targeting, a radionuclide or other diagnostic or therapeutic agent is attached to a small delivery molecule (targetable construct) that is cleared within minutes from the blood. A pre-targeting bispecific or multispecific antibody, which has binding sites for the targetable construct as well as a target antigen, is administered first, free antibody is allowed to clear from circulation and then the targetable construct is administered.

Pre-targeting methods are disclosed, for example, in Goodwin et al., U.S. Pat. No. 4,863,713; Goodwin et al., J. Nucl. Med. 29:226, 1988; Hnatowich et al., J. Nucl. Med. 28:1294, 1987; Oehr et al., J. Nucl. Med. 29:728, 1988; Klibanov et al., J. Nucl. Med. 29:1951, 1988; Sinitsyn et al., J. Nucl. Med.

30:66, 1989; Kalofonos et al., J. Nucl. Med. 31:1791, 1990; Schechter et al., Int. J. Cancer 48:167, 1991; Paganelli et al., Cancer Res. 51:5960, 1991; Paganelli et al., Nucl. Med. Commun. 12:211, 1991; U.S. Pat. No. 5,256,395; Stickney et al., Cancer Res. 51:6650, 1991; Yuan et al., Cancer Res. 51:3119, 1991; U.S. Pat. Nos. 6,077,499; 7,011,812; 7,300,644; 7,074,405; 6,962,702; 7,387,772; 7,052,872; 7,138,103; 6,090,381; 6,472,511; 6,962,702; and 6,962,702, each incorporated herein by reference.

A pre-targeting method of treating or diagnosing a disease or disorder in a subject may be provided by: (1) administering to the subject a DNL complex comprising a bispecific antibody or antibody fragment; (2) optionally administering to the subject a clearing composition, and allowing the composition to clear the antibody from circulation; and (3) administering to the subject the targetable construct, containing one or more chelated or chemically bound therapeutic or diagnostic agents.

Immunoconjugates

In preferred embodiments, an antibody or antibody fragment in a DNL complex may be directly attached to one or more therapeutic agents to form an immunoconjugate. Therapeutic agents may be attached, for example to reduced SH groups and/or to carbohydrate side chains. A therapeutic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic agent can be conjugated via a carbohydrate moiety in the Fc region of the antibody.

Methods for conjugating functional groups to antibodies via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching therapeutic agents to an antibody or other effector moiety involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted akyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach therapeutic agents to antibodies in vitro.

The specificity of the click chemistry reaction may be used as a substitute for the antibody-hapten binding interaction used in pretargeting with bispecific antibodies. In this alternative embodiment, the specific reactivity of e.g., cyclooctyne moieties for azide moieties or alkyne moieties for nitrone moieties may be used in an in vivo cycloaddition reaction. An antibody-based DNL complex is activated by incorporation of a substituted cyclooctyne, an azide or a nitrone moiety. A targetable construct is labeled with one or more diagnostic or therapeutic agents and a complementary reactive moiety. I.e., where the antibody comprises a cyclooctyne, the targetable construct will comprise an azide; where the antibody comprises a nitrone, the targetable construct will comprise an alkyne, etc. The DNL complex comprising an activated antibody is administered to a subject and allowed to localize to a targeted cell, tissue or pathogen, as disclosed for pretargeting protocols. The reactive labeled targetable construct is then administered. Because the cyclooctyne, nitrone or azide on the targetable construct is unreactive with endogenous biomolecules and highly reactive with the complementary moiety on the antibody, the specificity of the binding interaction results in the highly specific binding of the targetable construct to the tissue-localized antibody. Although the discussion above concerns click chemistry reactions with antibody effector moiety, the skilled artisan will realize that such reactions may be used to attach any functional groups to any effector moiety that may be incorporated into a DNL construct.

Therapeutic Agents

A wide variety of therapeutic reagents can be administered concurrently or sequentially with the subject DNL complexes. For example, drugs, toxins, oligonucleotides, immunomodulators, hormones, hormone antagonists, enzymes, enzyme inhibitors, radionuclides, angiogenesis inhibitors, other antibodies or fragments thereof, etc. The therapeutic agents recited here are those agents that useful for administration separately with a DNL complex as described above or else conjugated to a subject DNL complex. Therapeutic agents include, for example, chemotherapeutic drugs such as vinca alkaloids, anthracyclines, gemcitabine, epipodophyllotoxins, taxanes, antimetabolites, alkylating agents, antibiotics, SN-38, COX-2 inhibitors, antimitotics, anti-angiogenic and pro-apoptotic agents, particularly doxorubicin, methotrexate, TAXOL® (paclitaxel), CPT-11, camptothecans, proteosome inhibitors, mTOR inhibitors, HDAC inhibitors, tyrosine kinase inhibitors, and others.

Antisense molecules may include antisense molecules that correspond to bcl-2 or p53. However, other antisense molecules are known in the art, as described below, and any such known antisense molecule may be used. Second antibodies or fragments thereof may bind to an antigen selected from the group consisting of carbonic anhydrase IX, CCCL19, CCCL21, CSAp, CD1, CD1a, CD2, CD3, CD4, CD5, CD8, CD11A, CD14, CD15, CD16, CD18, CD19, IGF-1R, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD133, CD138, CD147, CD154, CXCR4, CXCR7, CXCL12, HIF-1a, AFP, PSMA, CEACAM1, CEACAM5, CEACAM6, B7, ED-B of fibronectin, Factor H, FHL-1, Flt-3, folate receptor, GROB, HMGB-1, hypoxia inducible factor (HIF), HM1.24, insulin-like growth factor-1 (IGF-1), IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-25, IP-10, MAGE, mCRP, MCP-1, MIP-1A, MIP-1B, MIF, MUC1, MUC2, MUC3, MUC4, MUC5, NCA-95, NCA-90, Ia, HM1.24, EGP-1, EGP-2, HLA-DR, tenascin, Le(y), RANTES, T101, TAC, Tn antigen, Thomson-Friedenreich antigens, tumor necrosis antigens, TNF-α, TRAIL receptor (R1 and R2), VEGFR, EGFR, PlGF, complement factors C3, C3a, C3b, C5a, C5, and an oncogene product.

The therapeutic agent may be selected from the group consisting of aplidin, azaribine, anastrozole, azacytidine, bleomycin, bortezomib, bryostatin-1, busulfan, calicheamycin, camptothecin, 10-hydroxycamptothecin, carmustine, CELEBREX® (celecoxib), chlorambucil, CISPLATIN® (cisplatinum), irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, egestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, testosterone propionate, thalidomide, thioguanine, thiotepa, teniposide, topotecan, uracil mustard, vinblastine, vinorelbine, vincristine, ricin, abrin, ribonuclease, ONCONASE® (ranpirnase), rapLR1, DNase I, Staphylococcal enterotoxin-A, pokeweed antiviral protein, gelonin, diphtheria toxin, Pseudomonas exotoxin, and *Pseudomonas* endotoxin.

Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

Additional potential therapeutic radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

The therapeutic agent may be an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

An immunomodulator of use may be selected from the group consisting of a cytokine, a lymphokine, a monokine, a stem cell growth factor, a lymphotoxin, a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), TGF-α, TGF-β, insulin-like growth factor (IGF), erythropoietin, thrombopoietin, tumor necrosis factor (TNF), TNF-α, TNF-β, a mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, interferon-λ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 and IL-25, LIF, kit-ligand, FLT-3, angiostatin, thrombospondin, endostatin and LT, and the like.

Exemplary anti-angiogenic agents may include angiostatin, endostatin, vasculostatin, canstatin, maspin, anti-VEGF binding molecules, anti-placental growth factor binding molecules, or anti-vascular growth factor binding molecules.

In certain embodiments, the DNL complex may comprise one or more chelating moieties, such as NOTA, DOTA, DTPA, TETA, Tscg-Cys, or Tsca-Cys. In certain embodiments, the chelating moiety may form a complex with a therapeutic or diagnostic cation, such as Group II, Group III, Group IV, Group V, transition, lanthanide or actinide metal cations, Tc, Re, Bi, Cu, As, Ag, Au, At, or Pb.

Other useful cancer chemotherapeutic drugs include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

A toxin can be of animal, plant or microbial origin. A toxin, such as *Pseudomonas* exotoxin, may also be complexed to or form the therapeutic agent portion of an immunoconjugate. Other toxins include ricin, abrin, ribonuclease (RNase), DNase I, Staphylococcal enterotoxin-A, pokeweed antiviral protein, ONCONASE® (ranpirnase), gelonin, diphtheria toxin, *Pseudomonas* exotoxin, and *Pseudomonas* endotoxin. See, for example, Pastan et al., Cell 47:641 (1986), Goldenberg, C A—A Cancer Journal for Clinicians 44:43 (1994), Sharkey and Goldenberg, C A—A Cancer Journal for Clinicians 56:226 (2006). Additional toxins suitable for use are known to those of skill in the art and are disclosed in U.S. Pat. No. 6,077,499, the Examples section of which is incorporated herein by reference.

The skilled artisan will realize that certain therapeutic agents recited above, particularly those that are proteins or peptides such as toxins or immunomodulators, may be incorporated into a DNL complex as an effector moiety by attachment to an AD or DDD moiety.

Interference RNA

In certain preferred embodiments the therapeutic agent may be a siRNA or interference RNA species. The siRNA, interference RNA or therapeutic gene may be attached to a carrier moiety that is conjugated to an antibody or fragment in a DNL construct. A variety of carrier moieties for siRNA have been reported and any such known carrier may be incorporated into a DNL construct for use. Non-limiting examples of carriers include protamine (Rossi, 2005, Nat Biotech 23:682-84; Song et al., 2005, Nat Biotech 23:709-17); dendrimers such as PAMAM dendrimers (Pan et al., 2007, Cancer Res. 67:8156-8163); polyethylenimine (Schiffelers et al., 2004, Nucl Acids Res 32:e149); polypropyleneimine (Taratula et al., 2009, J Control Release 140:284-93); polylysine (Inoue et al., 2008, J Control Release 126:59-66); histidine-containing reducible polycations (Stevenson et al., 2008, J Control Release 130:46-56); histone H1 protein (Haberland et al., 2009, Mol Biol Rep 26:1083-93); cationic comb-type copolymers (Sato et al., 2007, J Control Release 122:209-16); polymeric micelles (U.S. Patent Application Publ. No. 20100121043); and chitosan-thiamine pyrophosphate (Rojanarata et al., 2008, Pharm Res 25:2807-14). The skilled artisan will realize that in general, polycationic proteins or polymers are of use as siRNA carriers. The skilled artisan will further realize that siRNA carriers can also be used to carry other oligonucleotide or nucleic acid species, such as antisense oligonucleotides or short DNA genes.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL complexes.

Exemplary siRNA species known in the art are listed in Table 6. Although siRNA is delivered as a double-stranded molecule, for simplicity only the sense strand sequences are shown in Table 6.

TABLE 6

Exemplary siRNA Sequences

| Target | Sequence | SEQ ID NO |
|---|---|---|
| VEGF R2 | AATGCGGCGGTGGTGACAGTA | SEQ ID NO: 85 |
| VEGF R2 | AAGCTCAGCACACAGAAAGAC | SEQ ID NO: 86 |
| CXCR4 | UAAAAUCUUCCUGCCCACCdTdT | SEQ ID NO: 87 |
| CXCR4 | GGAAGCUGUUGGCUGAAAAdTdT | SEQ ID NO: 88 |
| PPARC1 | AAGACCAGCCUCUUUGCCCAG | SEQ ID NO: 89 |
| Dynamin 2 | GGACCAGGCAGAAAACGAG | SEQ ID NO: 90 |
| Catenin | CUAUCAGGAUGACGCGG | SEQ ID NO: 91 |
| E1A binding protein | UGACACAGGCAGGCUUGACUU | SEQ ID NO: 92 |
| Plasminogen activator | GGTGAAGAAGGGCGTCCAA | SEQ ID NO: 93 |
| K-ras | GATCCGTTGGAGCTGTTGGCGTAGTTCAAGAGACTCGCCAACAGCTCCAACTTTTGGAAA | SEQ ID NO: 94 |
| Sortilin 1 | AGGTGGTGTTAACAGCAGAG | SEQ ID NO: 95 |
| Apolipoprotein E | AAGGTGGAGCAAGCGGTGGAG | SEQ ID NO: 96 |
| Apolipoprotein E | AAGGAGTTGAAGGCCGACAAA | SEQ ID NO: 97 |
| Bcl-X | UAUGGAGCUGCAGAGGAUGdTdT | SEQ ID NO: 98 |
| Raf-1 | TTTGAATATCTGTGCTGAGAACACAGTTCTCAGCACAGATATTCTTTTT | SEQ ID NO: 99 |
| Heat shock transcription factor 2 | AATGAGAAAAGCAAAAGGTGCCCTGTCTC | SEQ ID NO: 100 |
| IGFBP3 | AAUCAUCAUCAAGAAAGGGCA | SEQ ID NO: 101 |
| Thioredoxin | AUGACUGUCAGGAUGUUGCdTdT | SEQ ID NO: 102 |
| CD44 | GAACGAAUCCUGAAGACAUCU | SEQ ID NO: 103 |
| MMP14 | AAGCCTGGCTACAGCAATATGCCTGTCTC | SEQ ID NO: 104 |
| MAPKAPK2 | UGACCAUCACCGAGUUUAUdTdT | SEQ ID NO: 105 |
| FGFR1 | AAGTCGGACGCAACAGAGAAA | SEQ ID NO: 106 |
| ERBB2 | CUACCUUUCUACGGACGUGdTdT | SEQ ID NO: 107 |
| BCL2L1 | CTGCCTAAGGCGGATTTGAAT | SEQ ID NO: 108 |
| ABL1 | TTAUUCCUUCUUCGGGAAGUC | SEQ ID NO: 109 |
| CEACAM1 | AACCTTCTGGAACCCGCCCAC | SEQ ID NO: 110 |
| CD9 | GAGCATCTTCGAGCAAGAA | SEQ ID NO: 111 |
| CD151 | CATGTGGCACCGTTTGCCT | SEQ ID NO: 112 |
| Caspase 8 | AACTACCAGAAAGGTATACCT | SEQ ID NO: 113 |
| BRCA1 | UCACAGUGUCCUUUAUGUAdTdT | SEQ ID NO: 114 |
| p53 | GCAUGAACCGGAGGCCCAUTT | SEQ ID NO: 115 |
| CEACAM6 | CCGGACAGTTCCATGTATA | SEQ ID NO: 116 |

The skilled artisan will realize that Table 6 represents a very small sampling of the total number of siRNA species known in the art, and that any such known siRNA may be utilized in the claimed methods and compositions.

Immunotoxins Comprising Ranpirnase (Rap)

Ribonucleases, in particular, Rap (Lee, Exp Opin Biol Ther 2008; 8:813-27) and its more basic variant, amphinase (Ardelt et al., Curr Pharm Biotechnol 2008:9:215-25), are potential anti-tumor agents (Lee and Raines, Biodrugs 2008; 22:53-8). Rap is a single-chain ribonuclease of 104 amino acids originally isolated from the oocytes of *Rana pipiens*. Rap exhibits cytostatic and cytotoxic effects on a variety of tumor cell lines in vitro, as well as antitumor activity in vivo. The amphibian ribonuclease enters cells via receptor-mediated endocytosis and once internalized into the cytosol, selectively degrades tRNA, resulting in inhibition of protein synthesis and induction of apoptosis.

Rap has completed a randomized Phase IIIb clinical trial, which compared the effectiveness of Rap plus doxorubicin with that of doxorubicin alone in patients with unresectable malignant mesothelioma, with the interim analysis showing that the MST for the combination was 12 months, while that of the monotherapy was 10 months (Mutti and Gaudino, Oncol Rev 2008; 2:61-5). Rap can be administered repeatedly to patients without an untoward immune response, with reversible renal toxicity reported to be dose-limiting (Mikulski et al., J Clin Oncol 2002; 20:274-81; Int J Oncol 1993; 3:57-64).

Conjugation or fusion of Rap to a tumor-targeting antibody or antibody fragment is a promising approach to enhance its potency, as first demonstrated for LL2-ONCONASE® (ranpirnase) (Newton et al., Blood 2001; 97:528-35), a chemical conjugate comprising Rap and a murine anti-CD22 monoclonal antibody (MAb), and subsequently for 2L-Rap-hLL1-γ4P, a fusion protein comprising Rap and a humanized anti-CD74 MAb (Stein et al., Blood 2004; 104:3705-11).

The method used to generate 2L-Rap-hLL1-γ4P allowed us to develop a series of structurally similar immunotoxins, referred to in general as 2L-Rap-X, all of which consist of two Rap molecules, each connected via a flexible linker to the N-terminus of one L chain of an antibody of interest (X). We have also generated another series of immunotoxins of the same design, referred to as 2LRap(Q)-X, by substituting Rap with its non-glycosylation form of Rap, designated as Rap(Q) to denote that the potential glycosylation site at Asn69 is changed to Gln (or Q, single letter code). For both series, we made the IgG as either IgG1(γ1) or IgG4(γ4), and to prevent the formation of IgG4 half molecules (Aalberse and Schuurman, Immunology 2002; 105:9-19), we converted the serine residue in the hinge region (S228) of IgG4 to proline (γ4P). A pyroglutamate residue at the N-terminus of Rap is required for the RNase to be fully functional (Liao et al., Nucleic Acids Res 2003; 31:5247-55).

The skilled artisan will recognize that the cytotoxic RNase moieties suitable for use in the present invention include polypeptides having a native ranpirnase structure and all enzymatically active variants thereof. These molecules advantageously have an N-terminal pyroglutamic acid resides that appears essential for RNase activity and are not substantially inhibited by mammalian RNase inhibitors. Nucleic acid that encodes a native cytotoxic RNase may be prepared by cloning and restriction of appropriate sequences, or using DNA amplification with polymerase chain reaction (PCR). The amino acid sequence of *Rana Pipiens* ranpirnase can be obtained from Ardelt et al., J. Biol. Chem., 256: 245 (1991), and cDNA sequences encoding native ranpirnase, or a conservatively modified variation thereof, can be generated synthesized by methods similar to the en bloc V-gene assembly method used in hLL2 humanization. (Leung et al., Mol. Immunol., 32: 1413, 1995). Methods of making cytotoxic RNase variants are known in the art and are within the skill of the routineer.

As described in the Examples below, Rap conjugates of targeting antibodies may be made using the DNL technology. The DNL Rap-antibody constructs show potent cytotoxic activity that can be targeted to disease-associated cells.

Diagnostic Agents

In various embodiments, the DNL complexes may be conjugated to, or may bind a targetable construct comprising one or more diagnostic agents. Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}$F, $^{52}$Fe, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{83}$Sr, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Therapeutic Treatment

The DNL complexes are of use for treating a variety of disease states, such as cancer, autoimmune disease or immune dysfunction. The methods may comprise administering a therapeutically effective amount of a DNL complex, either alone or in conjunction with one or more other therapeutic agents, administered either concurrently or sequentially.

Multimodal therapies may include therapy with other antibodies, such as anti-CD22, anti-CD19, anti-CD20, anti-CD21, anti-CD74, anti-CD80, anti-CD23, anti-CD45, anti-CD46, anti-MIF, anti-EGP-1, anti-CEACAM1, anti-CEACAM5, anti-CEACAM6, anti-pancreatic cancer mucin, anti-IGF-1R or anti-HLA-DR (including the invariant chain) antibodies in the form of naked antibodies, fusion proteins, or as immunoconjugates. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,612,180; 7,501,498; the Examples section of each of which is incorporated herein by reference.

In another form of multimodal therapy, subjects may receive therapeutic DNL complexes in conjunction with standard cancer chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

In a preferred multimodal therapy, both chemotherapeutic drugs and cytokines are co-administered with a therapeutic DNL complex. The cytokines, chemotherapeutic drugs and therapeutic DNL complex can be administered in any order, or together.

Therapeutic DNL complexes can be formulated according to known methods to prepare pharmaceutically useful compositions, whereby the therapeutic DNL complex is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The therapeutic DNL complex can be formulated for intravenous administration via, for example, bolus injection or continuous infusion. Preferably, the therapeutic DNL complex is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

More generally, the dosage of an administered therapeutic DNL complex for humans will vary depending upon such factors as the patient's age, weight, height, sex, general medical condition and previous medical history. It may be desirable to provide the recipient with a dosage of therapeutic DNL complex that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, a therapeutic DNL complex may be administered as one dosage every 2 or 3 weeks, repeated for a total of at least 3 dosages. Or, the therapeutic DNL complex may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

Additional pharmaceutical methods may be employed to control the duration of action of the therapeutic DNL complex. Control release preparations can be prepared through the use of polymers to complex or adsorb the DNL complex. For example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). The rate of release of a DNL complex from such a matrix depends upon the molecular weight of the DNL complex, the amount of DNL complex within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Cancer Therapy

In preferred embodiments, the DNL complexes are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Therapy of Autoimmune Disease

DNL complexes can be used to treat immune dysregulation disease and related autoimmune diseases, including Class-III autoimmune diseases, immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis obliterans, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis.

Avimers

In certain embodiments, the DNL complexes described herein may comprise one or more avimer sequences. Avimers are a class of binding proteins somewhat similar to antibodies in their affinities and specificities for various target molecules. They were developed from human extracellular receptor domains by in vitro exon shuffling and phage display (Silverman et al., 2005, Nat. Biotechnol. 23:1493-94; Silverman et al., 2006, Nat. Biotechnol. 24:220). The resulting multidomain proteins may comprise multiple independent binding domains, that may exhibit improved affinity (in some cases sub-nanomolar) and specificity compared with single-epitope binding proteins. (Id.) In various embodiments, avimers may be attached to, for example, DDD and/or AD sequences for use in the claimed methods and compositions. Additional details concerning methods of construction and use of avimers are disclosed, for example, in U.S. Patent Application Publication Nos. 20040175756 (now abandoned), 20050048512 (now abandoned), 20050053973 (now abandoned), 20050089932 (now abandoned) and 20050221384 (now abandoned), the Examples section of each of which is incorporated herein by reference.

Phage Display

In alternative embodiments, the effector moieties may comprise binding peptides and/or peptide mimetics of various target molecules, cells or tissues. Binding peptides may be identified by any method known in the art, including but not limiting to the phage display technique. Various methods of phage display and techniques for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, Science 228:1315-1317; Smith and Scott, 1993, Meth. Enzymol. 21:228-257). In addition to peptides, larger protein domains such as single-chain antibodies may also be displayed on the surface of phage particles (Arap et al., 1998, Science 279:377-380).

Targeting amino acid sequences selective for a given organ, tissue, cell type or target molecule may be isolated by panning (Pasqualini and Ruoslahti, 1996, Nature 380:364-366; Pasqualini, 1999, The Quart. J. Nucl. Med. 43:159-162). In brief, a library of phage containing putative targeting peptides is administered to an intact organism or to isolated organs, tissues, cell types or target molecules and samples containing bound phage are collected. Phage that bind to a target may be eluted from a target organ, tissue, cell type or target molecule and then amplified by growing them in host bacteria.

In certain embodiments, the phage may be propagated in host bacteria between rounds of panning. Rather than being lysed by the phage, the bacteria may instead secrete multiple copies of phage that display a particular insert. If desired, the amplified phage may be exposed to the target organs, tissues, cell types or target molecule again and collected for additional rounds of panning. Multiple rounds of panning may be performed until a population of selective or specific binders is obtained. The amino acid sequence of the peptides may be determined by sequencing the DNA corresponding to the targeting peptide insert in the phage genome. The identified targeting peptide may then be produced as a synthetic peptide by standard protein chemistry techniques (Arap et al., 1998, Smith et al., 1985).

In some embodiments, a subtraction protocol may be used to further reduce background phage binding. The purpose of subtraction is to remove phage from the library that bind to targets other than the target of interest. In alternative embodiments, the phage library may be prescreened against a control cell, tissue or organ. For example, tumor-binding peptides may be identified after prescreening a library against a control normal cell line. After subtraction the library may be screened against the molecule, cell, tissue or organ of interest. Other methods of subtraction protocols are known and may be used in the practice of the claimed methods, for example as disclosed in U.S. Pat. Nos. 5,840,841, 5,705,610, 5,670,312 and 5,492,807.

Aptamers

In other alternative embodiments, the subject DNL complex may comprise an aptamer. Methods of constructing and determining the binding characteristics of aptamers are well known in the art. For example, such techniques are described in U.S. Pat. Nos. 5,582,981, 5,595,877 and 5,637,459, the Examples section of each incorporated herein by reference. Methods for preparation and screening of aptamers that bind to particular targets of interest are well known, for example U.S. Pat. No. 5,475,096 and U.S. Pat. No. 5,270,163, the Examples section of each incorporated herein by reference.

Aptamers may be prepared by any known method, including synthetic, recombinant, and purification methods, and may be used alone or in combination with other ligands specific for the same target. In general, a minimum of approximately 3 nucleotides, preferably at least 5 nucleotides, are necessary to effect specific binding. Aptamers of sequences shorter than 10 bases may be feasible, although aptamers of 10, 20, 30 or 40 nucleotides may be preferred.

Aptamers may be isolated, sequenced, and/or amplified or synthesized as conventional DNA or RNA molecules. Alternatively, aptamers of interest may comprise modified oligomers. Any of the hydroxyl groups ordinarily present in aptamers may be replaced by phosphonate groups, phosphate groups, protected by a standard protecting group, or activated to prepare additional linkages to other nucleotides, or may be conjugated to solid supports. One or more phosphodiester linkages may be replaced by alternative linking groups, such as P(O)O replaced by P(O)S, P(O)NR$_2$, P(O)R, P(O)OR', CO, or CNR$_2$, wherein R is H or alkyl (1-20C) and R' is alkyl (1-20C); in addition, this group may be attached to adjacent nucleotides through O or S, Not all linkages in an oligomer need to be identical.

Kits

Various embodiments may concern kits containing DNL constructs and/or other components. Such components may include a targetable construct for use with such DNL complexes. In alternative embodiments it is contemplated that a targetable construct may be attached to one or more different therapeutic and/or diagnostic agents.

If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used for certain applications.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Various embodiments of the present invention are illustrated by the following examples, without limiting the scope thereof.

Example 1

Preparation of Dock-and-Lock (DNL) Constructs

DDD and AD Fusion Proteins

The DNL technique can be used to make dimers, trimers, tetramers, hexamers, etc. comprising virtually any antibody, antibody fragment, immunomodulator, cytokine, PEG moiety, toxin, antigen or xenoantigen or other effector moiety. For certain preferred embodiments, antibodies and cytokines may be produced as fusion proteins comprising either a dimerization and docking domain (DDD) or anchoring domain (AD) sequence. Although in preferred embodiments the DDD and AD moieties may be joined to antibodies, antibody fragments, cytokines or other effector moieties as fusion proteins, the skilled artisan will realize that other methods of conjugation exist, such as chemical cross-linking, click chemistry reaction, etc.

The technique is not limiting and any protein or peptide of use may be produced as an AD or DDD fusion protein for incorporation into a DNL construct. Where chemical cross-linking is utilized, the AD and DDD conjugates may comprise any molecule that may be cross-linked to an AD or DDD sequence using any cross-linking technique known in the art. In certain exemplary embodiments, a dendrimer or other polymeric moiety such as polyethyleneimine or polyethylene glycol (PEG), may be incorporated into a DNL construct, as described in further detail below.

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain ($V_H$ and $V_L$) sequences. Using molecular biology tools known to those skilled in the art, these IgG expression vectors can be converted into Fab-DDD or Fab-AD expression vectors.

To generate Fab-DDD expression vectors, the coding sequences for the hinge, CH2 and CH3 domains of the heavy chain were replaced with a sequence encoding the first 4 residues of the hinge, a 14 residue Gly-Ser linker and a DDD moiety, such as the first 44 residues of human RIIα (referred to as DDD1, SEQ ID NO:1). To generate Fab-AD expression vectors, the sequences for the hinge, CH2 and CH3 domains of IgG were replaced with a sequence encoding the first 4 residues of the hinge, a 15 residue Gly-Ser linker and an AD moiety, such as a 17 residue synthetic AD called AKAP-IS (referred to as AD1, SEQ ID NO:3), which was generated using bioinformatics and peptide array technology and shown to bind Mkt dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC, SEQ ID NO:117) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

(SEQ ID NO: 118)
GSGGGGSGGGG<u>SHIQIPPGLTELLQGYTVEVLRQQPPDLVEFAVEY</u>

<u>FTRLREARA</u>

Two oligonucleotides, designated RIIA 1-44 top and RIIA 1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

GSGGGGSGGGGSQIEYLAKQIVDNAIQQA (SEQ ID NO: 119)

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1—PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1—PGEMT® to generate the shuttle vector CH1-AD1-PGEMT®.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective PGEMT® shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Production and Purification of h679-Fab-AD1

The h679-Fd-AD1-pdHL2 vector was linearized by digestion with Sal I restriction endonuclease and transfected into Sp/EEE myeloma cells by electroporation. The di-cistronic expression vector directs the synthesis and secretion of both h679 kappa light chain and h679 Fd-AD1, which combine to form h679 Fab-AD1. Following electroporation, the cells were plated in 96-well tissue culture plates and transfectant clones were selected with 0.05 µM methotrexate (MTX). Clones were screened for protein expression by ELISA using microtiter plates coated with a BSA-IMP260 (HSG) conjugate and detection with HRP-conjugated goat anti-human Fab. BIAcore analysis using an HSG (IMP239) sensorchip was used to determine the productivity by measuring the initial slope obtained from injection of diluted media samples. The highest producing clone had an initial productivity of approximately 30 mg/L. A total of 230 mg of h679-Fab-AD1 was purified from 4.5 liters of roller bottle culture by single-step 1MP291 affinity chromatography. Culture media was concentrated approximately 10-fold by ultrafiltration before loading onto an IMP291-affigel column. The column was washed to baseline with PBS and h679-Fab-AD1 was eluted with 1M imidazole, 1 mM EDTA, 0.1M NaAc, pH 4.5. SE-HPLC analysis of the eluate shows a single sharp peak with a retention time consistent with a 50 kDa protein (not shown). Only two bands, which represent the polypeptide constituents of h679-AD1, were evident by reducing SDS-PAGE analysis (not shown).

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

Construction of N-DDD1-Fd-hMN-14-pdHL2

N-DDDI-Fd-hMN-14-pdHL2 is an expression vector for production of a stable dimer that comprises two copies of a fusion protein N-DDD1-Fab-hMN-14, in which DDD1 is linked to hMN-14 Fab at the amino terminus of $V_H$ via a flexible peptide spacer. The expression vector was engineered as follows. The DDD1 domain was amplified by PCR.

As a result of the PCR, an NcoI restriction site and the coding sequence for part of the linker containing a BamHI restriction were appended to the 5' and 3' ends, respectively. The 170 bp PCR amplimer was cloned into the PGEMT® vector and clones were screened for inserts in the T7 (5') orientation. The 194 bp insert was excised from the PGEMT® vector with NcoI and SalI restriction enzymes and cloned into the SV3 shuttle vector, which was prepared by digestion with those same enzymes, to generate the intermediate vector DDD1-SV3.

The hMN-14 Fd sequence was amplified by PCR. As a result of the PCR, a BamHI restriction site and the coding sequence for part of the linker were appended to the 5' end of the amplimer. A stop codon and EagI restriction site was appended to the 3' end. The 1043 bp amplimer was cloned into pGemT. The hMN-14-Fd insert was excised from PGEMT® with BamHI and EagI restriction enzymes and then ligated with DDD1-SV3 vector, which was prepared by digestion with those same enzymes, to generate the construct N-DDD1-hMN-14Fd-SV3.

The N-DDD1-hMN-14 Fd sequence was excised with XhoI and EagI restriction enzymes and the 1.28 kb insert fragment was ligated with a vector fragment that was prepared by digestion of C-hMN-14-pdHL2 with those same enzymes. The final expression vector was N-DDD1-Fd-hMN-14-pDHL2. The N-linked Fab fragment exhibited similar DNL complex formation and antigen binding characteristics as the C-linked Fab fragment (not shown).

Production and Purification of N-DDD1-Fab-hMN-14 and C-DDD1-Fab-hMN-14

The C-DDD1-Fd-hMN-14-pdHL2 and N-DDD1-Fd-hMN-14-pdHL2 vectors were transfected into Sp2/0-derived myeloma cells by electroporation. C-DDD1-Fd-hMN-14-pdHL2 is a di-cistronic expression vector, which directs the synthesis and secretion of both hMN-14 kappa light chain and hMN-14 Fd-DDD1, which combine to form C-DDD1-hMN-14 Fab. N-DDD1-hMN-14-pdHL2 is a di-cistronic expression vector, which directs the synthesis and secretion of both hMN-14 kappa light chain and N-DDD1-Fd-hMN-14, which combine to form N-DDD1-Fab-hMN-14. Each fusion protein forms a stable homodimer via the interaction of the DDD1 domain.

Following electroporation, the cells were plated in 96-well tissue culture plates and transfectant clones were selected with 0.05 pM methotrexate (MTX). Clones were screened for protein expression by ELISA using microtiter plates coated with WI2 (a rat anti-id monoclonal antibody to hMN-14) and detection with HRP-conjugated goat anti-human Fab. The initial productivity of the highest producing C-DDD1-Fab-hMN14 Fab and N-DDD1-Fab-hMN14 Fab clones was 60 mg/L and 6 mg/L, respectively.

Affinity Purification of N-DDD1-hMN-14 and C-DDD1-hMN-14 with AD1-Affigel

The DDD/AD interaction was utilized to affinity purify DDD 1-containing constructs. AD1-C is a peptide that was made synthetically consisting of the AD1 sequence and a carboxyl terminal cysteine residue, which was used to couple the peptide to Affigel following reaction of the sulfhydryl group with chloroacetic anhydride. DDD-containing dimer structures specifically bind to the AD1-C-Affigel resin at neutral pH and can be eluted at low pH (e.g., pH 2.5).

A total of 81 mg of C-DDD1-Fab-hMN-14 was purified from 1.2 liters of roller bottle culture by single-step AD1-C affinity chromatography. Culture media was concentrated approximately 10-fold by ultrafiltration before loading onto an AD1-C-affigel column. The column was washed to baseline with PBS and C-DDD1-Fab-hMN-14 was eluted with 0.1M Glycine, pH 2.5. SE-HPLC analysis of the eluate showed a single protein peak with a retention time consistent with a 107 kDa protein (not shown). The purify was also confirmed by reducing SDS-PAGE, showing only two bands of molecular size expected for the two polypeptide constituents of C-DDD1-Fab-hMN-14 (not shown).

A total of 10 mg of N-DDD1-hMN-14 was purified from 1.2 liters of roller bottle culture by single-step AD1-C affinity chromatography as described above. SE-HPLC analysis of the eluate showed a single protein peak with a retention time similar to C-DDD1-Fab-hMN-14 and consistent with a 107 kDa protein (not shown). Reducing SDS-PAGE showed only two bands attributed to the polypeptide constituents of N-DDD1-Fab-hMN-14 (not shown).

The binding activity of C-DDD1-Fab-hMN-14 was determined by SE-HPLC analysis of samples in which the test article was mixed with various amounts of WI2. A sample prepared by mixing WI2 Fab and C-DDD1-Fab-hMN-14 at a molar ratio of 0.75:1 showed three peaks, which were attributed to unbound C-DDD1-Fab-hMN14 (8.71 min), C-DDD1-Fab-hMN-14 bound to one WI2 Fab (7.95 min), and C-DDD1-Fab-hMN14 bound to two WI2 Fabs (7.37 min) (not shown). When a sample containing WI2 Fab and C-DDD1-Fab-hMN-14 at a molar ratio of 4 was analyzed, only a single peak at 7.36 minutes was observed (not shown). These results demonstrated that hMN14-Fab-DDD1 is dimeric and has two active binding sites. Very similar results were obtained when this experiment was repeated with N-DDD1-Fab-hMN-14.

A competitive ELISA demonstrated that both C-DDD1-Fab-hMN-14 and N-DDD1-Fab-hMN-14 bind to CEA with an avidity similar to hMN-14 IgG, and significantly stronger than monovalent hMN-14 Fab (not shown). ELISA plates were coated with a fusion protein containing the epitope (A3B3) of CEA for which hMN-14 is specific.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 (SEQ ID NO:2) appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

N-DDD2-Fd-hMN-14-pdHL2

N-DDD2-hMN-14-pdHL2 is an expression vector for production of N-DDD2-Fab-hMN-14, which possesses a dimerization and docking domain sequence of DDD2 (SEQ ID NO:2) appended to the amino terminus of the Fd. The DDD2 is coupled to the $V_H$ domain via a 15 amino acid residue Gly/Ser peptide linker. DDD2 has a cysteine residue preceding the dimerization and docking sequences, which are identical to those of DDD1. The fusion protein secreted is composed of two identical copies of hMN-14 Fab held together by non-covalent interaction of the DDD2 domains.

The expression vector was engineered as follows. Two overlapping, complimentary oligonucleotides (DDD2 Top and DDD2 Bottom), which comprise residues 1-13 of DDD2, were made synthetically. The oligonucleotides were annealed and phosphorylated with T4 polynucleotide kinase (PNK), resulting in overhangs on the 5' and 3' ends that are compatible for ligation with DNA digested with the restriction endonucleases NcoI and PstI, respectively.

The duplex DNA was ligated with a vector fragment, DDD1-hMN14 Fd-SV3 that was prepared by digestion with NcoI and PstI, to generate the intermediate construct DDD2-hMN14 Fd-SV3. A 1.28 kb insert fragment, which contained the coding sequence for DDD2-hMN14 Fd, was excised from the intermediate construct with XhoI and EagI restriction endonucleases and ligated with hMN14-pdHL2 vector DNA that was prepared by digestion with those same enzymes. The final expression vector is N-DDD2-Fd-hMN-14-pdHL2.

h679-Fd-AD2-pdHL2 h679-Fab-AD2, was designed to pair to C-DDD2-Fab-hMN-14. h679-Fd-AD2-pdHL2 is an expression vector for the production of h679-Fab-AD2, which possesses an anchoring domain sequence of AD2 (SEQ ID NO:4) appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 2

Generation of TF1 DNL Construct

A large scale preparation of a DNL construct, referred to as TF1, was carried out as follows. N-DDD2-Fab-hMN-14 (Protein L-purified) and h679-Fab-AD2 (IMP291-purified) were first mixed in roughly stoichiometric concentrations in 1 mM EDTA, PBS, pH 7.4. Before the addition of TCEP, SE-HPLC did not show any evidence of $a_2b$ formation (not shown). Instead there were peaks representing $a_4$ (7.97 min; 200 kDa), $a_2$ (8.91 min; 100 kDa) and B (10.01 min; 50 kDa) (not shown). Addition of 5 mM TCEP rapidly resulted in the formation of the $a_2b$ complex as demonstrated by a new peak at 8.43 min, consistent with a 150 kDa protein (not shown). Apparently there was excess B in this experiment as a peak attributed to h679-Fab-AD2 (9.72 min) was still evident yet no apparent peak corresponding to either $a_2$ or $a_4$ was observed (not shown). After reduction for one hour, the TCEP was removed by overnight dialysis against several changes of PBS. The resulting solution was brought to 10% DMSO and held overnight at room temperature.

When analyzed by SE-HPLC, the peak representing $a_2b$ appeared to be sharper with a slight reduction of the retention time by 0.1 min to 8.31 min (not shown), which, based on our previous findings, indicates an increase in binding affinity. The complex was further purified by IMP291 affinity chromatography to remove the kappa chain contaminants. As expected, the excess h679-AD2 was co-purified and later removed by preparative SE-HPLC (not shown).

TF1 is a highly stable complex. When TF1 was tested for binding to an HSG (IMP239) sensorchip, there was no apparent decrease of the observed response at the end of sample injection. In contrast, when a solution containing an equimolar mixture of both C-DDD1-Fab-hMN-14 and h679-Fab-AD1 was tested under similar conditions, the observed increase in response units was accompanied by a detectable drop during and immediately after sample injection (not shown), indicating that the initially formed $a_2b$ structure was unstable. Moreover, whereas subsequent injection of WI2 gave a substantial increase in response units for TF1, no increase was evident for the C-DDD1/AD1 mixture.

The additional increase of response units resulting from the binding of WI2 to TF1 immobilized on the sensorchip corresponds to two fully functional binding sites, each contributed by one subunit of N-DDD2-Fab-hMN-14. This was confirmed by the ability of TF1 to bind two Fab fragments of WI2 (not shown). When a mixture containing h679-AD2 and N-DDD1-hMN14, which had been reduced and oxidized exactly as TF1, was analyzed by BIAcore, there was little additional binding of WI2 (not shown), indicating that a disulfide-stabilized $a_2b$ complex such as TF1 could only form through the interaction of DDD2 and AD2.

Two improvements to the process were implemented to reduce the time and efficiency of the process. First, a slight molar excess of N-DDD2-Fab-hMN-14 present as a mixture of $a_4/a_2$ structures was used to react with h679-Fab-AD2 so that no free h679-Fab-AD2 remained and any $a_4/a_2$ structures not tethered to h679-Fab-AD2, as well as light chains, would be removed by IMP291 affinity chromatography. Second, hydrophobic interaction chromatography (HIC) has replaced dialysis or diafiltration as a means to remove TCEP following reduction, which would not only shorten the process time but also add a potential viral removing step. N-DDD2-Fab-hMN-14 and 679-Fab-AD2 were mixed and reduced with 5 mM TCEP for 1 hour at room temperature. The solution was brought to 0.75 M ammonium sulfate and then loaded onto a Butyl FF HIC column. The column was washed with 0.75 M ammonium sulfate, 5 mM EDTA, PBS to remove TCEP. The reduced proteins were eluted from the HIC column with PBS and brought to 10% DMSO. Following incubation at room temperature overnight, highly purified TF1 was isolated by IMP291 affinity chromatography (not shown). No additional purification steps, such as gel filtration, were required.

Example 3

Generation of TF2 DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP291 affinity chromatography. Before the addition of TCEP, SE-HPLC did not show any evidence of $a_2b$ formation (not shown). Addition of 5 mM TCEP rapidly resulted in the formation of $a_2b$ complex consistent with a 157 kDa protein expected for the binary structure (not shown). TF2 was purified to near homogeneity by IMP291 affinity chromatography (not shown). IMP291 is a synthetic peptide containing the HSG hapten to which the 679 Fab binds (Rossi et al., 2005, Clin Cancer Res 11:7122s-29s). SE-HPLC analysis of the IMP291 unbound fraction demonstrated the removal of $a_4$, $a_2$ and free kappa chains from the product (not shown).

The functionality of TF2 was determined by BIACORE® assay. TF2, C-DDD1-hMN-14+h679-AD1 (used as a control sample of noncovalent $a_2b$ complex), or C-DDD2-hMN-14+ h679-AD2 (used as a control sample of unreduced $a_2$ and b components) were diluted to 1 μg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response (not shown). The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Example 4

Production of TF10 DNL Construct

A similar protocol was used to generate a trimeric TF10 DNL construct, comprising two copies of a C-DDD2-Fab-hPAM4 and one copy of C-AD2-Fab-679. The TF 10 bispecific ([hPAM4]$_2$×h679) antibody was produced using the method disclosed for production of the (anti CEA)$_2$× anti HSG bsAb TF2, as described above. The TF10 construct bears two humanized PAM4 Fabs and one humanized 679 Fab.

The two fusion proteins (hPAM4-DDD2 and h679-AD2) were expressed independently in stably transfected myeloma cells. The tissue culture supernatant fluids were combined, resulting in a two-fold molar excess of hPAM4-DDD2. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP291-affigel resin, which binds with high specificity to the h679 Fab.

Example 5

Serum Stability of TF1 and TF2

TF1 and TF2 were designed to be DNL complexes that could be used in vivo where extensive dilution in blood and tissues would occur. The stability of TF2 in human sera was assessed using BIACORE. TF2 was diluted to 0.1 mg/ml in fresh human serum, which was pooled from four donors, and incubated at 37° C. under 5% $CO_2$ for seven days. Daily samples were diluted 1:25 and then analyzed by BIACORE using an IMP239 HSG sensorchip. An injection of WI2 IgG was used to quantify the amount of intact and fully active TF2. Serum samples were compared to control samples that were diluted directly from the stock. TF2 was highly stable in serum, retaining 98% of its bispecific binding activity after 7 days (not shown). Similar results were obtained for TF1 in either human or mouse serum (not shown).

Example 6

Biodistribution of TF2 in Tumor-Bearing Mice

Biodistribution studies were performed for TF2 in female athymic nude mice bearing s.c. human colorectal adenocarcinoma xenografts (LS174T). Cells were expanded in tissue culture until enough cells had been grown to inject 50 mice s.c. with 1×10$^7$ cells per mouse. After one week, tumors were measured and mice assigned to groups of 5 mice per time-point. The mean tumor size at the start of this study was 0.141±0.044 cm$^3$. All the mice were injected with 40 mg $^{125}$I-TF2 (250 pmoles, 2 μCi). They were then sacrificed and necropsied at 0.5, 2, 4, 16, 24, 48, and 72 hrs post-injection. A total of 35 mice were used in this study. Tumor as well as various tissues were removed and placed in a gamma-counter to determine percent-injected dose per gram (% ID/g) in tissue at each time-point.

Radioiodination of $^{125}$I-TF2 resulted in 2.7% unbound isotope with a specific activity of 1.48 mCi/mg. The labeled sample was then subjected to SE-HPLC alone and after mixing with a 20-fold molar excess of CEA. Approximately 83% of the TF2 eluted off with a retention time of 10.1 minutes (not shown). There was 9% aggregated material (RT=9.03 min) and 8% low molecular weight material (RT=14.37 min) in the labeled TF2 (not shown). When mixed with CEA, 95% of the labeled TF2 shifted to a high molecular weigh species (RT=7.25 min) (not shown). These results indicated that the labeled preparation was acceptable for administration to the tumor-bearing mice.

Peak tumor uptake occurred at 4 h post-injection (10.3.+−.2.1% ID/g). Between 16 and 24 h post-injection, the amount of TF2 in the tumor is not significantly different (5.3±1.1% ID/g and 5.37±0.7% ID/g), indicating that peptide could be administered anytime between these two time-points, depending on blood values, without impacting tumor targeting. Uptake and clearance of TF2 from normal tissues was very similar to what has been observed previously for TF1. Both TF1 and TF2 appeared to favor clearance through the RES system (spleen and liver).

Example 7

Production of AD- and DDD-Linked Fab and IgG Fusion Proteins from Multiple Antibodies Using the techniques described in the preceding Examples, the IgG and Fab fusion proteins shown in Table 7 were constructed and incorporated into DNL constructs. The fusion proteins retained the antigen-binding characteristics of the parent antibodies and the DNL constructs exhibited the antigen-binding activities of the incorporated antibodies or antibody fragments.

TABLE 7

| Fusion proteins comprising IgG or Fab | |
|---|---|
| Fusion Protein | Binding Specificity |
| C-AD1-Fab-h679 | HSG |
| C-AD2-Fab-h679 | HSG |
| C-(AD)$_2$-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |

TABLE 7-continued

Fusion proteins comprising IgG or Fab

| Fusion Protein | Binding Specificity |
|---|---|
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

Example 8

Generation of a Fusion Protein Comprising a Heat Shock Protein, AD2 and AD3 (Type-a Adaptor Module) and Use A fusion protein in which AD2 and AD3 are linked, respectively, to the amino and carboxyl termini of a heat shock protein such as HSP70 or gp96 can be further docked and locked with two peripheral modules, one consisting of a DDD2-linked homodimer ($X_2$) and the other consisting of a DDD3C-linked homodimer ($Y_2$) to form a complex composed of $X_2$ (adaptor)$Y_2$. One choice of the two peripheral modules is the Ig-like domains 1 and 2 of human CD22 and the extracellular region of human CD20, which upon conjugation to the HSP-based adaptor module is of use as a therapeutic vaccine for B cell lymphomas. Another choice of the two peripheral modules is the N-A1 and the A3-B3 domains of CEACAM5, which upon conjugation to the HSP-based adaptor module is of use as a therapeutic vaccine for CEA-expressing cancers. The two peripheral modules can also be hLL1 Fab and the extracellular region of HER2, which upon conjugation to the HSP-based adaptor module is of use as a therapeutic vaccine for cancers over-expressing HER2.

A vaccine comprising AD2-HSP70-AD3 stably linked to the N-A1 and the A3-B3 domains of CEACAM5 produced as described above is formulated in saline or other physiologically compatible solution and administered to patients following surgical removal of colorectal cancer. The therapeutic vaccine is given once weekly for a minimal of four weeks at a dosage in the range of 100 and 5000 µg, with the preferred dosage being about 500 µg. The route of injection is subcutaneous but the site of injection can be varied each time with the same site of injection repeated after a gap of one or more injections. For example, the first injection is given on the left thigh, the second injection on the right thigh, the third injection on the left arm, the fourth injection on the right arm, the fifth injection on the left thigh, the sixth injection on the right arm, etc. After the first cycle of four weekly injections, two more injections are given biweekly, followed by a regimen of monthly injections. The effect of the vaccine on eliciting anti-cancer immune response is evaluated by measuring (1) delayed hypersensitivity as an assessment of cellular immunity; (2) activity of cytolytic T cells in vitro; (3) levels of circulating CEA; (4) changes in tumor size using various imaging techniques such as CT or PET scan; and (5) other biomarkers associated with CEA-expressing cancers.

Example 9

Molecular Engineering of DDD3-CH2-CH3-AD2 and DDD3C-CH2-CH3-AD2

Two PCR reactions were performed to generate the DDD3 and DDD3C sequences using a human RIα cDNA clone (Invitrogen IMAGE clone #5531156) as a template. Both reactions used the oligonucleotide RIBglII right as the 3' PCR primer. The oligonucleotides RIBspHI Left and RI-C BspHI Left were used as 5' primers for DDD3 and DDD3C, respectively.

```
RI BglII Right
                                 (SEQ ID NO: 120)
5'-AGATCTGCCTTTTGCCTCCTCCTTCTC-3'

RI BspHI Left
                                 (SEQ ID NO: 121)
5'-TCATGAGCCTTCGAGAATGTGAGCTC-3'

RI-C BspHI Left
                                 (SEQ ID NO: 122)
5'-TCATGAGTTGTGGCGGAAGCCTTCGAGAATGTGAGC-3'
```

The Fc (CH2 and CH3 domains) was amplified using the pdHL2 vector as a template and the oligonucleotides Fc BglII Left and Fc Bam-EcoRI Right as primers. Each of the amplimers was cloned in the PGEMT® PCR cloning vector. The Fc insert fragment was excised from PGEMT® with BglII and EcoRI restriction enzymes and cloned into those same sites in the SV3 shuttle vector to generate the intermediate clone Fc-SV3.

The DDD3 and DDD3C inserts were then excised from the PGEMT® vectors with BspHI and BglII and ligated with Fc-SV3 vector that was digested with NcoI (BspHI compatible ends) and BglII to generate the shuttle vectors DDD3-Fc-SV3 and DDD3C-Fc-SV3, respectively. Finally, the expression cassettes were excised from the SV3 shuttle vectors with XbaI and BamHI and ligated with AD2-pdHL2 vector that was prepared by digestion of h679-AD2-pdHL2 with XbaI and BamHI. The final expression constructs are DDD3-Fc-AD2-pdHL2 and DDD3C-Fc-AD2-pdHL2.

Example 10

Hexavalent DNL Constructs

The DNL technology described above for formation of trivalent DNL complexes was applied to generate hexavalent IgG-based DNL structures (HIDS). Because of the increased number of binding sites for target antigens, hexavalent constructs might be expected to show greater affinity and/or efficacy against target cells. Two types of modules, which were produced as recombinant fusion proteins, were combined to generate a variety of HIDS. Fab-DDD2 modules were as described for use in generating trivalent Fab structures (Rossi et al. *Proc Natl Acad Sci USA*. 2006; 103(18): 6841-6). The Fab-DDD2 modules form stable homodimers that bind to AD2-containing modules. To generate HIDS, two types of IgG-AD2 modules were created to pair with the Fab-DDD2 modules: C-H-AD2-IgG and N-L-AD2-IgG.

C-H-AD2-IgG modules have an AD2 peptide fused to the carboxyl terminus (C) of the heavy (H) chain of IgG via a 9 amino acid residue peptide linker. The DNA coding sequences for the linker peptide (GSGGGGSGG, SEQ ID NO:136) followed by the AD2 peptide (CGQIEYLAKQIVDNAIQQAGC, SEQ ID NO:4) are coupled to the 3' end of the CH3 (heavy chain constant domain 3) coding sequence by standard recombinant DNA methodologies, resulting in a contiguous open reading frame. When the heavy chain-AD2 polypeptide is co-expressed with a light chain polypeptide, an IgG molecule is formed possessing two AD2 peptides, which can therefore bind two Fab-DDD2 dimers. The C-H-AD2-IgG module can be combined with any Fab-DDD2 module to generate a wide variety of hexavalent structures composed of an Fc fragment and six Fab fragments. If the C-H-AD2-IgG module and the Fab-DDD2 module are derived from the same parental monoclonal antibody (MAb) the resulting HIDS is monospecific with 6 binding arms to the same antigen. If the modules are instead derived from two different MAbs then the resulting HIDS are bispecific, with two binding arms for the specificity of the C-H-AD2-IgG module and 4 binding arms for the specificity of the Fab-DDD2 module.

N-L-AD2-IgG is an alternative type of IgG-AD2 module in which an AD2 peptide is fused to the amino terminus (N) of the light (L) chain of IgG via a 13 amino acid residue peptide linker. The L chain can be either Kappa (K) or Lambda (X) and will also be represented as K. The DNA coding sequences for the AD2 peptide (CGQIEYLAKQIVDNAIQQAGC, SEQ ID NO:4) followed by the linker peptide (GGGGSGGGSGGG, SEQ ID NO:174) are coupled to the 5' end of the coding sequence for the variable domain of the L chain ($V_L$), resulting in a contiguous open reading frame. When the AD2-kappa chain polypeptide is co-expressed with a heavy chain polypeptide, an IgG molecule is formed possessing two AD2 peptides, which can therefore bind two Fab-DDD2 dimers. The N-L-AD2-IgG module can be combined with any Fab-DDD2 module to generate a wide variety of hexavalent structures composed of an Fc fragment and six Fab fragments.

Example 11

Creation of C-H-AD2-IgG-pdHL2 Expression Vectors

The pdHL2 mammalian expression vector has been used to mediate the expression of many recombinant IgGs. A plasmid shuttle vector was produced to facilitate the conversion of any IgG-pdHL2 vector into a C-H-AD2-IgG-pdHL2 vector. The gene for the Fc (CH2 and CH3 domains) was amplified using the pdHL2 vector as a template and Fc BglII Left and Fc Bam-EcoRI Right primers. The amplimer was cloned in the PGEMT® PCR cloning vector. The Fc insert fragment was excised from PGEMT® with XbaI and BamHI restriction enzymes and ligated with AD2-pdHL2 vector that was prepared by digestion of h679-Fab-AD2-pdHL2 with XbaI and BamHI, to generate the shuttle vector Fc-AD2-pdHL2.

```
Fc BglII Left
                                    (SEQ ID NO: 175)
5'-AGATCTGGCGCACCTGAACTCCTG-3'

Fc Bam-EcoRI Right
                                    (SEQ ID NO: 176)
5'-GAATTCGGATCCTTTACCCGGAGACAGGGAGAG-3'
```

To convert any IgG-pdHL2 expression vector to a C-H-AD2-IgG-pdHL2 expression vector, an 861 bp BsrGI/NdeI restriction fragment is excised from the former and replaced with a 952 bp BsrGI/NdeI restriction fragment excised from the Fc-AD2-pdHL2 vector. BsrGI cuts in the CH3 domain and NdeI cuts downstream (3') of the expression cassette.

Example 12

Production of AD2-Linked IgG Species

Production of C-H-AD2-hLL2 IgG

Epratuzumab, or hLL2 IgG, is a humanized anti-human CD22 MAb. An expression vector for C-H-AD2-hLL2 IgG was generated from hLL2 IgG-pdHL2, as described in the Example above, and used to transfect Sp2/0 myeloma cells by electroporation. Following transfection, the cells were plated in 96-well plates and transgenic clones were selected in media containing methotrexate. Clones were screened for C-H-AD2-hLL2 IgG productivity by a sandwich ELISA using 96-well microtiter plates coated with an hLL2-specific anti-idiotype MAb and detection with peroxidase-conjugated anti-human IgG. Clones were expanded to roller bottles for protein production and C-H-AD2-hLL2 IgG was purified from the spent culture media in a single step using Protein-A affinity chromatography. SE-HPLC analysis resolved two protein peaks (not shown). The retention time of the slower eluted peak was similar to hLL2 IgG (not shown). The retention time of the faster eluted peak was consistent with a ~300 kDa protein (not shown). It was later determined that this peak represents disulfide linked dimers of C-H-AD2-hLL2-IgG. This dimer is reduced to the monomeric form during the DNL reaction. SDS-PAGE analysis demonstrated that the purified C-H-AD2-hLL2-IgG consisted of both monomeric and disulfide-linked dimeric forms of the module (not shown). Protein bands representing these two forms are evident by SDS-PAGE under non-reducing conditions, while under reducing conditions all of the forms are reduced to two bands representing the constituent polypeptides (Heavy chain-AD2 and kappa chain). No other contaminating bands were detected.

Production of C-H-AD2-hA20 IgG hA20 IgG is a humanized anti-human CD20 MAb. An expression vector for C-H-AD2-hA20 IgG was generated from hA20 IgG-pDHL2, as described above, and used to transfect Sp2/0 myeloma cells by electroporation. Following transfection, the cells were plated in 96-well plates and transgenic clones were selected in media containing methotrexate. Clones were screened for C-H-AD2-hA20 IgG productivity by a sandwich ELISA using 96-well microtiter plates coated with a hA20-specific anti-idiotype MAb and detection with peroxidase-conjugated anti-human IgG. Clones were expanded to roller bottles for protein production and C-H-AD2-hA20 IgG was purified from the spent culture media in a single step using Protein-A affinity chromatography. SE-HPLC and SDS-PAGE analyses gave very similar results to those obtained for C-H-AD2-hLL2 IgG (not shown).

Production of N-L-AD2-hA20 IgG

A 197 bp DNA duplex comprising the coding sequence for the light chain leader peptide, AD2, a 13-residue peptide linker and the first four residues of hA20 Vk (all in frame) was generated as follows. Two 100-mer synthetic oligonucleotides, which overlap by 35 base-pairs, were made fully duplex by primer extension using Taq polymerase. The sequence was amplified by PCR, which appended XbaI and PvuII restriction sites to the 5' and 3' ends, respectively. The amplimer was cloned into PGEMT®.

The 197 bp XbaI/PvuII fragment was excised from PGEMT® and ligated with the hA20 $V_K$ shuttle vector h2B8-$V_K$-pBR2, which was prepared by digestion with XbaI and PvuII. The new shuttle vector is AD2-K-hA20-pBR2. A 536 bp XbaI/Bam HI restriction fragment was excised from AD2-K-hA20-pBR2 and ligated with hA20-IgG-pDHL2 vector that was prepared by digestion with XbaI and Bam HI to generate the expression vector N-L-AD2-hA20-IgG-pdHL2.

N-L-AD2-hA20-IgG-pdHL2 was used to transfect Sp2/0 myeloma cells by electroporation. Following transfection, the cells were plated in 96-well plates and transgenic clones were selected in media containing methotrexate. Clones were screened for N-L-AD2-hA20 IgG productivity by a sandwich ELISA using 96-well microtiter plates coated with a hA20-specific anti-idiotype MAb and detection with peroxidase-conjugated anti-human IgG. Clones were expanded to roller bottles for protein production and N-L-AD2-hA20 IgG was purified from the spent culture media in a single step using Protein-A affinity chromatography.

Size exclusion HPLC showed that the majority of the N-L-AD2-hA20 IgG in the prep is in a monomeric form with a retention time similar to IgG (not shown). Two additional peaks likely representing disulfide linked dimeric and trimeric forms and each accounting for approximately 15% of the total protein were also observed (not shown). Mild reduction of the prep, as is used in the DNL reaction, resulted in the conversion of the dimeric and trimeric forms to the monomeric form (not shown).

Example 13

Generation of Hexavalent DNL Constructs

Generation of Hex-hA20

The DNL method was used to create Hex-hA20, a monospecific anti-CD20 HIDS, by combining C-H-AD2-hA20 IgG with hA20-Fab-DDD2. The Hex-hA20 structure contains six anti-CD20 Fab fragments and an Fc fragment, arranged as four Fab fragments and one IgG antibody. Hex-hA20 was made in four steps.

Step 1, Combination: A 210% molar equivalent of (hA20-Fab-DDD2)$_2$ was mixed with C-H-AD2-hA20 IgG. This molar ratio was used because two Fab-DDD2 dimers are coupled to each C-H-AD2-hA20 IgG molecule and an additional 10% excess of the former ensures that the coupling reaction is complete. The molecular weights of C-H-AD2-hA20 IgG and (hA20-Fab-DDD2)$_2$ are 168 kDa and 107 kDa, respectively. As an example, 134 mg of hA20-Fab-DDD2 would be mixed with 100 mg of C-H-AD2-hA20 IgG to achieve a 210% molar equivalent of the former. The mixture is typically made in phosphate buffered saline, pH 7.4 (PBS) with 1 mM EDTA.

Step 2, Mild Reduction: Reduced glutathione (GSH) was added to a final concentration of 1 mM and the solution is held at room temperature (16-25° C.) for 1-24 hours.

Step 3, Mild Oxidation: Following reduction, oxidized glutathione (GSSH) was added directly to the reaction mixture to a final concentration of 2 mM and the solution was held at room temperature for 1-24 hours.

Step 4, Isolation of the DNL product: Following oxidation, the reaction mixture was loaded directly onto a Protein-A affinity chromatography column. The column was washed with PBS and the Hex-hA20 was eluted with 0.1M glycine, pH 2.5. Since excess hA20-Fab-DDD2 was used in the reaction, there was no unconjugated C-H-AD2-hA20 IgG, or incomplete DNL structures containing only one (hA20-Fab-DDD2)$_2$ moiety. The unconjugated excess hA20-Fab-DDD2 does not bind to the affinity resin. Therefore, the Protein A-purified material contains only the desired product.

The calculated molecular weight from the deduced amino acid sequences of the constituent polypeptides is 386 kDa. Size exclusion HPLC analysis showed a single protein peak with a retention time consistent with a protein structure of 375-400 kDa (not shown). SDS-PAGE analysis under non-reducing conditions showed a cluster of high molecular weight bands indicating a large covalent structure (not shown). SDS-PAGE under reducing conditions showed the presence of only the three expected polypeptide chains: the AD2-fused heavy chain (HC-AD2), the DDD2-fused Fd chain (Fd-DDD2), and the kappa chains (not shown).

Generation of Hex-hLL2

The DNL method was used to create a monospecific anti-CD22 HIDS (Hex-hLL2) by combining C-H-AD2-hLL2 IgG with hLL2-Fab-DDD2. The DNL reaction was accomplished as described above for Hex-hA20. The calculated molecular weight from the deduced amino acid sequences of the constituent polypeptides is 386 kDa. Size exclusion HPLC analysis showed a single protein peak with a retention time consistent with a protein structure of 375-400 kDa (not shown). SDS-PAGE analysis under non-reducing conditions showed a cluster of high molecular weight bands, which were eliminated under reducing conditions to leave only the three expected polypeptide chains: HC-AD2, Fd-DDD2, and the kappa chain (not shown).

Generation of DNL1 and DNL1C

The DNL method was used to create bispecific HIDS by combining C-H-AD2-hLL2 IgG with either hA20-Fab-DDD2 to obtain DNL1 or hMN-14-DDD2 to obtain DNL1C. DNL1 has four binding arms for CD20 and two for CD22. As hMN-14 is a humanized MAb to carcinoembryonic antigen (CEACAM5), DNL1C has four binding arms for CEACAM5 and two for CD22. The DNL reactions were accomplished as described for Hex-hA20 above.

For both DNL1 and DNL1C, the calculated molecular weights from the deduced amino acid sequences of the constituent polypeptides are ~386 kDa. Size exclusion HPLC analysis showed a single protein peak with a retention time consistent with a protein structure of 375-400 kDa for each structure (not shown). SDS-PAGE analysis under non-reducing conditions showed a cluster of high molecular weight bands, which were eliminated under reducing conditions to leave only the three expected polypeptides: HC-AD2, Fd-DDD2, and the kappa chain (not shown).

Generation of DNL2 and DNL2C

The DNL method was used to create bispecific HIDS by combining C-H-AD2-hA20 IgG with either hLL2-Fab-DDD2 to obtain DNL2 or hMN-14-DDD2 to obtain DNL2C. DNL2 has four binding arms for CD22 and two for CD20. DNL2C has four binding arms for CEACAM5 and two for CD20. The DNL reactions were accomplished as described for Hex-hA20.

For both DNL2 and DNL2C, the calculated molecular weights from the deduced amino acid sequences of the constituent polypeptides are ~386 kDa. Size exclusion HPLC analysis showed a single protein peak with a retention time consistent with a protein structure of 375-400 kDa for each structure (not shown). SDS-PAGE analysis under non-reducing conditions showed high molecular weight bands, but under reducing conditions consisted solely of the three expected polypeptides: HC-AD2, Fd-DDD2, and the kappa chain (not shown).

Generation of K-Hex-hA20

The DNL method was used to create a monospecific anti-CD20 HIDS (K-Hex-hA20) by combining N-L-AD2-hA20 IgG with hA20-Fab-DDD2. The DNL reaction was accomplished as described above for Hex-hA20.

The calculated molecular weight from the deduced amino acid sequences of the constituent polypeptides is 386 kDa. SDS-PAGE analysis under non-reducing conditions showed a cluster of high molecular weight bands, which under reducing conditions were composed solely of the four expected polypeptides: Fd-DDD2, H-chain, kappa chain, and AD2-kappa (not shown).

Generation of DNL3

A bispecific HIDS was generated by combining N-L-AD2-hA20 IgG with hLL2-Fab-DDD2. The DNL reaction was accomplished as described above for Hex-hA20. The calculated molecular weight from the deduced amino acid sequences of the constituent polypeptides is 386 kDa. Size exclusion HPLC analysis showed a single protein peak with a retention time consistent with a protein structure of 375-400 kDa (not shown). SDS-PAGE analysis under non-reducing conditions showed a cluster of high molecular weight bands that under reducing conditions showed only the four expected polypeptides: Fd-DDD2, H-chain, kappa chain, and AD2-kappa (not shown).

Example 14

In Vitro Characterization of Hexavalent DNL Constructs

Stability in Serum

The stability of DNL1 and DNL2 in human serum was determined using a bispecific ELISA assay. The protein structures were incubated at 10 µg/ml in fresh pooled human sera at 37° C. and 5% $CO_2$ for five days. For day 0 samples, aliquots were frozen in liquid nitrogen immediately after dilution in serum. ELISA plates were coated with an anti-Id to hA20 IgG and bispecific binding was detected with an anti-Id to hLL2 IgG. Both DNL1 and DNL2 were highly stable in serum and maintained complete bispecific binding activity.

Binding Activity

The HIDS generated as described above retained the binding properties of their parental Fab/IgGs. Competitive ELISAs were used to investigate the binding avidities of the various HIDS using either a rat anti-idiotype MAb to hA20 (WR2) to assess the binding activity of the hA20 components or a rat anti-idiotype MAb to hLL2 (WN) to assess the binding activity of the hLL2 components. To assess hA20 binding, ELISA plates were coated with hA20 IgG and the HIDS were allowed to compete with the immobilized IgG for WR2 binding. To assess hLL2 binding, plates were coated with hLL2 IgG and the HIDS were allowed to compete with the immobilized IgG for WN binding. The relative amount of anti-Id bound to the immobilized IgG was detected using peroxidase-conjugated anti-Rat IgG.

Examining the relative CD20 binding avidities (FIG. 1A), DNL2, which has two CD20 binding groups, showed a similar binding avidity to hA20 IgG, which also has two CD20-binding arms (FIG. 1A). DNL1, which has four CD20-binding groups, had a stronger (~4-fold) relative avidity than DNL2 or hA20 IgG (FIG. 1A). Hex-hA20, which has six CD20-binding groups, had an even stronger (~10-fold) relative avidity than hA20 IgG (FIG. 1A).

Similar results were observed for CD22 binding (FIG. 1B). DNL1, which has two CD20 binding groups, showed a similar binding avidity to hLL2 IgG, which also has two CD22-binding arms (FIG. 1B). DNL2, which has four CD22-binding groups, had a stronger (>5-fold) relative avidity than DNL1 or hLL2 IgG. Hex-hLL2, which has six CD22-binding groups, had an even stronger (>10-fold) relative avidity than hLL2 IgG (FIG. 1B).

As both DNL2 and DNL3 contain two hA20 Fabs and four hLL2 Fabs, they showed similar strength in binding to the same anti-id antibody (not shown).

Some of the HIDS were observed to have potent anti-proliferative activity on lymphoma cell lines. DNL1, DNL2 and Hex-hA20 inhibited cell growth of Daudi Burkitt Lymphoma cells in vitro (FIG. 2). Treatment of the cells with 10 nM concentrations was substantially more effective for the HIDS compared to rituximab (not shown). Using a cell counting assay, the potency of DNL1 and DNL2 was estimated to be more than 100-fold greater than that of rituximab, while the Hex-hA20 was shown to be even more potent (not shown). This was confirmed with an MTS proliferation assay in which dose-response curves were generated for Daudi cells treated with a range of concentrations of the HIDS (not shown). Compared to rituximab, the bispecific HIDS (DNL1 and DNL2) and Hex-hA20 were >100-fold and >10000-fold more potent, respectively.

Example 15

In Vivo Anti-Tumor Activity of Hexavalent DNL Constructs

Figure 3:
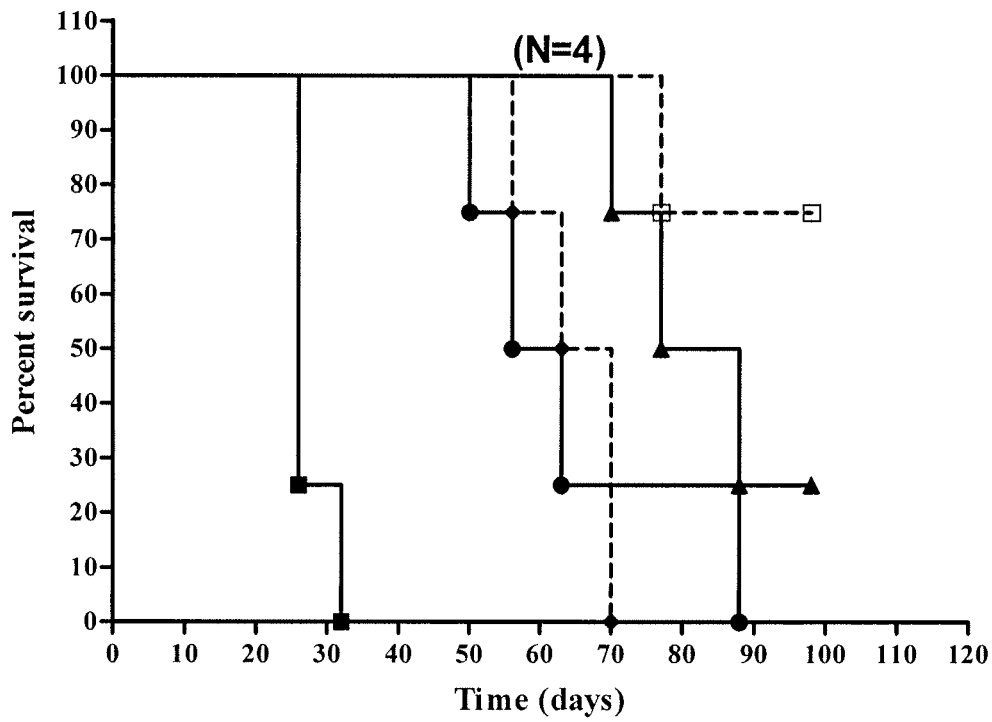
FIG. 3. In vivo therapy of mice bearing human Burkitt Lymphoma (Daudi) treated with DNL2 or Hex-hA20. Mice (4/group) were inoculated i.v. with $1.5 \times 10^7$ Daudi cells (day 0). On days 1, 4 and 7, mice were administered either 4 µg or 20 µg of DNL2 or Hex-hA20 intraperitoneally (i.p.). Mice were sacrificed if they developed either hind-limb paralysis or lost >20% body weight. The results are plotted as % survival vs. time (days). Median survival and long term survivors are shown.

The HIDS were shown to have therapeutic efficacy in vivo using a human Burkitt Lymphoma model in mice (FIG. 3). Low doses (12 µg) of DNL2 and Hex-hA20 more than doubled the survival times of tumor bearing mice. Treatment with higher doses (60 µg) resulted in long-term survivors.

Example 16

Comparative Effects of Hexavalent DNL Constructs and Parent IgG on Lymphoma Cell Lines Dose-response curves for HIDS (DNL1, DNL2, Hex-hA20) versus a parent IgG (hA20 IgG) were compared for three different lymphoma cell lines (FIG. 4), using an MTS proliferation assay. In Daudi lymphoma cells (FIG. 4, top panel), the bispecific structures DNL1 (not shown) and DNL2 showed >100-fold more potent anti-proliferative activity and Hex-hA20 showed >10,000-fold more potent activity than the parent hA20 IgG. Hex-hLL2 and the control structures (DNL1-C and DNL2-C) had very little anti-proliferative activity in this assay (not shown).

In Raji lymphoma cells (FIG. 4, middle panel), Hex-hA20 displayed potent anti-proliferative activity, but DNL2 showed only minimal activity compared with hA20 IgG. In Ramos lymphoma cells (FIG. 4, bottom panel), both DNL2 and Hex-hA20 displayed potent anti-proliferative activity, compared with hA20 IgG. These results show that the increased potency of HIDS relative to the parent IgGs is not limited to particular cell lines, but rather is a general phenomenon for cells displaying the appropriate targets.

Example 17

CDC and ADCC Activity of Hexavalent DNL Constructs

In vivo, anti-CD20 monoclonal antibodies such as rituximab and hA20 can utilize complement-dependent cytotoxicity (CDC), antibody-dependent cellular cytotoxicity (ADCC) and signal transduction induced growth inhibition/apoptosis for tumor cell killing. The hexavalent DNL structures (DNL1, DNL2, Hex-hA20) were tested for CDC activity using Daudi cells in an in vitro assay. Surprisingly, none of the hexavalent structures that bind CD20 exhibited CDC activity (not shown). The parent hA20 IgG exhibited potent CDC activity (not shown), while as expected the hLL2 antibody against CD22 showed no activity (not shown). The lack of effect of DNL2 and Hex-hA20 was of interest, since they comprise hA20-IgG-Ad2, which showed similar positive CDC activity to hA20 IgG (not shown).

DNL1 was assayed for ADCC activity using freshly isolated peripheral blood mononuclear cells. Both rituximab and hA20 IgG showed potent activity on Daudi cells, while DNL1 did not exhibit any detectable ADCC activity (not shown).

These data suggest that the Fc region may become inaccessible for effector functions (CDC and ADCC) when four additional Fab groups are tethered to its carboxyl termini. Therefore, the hexavalent DNL structures appear to rely only on signal transduction induced growth inhibition/apoptosis for in vivo anti-tumor activity.

Example 18

Formation of PEGylated DNL Constructs

Generation of PEG-AD2 Modules

In certain embodiments, PEG moieties may be incorporated into DNL complexes, for example to provide for a reproducible and homogeneous PEGylated product of an effector moiety, such as a cytokine. The Examples below provide compositions and methods of use of such DNL-based PEGylation products. As a first step, peptide subunits capable of covalent conjugation to PEG moieties for incorporation into DNL complexes were synthesized.

```
Synthesis of IMP350
                                       (SEQ ID NO: 123)
CGQIEYLAKQIVDNAIQQAGC(SS-tbu)-NH2
```

IMP350, incorporating the sequence of AD2, was made on a 0.1 mmol scale with Sieber Amide resin using Fmoc methodology on an automated peptide synthesizer. Starting from the C-terminus the protected amino acids used were Fmoc-Cys(t-Buthio)-OH, Fmoc-Gly-OH, Fmoc-Ala-OH, Fmoc-Gln(Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH and Fmoc-Cys(Trt)-OH. The peptide was cleaved from the resin and purified by reverse phase (RP)-HPLC.

Synthesis of $PEG_{20}$-IMP350

IMP350 (0.0104 g) was mixed with 0.1022 g of mPEG-OPTE (20kDa, Nektar Therapeutics) in 7 mL of 1M Tris buffer at pH 7.81. Acetonitrile, 1 mL, was then added to dissolve some suspended material. The reaction was stirred at room temperature for 3 h and then 0.0527 g of TCEP was added along with 0.0549 g of cysteine. The reaction mixture was stirred for 1.5 h and then purified on a PD-10 desalting column, which was equilibrated with 20% methanol in water. The sample was eluted, frozen and lyophilized to obtain 0.0924 g of crude $PEG_{20}$-IMP350 (MH+ 23508 by MALDI).

```
Synthesis of IMP360
                                       (SEQ ID NO: 124)
CGQIEYLAKQIVDNAIQQAGC(SS-tbu)-G-EDANS
```

IMP360, incorporating the AD2 sequence, was synthesized on a 0.1 mmol scale with Fmoc-Gly-EDANS resin using Fmoc methodology on an automated peptide synthesizer. The Fmoc-Gly-OH was added to the resin manually using 0.23 g of Fmoc-Gly-OH, 0.29 g of HATU, 26 μL of DIEA, 7.5 mL of DMF and 0.57 g of EDANS resin (Nova Biochem). The reagents were mixed and added to the resin. The reaction was mixed at room temperature for 2.5 hr and the resin was washed with DMF and IPA to remove the excess reagents. Starting from the C-terminus the protected amino acids used were Fmoc-Cys(t-Buthio)-OH, Fmoc-Gly-OH, Fmoc-Ala-OH, Fmoc-Gln(Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH and Fmoc-Cys(Trt)-OH. The peptide was cleaved from the resin and purified by RP-HPLC.

Generation of IMP362 and IMP413

The two linear PEG-AD2 modules were prepared by coupling IMP360 to mPEG-OPTE (Nectar Therapeutics, San Carlos, Calif.) of 20-kDa or 30-kDa, resulting in IMP362 or IMP413, respectively. To prepare IMP362, IMP360 (11.5 mg) was mixed with 20-kDa mPEG-OPTE (127 mg) in 7 mL of 1M Tris-HCL, pH 7.8. Acetonitrile (1 mL) was added to dissolve some suspended material. The reaction was stirred at room temperature for 4 h to effect the attachment of mPEG to the amino-terminal cysteine via an amide bond. Subsequently, 41 mg of Tris[2-carboxyethyl]phosphine hydrochloride (TCEP) and 43 mg of cysteine were added to de-protect the remaining cysteine. The reaction mixtures were stirred for 1 h and desalted using PD-10 columns, which had been equilibrated with 20% methanol in water. The samples were lyophilized to obtain approximately 150 mg of IMP362 (MH+ 23713). IMP413 (MH$^+$34499) was made similarly using 30-kDa mPEG-OPTE (190 mg).

Synthesis of IMP413 ($PEG_{30}$-IMP360)

For synthesis of IMP413, IMP360 (0.0103 g) was mixed with 0.1601 g of mPEG-OPTE (30 kDa, Nektar Therapeutics) in 7 mL of 1M Tris buffer at pH 7.81. Acetonitrile (1 mL) was then added to dissolve some suspended material. The reaction was stirred at room temperature for 4.5 h and then 0.0423 g of TCEP was added along with 0.0473 g of cysteine. The reaction mixture was stirred for 2 h followed by dialysis for two days. The dialyzed material was frozen and lyophilized to obtain 0.1552 g of crude IMP413 (MH$^+$ 34499).

```
Synthesis of IMP421
                                       (SEQ ID NO: 125)
IMP421 Ac-C-PEG3-C(S-tBu)GQIEYLAKQIVDNAIQQAGC
(S-tBu)G-NH2
```

The AD2-containing peptide (IMP421, MH$^+$ 2891 was made for derivatizing mPEG2-MAL-40K (Nectar Therapeutics) to obtain the branched PEG-AD2 module (IMP457). IMP421 was made on NOVASYN® TGR resin (487.6 mg, 0.112 mmol) by adding the following amino acids to the resin in the order shown: Fmoc-Gly-OH, Fmoc-Cys(t-Buthio)-OH, Fmoc-Gly-OH, Fmoc-Ala-OH, Fmoc-Gln(Trt)-OH, Fmoc-Gln(Trt)-OH, Fmoc-Ile-OH, Fmoc-Ala-OH, Fmoc-Asn(Trt)-OH, Fmoc-Asp(OBut)-OH, Fmoc-Val-OH, Fmoc-Ile-OH, Fmoc-Gln(Trt)-OH, Fmoc-Lys(Boc)-OH, Fmoc-Ala-OH, Fmoc-Leu-OH, Fmoc-Tyr(But)-OH, Fmoc-Glu(OBut)-OH, Fmoc-Ile-OH, Fmoc-Gln(Trt)-OH, Fmoc-Gly-OH, Fmoc-Cys(t-Buthio)-OH, Fmoc-NH-PEG$_3$-COOH, Fmoc-Cys(Trt)-OH. The N-terminal amino acid was protected as an acetyl derivative. The peptide was then cleaved from the resin and purified by RP-HPLC to yield 32.7 mg of a white solid.

Synthesis of IMP457

IMP421, incorporating the sequence of AD2, was synthesized by standard chemical means. To a solution of 15.2 mg (5.26 μmol) IMP421 (F.W. 2890.50) and 274.5 mg (6.86 mop mPEG2-MAL-40K in 1 mL of acetonitrile was added 7 mL 1M Tris pH 7.8 and allowed to react at room temperature for 3 h. The excess mPEG2-MAL-40K was quenched with 49.4 mg L-cysteine, followed by S-S-tBu deprotection over one hour with 59.1 mg TCEP. The reaction mixture was dialyzed overnight at 2-8° C. using two 10K dialysis cassettes (4 ml in each cassette) into 5 L of 5 mM ammonium acetate, pH 5.0. Three more 5 L buffer changes of 5 mM ammonium acetate, pH 5.0 were made the next day with each dialysis lasting at least 2½ h. The purified product (19.4 mL) was transferred into two 20 mL scintillation vials, frozen and lyophilized to yield 246.7 mg of a white solid. MALDI-TOF gave results of mPEG2-MAL-40K 42,982 and IMP457 45,500.

Generation of DDD Module Based on Interferon (IFN)-α2b

Construction of IFN-α2b-DDD2-pdHL2 for Expression in Mammalian Cells

The cDNA sequence for IFN-α2b was amplified by PCR, resulting in a sequence comprising the following features, in which XbaI and BamHI are restriction sites, the signal peptide is native to IFN-α2b, and 6 His (SEQ ID NO:126) is a hexahistidine tag (SEQ ID NO: 126): XbaI - - - Signal peptide - - - IFNα2b - - - 6 His (SEQ ID NO: 126) - - - BamHI. The resulting secreted protein consists of IFN-α2b fused at its C-terminus to a polypeptide consisting of SEQ ID NO:127.

(SEQ ID NO: 127)
KSHHHHHHGSGGGGSGGGCGHIQIPPGLTELLQGYTVEVLRQQPPDLVEF

AVEYFTRLREARA

PCR amplification was accomplished using a full length human IFNα2b cDNA clone (Invitrogen ULTIMATE™ ORF human clone cat# HORF01Clone ID IOH35221) as a template and the following oligonucleotides as primers:

IFNA2 Xba I Left
(SEQ ID NO: 128)
5'-TCTAGACACAGGACCTCATCATGGCCTTGACCTTTGCTTTACTGG-3'

IFNA2 BamHI right
(SEQ ID NO: 129)
5'-GGATCCATGATGGTGATGATGGTGTGACTTTTCCTTACTTCTTAAAC

TTTCTTGC-3'

The PCR amplimer was cloned into the pGEM®-T vector. A DDD2-pdHL2 mammalian expression vector was prepared for ligation with IFN-α2b by digestion with XbaI and Bam HI restriction endonucleases. The IFN-α2b amplimer was excised from PGEMT® with XbaI and Bam HI and ligated into the DDD2-pdHL2 vector to generate the expression vector IFN-α2b-DDD2-pdHL2.

Mammalian Expression of IFN-α2b-DDD2

IFN-α2b-DDD2-pdHL2 was linearized by digestion with SalI enzyme and stably transfected into Sp/EEE myeloma cells by electroporation (see. e.g., U.S. Pat. No. 7,537,930, the Examples section of which is incorporated herein by reference). Two clones were found to have detectable levels of IFN-α2b by ELISA. One of the two clones, designated 95, was adapted to growth in serum-free media without substantial decrease in productivity. The clone was subsequently amplified with increasing methotrexate (MTX) concentrations from 0.1 to 0.8 μM over five weeks. At this stage, it was sub-cloned by limiting dilution and the highest producing sub-clone (95-5) was expanded. The productivity of 95-5 grown in shake-flasks was estimated to be 2.5 mg/L using commercial rIFN-α2b (Chemicon IF007, Lot 06008039084) as a standard.

Purification of IFN-α2b-DDD2 from Batch Cultures Grown in Roller Bottles

Clone 95-5 was expanded to 34 roller bottles containing a total of 20 L of serum-free Hybridoma SFM with 0.8 μM MTX and allowed to reach terminal culture. The supernatant fluid was clarified by centrifugation, filtered (0.2 μM). The filtrate was diafiltered into 1× binding buffer (10 mM imidazole, 0.5 M NaCl, 50 mM $NaH_2PO_4$, pH 7.5) and concentrated to 310 mL in preparation for purification by immobilized metal affinity chromatography (IMAC). The concentrate was loaded onto a 30-mL Ni-NTA column, which was washed with 500 mL of 0.02% Tween 20 in 1× binding buffer and then 290 mL of 30 mM imidazole, 0.02% Tween 20, 0.5 M NaCl, 50 mM $NaH_2PO_4$, pH 7.5. The product was eluted with 110 mL of 250 mM imidazole, 0.02% Tween 20, 150 mM NaCl, 50 mM $NaH_2PO_4$, pH 7.5. Approximately 6 mg of IFNα2b-DDD2 was purified.

Characterization of IFN-α2b-DDD2

The purity of IFN-α2b-DDD2 was assessed by SDS-PAGE under reducing conditions (not shown). The Coomassie blue-stained gel showed that the batch produced from roller bottles was purer than an earlier batch (not shown). IFN-α2b-DDD2 was the most heavily stained band and accounted for approximately 50% of the total protein (not shown). The product resolved as a doublet with an $M_r$ of ~26 kDa, which is consistent with the calculated MW of IFN-α2b-DDD2-SP (26 kDa). There was one major contaminant with a $M_r$ of 34 kDa and many faint contaminating bands (not shown).

Example 19

Generation of PEGylated IFN-α2b by DNL

Preparation and Purification of α2b-362 (IFN-α2b-DDD2-IMP362)

The structure of α2b-362 has two copies of IFNα2b-DDD2 coupled to a 20 kDa PEG-AD. A DNL reaction was performed by the addition of 11 mg of reduced and lyophilized IMP362 in 10-fold molar excess to 2.25 mg (3.5 ml) of IFN-α2b-DDD2 in 250 mM imidazole, 0.02% Tween 20, 150 mM NaCl, 1 mM EDTA, 50 mM $NaH_2PO_4$, pH 7.5. After 6 h at room temperature in the dark, the reaction mixture was dialyzed against CM Loading Buffer (150 mM NaCl, 20 mM NaAc, pH 4.5) at 4° C. in the dark. The solution was loaded onto a 1-mL Hi-Trap CM-FF column (Amersham), which was pre-equilibrated with CM Loading buffer. After sample loading, the column was washed with CM loading buffer to baseline, followed by washing with 15 mL of 0.25 M NaCl, 20 mM NaAc, pH 4.5. The PEGylated product was eluted with 12.5 mL of 0.5 M NaCl, 20 mM NaAc, pH 4.5.

The conjugation process was analyzed by SDS-PAGE with Coomassie blue staining, fluorescence imaging and anti-IFNα immunoblotting (not shown). To normalize the samples for direct protein mass comparison, each fraction eluted from the CM-FF column was concentrated to 3.5 mL to match the reaction volume. Under non-reducing conditions, the Coomassie blue-stained gel revealed the presence of a major band at a $M_r$ of 110 kDa in the reaction mixture, which was absent in the unbound or 0.25 M NaCl wash fraction, but evident in the 0.5 M NaCl fraction (not shown). Fluorescence imaging, which was used to detect the EDANS tag on IMP362, demonstrated that the 110 kDa band contained IMP362 and the presence of excess IMP362 in the reaction mixture and the unbound fraction, which did not stain with Coomassie blue (not shown). Anti-IFNα immunoblotting confirmed the association of IFN-α2b with the 110 kDa band (not shown).

These data together indicate that the DNL reaction resulted in the site-specific and covalent conjugation of IMP362 with a dimer of IFN-α2b. Under reducing conditions, which breaks the disulfide linkage, the components of the DNL structures were resolved (not shown). The calculated MW of α2b-362 was ~75 kDa, which matches well the mass of 76,728 Da determined by MALDI TOF. The observed discrepancy between the calculated mass and the estimated Mr by SDS-PAGE is due to PEG, which is known to inflate the molecular size when PEGylated products are analyzed by SDS-PAGE or SE-HPLC. Overall, the DNL reaction resulted in a near quantitative yield of a homogeneous product that was >90% pure after purification by cation-exchange chromatography (not shown).

Preparation and Purification of α2b-457 (IFN-α2b-DDD2-IMP457)

A DNL reaction was performed by the addition of 2.5 mg of reduced and lyophilized IMP457 in 10-fold molar excess to 1 mg (1.7 ml) of IFN-α2b-DDD2 in 250 mM imidazole, 0.02% Tween 20, 150 mM NaCl, 1 mM EDTA, 50 mM $NaH_2PO_4$, pH 7.5. After 60 h at room temperature, 1 mM oxidized glutathione was added to the reaction mixture, which was then held for an additional 2 h. The mixture was diluted 1:20 with CM Loading Buffer (150 mM NaCl, 20 mM NaAc, pH 4.5) and titrated to pH 4.5 with acetic acid. The solution was loaded onto a 1-mL CM-FF column, which was pre-equilibrated with CM Loading Buffer. After sample loading, the column was washed with CM Loading Buffer to baseline, followed by washing with 15 mL of 0.25M NaCl, 20 mM NaAc, pH 4.5. The PEGylated product was eluted with 20 mL of 0.5 M NaCl, 20 mM NaAc, pH 4.5, then concentrated to 2 mL and diafiltered into 0.4 M PBS, pH 7.4. The final yield was approximately 1 mg of α2b-457 of >90% purity as determined by SDS-PAGE and IFNα ELISA.

Preparation and Purification of α2b-413 (IFN-α2b-DDD2-IMP413)

The structure of α2b-413 has two copies of IFNα2b-DDD2 coupled to a 30 kDa PEG-AD2. α2b-413 was prepared as described immediately above using IMP413 instead of IMP362.

Example 20

In Vitro Potency of IFN-α2b-DDD2, α2b-362, and α2b-413

In Vitro Anti-Proliferative Assay

IFN-α2b-DDD2 and α2b-362 were assayed for inhibition of growth of Burkitt's lymphoma (Daudi) cells. Briefly, IFN-α2b standard (Chemicon IF007, Lot 06008039084), IFN-α2b-DDD2 and α2b-362 were each diluted to 500 pM in RPMI 1640 media supplemented with 10% FBS, from which three-fold serial dilutions in triplicate were made in 96-well tissue culture plates (50 µl, sample/well). Daudi cells were diluted to $4 \times 10^5$ cells/mL and 50 µL were added to each well (20K/well). The concentration range for each test reagent was 500 pM to 0.008 pM. After 4 days at 37° C., MTS dye was added to the plates (20 µL per well) and after 3 h the plates were read with an ENVISION® plate reader (Perkin Elmer, Boston Mass.) at 490 nm. Dose-response curves were generated (not shown) and 50% effective concentration ($EC_{50}$) values were obtained by sigmoidal fit non-linear regression.

We compared the anti-proliferative activity of α2b-362 and α2b-413 with PEGINTRON® and PEGASYS® in Daudi lymphoma cells, with the finding that α2b-362 and α2b-413 had 2-3-fold lower $EC_{50}$ values than PEGINTRON (~$1 \times 10^{12}$ U/mmol vs. $2.2 \times 10^{12}$ U/mmol), but were comparable to PEGASYS (not shown).

Anti-Viral Assay

The reduction of viral cytopathic effect (CPE) was determined by an independent laboratory (PBL Interferon Source, Piscataway, N.J.) using encephalomyocarditis virus (EMCV) and human lung epithelial A549 cells. Plates were stained with crystal violet and the OD was measured by spectrophotometry on a 96-well plate reader following solubilization of the dye. The data were analyzed using a sigmoidal fit (variable slope) non-linear regression. The anti-viral titer was determined by comparison of $EC_{50}$ values with that of an IFNα standard.

The biological activities of α2b-362 and α2b-413 were compared with PEGINTRON® and PEGASYS® by measuring the cytopathic effect (CPE) of encephalomyocarditis virus (EMCV) on human lung epithelial A549 cells and the resulting $EC_{50}$ values were calculated to determine the anti-viral specific activities based on a validated IFN-α2b standard. On a molar basis, α2b-362, α2b-413, and PEGINTRON all have similar specific activities (averaging $7 \times 10^{12}$ to $9 \times 10^{12}$ U/mmol) and are about 5-fold more potent than PEGASYS (not shown). These data indicate that site-specific PEGylation by DNL may preserve biological activity better, particularly when using large PEG molecules. In addition, a cell-based kit, which utilizes a transgenic human pro-monocyte cell line carrying a reporter gene fused to an interferon-stimulated response element, was used to determine the specific activities of α2b-362 and α2b-413 to be 2940 IU/pmol and 816 IU/pmol, respectively, both of which were higher than PEGASYS (170 IU/pmol) but lower than PEGINTRON (3400 IU/pmol) (not shown).

Example 21

In Vivo Evaluation of α2b-413 and α2b-362

Pharmacokinetics

The study was performed in adult female Swiss-Webster mice (~35 g). There were 4 different treatment groups of 2 mice each. Each reagent (test and control) was administered at equimolar protein doses (3 µg of rhuIFN-α2a, 5 µg of PEGINTRON®, 11 µg of α2b-362, and 13 µg of α2b-413) as a single bolus i.v. injection. Mice were bled via the retro-orbital method at various time-points (pre-dose, 5-min, 2-, 8-, 24-, 48-, 72-, 96-, and 168-h post-injection). The blood was allowed to clot, centrifuged, and the serum was isolated and stored at ~70° C. until assayed for IFN-α concentration and subsequent PK-analysis.

Concentrations of IFN-α in the serum samples were determined using a human interferon alpha ELISA kit following the manufacturer's instructions (PBL Interferon Source). Briefly, the serum samples were diluted appropriately according to the human IFN-α standard provided in the kit. An antibody coupled to the microtiter plate wells captured interferon. A second antibody was then used to reveal the bound interferon, which was quantified by anti-secondary antibody conjugated to horseradish peroxidase (HRP) following the addition of Tetramethyl benzidine (TMB) substrate. The plates were read at 450 nm.

The PK properties of each agent are summarized in Table 8. As expected, rhIFN-α2a had the most rapid clearance from the blood of injected mice. Its clearance was approximately 3-fold faster than the PEGINTRON® and more than 13-fold faster than the DNL-IFN reagents. The PEGINTRON® was in turn cleared greater than 4-fold faster than α2b-362 or α2b-413. There was little difference in the elimination rates between α2b-362 and α2b-413.

TABLE 8

Blood Pharmacokinetic Analysis of Interferon-α2b Containing DNL Molecules
Administered as Intravenous Injections to Naïve Swiss-Webster Mice.

| Animal Number | IFN Dose (pmol) | $C_{max}$ (pM) | $T_{1/2\alpha}$ (hours) | $T_{1/2\beta}$ (hours) | $AUC_{0.08\to\infty}$ (h*pM) | Elimination Rate (1/h) | $MRT_{0.08\to\infty}$ (h) |
|---|---|---|---|---|---|---|---|
| Recombinant Human Interferon-α2a | | | | | | | |
| Animal No. 1 | 160 | 16,411 | 0.29 | 10.53 | 7,011 | 2.34 | 0.63 |
| Animal No. 2 | 160 | 21,835 | 0.31 | 7.14 | 10,147 | 2.15 | 0.78 |
| i. Mean | 160 | 19,123 | 0.30 | 8.84 | 8,579 | 2.25 | 0.71 |
| PEGINTRON ® | | | | | | | |
| Animal No. 1 | 160 | 87,090 | 0.53 | 6.29 | 137,790 | 0.63 | 5.42 |
| Animal No. 2 | 160 | 105,774 | 0.43 | 5.11 | 150,905 | 0.70 | 4.79 |
| ii. Mean | 160 | 96,432 | 0.48 | 5.70 | 144,348 | 0.67 | 5.11 |
| IFN-α2b-IMP362 | | | | | | | |
| Animal No. 1 | 320 | 60,833 | 1.72 | 7.54 | 379,462 | 0.16 | 9.03 |
| Animal No. 2 | 320 | 97,089 | 1.43 | 10.14 | 570,336 | 0.17 | 11.56 |
| iii. Mean | 320 | 78,961 | 1.58 | 8.84 | 474,899 | 0.17 | 10.30 |
| IFN-α2b-IMP413 | | | | | | | |
| Animal No. 1 | 320 | 152,923 | 0.69 | 12.85 | 1,012,470 | 0.15 | 16.75 |
| Animal No. 2 | 320 | 100,495 | 4.03 | 28.53 | 1,179,056 | 0.09 | 26.56 |
| iv. Mean | 320 | 126,709 | 2.36 | 20.69 | 1,095,763 | 0.12 | 21.66 |

In terms of mean residence time (MRT), there is a clear correlation with size among the various reagents. The 19-kDa rhIFN-α2a had a MRT that was 7-fold less than the 31 kDa PEGINTRON® (0.7 h versus 5.1 h, respectively), which had a 2-fold lower MRT when compared to the 70 kDa α2b-362 (10.3 h). The MRT for the 80 kDa α2b-413 (21.7 h) was 2-fold longer than α2b-362. Finally, a test for bioequivalence showed that none of the reagents tested were the same in terms of PK, indicating that the differences are genuine (i.e., circulating half-life for α2b-413>α2b-362>PEGINTRON®>rhIFN-α2a).

Anti-Tumor Therapeutic Efficacy

An in vivo tumor therapy study demonstrated that the DNL-PEGylated interferons were more potent and longer-lasting compared to PEGINTRON®. Eight-week-old female C.B.-17 SCID mice were injected i.v. with a human Burkitt's lymphoma cell-line (Daudi) at $1.5\times10^7$ cells per animal. There were 10 different treatment groups of 5 mice each. Equivalent units of activity of PEGINTRON®, α2b-362 and α2b-413 were administered once every 7 days via s.c. injection in either the left or right flank at three different doses (3500, 7000, and 14000 Units). Therapy commenced 1 day after the Daudi cells were transplanted.

Mice were observed daily for signs of distress and paralysis. They were weighed weekly. In the event a mouse lost greater than 15% of its body weight (but <20%) it was weighed every 2 days until it either gained back its weight to <15% loss or was sacrificed due to >20% loss. Mice were also terminated when hind-limb paralysis developed or if they became otherwise moribund.

Figure 5:
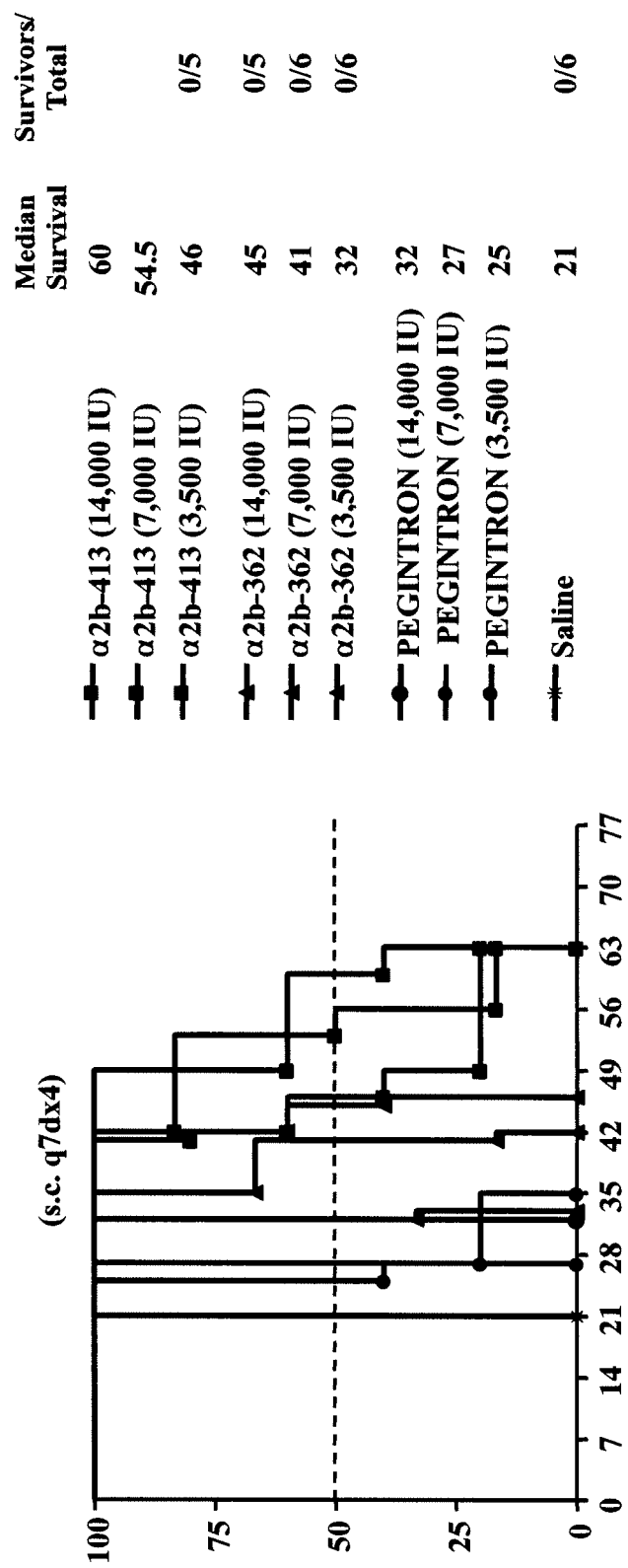
FIG. 5. Evaluation of the therapeutic efficacy of IFNα constructs in mice bearing Burkitt's lymphoma (Daudi). Eight-week-old female SCID mice were injected i.v. with $1.5 \times 10^7$ Daudi cells. Groups of 5 mice were administered PEGINTRON®, α2b-362 and α2b-413 at doses of 3,500, 7,000 or 14,000 Units once per week for 4 weeks. Therapy commenced 1 day after the Daudi cells were transplanted. Injection times are indicated with arrows. Survival curves and median survival are shown for each group.

Survival curves generated from this study are shown in FIG. 5. PEGINTRON®, α2b-362, and α2b-413 all demonstrated significant improvement in survival when compared to saline control mice (P<0.0016). Except for the 3,500 IU dose of α2b-362, both α2b-413 and α2b-362 were superior to PEGINTRON® when administered at equal activity doses (P<0.0027). α2b-362 showed more than twice the potency of PEGINTRON®. Doses of 7,000 IU and 3,500 IU of α2b-362 were superior to 14,000 IU (P=0.0016) and 7,000 IU (P=0.0027) doses of PEGINTRON®, respectively. α2b-413 is more than four times as potent as PEGINTRON® since a 3,500 IU dose of the former was superior to 14,000 IU of the latter (P=0.0027). α2b-413 was significantly better than α2b-362 (P<0.0025) when administered at equivalent doses. However, there were no statistically significant differences among the three doses of α2b-413, even though the 14,000 IU dose resulted in a median survival of 60 days in comparison to the 3,500 IU dose and its 46 day median survival (P=0.1255). The in vivo efficacy observed for α2b-362, α2b-413, and PEGINTRON® thus correlate well with the PK data.

The increased bioavailability of α2b-362 and α2b-413 demonstrated by PK analysis contributes to the enhanced in vivo anti-tumor potency of DNL-PEGylated IFNα. In turn, these two factors allow for a less frequent dosing schedule used in tumor therapy. This was demonstrated with a similar in vivo tumor therapy study as above, in which equal units of activity of PEGINTRON® or α2b-413 were administered with varied dosing schedules. This study was performed in 8-week-old female SCID mice injected i.v. with Daudi $1.5\times10^7$ cells. There were 7 different treatment groups of 6-7 mice each. Each reagent (test and control) was administered at 14,000 IU via a s.c. injection in either the left or right flank. Therapy was commenced 1 day after the Daudi-cells were administered to the mice. One set of mice was dosed once a week for 4 weeks (q7dx4), another dosed on a bi-weekly schedule over 8 weeks (q2wkx4), while the third set of mice was dosed once every 3 weeks over 12 weeks (q3wkx4). All the mice received a total of 4 injections.

Figure 6:
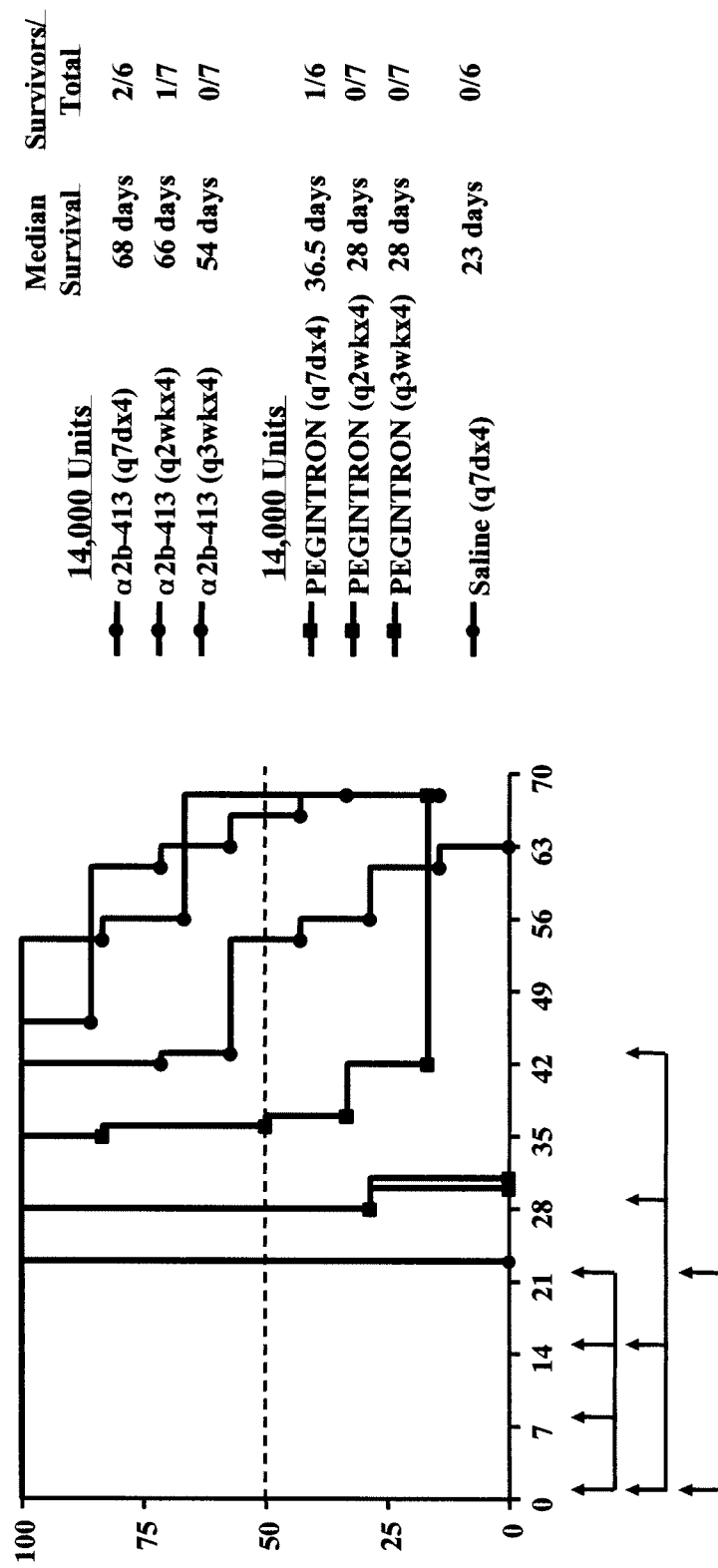
FIG. 6. Evaluation of the dosing schedule for therapy of tumor-bearing mice. Eight-week-old female SCID mice were injected i.v. with $1.5 \times 10^7$ Daudi-cells. Groups of 6-7 mice were administered 14,000 IU of either PEGINTRON® or α2b-413 via a s.c. injection. Therapy was commenced 1 day after the Daudi cells were administered to the mice. Groups were dosed once a week (q7dx4), once every other week (q2wkx4) or once every 3 weeks (q3wkx4). Injection times are indicated with arrows. All the mice received 4 injections in total. Survival curves and median survival are shown for each group.

Survival curves generated from this study are shown in FIG. 6. All animals that received either form of interferon at any of the various schedules had significantly improved survival in comparison to saline control mice (P<0.0009). Importantly, all the IFN-IMP413-treated mice had significantly improved survival when compared to those animals treated at the same schedule with PEGINTRON® (P<0.0097). Of note, those mice treated every other week with IFN-IMP413 (q2wkx4) not only had significantly improved survival in comparison to those treated with PEGINTRON® at the same schedule (MST=>54 days versus 28 days, respectively; P=0.0002), but were also significantly better than those animals treated weekly (q7dx4) with PEGINTRON® (MST=36.5 days; P=0.0049). Further, survival of mice treated every three weeks with IFN-IMP413 (q3wkx4) was significantly better than those treated with PEGINTRON® every two weeks (MST=54 days versus 28 days; P=0.002) and approaches significance when compared to those treated weekly with PEGINTRON® (P=0.0598).

pmol dose of α2b-413 also improved survival in comparison to PEGINTRON® (P=0.002) (not shown). At 10 pmol, there was no difference between α2b-457 and α2b-413 but both significantly improved survival over PEGINTRON® treated mice (P<0.001) (not shown).

TABLE 9

Comparison of PK parameters.

| Injected Material | Animal # | $C_{max}$ (pmol/L) | $T_{max}$ (h) | $T_{1/2}$ (h) | $AUC_{0\to\infty}$ (h*pmole/L) | Cl (L/h) | $MRT_{0\to\infty}$ (h) |
|---|---|---|---|---|---|---|---|
| α2b-457 | 1 | 4,326 | 24 | 16.9 | 169,119 | 0.0012 | 34.7 |
|  | 2 | 6,538 | 24 | 16.6 | 249,852 | 0.0008 | 33.4 |
|  | 3 | 5,424 | 24 | 16.3 | 192,651 | 0.0010 | 29.9 |
|  | 4 | 5,052 | 8 | 15.9 | 194,122 | 0.0010 | 31.6 |
|  |  | 5,335 ± 923 | 20 ± 8 | 16.4 ± 0.4 | 201,436 ± 34,250 | 0.0010 ± 0.0002 | 32.4 ± 2.1 |
| α2b-413 | 1 | 3,014 | 24 | 15.5 | 123,440 | 0.0016 | 30.1 |
|  | 2 | 4,104 | 8 | 20.5 | 170,183 | 0.0012 | 30.1 |
|  | 3 | 2,888 | 24 | 11.3 | 92,415 | 0.0022 | 24.1 |
|  | 4 | 4,122 | 8 | 14.9 | 166,127 | 0.0012 | 27.0 |
|  |  | 3,532 ± 673 | 16 ± 9.2 | 15.6 ± 3.8 | 138,041 ± 37,044 | 0.0016 ± 0.0005 | 27.8 ± 2.9 |
| PEGASYS ® | 1 | 1,948 | 24 | 14.5 | 64,294 | 0.0016 | 33.1 |
|  | 2 | 1,887 | 24 | 14.6 | 58,596 | 0.0017 | 33.3 |
|  | 3 | 1,902 | 24 | 15.0 | 59,147 | 0.0017 | 34.1 |
|  | 4 | 2,377 | 24 | 15.3 | 47,116 | 0.0013 | 33.5 |
|  |  | 2,029 ± 234 | 24 | 14.9 ± 0.4 | 64,038 ± 7,192 | 0.0016 ± 0.0002 | 33.5 ± 0.4 |
| PEGINTRON ® | 1 | 1,885 | 8 | 9.4 | 34,063 | 0.0029 | 17.1 |
|  | 2 | 1,301 | 8 | 8.4 | 24,667 | 0.0041 | 15.5 |
|  | 3 | 1,609 | 8 | 9.8 | 32,833 | 0.0030 | 18.5 |
|  | 4 | 2,521 | 8 | 9.6 | 50,129 | 0.0020 | 17.3 |
|  |  | 1,829 ± 519 | 8 | 9.3 ± 0.6 | 35,423 ± 10,654 | 0.0030 ± 0.0008 | 17.1 ± 1.3 |

In another study, we found that administering α2b-413 at 14,000 IU every 4 weeks increased the median survival to 56 days from 23 days of the saline control and was more potent than PEGINTRON® given 14,000 IU every week (not shown).

Example 22

In Vitro and In Vivo Characterization of α2b-457

For a better comparison with PEGASYS®, we conjugated IFNα2b-DDD2 to IMP457, an AD2-module of 40-kDa branched PEG, and obtained a resulting α2b-457. Gel electrophoresis showed that α2b-457 was of substantial purity in a 0.5 M NaCl fraction eluted from a CM column (not shown).

The in vitro biological activities of α2b-457 were determined by three different assays to be lower than PEGINTRON®, comparable to α2b-413, and considerably higher than PEGASYS® (not shown). The PK data obtained in mice with a single s.c. injection indicate a longer circulating half-life of α2b-457 than either α2b-413 or PEGASYS®, with all three clearing much slower than PEGINTRON® (not shown).

Table 9 summarizes the key PK parameters calculated. The observed differences between α2b-457 and each of α2b-413, PEGASYS®, and PEGINTRON®, or between α2b-413 and PEGASYS® or PEGINTRON®, are significant by statistical analysis (Table 10). When given once every four weeks at a low dose of 20 pmol, α2b-457 was more effective than PEGINTRON® given as a mole-equivalent dose once weekly. Administration of α2b-457 extended the median survival of Daudi-bearing mice to 47 days from 23 days when compared to the saline group (not shown). In the same study, α2b-457 at 20 pmol was significantly better than either α2b-413 or PEGINTRON® at 20 pmol (MST=47 days versus 41 and 37 days, respectively; P<0.0151) (not shown). The 20

TABLE 10

Statistical analysis of PK parameters

|  | AUC | P-value | Cmax | P-value |
|---|---|---|---|---|
| α2b-457 vs. | Fraction of α2b-457 |  | Fraction of α2b-457 |  |
| α2b-413 | 0.68 | 0.0457 | 0.66 | 0.0196 |
| PEGASYS ® | 0.32 | 0.0027 | 0.38 | 0.0041 |
| PEGINTRON ® | 0.18 | 0.0001 | 0.34 | 0.0006 |
| α2b-413 vs. | Fraction of α2b-413 |  | Fraction of α2b-413 |  |
| PEGASYS ® | 0.46 | 0.0202 | 0.57 | 0.0056 |
| PEGINTRON ® | 0.26 | 0.0018 | 0.52 | 0.0071 |

These studies demonstrated that DNL-PEGylation of IFNα2b resulted in improved and long-lasting efficacy, even when compared with other PEGylated forms of IFNα2b, allowing for less frequent dosing. Similar enhancements are realized when this technology is applied to other cytokines (such as G-CSF and EPO), growth factors, enzymes, antibodies, immunomodulators, hormones, peptides, drugs, interference RNA, oligonucleotides, vaccines and other biologically active agents.

Example 23

Generation of DDD Module Based on Granulocyte-Colony Stimulating Factor (G-CSF)

Construction of G-CSF-DDD2-pdHL2 for Expression in Mammalian Cells

The cDNA sequence for G-CSF was amplified by PCR resulting in an amplified construct similar to that disclosed above for INF-α2b. The resulting secreted protein consisted of G-CSF fused at its C-terminus to a polypeptide consisting of SEQ ID NO:127. PCR amplification was accomplished using a full-length human G-CSF cDNA clone (Invitrogen IMAGE human cat#97002RG Clone ID 5759022) as a template and oligonucleotide primers. The PCR amplimer was cloned into the pGEM®-T vector. A DDD2-pdHL2 mammalian expression vector was prepared for ligation with G-CSF by digestion with XbaI and Bam HI restriction endonucleases. The G-CSF amplimer was excised from PGEMT® with XbaI and Bam HI and ligated into the DDD2-pdHL2 vector to generate the expression vector G-CSF-DDD2-pdHL2.

Mammalian Expression of G-CSF-DDD2

G-CSF-pdHL2 was linearized by digestion with SalI enzyme and stably transfected into Sp/EEE myeloma cells by electroporation. Clones were selected with media containing 0.15 µM MTX. Clone #4 was shown to produce 0.15 mg/L of G-CSF-DDD2 by sandwich ELISA.

Purification of G-CSF-DDD2 from Batch Cultures Grown in Roller Bottles

Approximately 3 mg of G-CSF-DDD2 is purified as descried above for INF-α2b. Clone 4 is expanded to 34 roller bottles containing a total of 20 L of Hybridoma SFM with 0.4 µM MTX and allowed to reach terminal culture. The supernatant fluid is clarified by centrifugation, filtered (0.2 µM), diafiltered into 1× Binding buffer (10 mM Imidazole, 0.5 M NaCl, 50 mM $NaH_2PO_4$, pH 7.5 and concentrated. The concentrate is loaded onto a Ni-NTA column, which is washed with 0.02% Tween 20 in 1× binding buffer and then 30 mM imidazole, 0.02% Tween 20, 0.5 M NaCl, 50 mM $NaH_2PO_4$, pH 7.5. The product is eluted with 250 mM imidazole, 0.02% Tween 20, 150 mM NaCl, 50 mM $NaH_2PO_4$, pH 7.5.

Generation of PEGylated G-CSF by DNL

A DNL reaction is performed by the addition of reduced and lyophilized IMP413 in 10-fold molar excess to G-CSF-DDD2 in PBS. After 6 h at room temperature in the dark, the reaction mixture is purified by immobilized metal affinity chromatography using Ni-NTA.

Example 24

Generation of DDD Module Based on Erythropoietin (EPO)

Construction of G-CSF-DDD2-pdHL2 for Expression in Mammalian Cells

The cDNA sequence for EPO was amplified by PCR resulting in an amplified construct similar to that disclosed above for INF-α2b. The resulting secreted protein consists of EPO fused at its C-terminus to a polypeptide consisting of SEQ ID NO:127. PCR amplification was accomplished using a full-length human EPO cDNA clone as a template and oligonucleotide primers. The PCR amplimer was cloned into the pGEM®-T vector. A DDD2-pdHL2 mammalian expression vector was prepared for ligation with EPO by digestion with XbaI and Bam HI restriction endonucleases. The EPO amplimer was excised from PGEMT® with XbaI and Bam HI and ligated into the DDD2-pdHL2 vector to generate the expression vector EPO-DDD2-pdHL2.

Mammalian Expression of EPO-DDD2

EPO-pdHL2 was linearized by digestion with SalI enzyme and stably transfected into Sp/EEE myeloma cells by electroporation. Clones were selected with media containing 0.15 µM MTX. Clones #41, 49 and 37 each were shown to produce ~0.5 mg/L of EPO by an ELISA using Nunc Immobilizer Nickel-Chelate plates to capture the His-tagged fusion protein and detection with anti-EPO antibody.

Purification of EPO from Batch Cultures Grown in Roller Bottles

Approximately 2.5 mg of EPO-DDD2 was purified by IMAC from 9.6 liters of serum-free roller bottle culture. SDS-PAGE and immunoblot analysis indicated that the purified product constituted approximately 10% of the total protein following IMAC (not shown). Under reducing conditions the EPO-DDD2 polypeptide was resolved as a broad band with a $M_r$ (40-45 kDa), greater than its calculated mass (28 kDa) due to extensive and heterogeneous glycosylation. Under non-reducing conditions the EPO-DDD2 primarily resolved as a disulfide-linked covalent dimer (mediated by DDD2) with a $M_r$ of 80-90 kDa.

DNL Conjugation of EPO-DDD2 with a Fab-AD2 Module h679 is a humanized monoclonal antibody that is highly specific for the hapten HSG (histamine-succinyl-glycine). Production of an h679-Fab-AD2 module has been described previously (Rossi et al., Proc. Natl. Acad. Sci. USA. 2006; 103:6841). A small-scale preparation of EPO-679 (EPO-DDD2×h679-Fab-AD2) was made by DNL. EPO-DDD2 (1 mg) was reacted overnight with h679-Fab-AD2 (1 mg) in PBS containing 1 mM reduced glutathione and 2 mM oxidized glutathione. The DNL conjugate was purified by HSG-based affinity chromatography as described previously (Rossi et. al, Proc. Natl. Acad. Sci. USA. 2006; 103:6841). The structure of EPO-679 contained two EPO moieties and h679-Fab. Coomassie blue staining of SDS-PAGE gels demonstrated the creation of EPO-679 (not shown). The DNL product, which resolved as a broad band with a $M_r$ of 150-170 kDa under non-reducing conditions, was highly purified and consisted only of the three constituent polypeptides (EPO, h679-Fd-AD2 and h679 Kappa) as demonstrated by SDS-PAGE under reducing conditions (not shown).

Biological Activity of EPO-DDD2 and EPO-679

EPO-DDD2 and EPO-679 were assayed for their ability to stimulate the growth of EPO-responsive TF1 cells (ATCC) using recombinant human EPO (Calbiochem) as a positive control. TF1 cells were grown in RPMI 1640 media supplemented with 20% FBS without GM-CSF supplementation in 96-well plates containing $1 \times 10^4$ cells/well. The concentrations (units/ml) of the EPO constructs were determined using a commercial kit (Human erythropoietin ELISA kit, Stem Cell Research, Cat#01630). Cells were cultured in the presence of rhEPO, EPO-DDD2 or EPO-679 at concentrations ranging from 900 U/ml to 0.001 U/ml for 72 hours. The viable cell densities were compared by MTS assay using 20 µl of MTS reagent/well incubated for 6 hours before measuring the OD490 in a 96-well plate reader. Dose response curves and EC50 values were generated (not shown). Both EPO-DDD2 and EPO-679 showed in vitro biological activity at approximately 10% of the potency of rhEPO (not shown).

Generation of PEGylated EPO by DNL

The structure of EPO-413 has two copies of EPO coupled to a 30 kDa PEG. A DNL reaction is performed by the addition of reduced and lyophilized IMP413 in 10-fold molar excess to EPO-DDD2 in PBS. After 6 h at room temperature in the dark, the reaction mixture is purified by immobilized metal affinity chromatography using Ni-NTA.

Example 25

PEGylation of Fab Antibody Fragments

The C-DDD2-Fd-hMN14-pdHL2 vector is transfected into Sp/EEE cells and used to produce C-DDD2-Fab-hMN-14. The di-cistronic expression vector directs the synthesis and secretion of both hMN-14 kappa light chain and C-DDD2-Fd-hMN-14, which combine to form C-DDD2-Fab-hMN14. The C-DDD2-Fab-hMN-14 spontaneously forms dimers, which are mixed with an equimolar amount of IMP362, IMP413 or IMP457, resulting in the production of a PEGylated C-DDD2-Fab-hMN-14 dimer. The hMN-14 Fab moiety retains its binding specificity for the CEA antigen. Injection into nude mice bearing a CEACAM5-expressing tumor shows that the PEGylated C-DDD2-Fab-hMN-14 exhibits a significantly prolonged circulating half-life compared to non-PEGylated hMN-14 F(ab)$_2$, resulting in improved efficacy with a less frequent dosing schedule.

The skilled artisan will realize that the techniques disclosed in the Examples above may be utilized to make PEGylated Fab constructs using sequences from any murine, chimeric, humanized or human antibody.

Example 26

Cytokine-Antibody DNL Constructs with Enhanced Efficacy

In certain preferred embodiments, the subject DNL complexes may comprise antibody-cytokine constructs, more preferably tetrameric cytokines attached to IgG antibodies. The cytokine-antibody DNL constructs have substantially enhanced efficacy compared to cytokines alone, antibody alone, unconjugated combinations of cytokine and antibody, or PEGylated cytokines. Exemplary methods for making such cytokine-MAb DNL constructs are provided below.

General Methods

Cell lines. Cell lines suitable for transfection and protein production are known in the art, such as Sp/EEE and Sp/ESF cells (see, e.g., U.S. Pat. Nos. 7,531,327; 7,537,930 and 7,608,425, the Examples section of each of which is incorporated herein by reference.) Sp/ESF cells, an enhanced variant of Sp2/0-Ag14 (ATCC, Manassas, Va.), were maintained in Hybridoma Serum-Free Media (H-SFM) supplemented with 2 mM L-glutamine and 100 units/mL penicillin-streptomycin. Daudi, Ramos, Raji, NAMALWA and Jeko-1 (ATCC) human lymphomas were maintained in RPMI 1640 media containing 10% FBS and supplemented with 1 mM sodium pyruvate, 10 mM L-glutamine, 25 mM HEPES, and 100 units/mL penicillin-streptomycin.

MAb-IFNα constructs. 20-2b was produced by DNL via the combination of two DNL modules, $C_{H3}$-AD2-IgG-v-mab and IFNα2b-DDD2, which were each expressed in Sp/ESF. Additional DNL-generated MAb-IFNα constructs, of similar design as 20-2b (humanized IgG1+4 IFNα2b) but with different targeting MAbs, were used as controls in several experiments: 22-2b has $C_{H3}$-AD2-IgG-e-mab (epratuzumab) as its AD2 module, which is directed against CD22 and binds lymphoma; 734-2b has $C_{H3}$-AD2-IgG-h734 as its AD2 module, which is directed against the hapten, In-DTPA and does not bind to any animal proteins or tissues; and R1-2b uses $C_{H3}$-AD2-IgG-hR1, which binds human insulin-like growth factor 1 receptor (IGF-1R).

Analytical methods. Protein concentrations of IFNα constructs were measured using a commercial human IFNα2 ELISA kit following the manufacturer's suggested protocol (PBL Interferon Source, Piscataway, N.J.) and confirmed by size-exclusion HPLC. Reducing and non-reducing SDS-PAGE analyses were performed using 4-20% gradient Tris-glycine gels (Cambrex Bio Science, Rockland, Me.). All colorimetric (ELISA and MTS), luminescence (reporter) and fluorometric (CDC and ADCC) assays were quantified with an ENVISION™ 2100 multilabel plate reader (PerkinElmer, Waltham, Mass.).

IFNα activity measurements. IFNα2b specific activities were determined using the ILITE™ Human Interferon Alpha Cell-Based Assay Kit following the manufacturer's suggested protocol (PBL Interferon Source). PEGASYS®, 20-2b, and seven more MAb-IFNα constructs were diluted to 10, 2.5 and 0.625 ng/mL in 1% BSA-PBS. PEGINTRON® was diluted to 1, 0.25 and 0.0625 ng/mL. Each dilution was assayed in triplicate with overnight incubation with the supplied cells. Specific activities were extrapolated from a standard curve generated with the supplied standard. Antiviral activities were determined with an in vitro viral challenge assay using encephalomyocarditis (EMC) virus on A549 cells by an independent analytical laboratory (PBL Interferon Source).

In vitro proliferation. Daudi or Jeko-1 were plated at 5,000 cells/well in 96-well plates and incubated at 37° C. for four (Daudi) or five (Jeko-1) days in the presence of increasing concentrations of the indicated agents. Viable cell densities were determined using a CELLTITER 96® Cell Proliferation Assay (Promega, Madison, Wis.).

Ex-vivo depletion of Daudi and Ramos lymphoma cells from whole blood. The effects of 20-2b on NHL cells as well as peripheral blood lymphocytes in whole human blood from health volunteers were evaluated ex-vivo using flow cytometry and compared to those of v-MAb, 734-2b or a combination of v-MAb and 734-2b. Daudi or Ramos ($5 \times 10^4$ cells) were mixed with heparinized whole blood (150 µl) and incubated with test MAbs at 0.01, 0.1 or 1 nM for 2 days at 37° C. and 5% $CO_2$. Cells were stained with FITC-labeled anti-CD3, anti-CD19, or mouse $IgG_1$ isotype control. Following lysis of erythrocytes, cells were analyzed using a FACSCALIBUR™ (BD Biosciences). Both Daudi and Ramos cells are CD19+ and in the monocyte gate. The normal B- and T-cells are CD19+ and CD3+ cells, respectively, in the lymphocyte gate. Student t-test was used to evaluate statistical significance ($P<0.05$).

In vivo efficacy in mice. Studies were performed in female C.B.17 homozygous severe combined immune deficient (SCID) mice of approximately 20 g (Taconic, Germantown, N.Y.). Each mouse was inoculated i.v. with $1.5 \times 10^7$ Daudi, $2.5 \times 10^6$ Raji or $5 \times 10^6$ NAMALWA cells on day 0. Treatment doses were all administered by subcutaneous injection. Saline was used as a control treatment. Animals monitored daily were humanely sacrificed when hind-limb paralysis developed or if they became otherwise moribund. Additionally, mice were sacrificed if they lost more than 20% of initial body weight. Survival curves were analyzed using Kaplan-Meier plots (log-rank analysis). Some outliers determined by critical Z test were censored from analyses.

Generation of a DNL Conjugate Comprising Four IFN-α2b-DDD2 Moieties Linked to $C_{H3}$-AD2-IgG A DNL complex comprising four IFN-α2b-DDD2 moieties linked to $C_{H3}$-AD2-IgG was made as follows. Briefly, a chosen $C_{H3}$-AD2-IgG was combined with approximately two mole-equivalents of IFN-α2b-DDD2 and the mixture was reduced under mild conditions overnight at room temperature after adding 1 mM EDTA and 2 mM reduced glutathione (GSH). Oxidized glutathione was added to 2 mM and the mixture was held at room temperature for an additional 12-24 hours. The DNL conjugate was purified over a Protein A affinity column. Four such DNL conjugates designed 20-2b, 22-2b, hR1-2b, and 243-2b, each comprising four copies of IFN-α2b anchored on $C_{H3}$-AD2-IgG-hA20 (with specificity for CD20), $C_{H3}$-AD2-IgG-hLL2 (with specificity for CD22), $C_{H3}$-AD2-IgG-hR1 (with specificity for IGF-1R) and $C_{H3}$-AD2-IgG-hL243 (with specificity for HLA-DR), respectively, were prepared. SE-HPLC analyses of 20-2b generated from mammalian (m) or E. coli (e)-produced IFN-α2b-DDD2 each showed a major peak having a retention time consistent with a covalent complex composed of an IgG and 4 IFN-α2b groups (not shown). Similar SE-HPLC profiles were observed for the other three IFN-IgG conjugates.

In Vitro Activity of the IFN-IgG Conjugates.

Figure 7:
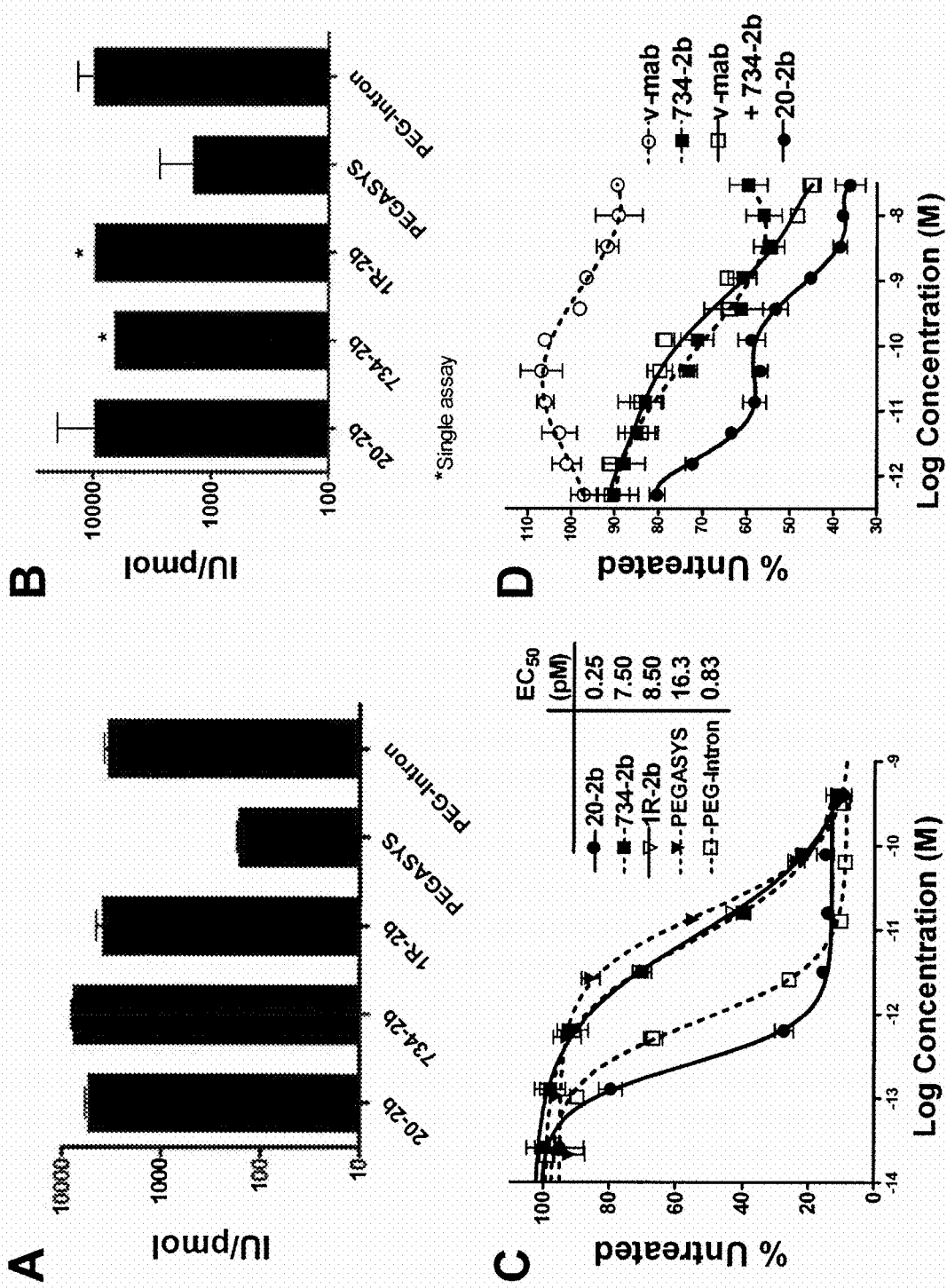
FIG. 7. In vitro IFNα activity in a cytokine-MAb DNL construct compared to PEGylated or native IFNα. Specific activities (IU/pmol) measured as described in the Examples. The activity of known concentrations of each test article was extrapolated from a rhIFNα2b standard curve. Cultures were grown in the presence of increasing concentrations of 20-2b (●), 734-2b (■), v-MAb (○), v-MAb+734-2b (□), PEGASYS® (▼), PEGINTRONte (◆) or 1R-2b (▽) and the relative viable cell densities were measured with MTS. The % of the signal obtained from untreated cells was plotted vs. the log of the molar concentration. Dose-response curves and $EC_{50}$ values were generated using Prism software. Error bars, SD. (A) Cell-based reporter gene assay. (B) Viral protection assay with EMC virus and A549 cells. (C) In vitro lymphoma proliferation assays using Daudi cells. (D) In vitro lymphoma proliferation assays using Jeko-1 cells.

The in vitro IFNα biological activity of 20-2b was compared to that of commercial PEGylated IFNα2 agents, PEGASYS® and PEGINTRON®, using cell-based reporter, viral protection, and lymphoma proliferation assays. Specific activities were determined using a cell-based kit, which utilizes a transgenic human pro-monocyte cell line carrying a reporter gene fused to an interferon-stimulated response element (FIG. 7A-7D). The specific activity of 20-2b (5300 IU/pmol) was greater than both PEGASYS® (170 IU/pmol) and PEGINTRON® (3400 IU/pmol) (FIG. 7A). 734-2b, 1R-2b and five additional MAb-IFNα constructs (data not shown), which were produced similarly to 20-2b, each exhibited similar specific activities (4000-8000 IU/pmol), demonstrating the consistency of the DNL method for generating such structures (FIG. 7A). Having four IFNα2b groups contributed to the enhanced potency of MAb-IFNα. When normalized to IFNα equivalents, the specific activity/IFNα was about 10-fold greater than PEGASYS® and only about 2-fold less than PEGINTRON®.

Comparison of MAb-IFNα, PEGASYS® and PEGINTRON® in an in vitro viral protection assay demonstrated that MAb-IFNα retains IFNα2b antiviral activity with specific activities similar to PEGINTRON® and 10-fold greater than PEGASYS® (FIG. 7B).

IFNα2b can have a direct antiproliferative or cytotoxic effect on some tumor lines. The activity of 20-2b was measured in an in vitro proliferation assay with a Burkitt lymphoma cell line (Daudi) that is highly sensitive to IFNα (FIG. 7C). Each of the IFNα2 agents efficiently inhibited (>90%) Daudi in vitro with high potency ($EC_{50}$=4-10 pM). However, 20-2b ($EC_{50}$=0.25 pM) was about 30-fold more potent than the non-targeting MAb-IFNα constructs. The parent anti-CD20 MAb of 20-2b has anti-proliferative activity in vitro on many lymphoma cell lines, including Daudi (Rossi et al., 2008, Cancer Res 68:8384-92), at considerably greater concentrations ($EC_{50}$>10 nM). The in vitro activity of 20-2b was also assessed using Jeko-1, which is a mantle cell lymphoma line that has lower sensitivity to both IFNα and anti-CD20 (FIG. 7D). Jeko-1 is only modestly sensitive to the parent anti-CD20 MAb, having 10% maximal inhibition ($I_{max}$) with an $EC_{50}$ near 1 nM. As shown with 734-2b, Jeko-1 ($I_{max}$=43%; $EC_{50}$=23 pM) is less responsive to IFNα2b than Daudi ($I_{max}$=90%; $EC_{50}$=7.5 pM). Compared to 734-2b, 20-2b inhibited Jeko-1 to a greater extent ($I_{max}$=65%) and exhibited a biphasic dose-response curve (FIG. 7D). At <10 pM, a low-concentration response attributed to IFNα2b activity was observed, which plateaus at $I_{max}$=43%, similar to 734-2b. A high-concentration response was evident above 100 pM, where $I_{max}$ reached 65%. The low-concentration IFNα2b response of 20-2b ($EC_{50}$=0.97 pM) was 25-fold more potent than 734-2b, similar to the results with Daudi.

A combination of the parent anti-CD20 antibody and 734-2b (v-mab+734-2b) was assayed to elucidate whether the increased potency of 20-2b is due to an additive/synergistic effect of CD20 and IFNα signaling. The dose response curve for v-mab+734-2b was largely similar to 734-2b alone, except at >1 nM, where inhibition increased for the former but not the latter. These results suggest that MAb targeting is responsible for the lower $EC_{50}$ of 20-2b, but its greater $I_{max}$ is apparently due to the additive activity of IFNα2b and CD-20 signaling. The effect of CD20 signaling was only evident in the high-concentration response for 20-2b ($EC_{50}$=0.85 nM), which parallels the response to v-MAb ($EC_{50}$=1.5 nM). A biphasic dose-response curve was not obvious for v-mab+734-2b, because the two responses overlap. However, an additive effect was evident at >1 nM concentrations. The $I_{max}$ of 20-2b (65%) was greater than the added responses of IFNα2b ($I_{max}$=43%) and v-MAb ($I_{max}$=10%), suggesting possible synergism between the actions of IFNα2b and v-MAb.

ADCC Activity

Figure 8:
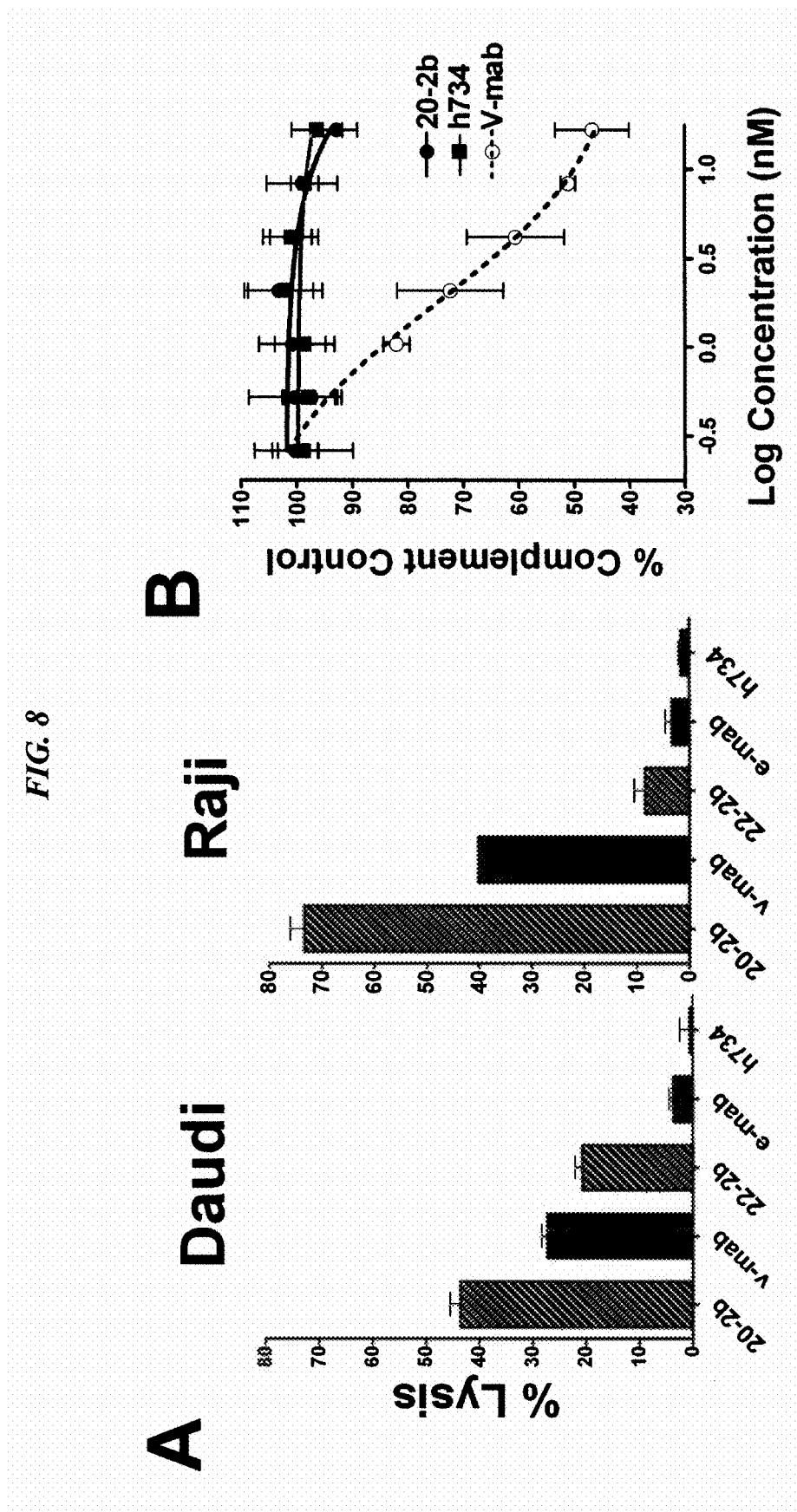
FIG. 8. (A) ADCC effector functions of 20-2b. Daudi or Raji cells were incubated with 20-2b, 22-2b, v-MAb, epratuzumab (e-MAb), or h734 at 5 µg/ml in the presence of freshly isolated PBMCs for 4 h before quantification of cell lysis. (B) CDC effector functions of 20-2B. Daudi cells were incubated with serial dilutions of 20-2b (●), 734-2b (■) or v-MAb (○) in the presence of human complement. The % complement control (number of viable cells in the test sample compared to cells treated with complement only) was plotted vs. the log of the nM concentration. Error bars, SD.

IFNα can potentiate ADCC activity, which is a fundamental mechanism of action (MOA) for anti-CD20 immunotherapy, by activating NK cells and macrophages. We compared ADCC of 20-2b and v-MAb with two NHL cell lines using peripheral blood mononuclear cells (PBMCs) as effector cells. Replicate assays using PBMCs from multiple donors consistently demonstrated that 20-2b had enhanced ADCC compared to v-MAb, as shown for both Daudi and Raji cells (FIG. 8A). This effect was also shown with 22-2b, a MAb-IFNα comprising the anti-CD22 MAb, epratuzumab, which shows modest ADCC (Carnahan et al., 2007, Mol Immunol 44:1331-41.

CDC Activity

CDC is thought to be an important mechanism of action for Type-I anti-CD20 MAbs (including v-MAb and rituximab). However, this function is lacking in the Type-II MAbs, represented by tositumomab (Cardarelli et al., 2002, Cancer Immunol Immunother 51:15-24), which nonetheless has anti-lymphoma activity. Unlike v-MAb, 20-2b does not show CDC activity in vitro (FIG. 8B). These results are consistent with those for other DNL structures based on the $C_{H3}$-AD2-IgG-v-mab module, in which complement fixation is apparently impaired, perhaps by steric interference (Rossi et al., 2008).

Pharmacokinetic (PK) Analysis of 20-2b.

The pharmacokinetic (PK) properties of 20-2b were evaluated in male Swiss-Webster mice and compared to those of PEGASYS®, PEGINTRON® and α2b-413 (PEGylated IFN made by DNL). Concentrations of IFN-α in the serum samples at various times were determined by ELISA following the manufacturer's instructions. Briefly, the serum samples were diluted appropriately according to the human IFN-α standard provided in the kit. An antibody bound to the microtiter plate wells captures interferon. A second antibody was then used to reveal the bound interferon, which was quantified by anti-secondary antibody conjugated to horse-radish peroxidase (HRP) following the addition of Tetramethyl benzidine (TMB). The plates were read at 450 nm.

Figure 9:
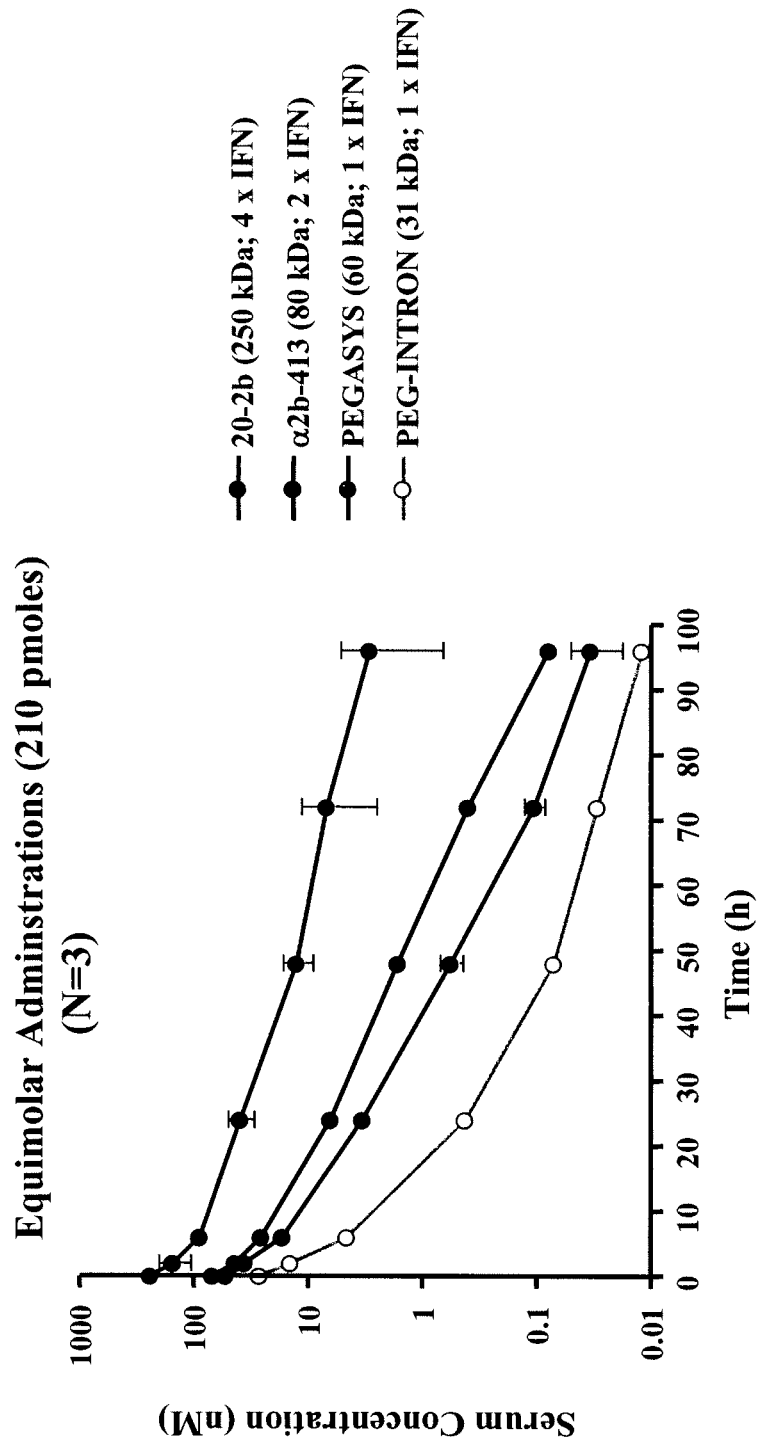
FIG. 9. Results of pharmacokinetic analyses in Swiss-Webster mice. Mice were administered 20-2b, α2b-413, PEGINTRON or PEGASYS® and serum samples were analyzed for IFNα2b concentration by ELISA over 96 hours.

FIG. 9 presents the results of the PK analysis, which showed significantly slower elimination and longer serum residence of 20-2b compared to the other agents. At an injected dose of 210 pmol, the calculated pharmacokinetic serum half-life in hours was 8.0 hr (20-2b), 5.7 hr (α2b-413), 4.7 hr (PEGASYS®) and 2.6 hr (PEGINTRON®). The elimination rate (1/h) was 0.087 (20-2b), 0.121 (α2b-413), 0.149 (PEGASYS®) and 0.265 (PEGINTRON®). The calculated $MRT_{0.08 \to \infty}$ (hr) was 22.2 (20-2b), 12.5 (α2b-413), 10.7 (PEGASYS®) and 6.0 (PEGINTRON®). Because the pharmacokinetic parameters are determined more by the nature of the complex than the individual antibody or cytokine, it is expected that the PK characteristics of the cytokine-DNL complex are generalizable to other cytokine moieties and antibody moieties and are not limited to the specific 20-2b construct discussed above.

Example 27

In Vivo Activity of 20-2b

Serum Stability 20-2b was stable in human sera (≥10 days) or whole blood (≥6 days) at 37° C. (not shown). Concentration of 20-2b complex was determined using a bispecific ELISA assay.

There was essentially no detectable change in serum 20-2b levels in either whole blood or serum over the time period of the assay.

Ex Vivo Efficacy of 20-2b Against Lymphoma Cells from Whole Human Blood

We compared the abilities of 20-2b, v-MAb, 734-2b, or v-mab+734-2b to eliminate lymphoma or normal B-cells from whole blood in an ex vivo setting (FIG. 10). The therapeutic efficacy of naked anti-CD20 MAbs is believed to be achieved via three mechanisms of action (MOA)—signaling-induced apoptosis or growth arrest, ADCC, and CDC (Glennie et al., 2007, Mol Immunol 44:3823-37). In this assay, v-MAb can employ all three MOA, while, based on the in vitro findings, 20-2b can potentially take advantage of signaling and enhanced ADCC, but not CDC. In this short-term model, the IFN$\alpha$2b groups of 20-2b and 734-2b can act directly on tumor cells, augment the ADCC activity of v-MAb, and possibly have some immunostimulatory effects. However, the full spectrum of IFN$\alpha$-mediated activation of the innate and adaptive immune systems that might occur in vivo is not realized in this two-day ex vivo assay.

At 0.01 nM, 20-2b depleted Daudi cells (60.5%) significantly more than v-MAb (22.8%), 734-2b (38.6%) or v-mab+734-2b (41.7%) (FIG. 10). At 0.1 nM, 20-2b and v-mab+734-2b depleted Daudi to a similar extent (88.9%), which was more than for v-MAb (82.4%) or 734-2b (40.7%) (FIG. 10). At 1 nM, each agent depleted Daudi >95%, except for 734-2b (55.7%) (FIG. 10). Each of the differences indicated were statistically significant ($P<0.01$).

Ramos is less sensitive than Daudi to both IFN$\alpha$2b and v-MAb. The effect of 734-2b was only moderate, resulting in <20% depletion of Ramos at each concentration (FIG. 10). At both 0.01 and 0.1 nM, 20-2b depleted Ramos more than v-mab+734-2b, which in turn eliminated more cells than v-MAb (FIG. 10). At 1 nM, all treatments besides 734-2b resulted in similar Ramos depletion (75%) (FIG. 10). Each of the differences indicated were statistically significant ($P<0.02$).

As demonstrated with 734-2b, IFN$\alpha$2b alone does not deplete normal B-cells in this assay. At these low concentrations, 20-2b, v-MAb, and v-mab+734-2b each show similar dose-responsive depletion of B-cells, which is markedly less than the depletion of either Daudi or Ramos. None of the treatments resulted in significant depletion of T-cells (data not shown).

In Vivo Efficacy of 20-2b in SCID Mice

A limitation of the mouse model is the very low sensitivity of murine cells to human IFN$\alpha$2b. The overall therapeutic advantage of 20-2b that might be achieved in humans can involve the enhancement of both innate and adaptive immunity. With these limitations in mind, we studied the anti-lymphoma in vivo efficacy of 20-2b against disseminated Burkitt lymphoma models in SCID mice. We initially tested a highly sensitive early Daudi model (FIG. 11A). One day after inoculation, groups were administered a single low dose of 20-2b, v-MAb, or 734-2b. A single dose of v-MAb or 734-2b at 0.7 pmol (170 ng) resulted in significant improvement in survival when compared to saline for v-MAb ($P<0.0001$), but not for the irrelevant MAb-IFN$\alpha$ control, 734-2b (FIG. 11A). This improvement was modest, with the median survival time (MST) increasing from 27 days for saline to 34 days for v-MAb. However, a single dose of 0.7 pmol (170 ng) of 20-2b improved the MST by more than 100 days over both saline control and v-MAb groups ($P<0.0001$) (FIG. 11A). The study was terminated after 19 weeks, at which time the 7 long-term survivors (LTS) in the 0.7 pmol 20-2b treatment group were necropsied with no visible evidence of disease found (cured) (FIG. 11A). Remarkably, even the lowest dose of 0.07 pmol (17 ng) of 20-2b more than doubled the MST (FIG. 11A).

Next, we assessed the efficacy of 20-2b in a more challenging advanced Daudi model, in which mice were allowed to develop a substantially greater tumor burden prior to treatment (FIG. 11B). Seven days after tumor inoculation, groups were administered a single low dose (0.7, 7.0 or 70 pmol) of 20-2b, v-MAb, 734-2b, or PEGASYS®. The MST for the saline control mice was 21 days (FIG. 11B). The highest dose (70 pmol) of PEGASYS® or 734-2b, each of which have enhanced Pk (compared to recombinant IFN$\alpha$2b) but do not target tumor, doubled the MST (42 days; $P<0.0001$) (FIG. 11B). Treatment with 20-2b at a 100-fold lower dose (0.7 pmol) produced similar results (38.5 days) as the highest dose (70 pmol) of either PEGASYS® or 734-2b (FIG. 11B). Treatment with 20-2b at a 10-fold lower dose (7 pmol) resulted in significantly improved survival (80.5 days, 20% LTS) over treatment with 70 pmol of PEGASYS® or 734-2b ($P<0.0012$) (FIG. 11B). At the highest dose tested (70 pmol), 20-2b improved the MST to >105 days with 100% LTS (FIG. 11B). We have demonstrated previously with the early tumor model that v-MAb can increase survival of Daudi-bearing mice at relatively low doses (3.5 pmol) while higher doses result in LTS. However, in this advanced tumor model, a single dose of 70 pmol of v-MAb had only a modest, though significant, effect on survival (MST=24 days, $P=0.0001$) (FIG. 11B).

We subsequently assayed 20-2b in more challenging models, which are less sensitive than Daudi to direct inhibition by IFN$\alpha$ and less responsive to immunotherapy with v-MAb. Raji is ~1000-fold less sensitive to the direct action of IFN$\alpha$2b compared to Daudi. However, Raji has a similar CD20 antigen density to Daudi (Stein et al., 2006, Blood 108:2736-44) and is responsive to v-MAb, albeit considerably less so than Daudi (Goldenberg et al., 2009, Blood 113, 1062-70). The efficacy of 20-2b was studied in an advanced Raji model with therapy beginning five days after tumor inoculation (FIG. 12A). Groups were administered a total of 6 injections (250 pmol each) over two weeks. 734-2b did not improve survival over saline (MST=16 days), consistent with the insensitivity of Raji to IFN$\alpha$ (FIG. 12A). V-MAb significantly improved survival over saline (MST=26 days, $P<0.0001$) (FIG. 12A). 20-2b was superior to all other treatments (MST=33 days, $P<0.0001$) (FIG. 12A).

Finally, we investigated the efficacy of 20-2b with NAMA-LWA (FIG. 12B), a human lymphoma that has low sensitivity to the direct action of IFN$\alpha$, ~25-fold lower CD20 antigen density compared to Daudi or Raji, and is considered to be resistant to anti-CD20 immunotherapy (Stein et al., 2006). Groups were administered a total of 6 doses (250 pmol each) of either 20-2b or 734-2b. Another group was administered a total of 7 doses (3.5 nmol each) of v-MAb. The group treated with saline had an MST of 17 days (FIG. 12B). Treatment with 734-2b very modestly, though significantly, improved survival (MST=20 days, $P=0.0012$) (FIG. 12B). 20-2b (MST=34 days) was superior to 734-2b ($P=0.0004$) as well as v-MAb (MST=24 days, $P=0.0026$), which was given at a 14-fold higher dose (FIG. 12B).

Conclusions

The results demonstrate unequivocally that targeting of IFN$\alpha$ with an anti-CD20 MAb makes the immunocytokine more potent and effective than either agent alone or in combination. MAb targeting of IFN$\alpha$ to tumors may allow a less frequent dosing schedule of a single agent, reduce or eliminate side effects associated with IFN therapy, and result in profoundly enhanced efficacy. Additionally, targeted IFN$\alpha$ can induce an acute tumor-directed immune response and possibly evoke immune memory via pleiotropic stimulation of innate and adaptive immunity (Belardelli et al, 2002, Cytokine Growth Factor Rev 12:119-34). Other groups have produced MAb-IFNα made by chemical conjugation that revealed some of the potential clinical benefits of such constructs (Pelham et al., 1983, Cancer Immunol Immunother 15:210-16; Ozzello et al., 1998, Breast Cancer Res Treat 48:135-47). A recombinant MAb-IFNα comprising murine IFNα and an anti-HER2/neu MAb exhibited potent inhibition of a transgenic (HER2/neu) murine B-cell lymphoma in immunocompetent mice and was also capable of inducing a protective adaptive immune response with immunologic memory (Huang et al., 2007, J Immunol 179:6881-88).

We expect that therapy with 20-2b will stimulate localized recruitment and activation of a number of immune cells, including NK, T4, T8, and dendritic cells, resulting in enhanced cytotoxicity and ADCC, and may potentially induce tumor-directed immunologic memory. However, murine cells are exceedingly less sensitive (~4 logs) than human cells to human IFNα2b (Kramer et al., 1983, J Interferon Res 3:425-35; Weck et al., 1981, J Gen Virol 57:233-37). Therefore, very little, if any, of the anti-lymphoma activity of 20-2b in the mouse model in vivo studies described above can be attributed to IFNα2b activation of the mouse immune response. Rather, killing is due primarily to the direct action of IFNα2b on the lymphoma cells.

We have shown that 20-2b has augmented ADCC, which may be the most important MOA of anti-CD20 immunotherapy. However, since human IFNα2b is only a very weak stimulator of the murine host's immune effector cells, an IFNα-enhanced ADCC is probably not realized as it might be in humans. Even with these limitations, the in vivo results demonstrate that 20-2b can be a highly effective anti-lymphoma agent, exhibiting more than 100-times the potency of v-MAb or a non-targeting MAb-IFNα in the IFNα-sensitive Daudi model. Even with lymphoma models that are relatively insensitive to the direct action of IFNα (Raji/NAMALWA) or are resistant to anti-CD20 immunotherapy (NAMALWA), 20-2b showed superior efficacy to either v-MAb or non-targeted MAb-IFNα.

Fusion of IFNα2b to v-MAb increases its in vivo potency by extending circulation times and enabling tumor targeting. The therapeutic significance of Pk was demonstrated in the Daudi model, where the slower clearing PEGASYS® was superior to the faster clearing PEGINTRON®, which has a higher specific activity (data not shown). 20-2b was considerably more potent than either PEGASYS® or 734-2b, suggesting that lymphoma targeting via the anti-CD20 MAb is critical to its superior potency and efficacy. Surprisingly, the impact of targeting was evident even in the in vitro assays. In the in vitro proliferation experiments, which only allow for lymphoma inhibition via signaling, 20-2b showed activity at a 25-fold lower concentration compared to non-targeting MAb-IFNα, either alone or when combined with v-MAb. The ex vivo setting allows the involvement of all three of the anti-CD20 MOA. Even without CDC activity, 20-2b was more effective at depleting lymphoma from blood than IFNα or v-MAb, either alone or in combination, demonstrating the significance of targeting. The influence of MAb targeting in the in vitro/ex vivo studies is somewhat surprising, because the MAbs, effector, and target cells are all confined throughout the experiments. We expect that 20-2b will have a substantially greater impact in vivo in human patients.

The IFNα2b and v-MAb components of 20-2b can apparently act additively or synergistically, to contribute to its enhanced potency. The in vitro proliferation assays suggest at least an additive effect, which was substantiated with the results of the ex vivo studies where the combination of v-MAb and 734-2b was superior to either agent alone. This may be accomplished ex vivo via increased ADCC activity of v-MAb as part of 20-2b or when combined with 734-2b, yet ADCC is not functional in the in vitro proliferation assays, suggesting additional mechanisms. The signal transduced by v-MAb-bound CD20 may potentiate the IFNα signal, resulting in enhanced potency. Alternatively, the binding of v-MAb, which is a slowly internalizing MAb, may prevent the internalization/down-regulation of the Type-I IFN receptors, resulting in a more prolonged and effective IFNα-induced signal.

Example 28

Generation of hR1-17S, a DNL Conjugate Comprising Four N-DDD2-G-CSF(C17S) Moieties Linked to $C_{H3}$-AD2-IgG-hR1 hR1-17S was produced by combining $C_{H3}$-AD2-IgG-hR1 with excess N-DDD2-G-CSF(C17S) under redox conditions following purification by Protein A affinity chromatography. SE-HPLC analysis of the protein A-purified hR1-17S showed a major peak and a shoulder of a higher molecular size (not shown). The retention time of the major peak was consistent with a covalent complex composed of an IgG and 4 G-CSF groups. The shoulder was likely due to a non-covalent dimer of the IgG-G-CSF conjugate. SDS-PAGE analysis with Coomassie blue staining and anti-G-CSF immunoblot analysis showed that under non-reducing conditions the product had an Mr consistent with the deduced MW of ~260 kDa (not shown). Under reducing conditions, bands representing the three constituent polypeptides of hR1-17S(N-DDD2-G-CSF (C17S), Heavy chain-ADZ, and light chain) were detected (not shown).

Example 29

Generation of 734-EPO, a DNL Conjugate Comprising Four EPO-DDD2 Moieties Linked to C.sub.H3-AD2-IgG-h734

734-EPO was produced as described above for 20-2b. SE-HPLC analysis of the protein A-purified 734-EPO showed a major peak and a shoulder of a higher molecular size (not shown). The retention time of the major peak was consistent with a covalent complex composed of an IgG and 4 EPO groups. The shoulder was likely due to a non-covalent dimer of the IgG-EPO conjugate. SDS-PAGE analysis with Coomassie blue staining and anti-EPO immunoblot analysis showed that under non-reducing conditions the product had a Mr of >260 kDa (not shown), consistent with the deduced MW of .about.310 kDa. Under reducing conditions the bands representing the three constituent polypeptides of 734-EPO (EPO-DDD2, Heavy chain-AD2, and light chain) were evident and appeared to be similar in quantity (not shown). Non-product contaminants were not detected.

EPO-DDD2 and 734-EPO were assayed for their ability to stimulate the growth of EPO-responsive TF1 cells (ATCC) using recombinant human EPO (Calbiochem) as a positive control. TF1 cells were grown in RPMI 1640 media supplemented with 20% FBS without GM-CSF supplementation in 96-well plates containing $1\times10^4$ cells/well. The concentrations (units/ml) of the EPO constructs were determined using a commercial kit (Human erythropoietin ELISA kit, Stem Cell Research, Cat #01630). Cells were cultured in the presence of rhEPO, EPO-DDD2 or 734-EPO at concentrations ranging from 900 u/ml to 0.001 U/ml for 72 hours. The viable cell densities were compared by MTS assay using 200 of MTS reagent/well incubated for 6 hours before measuring the OD490 in a 96-well plate reader. Dose response curves and $EC_{50}$ values were determined. Both EPO-DDD2 and 734-EPO showed in vitro biological activity that was approximately 10% of rhEPO (not shown).

Example 30

Tetrameric G-CSF with Improved Biological Activity

The Dock-and-Lock (DNL) method was applied to produce three IgG-AD2 fusion proteins, each of which was combined with the dimer of a G-CSF-DDD2 fusion protein to generate a stably tethered complex comprising an intact IgG linked at its CH3 termini to four molecules of G-CSF. The humanized IgGs fused to AD2 were hA20 (anti-CD20), hMN14 (anti-CEACAM5), and h734 (anti-indium-DTPA). In G-CSF-DDD2, the unpaired cysteine (C17) of wild-type G-CSF was replaced with a serine. As expected, a dimeric form of G-CSF-DDD2 was predominantly obtained following purification. Reacting G-CSF-DDD2 to each of the three IgG-AD2 modules resulted in hA20-G-CSF, hMN14-G-CSF and h734-G-CSF, respectively. IgG-G-CSF was purified from the reaction mixture by Protein A chromatography.

The purity, size, and composition of each IgG-G-CSF were confirmed by SDS-PAGE, size-exclusion HPLC, and western blotting (not shown). An in vitro proliferation assay using Kasumi-1 (a myeloid leukemia cell line) showed that IgG-G-CSF complexes were more potent compared with recombinant hG-CSF (not shown). ADCC studies of hA20-G-CSF were performed in CD20-positive Daudi cells with the PBMCs isolated from two different donors. For both donors, enhanced ADCC was observed for hA20-G-CSF compared to the parental hA20 IgG (veltuzumab): donor 006, 35% vs. 20% (P<0.0191); donor 010, 60% vs. 50% (not statistically significant). The concentration of each agent tested was 5 µg/mL.

In vivo studies in normal mice also revealed the spleen of the treated group had an average weight that was about 2- to 3-times that of the untreated group (P=0.0061) (not shown). In addition, the numbers of monocytes and neutrophils in the blood of the treated mice, when measured at day 9, were increased about 5- and 2-fold, respectively, compared to the untreated mice (not shown). The three IgG-G-CSF complexes represent a novel class of bioactive immunocytokines comprising tetrameric G-CSF anchored onto an IgG, which are expected to show improved pharmacokinetics and additional targeting specificity conferred by the built-in IgG. Because rituximab (anti-CD20) therapy causes neutropenia in patients, the potential of hA20-IgG-G-CSF to enhance the potency of an anti-CD20 antibody yet prevent neutropenia is advantageous.

Example 31

Tetrameric Erythropoietin with Improved Biological Activity

We combined a recombinant fusion protein comprising erythropoietin attached to a DDD sequence with either (1) a recombinant 40 kDa PEG-AD module to generate a PEGylated dimeric Epo; (2) a recombinant Fab-AD module to generate a dimeric Epo-Fab construct; or (3) a recombinant IgG-AD module to generate a tetrameric Epo-IgG conjugate. Epo-DDD2 was generated by recombinant fusion of the DDD2 peptide to the carboxyl terminus of human Epo via an 18 amino acid linker peptide. $C_H1$-AD2-Fab was generated by recombinant fusion of the AD2 peptide to the carboxyl terminus of the $C_H1$ domain of a Fab via a 15 amino acid linker peptide. IMP457 was generated by forming a sulfide linkage between the maleimide group of mPEG2-MAL-40K to the N-terminal cysteine residue of the AD2 peptide IMP421.

DNL modules for IgG-AD2, Fab-AD2 and Epo-DDD2 were purified from the supernatant fluid of separate recombinant myeloma cultures by Protein A, Protein L and immobilized metal affinity chromatography (IMAC), respectively. Combining an IgG-AD2 module with slightly more than two molar equivalents of Epo-DDD2 module under mild redox conditions resulted in the formation of a covalent complex comprising one IgG and 4 Epo groups via the docking of each of the two AD2 domains on IgG with a dimer of Epo-DDD2, and subsequent formation of disulfide bonds (locking) between DDD2 and AD2. IgG-Epo, which was purified by Protein A following the DNL reaction, was detected by non-reducing SDS-PAGE and size-exclusion HPLC (SE-HPLC), where it was resolved as a single predominant protein peak with a retention time consistent with a 255-kDa protein (not shown). Combining Fab-AD2 and Epo-DDD2 modules by DNL resulted in the formation of a covalent complex comprising one Fab and 2 Epo groups (not shown). Fab-Epo was purified by Protein L and analyzed by non-reducing SDS-PAGE and SE-HPLC, where it was resolved as a single predominant protein peak with a retention time consistent with a 100-kDa protein (not shown). Combining a PEG-AD2 module (IMP457) and Epo-DDD2 resulted in the formation of a covalent complex comprising 40 kDa branched PEG and 2 Epo groups. 457-Epo, which was purified by Q-Sepharose IEC at pH-6, was detected by non-reducing SDS-PAGE with Coomassie blue and Iodine staining (not shown).

The in vitro potency of various Epo constructs was measured by their ability to stimulate the proliferation of the cytokine-dependent TF1 cell line (not shown). TF1 cells were incubated with serial dilutions of rhEpo, ARANESP®, Epo-DDD2, Fab-Epo, IgG-Epo, or 457-Epo. The results showed that the Epo-DDD2 module and each DNL construct maintained Epo biological activity (not shown). IgG-Epo, Fab-Epo and 457-Epo all stimulated of proliferation of the cytokine-dependent TF1 cell line with similar potency to rhEpo (not shown).

In vivo activity of IgG-Epo was determined by its effects on hematocrit levels. Normal Swiss-Webster mice (n=4) were administered a single i.v. injection (3.2 µg) of IgG-Epo and the hematocrit was measured after five days. The results showed that a single i.v. administration of IgG-hEpo produced a significant (P=0.0107) increase in hematocrit compared to untreated mice (not shown). The DNL method provides a novel approach for efficiently tethering cytokines, such as Epo, to a variety of molecules including IgG, Fab and PEG, which enhances their in vivo biological activity by improving their pharmacokinetics and stability.

Example 32

Antibody-Dendrimer DNL Complex for siRNA

For some embodiments, the DNL complexes of the present invention may be used for delivery of inhibitory RNA or DNA species. These may include, but are not limited to, synthetic genes, siRNA and/or RNAi. The inhibitory RNA species may be conjugated directly to an AD or DDD moiety, or may alternatively be attached to nucleic acid carrier molecules, as described herein.

Cationic polymers, such as polylysine, polyethylenimine, or polyamidoamine (PAMAM)-based dendrimers, form complexes with nucleic acids. However, their potential applications as non-viral vectors for delivering therapeutic genes or siRNAs remain a challenge. One approach to improve selectivity and potency of a dendrimeric nanoparticle may be achieved by conjugation with an antibody that internalizes upon binding to target cells.

We synthesized and characterized a novel immunoconjugate, designated E1-G5/2, which was made by the DNL method to comprise half of a generation 5 (G5) PAMAM dendrimer (G5/2) site-specifically linked to a stabilized dimer of Fab derived from hRS7, a humanized antibody that is rapidly internalized upon binding to the Trop-2 antigen expressed on various solid cancers.

Methods

E1-G5/2 was prepared by combining two self-assembling modules, AD2-G5/2 and hRS7-Fab-DDD2, under mild redox conditions, followed by purification on a Protein L column. To make AD2-G5/2, we derivatized the AD2 peptide with a maleimide group to react with the single thiol generated from reducing a G5 PAMAM with a cystamine core and used reversed-phase HPLC to isolate AD2-G5/2. We produced hRS7-Fab-DDD2 as a fusion protein in myeloma cells, as described in the Examples above.

The molecular size, purity and composition of E1-G5/2 were analyzed by size-exclusion HPLC, SDS-PAGE, and Western blotting. The biological functions of E1-G5/2 were assessed by binding to an anti-idiotype antibody against hRS7, a gel retardation assay, and a DNase protection assay.

Results

E1-G5/2 was shown by size-exclusion HPLC to consist of a major peak (>90%) flanked by several minor peaks (not shown). The three constituents of E1-G5/2 (Fd-DDD2, the light chain, and AD2-G5/2) were detected by reducing SDS-PAGE and confirmed by Western blotting (not shown). Anti-idiotype binding analysis revealed E1-G5/2 contained a population of antibody-dendrimer conjugates of different size, all of which were capable of recognizing the anti-idiotype antibody, thus suggesting structural variability in the size of the purchased G5 dendrimer (not shown). Gel retardation assays showed E1-G5/2 was able to maximally condense plasmid DNA at a charge ratio of 6:1 (+/−), with the resulting dendriplexes completely protecting the complexed DNA from degradation by DNase I (not shown).

Conclusion

The DNL technique can be used to build dendrimer-based nanoparticles that are targetable with antibodies. Such agents have improved properties as carriers of drugs, plasmids or siRNAs for applications in vitro and in vivo.

Example 33

Maleimide AD2 Conjugate for DNL Dendrimers

The peptide IMP498 up to and including the PEG moiety was synthesized on a peptide synthesizer by the Fmoc method on Sieber Amide resin (0.1 mmol scale). The maleimide was added manually by mixing the β-maleimidopropionic acid NHS ester with diisopropylethylamine and DMF with the resin for 4 hr. The peptide was cleaved from the resin with 15 mL TFA, 0.5 mL H$_2$O, 0.5 mL triisopropylsilane, and 0.5 mL thioanisole for 3 hr at room temperature. The peptide was purified by reverse phase HPLC using H$_2$O/CH$_3$CN TFA buffers to obtain about 90 mg of purified product after lyophilization.

Synthesis of Reduced G5 Dendrimer (G5/2)

The G-5 dendrimer (10% in MeOH, Dendritic Nanotechnologies), 2.03 g, 7.03×10$^{-6}$ mol was reduced with 0.1426 TCEP.HCl 1:1 MeOH/H$_2$O (~4 mL) and stirred overnight at room temperature. The reaction mixture was purified by reverse phase HPLC on a C-18 column eluted with 0.1% TFA H$_2$O/CH$_3$CN buffers to obtain 0.0633 g of the desired product after lyophilization.

Synthesis of G5/2 Dendrimer-AD2 Conjugate

The G5/2 dendrimer, 0.0469 g (3.35×10$^{-6}$ mol) was mixed with 0.0124 g of IMP498 (4.4×10$^{-6}$ mol) and dissolved in 1:1 MeOH/1M NaHCO$_3$ and mixed for 19 hr at room temperature followed by treatment with 0.0751 g dithiothreitol and 0.0441 g TCEP.HCl. The solution was mixed overnight at room temperature and purified on a C4 reverse phase HPLC column using 0.1% TFA H$_2$O/CH$_3$CN buffers to obtain 0.0033 g of material containing the conjugated AD2 and dendrimer as judged by gel electrophoresis and Western blot.

Example 34

Targeted Delivery of siRNA Using Protamine Linked Antibodies

Summary

RNA interference (RNAi) has been shown to down-regulate the expression of various proteins such as HER2, VEGF, Raf-1, bcl-2, EGFR and numerous others in preclinical studies. Despite the potential of RNAi to silence specific genes, the full therapeutic potential of RNAi remains to be realized due to the lack of an effective delivery system to target cells in vivo.

To address this critical need, we developed novel DNL constructs having multiple copies of human protamine tethered to a tumor-targeting, internalizing hRS7 (anti-Trop-2) antibody for targeted delivery of siRNAs in vivo. A DDD2-L-thP1 module comprising truncated human protamine (thP1, residues 8 to 29 of human protamine 1) was produced, in which the sequences of DDD2 and thP1 were fused respectively to the N- and C-terminal ends of a humanized antibody light chain (not shown). The sequence of the truncated hP1 (thP1, SEQ ID NO:131) is shown below. Reaction of DDD2-L-thP1 with the antibody hRS7-IgG-AD2 under mild redox (SEQ ID NO: 130)

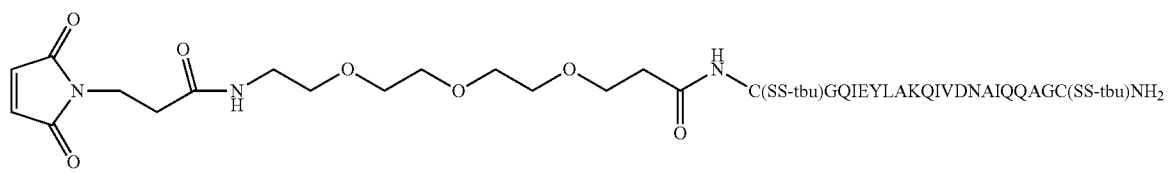

IMP498 conditions, as described in the Examples above, resulted in the formation of an E1-L-thP1 complex (not shown), comprising four copies of thP1 attached to the carboxyl termini of the hRS7 heavy chains.

```
tHP1
    RSQSRSRYYRQRQRSRRRRRRS      (SEQ ID NO: 131)
```

The purity and molecular integrity of E1-L-thP1 following Protein A purification were determined by size-exclusion HPLC and SDS-PAGE (not shown). In addition, the ability of E1-L-thP1 to bind plasmid DNA or siRNA was demonstrated by the gel shift assay (not shown). E1-L-thP1 was effective at binding short double-stranded oligonucleotides (not shown) and in protecting bound DNA from digestion by nucleases added to the sample or present in serum (not shown).

The ability of the E1-L-thP1 construct to internalize siRNAs into Trop-2-expressing cancer cells was confirmed by fluorescence microscopy using FITC-conjugated siRNA and the human Calu-3 lung cancer cell line (not shown).

Methods

The DNL technique was employed to generate E1-L-thP1. The hRS7 IgG-AD module, constructed as described in the Examples above, was expressed in myeloma cells and purified from the culture supernatant using Protein A affinity chromatography. The DDD2-L-thP1 module was expressed as a fusion protein in myeloma cells and was purified by Protein L affinity chromatography. Since the CH3-AD2-IgG module possesses two AD2 peptides and each can bind to a DDD2 dimer, with each DDD2 monomer attached to a protamine moiety, the resulting E1-L-thP1 conjugate comprises four protamine groups. E1-L-thp1 was formed in nearly quantitative yield from the constituent modules and was purified to near homogeneity (not shown) with Protein A.

DDD2-L-thP1 was purified using Protein L affinity chromatography and assessed by size exclusion HPLC analysis and SDS-PAGE under reducing and nonreducing conditions (data not shown). A major peak was observed at 9.6 min (not shown). SDS-PAGE showed a major band between 30 and 40 kDa in reducing gel and a major band about 60 kDa (indicating a dimeric form of DDD2-L-thP1) in nonreducing gel (not shown). The results of Western blotting confirmed the presence of monomeric DDD2-L-tP1 and dimeric DDD2-L-tP1 on probing with anti-DDD antibodies (not shown).

To prepare the E1-L-thP1, hRS7-IgG-AD2 and DDD2-L-thP1 were combined in approximately equal amounts and reduced glutathione (final concentration 1 mM) was added. Following an overnight incubation at room temperature, oxidized glutathione was added (final concentration 2 mM) and the incubation continued for another 24 h. E1-L-thP1 was purified from the reaction mixture by Protein A column chromatography and eluted with 0.1M sodium citrate buffer (pH 3.5). The product peak was neutralized, concentrated, dialyzed with PBS, filtered, and stored in PBS containing 5% glycerol at 2 to 8° C. The composition of E1-L-thP1 was confirmed by reducing SDS-PAGE (not shown), which showed the presence of all three constituents (AD2-appended heavy chain, DDD2-L-htP1, and light chain).

The ability of DDD2-L-thP1 (not shown) and E1-L-thP1 (not shown) to bind DNA was evaluated by gel shift assay. DDD2-L-thP1 retarded the mobility of 500 ng of a linear form of 3-kb DNA fragment in 1% agarose at a molar ratio of 6 or higher (not shown). E1-L-thP1 retarded the mobility of 250 ng of a linear 200-bp DNA duplex in 2% agarose at a molar ratio of 4 or higher (not shown), whereas no such effect was observed for hRS7-IgG-AD2 alone (not shown). The ability of E1-L-thP1 to protect bound DNA from degradation by exogenous DNase and serum nucleases was also demonstrated (not shown).

The ability of E1-L-thP1 to promote internalization of bound siRNA was examined in the Trop-2 expressing ME-180 cervical cell line (not shown). Internalization of the E1-L-thP1 complex was monitored using FITC conjugated goat anti-human antibodies. The cells alone showed no fluorescence (not shown). Addition of FITC-labeled siRNA alone resulted in minimal internalization of the siRNA (not shown). Internalization of E1-L-thP1 alone was observed in 60 minutes at 37° C. (not shown). E1-L-thP1 was able to effectively promote internalization of bound FITC-conjugated siRNA (not shown). E1-L-thP1 (10 µg) was mixed with FITC-siRNA (300 nM) and allowed to form E1-L-thP1-siRNA complexes which were then added to Trop-2-expressing Calu-3 cells. After incubation for 4 h at 37° C. the cells were checked for internalization of siRNA by fluorescence microscopy (not shown).

The ability of E1-L-thP1 to induce apoptosis by internalization of siRNA was examined (FIG. 13). E1-L-thP1 (10 µg) was mixed with varying amounts of siRNA (AllStars Cell Death siRNA, Qiagen, Valencia, Calif.). The E1-L-thP1-siRNA complex was added to ME-180 cells. After 72 h of incubation, cells were trypsinized and annexin V staining was performed to evaluate apoptosis. The Cell Death siRNA alone or E1-L-thP1 alone had no effect on apoptosis (FIG. 13). Addition of increasing amounts of E1-L-thP1-siRNA produced a dose-dependent increase in apoptosis (FIG. 13). These results show that E1-L-thP1 could effectively deliver siRNA molecules into the cells and induce apoptosis of target cells.

Conclusions

The DNL technology provides a modular approach to efficiently tether multiple protamine molecules to the anti-Trop-2 hRS7 antibody resulting in the novel molecule E1-L-thP1. SDS-PAGE demonstrated the homogeneity and purity of E1-L-thP1. DNase protection and gel shift assays showed the DNA binding activity of E1-L-thP1. E1-L-thP1 internalized in the cells like the parental hRS7 antibody and was able to effectively internalize siRNA molecules into Trop-2-expressing cells, such as ME-180 and Calu-3.

The skilled artisan will realize that the DNL technique is not limited to any specific antibody or siRNA species. Rather, the same methods and compositions demonstrated herein can be used to make targeted delivery complexes comprising any antibody, any siRNA carrier and any siRNA species. The use of a bivalent IgG in targeted delivery complexes would result in prolonged circulating half-life and higher binding avidity to target cells, resulting in increased uptake and improved efficacy.

Example 35

Apoptosis of Pancreatic Cancer Using siRNAs Against CD74 and CEACAM6

The siRNAs for CD74 (sc-35023, Santa Cruz Biotechnology, Santa Cruz, Calif.) and CEACAM6 [sense strand 5'-CCGGACAGUUCCAUGUAUAdTdT-3' (SEQ ID NO:132)], are obtained from commercial sources. Sense and antisense siRNAs are dissolved in 30 mM HEPES buffer to a final concentration of 20 µM, heated to 90° C. for 1 min and incubated at 37° C. for 60 min to form duplex siRNA. The duplex siRNA is mixed with E1-L-thP1 and incubated with BxPC-3 (CEACAM6-siRNA) and Capan2 (CD74-siRNA) cells. After 24 h, the changes in the levels of mRNA for the corresponding proteins are determined by real time quantitative PCR analysis. The levels CD74 and CEACAM6 proteins are determined by Western blot analysis and immunohistochemistry. Controls include nonspecific siRNA and the non-targeting DNL complex 20-L-thP1, which contains a humanized anti-CD20 antibody (hA20).

The effects of reduced expression of CD74 and CEACAM6 on the growth of pancreatic cancer cells is determined using the clonogenic assay. About 1×10³BxPC-3 cells are plated and treated with E1-L-thP1 carrying CEACAM6-siRNA. Media is changed every 3-4 days and after 14 days colonies are fixed with 4% para-formaldehyde solution, stained with 0.5% trypan blue and counted. Similar experiments are performed for Capan2 cells using E1-L-thP1 carrying CD74-siRNA. The effect of E1-L-thP1 carrying both CEACAM6- and CD74-siRNAs on inhibiting the growth of BxPC-3 and Capan2 cells is determined. Cell proliferation by the MTS assay is performed.

Two xenograft models are established in female athymic nu/nu mice (5 weeks of age, weighing 18-20 g). The subcutaneous model has BxPC-3 (ATCC No. CRL-1687) and Capan2 (ATCC No. HTB-80) implanted in opposite flanks of each animal with treatment initiated once tumors reach 50 mm³. The orthotopic model bears only BxPC-3 cells and treatment is started 2 weeks after implantation.

For the subcutaneous model, the efficacy of E1-L-thP1 to deliver a mixture of CEACAM6- and CD74-siRNAs is assessed and compared to that of E1-L-thP1 to deliver CEACAM6-, CD74-, or control siRNA individually. Additional controls are saline and the use of 20-L-thP1 instead of E1-L-thP1 to deliver the specific and control siRNAs. The dosage, schedule, and administration are 150 µg/kg based on siRNA, twice weekly for 6 weeks, and via tail vein injection (Table 11). Cells are expanded in tissue culture, harvested with Trypsin/EDTA, and re-suspended with matrigel (1:1) to deliver 5×10⁶ cells in 300 µL.

Animals are monitored daily for signs of toxicity and weighed twice weekly. Tumor dimensions are measured weekly and tumor volumes calculated.

The orthotopic model is set up as follows. Briefly, nude mice are anesthetized and a left lateral abdominal incision is made. The spleen and attached pancreas are exteriorized with forceps. Then 50 µL of a BxPC-3 cell suspension (2×10⁶ cells) is injected into the pancreas. The spleen and pancreas are placed back into the abdominal cavity and the incision closed. Therapy begins two weeks after implantation. Mice are treated systemically with CEACAM6- or control siRNA bound to E1-L-thP1 or 20-L-thP1 with the same dosing schedule and route as the subcutaneous model. Animals are monitored daily and weighed weekly.

TABLE 11

| Group | (N) | Treatment | Dose/Schedule |
|---|---|---|---|
| Specific Therapy | | | |
| 1 | 12 | E1-L-thP1-CEACAM6-siRNA | 150 µg/kg i.v. (twice weekly × 6) |
| 2 | 12 | E1-L-thP1-CD74-siRNA | 150 µg/kg i.v. (twice weekly × 6) |
| 3 | 12 | E1-L-thP1-CEACAM6-siRNA + E1-L-thP1-CD74-siRNA | 150 µg/kg each i.v. (twice weekly × 6) |
| Controls | | | |
| 4 | 12 | Saline | 100 µL i.v. (twice weekly × 6) |
| 5 | 12 | 20-L-thP1-CEACAM6-siRNA | 150 µg/kg i.v. (twice weekly × 6) |
| 6 | 12 | 20-L-thP1-CD74-siRNA | 150 µg/kg i.v. (twice weekly × 6) |
| 7 | 12 | E1-L-thP1-control-siRNA | 150 µg/kg each i.v. (twice weekly × 6) |
| 8 | 12 | 20-L-thP1-control-siRNA | 150 µg/kg each i.v. (twice weekly × 6) |

The results of the study show that both CEACAM6 and CD74 siRNA are internalized into pancreatic cancer cells by the E1-L-thP1 DNL construct and induce apoptosis of pancreatic cancer, while the control DNL construct with non-targeting anti-CD20 antibody is ineffective to induce siRNA uptake or cancer cell death.

Example 36

Ribonuclease Based DNL Immunotoxins Comprising Quadruple Ranpirnase (Rap) Conjugated to B-Cell Lymphoma-Targeting Antibodies We applied the DNL method to generate a novel class of immunotoxins, each of which comprises four copies of Rap site-specifically linked to a bivalent IgG. We combined a recombinant Rap-DDD module, produced in *E. coli*, with recombinant, humanized IgG-AD modules, which were produced in myeloma cells and targeted B-cell lymphomas and leukemias via binding to CD20 (hA20, veltuzumab), CD22 (hLL2, epratuzumab) or HLA-DR (hL243, IMMU-114), to generate 20-Rap, 22-Rap and C2-Rap, respectively. For each construct, a dimer of Rap was covalently tethered to the C-terminus of each heavy chain of the respective IgG. A control construct, 14-Rap, was made similarly, using labetuzumab (hMN-14), that binds to an antigen (CEACAM5) not expressed on B-cell lymphomas/leukemias.

Rap-DDD2
(SEQ ID NO: 133)
<u>pQDWLTFQKKHITNTRDVDCDNIMSTNLFHCKDKNTFIYSRPEPVKAICK</u>

<u>GIIASKNVLTTSEFYLSDCNVTSRPCKYKLKKSTNKFCVTCENQAPVHFV</u>

<u>GVGSC</u>*GGGGSLE*CGHIQIPPGLTELLQGYTVEVLRQQPPDLVEFAVEYFT

RLREARAVEHHHHHH

The deduced amino acid sequence of secreted Rap-DDD2 is shown above (SEQ ID NO:133). Rap, underlined; linker, italics; DDD2, bold; pQ, amino-terminal glutamine converted to pyroglutamate. Rap-DDD2 was produced in *E. coli* as inclusion bodies, which were purified by IMAC under denaturing conditions, refolded and then dialyzed into PBS before purification by Q-Sepharose anion exchange chromatography. SDS-PAGE under reducing conditions resolved a protein band with a Mr appropriate for Rap-DDD2 (18.6 kDa) (not shown). The final yield of purified Rap-DDD2 was 10 mg/L of culture.

The DNL method was employed to rapidly generate a panel of IgG-Rap conjugates. The IgG-AD modules were expressed in myeloma cells and purified from the culture supernatant using Protein A affinity chromatography. The Rap-DDD2 module was produced and mixed with IgG-AD2 to form a DNL complex. Since the CH3-AD2-IgG modules possess two AD2 peptides and each can tether a Rap dimer, the resulting IgG-Rap DNL construct comprises four Rap groups and one IgG. IgG-Rap is formed nearly quantitatively from the constituent modules and purified to near homogeneity with Protein A.

Prior to the DNL reaction, the CH3-AD2-IgG exists as both a monomer, and a disulfide-linked dimer (not shown). Under non-reducing conditions, the IgG-Rap resolves as a cluster of high molecular weight bands of the expected size between those for monomeric and dimeric CH3-AD2-IgG (not shown). Reducing conditions, which reduces the conjugates to their constituent polypeptides, shows the purity of the IgG-Rap and the consistency of the DNL method, as only bands representing heavy-chain-AD2 (HC-AD2), kappa light chain and Rap-DDD2 were visualized (not shown).

Reversed phase HPLC analysis of 22-Rap (not shown) resolved a single protein peak at 9.10 min eluting between the two peaks of CH3-AD2-IgG-hLL2, representing the monomeric (7.55 min) and the dimeric (8.00 min) forms. The Rap-DDD2 module was isolated as a mixture of dimer and tetramer (reduced to dimer during DNL), which were eluted at 9.30 and 9.55 min, respectively (not shown).

LC/MS analysis of 22-Rap was accomplished by coupling reversed phase HPLC using a C8 column with ESI-TOF mass spectrometry (not shown). The spectrum of unmodified 22-Rap identifies two major species, having either two G0F (G0F/G0F) or one G0F plus one G1F (G0F/G1F) N-linked glycans, in addition to some minor glycoforms (not shown). Enzymatic deglycosylation resulted in a single deconvoluted mass consistent with the calculated mass of 22-Rap (not shown). The resulting spectrum following reduction with TCEP identified the heavy chain-AD2 polypeptide modified with an N-linked glycan of the G0F or G1F structure as well as additional minor forms (not shown). Each of the three subunit polypeptides comprising 22-Rap were identified in the deconvoluted spectrum of the reduced and deglycosylated sample (not shown). The results confirm that both the Rap-DDD2 and HC-AD2 polypeptides have an amino terminal glutamine that is converted to pyroglutamate (pQ); therefore, 22-Rap has 6 of its 8 constituent polypeptides modified by pQ.

In vitro cytotoxicity was evaluated in three NHL cell lines. Each cell line expresses CD20 at a considerably higher surface density compared to CD22; however, the internalization rate for hLL2 (anti-CD22) is much faster than hA20 (anti-CD20). 14-Rap shares the same structure as 22-Rap and 20-Rap, but its antigen (CEACAM5) is not expressed by the NHL cells. In FIG. 14, Left panel: Cells were treated continuously with IgG-Rap as single agents or with combinations of the parental MAbs plus rRap. Both 20-Rap and 22-Rap killed each cell line at concentrations above 1 nM, indicating that their action is cytotoxic as opposed to merely cytostatic. 20-Rap was the most potent IgG-Rap, suggesting that antigen density may be more important than internalization rate. Similar results were obtained for Daudi and Ramos, where 20-Rap (EC50-0.1 nM) was 3-6-fold more potent than 22-Rap. The rituximab-resistant mantle cell lymphoma line, Jeko-1, exhibits increased CD20 but decreased CD22, compared to Daudi and Ramos. Importantly, 20-Rap exhibited very potent cytotoxicity ($EC_{50}$~20 pM) in Jeko-1, which was 25-fold more potent than 22-Rap.

As shown in FIG. 14. Right panel: Expectedly, washing the cells after 1-h treatment significantly decreased the cytotoxicity (~50-fold) of each agent. Again, 20-Rap was the most potent, suggesting that its slower internalization rate is not limiting. 14-Rap shows increased cytotoxicity compared to rRap (in combination with MAbs), indicating that the quadruple Rap structure of the IgG-Rap may enhance its internalization. Washing after the 1-h incubation reduced the cytotoxicity of 14-Rap more than the targeting 22-Rap and 20-Rap.

IgG-Rap was evaluated with three ALL cell lines (FIG. 15). The relative antigen density was similar among the three lines, with HLA-DR>>CD22>CD20. None of the parental MAbs, either alone or combined with rRap, were cytotoxic in these assays. However, the non-targeting 14-Rap showed some activity, similar to the results with NHL lines. For each cell line, C2-Rap, which targets the most abundant antigen (HLA-DR), gave the most potent response, which was ~50-fold greater than 22-Rap. For the ALL lines, which have very low CD20 antigen density, 20-Rap showed modest cytotoxicity, which was similar to that of the non-targeting 14-Rap. This is in contrast to the results for the NHL lines, which have high CD20 density and were most responsive to 20-Rap. Thus, the efficacy of IgG-Rap correlates with the relative abundance of the targeted antigen.

The DNL method provides a modular approach to efficiently tether multiple cytotoxins onto a targeting antibody, resulting in novel immunotoxins that are expected to show higher in vivo potency due to improved pharmacokinetics and targeting specificity. LC/MS, RP-HPLC and SDS-PAGE demonstrated the homogeneity and purity of IgG-Rap. Targeting Rap with a MAb to a cell surface antigen enhanced its tumor-specific cytotoxicity. Antigen density and internalization rate are both critical factors for the observed in vitro potency of IgG-Rap. In vitro results show that CD20-, CD22-, or HLA-DR-targeted IgG-Rap have potent biologic activity for therapy of B-cell lymphomas and leukemias.

Example 37

High Potency of a Rap-Anti-Trop-2 IgG DNL Construct Against Carcinomas

Using the same techniques described the Example above, an E1-Rap DNL construct, comprising hRS7-IgG-Ad2 (anti-Trop-2) linked to four copies of Rap-DDD2 was produced and showed potent in vitro growth inhibitory properties against a variety of carcinoma cell lines (not shown). In breast (MDA-MB-468), cervical (ME-180), and pancreatic (BxPC-3 and Capan-1) tumor lines, all of which express high levels of Trop-2, E1-Rap was very potent, showing $EC_{50}$ in the subnanomolar range (5 to 890 pM), which was 1,000- to 100,00-fold higher than untargeted Rap or the combination of Rap and hRS7. In cell lines expressing moderate levels of Trop-2, such as the three prostate cancer lines (PC-3, DU 145, and LNCaP), E1-Rap was less potent, but still showed $EC_{50}$ in the nanomolar range (1 to 890 nM). The cell binding data obtained for these solid cancer cell lines suggest that the sensitivity of a cell line to E1-Rap appears to correlate with its Trop-2 expression on the cell surface. No toxicity was observed for E1-Rap in the prostate cancer line, 22Rv1, which fails to bind hRS7. These results show the efficacy of E1-Rap as a new therapeutic for Trop-2-positive solid tumors, including breast, colon, stomach, lung, ovarian, endometrial, cervical, pancreatic, and prostatic carcinomas.

Example 38

$^{18}$F-Labeling of DNL Constructs for PET Imaging

The DNL constructs described herein may be of use for detection, diagnosis and imaging as well as for therapy. In certain preferred embodiments, the imaging may involve PET scanning using $^{18}$F labeled constructs as disclosed below.

Production and Use of a Serum-Stable $^{18}$F-Labeled Peptide IMP449

```
IMP449
                                        (SEQ ID NO: 134)
NOTA-ITC benzyl-D-Ala-D-Lys(HSG)-D-Tyr-D-Lys(HSG)-
NH₂
```

The peptide, IMP448 D-Ala-D-Lys(HSG)-D-Tyr-D-Lys(HSG)-NH$_2$ (SEQ ID NO:135) was made on Sieber Amide resin by adding the following amino acids to the resin in the order shown: Aloc-D-Lys(Fmoc)-OH, Trt-HSG-OH, the Aloc was cleaved, Fmoc-D-Tyr(But)-OH, Aloc-D-Lys(Fmoc)-OH, Trt-HSG-OH, the Aloe was cleaved, Fmoc-D-Ala-OH with final Fmoc cleavage to make the desired peptide. The peptide was then cleaved from the resin and purified by HPLC to produce IMP448, which was then coupled to ITC-benzyl NOTA.

IMP448 (0.0757 g, 7.5×10$^{-5}$ mol) was mixed with 0.0509 g (9.09×10$^{-5}$ mol) ITC benzyl NOTA and dissolved in 1 mL water. Potassium carbonate anhydrous (0.2171 g) was then slowly added to the stirred peptide/NOTA solution. The reaction solution was pH 10.6 after the addition of all the carbonate. The reaction was allowed to stir at room temperature overnight. The reaction was carefully quenched with 1M HCl after 14 hr and purified by HPLC to obtain 48 mg of IMP449.

In Vivo Studies With TF10 DNL Construct and $^{18}$F-Labeled Peptide $^{18}$F-labeled IMP449 was prepared as follows. The $^{18}$F, 54.7 mCi in ~0.5 mL was mixed with 3 µL 2 mM Al in 0.1M NaOAc pH 4 buffer. After 3 mM 10 µL of 0.05 M IMP449 in 0.5 M pH 4 NaOAc buffer was added and the reaction was heated in a 96° C. heating block for 15 min. The crude labeled peptide was then purified by HPLC on a C$_{18}$ column. The HPLC purified peptide sample was further processed by diluting the fractions of interest two fold in water and placing the solution in the barrel of a 1 cc WATERS® HLB column. The cartridge was eluted with 3×1 mL water to remove acetonitrile and TFA followed by 400 µL 1:1 EtOH/H$_2$O to elute the $^{18}$F-labeled peptide. The purified [Al$^{18}$F] IMP449 eluted as a single peak on an analytical HPLC C$_{18}$ column (not shown).

Taconic nude mice bearing the four slow-growing sc CaPan1 xenografts were used for in vivo studies. Three of the mice were injected with TF10 (162 µg) followed with [Al$^{18}$F] IMP449 18 h later. TF 10 is a humanized bispecific antibody of use for tumor imaging studies, with divalent binding to the PAM-4 defined tumor antigen and monovalent binding to HSG (see, e.g., Gold et al., 2007, J. Clin. Oncol. 25(18S): 4564) and was prepared as described above. One mouse was injected with peptide alone. All of the mice were necropsied at 1 h post peptide injection. Tissues were counted immediately. Comparison of mean distributions showed substantially higher levels of $^{18}$F-labeled peptide localized in the tumor than in any normal tissues in the presence of tumor-targeting bispecific antibody.

Tissue uptake was similar in animals given the [Al$^{18}$F] IMP449 alone or in a pretargeting setting (not shown). Uptake in the human pancreatic cancer xenograft, CaPan1, at 1 h was increased 5-fold in the pretargeted animals as compared to the peptide alone (4.6±0.9% ID/g vs. 0.89% ID/g). Exceptional tumor/nontumor ratios were achieved at this time (e.g., tumor/blood and liver ratios were 23.4±2.0 and 23.5±2.8, respectively).

Example 39

In Vivo Imaging Using $^{18}$F Pretargeted DNL Constructs and Comparison with $^{18}$F[FDG]

In vivo imaging techniques using pretargeting with bispecific DNL constructs and labeled targeting peptides were used to successfully detect tumors of relatively small size. The $^{18}$F was purified on a WATERS® ACCELL™ Plus QMA Light cartridge. The $^{18}$F eluted with 0.4 M KHCO$_3$ was mixed with 3 µL 2 mM Al$^{3+}$ in a pH 4 acetate buffer. The Al$^{18}$F solution was then injected into the ascorbic acid IMP449 labeling vial and heated to 105° C. for 15 min. The reaction solution was cooled and mixed with 0.8 mL DI water. The reaction contents were loaded on a WATERS® OASIS® lcc HLB Column and eluted with 2×2004 1:1 EtOH/H$_2$O. TF2 was prepared as described above. TF2 binds divalently to carcinoembryonic antigen (CEA) and monovalently to the synthetic hapten, HSG (histamine-succinyl-glycine).

Biodistribution and MicroPET Imaging

Six-week-old NCr nu-m female nude mice were implanted s.c. with the human colonic cancer cell line, LS174T (ATCC, Manassas, Va.). When tumors were visibly established, pretargeted animals were injected intravenously with 162 mg (~1 nmole/0.1 mL) TF2 or TF10 (control non-targeting tri-Fab bsMAb), and then 16-18 h later, ~0.1 nmole of [Al$^{18}$F] IMP449 (84 µCi, 3.11 MBq/0.1 mL) was injected intravenously. Other non-pretargeted control animals received $^{18}$F alone (150 µCi, 5.5 MBq), Al$^{18}$F complex alone (150 mCi, 5.55 MBq), the [Al$^{18}$F] IMP449 peptide alone (84 µCi, 3.11 MBq), or [$^{18}$F]FDG (150 µCi, 5.55 MBq). $^{18}$F and [$^{18}$F]FDG were obtained on the day of use from IBA Molecular (Somerset, N.J.). Animals receiving [$^{18}$F]FDG were fasted overnight, but water was given ad libitum.

At 1.5 h after the radiotracer injection, animals were anesthetized, bled intracardially, and necropsied. Tissues were weighed and counted together with a standard dilution prepared from each of the respective products. Due to the short physical half-life of $^{18}$F, standards were interjected between each group of tissues from each animal. Uptake in the tissues is expressed as the counts per gram divided by the total injected activity to derive the percent-injected dose per gram (% ID/g).

Two types of imaging studies were performed. In one set, 3 nude mice bearing small LS174T subcutaneous tumors received either the pretargeted [Al$^{18}$F] IMP449, [Al$^{18}$F] IMP449 alone (not pretargeted), both at 135 µCi (5 MBq; 0.1 nmol), or [$^{18}$F]FDG (135 µCi, 5 MBq). At 2 h after the intravenous radiotracer injection, the animals were anesthetized with a mixture of O$_2$/N$_2$O and isoflurane (2%) and kept warm during the scan, performed on an INVEON® animal PET scanner (Siemens Preclinical Solutions, Knoxyille, Tenn.).

Representative coronal cross-sections (0.8 mm thick) in a plane located approximately in the center of the tumor were displayed, with intensities adjusted until pixel saturation occurred in any region of the body (excluding the bladder) and without background adjustment.

In a separate dynamic imaging study, a single LS174T-bearing nude mouse that was given the TF2 bsMAb 16 h earlier was anesthetized with a mixture of O$_2$/N$_2$O and isoflurane (2%), placed supine on the camera bed, and then injected intravenously with 219 µCi (8.1 MBq) [Al$^{18}$F] IMP449 (0.16 nmol). Data acquisition was immediately initiated over a period of 120 minutes. The scans were reconstructed using OSEM3D/MAP. For presentation, timeframes ending at 5, 15, 30, 60, 90, and 120 min were displayed for each cross-section (coronal, sagittal, and transverse). For sections containing tumor, at each interval the image intensity was adjusted until pixel saturation first occurred in the tumor. Image intensity was increased as required over time to maintain pixel saturation within the tumor. Coronal and sagittal cross-sections without tumor taken at the same interval were adjusted to the same intensity as the transverse section containing the tumor. Background activity was not adjusted.

Results

Several animals were imaged to analyze the biodistribution of [Al$^{18}$F] IMP449 alone or [Al$^{18}$F] IMP449 pretargeted with TF2, as well [$^{18}$F]FDG. Static images initiated at 2.0 h after the radioactivity was injected corroborated the previous tissue distribution data showing uptake almost exclusively in the kidneys (FIG. 16). A 21-mg tumor was easily visualized in the pretargeted animal, while the animal given the [Al$^{18}$F] IMP449 alone failed to localize the tumor, having only renal uptake. No evidence of bone accretion was observed, suggesting that the Al$^{18}$F was bound firmly to IMP449.

This was confirmed in another pretargeted animal that underwent a dynamic imaging study that monitored the distribution of the [Al$^{18}$F] IMP449 in 5-min intervals over 120 minutes (FIG. 17). Coronal and sagittal slices showed primarily cardiac, renal, and some hepatic uptake over the first 5 min, but heart and liver activity decreased substantially over the next 10 min, while the kidneys remained prominent throughout the study. There was no evidence of activity in the intestines or bone over the full 120-min scan. Uptake in a 35-mg LS174T tumor was first observed at 15 min, and by 30 min, the signal was very clearly delineated from background, with intense tumor activity being prominent during the entire 120-min scanning.

In comparison, static images from an animal given [$^{18}$F] FDG showed the expected pattern of radioactivity in the bone, heart muscle, and brain observed previously (McBride et al., 2006, J. Nucl. Med. 47:1678; Sharkey et al., 2008, Radiology 246:497), with considerably more background activity in the body (FIG. 16). Tissue uptake measured in the 3 animals necropsied at the conclusion of the static imaging study confirmed much higher tissue $^{18}$F radioactivity in all tissues (not shown). While tumor uptake with [$^{18}$F]FDG was higher in this animal than in the pretargeted one, tumor/blood ratios were more favorable for pretargeting; and with much less residual activity in the body, tumor visualization was enhanced by pretargeting.

This Example describes a direct, facile, and rapid method of binding $^{18}$F to various compounds via an aluminum conjugate. The [Al$^{18}$F] peptide was stable in vitro and in vivo when bound by a NOTA-based chelate. Yields were within the range found with conventional $^{18}$F labeling procedures. These results further demonstrate the feasibility of PET imaging using metal $^{18}$F-chelates pretargeted with DNL constructs.

Example 40

Production and Use of a DNL Construct Comprising Two Different Antibody Moieties and a Cytokine In certain embodiments, the trimeric DNL constructs may comprise three different effector moieties, for example two different antibody moieties and a cytokine moiety. As discussed above, 20-2b, a monospecific immunocytokine generated by the dock-and-lock (DNL) method to comprise tetrameric IFN-α2b covalently linked to veltuzumab (anti-CD20) exhibited very potent anti-tumor activity in vitro and in human lymphoma xenografts. However, lymphomas and leukemias that express little or no CD20 are expected to be resistant to therapy with 20-2b. HLA-DR is expressed on many hematopoietic tumors and some solid cancers. A bispecific immunocytokine that could target IFN-α to both CD20 and HLA-DR might be a more effective therapeutic against a wide variety of hematopoietic malignancies, including those that express CD20, HLA-DR, or both. Since each component of the multifunctional complex (veltuzumab, anti-HLA-DR F(ab)$_2$, and IFN-α2b) has anti-tumor activity independently, we evaluated if the bispecific immunocytokine can potentially be even more potent than the monospecific immunocytokine, 20-2b.

We report here the generation and characterization of the first bispecific MAb-IFNα, designated 20-C$_2$-2b, which comprises two copies of IFN-α2b and a stabilized F(ab)$_2$ of hL243 (humanized anti-HLA-DR; IMMU-114) site-specifically linked to veltuzumab (humanized anti-CD20). In vitro, 20-C2-2b inhibited each of four lymphoma and eight myeloma cell lines, and was more effective than monospecific CD20-targeted MAb-IFNα or a mixture comprising the parental antibodies and IFNα in all but one (HLA-DR$^-$/CD20$^-$) myeloma line, suggesting that 20-C$_2$-2b should be useful in the treatment of various hematopoietic malignancies. The 20-C$_2$-2b displayed greater cytotoxicity against KMS12-BM (CD20$^+$/HLA-DR$^+$ myeloma) than monospecific MAb-IFNα that targets only HLA-DR or CD20, indicating that all three components in 20-C$_2$-2b can contribute to toxicity. Our findings indicate that a given cell's responsiveness to MAb-IFNα depends on its sensitivity to IFNα and the specific antibodies, as well as the expression and density of the targeted antigens.

Because 20-C$_2$-2b has antibody-dependent cellular cytotoxicity (ADCC), but not CDC, and can target both CD20 and HLA-DR, it is useful for therapy of a broad range of hematopoietic cancers that express either or both antigens. The bispecific immunocytokine appears to be particularly effective in the elimination of the putative cancer stem cells associated with myeloma, which are resistant to current therapy regimens and reportedly express CD20.

Antibodies and Cell Culture

The abbreviations used in the following discussion are: 20 (C$_H$3-AD2-IgG-v-mab, anti-CD20 IgG DNL module); C2 (C$_H$1-DDD2-Fab-hL243, anti-HLA-DR Fab$_2$ DNL module); 2b (dimeric IFNα2B-DDD2 DNL module); 734 (anti-inDTPA IgG DNL module used as non-targeting control). The following MAbs were provided by Immunomedics, Inc.: veltuzumab or v-mab (anti-CD20 IgG$_1$), hL243γ4p (Immu-114, anti-HLA-DR IgG$_4$), a murine anti-IFNα MAb, and rat anti-idiotype MAbs to v-mab (WR2) and hL243 (WT).

Sp/ESF cells, a cell line derived from Sp2/0 with superior growth properties were maintained in Hybridoma Serum-Free Media. The NHL and MM cells were grown in RPMI 1640 medium with 10% FBS, 1 mM sodium pyruvate, 10 mM L-glutamine, and 25 mM HEPES. Daudi, Ramos, Raji, Jeko-1, NCI-H929, and U266 human lymphoma cell lines were purchased from ATCC (Manassas, Va.). The sources of MM cell lines are as follows: KMS11, KMS12-PE, and KMS12-BM from Dr. Takemi Otsuki (Kawasaki Medical School, Okayama, Japan); CAG, OPM-6 and MM.1R from Dr. Joshua Epstein (University of Arkansas, Little Rock, Ak.), Dr. Kenji Oritani (Osaka University, Osaka, Japan) and Dr. Steven Rosen (Northwestern University, Chicago, Ill.), respectively. All cell lines were authenticated by the supplier, obtained within 6 months of their use and passaged less than 50 times. We did not re-authenticate the cell lines.

DNL Constructs

Monospecific MAb-IFNα (20-2b-2b, 734-2b-2b and $C_2$-2b-2b) and the bispecific HexAb (20-C2-C2) were generated by combination of an IgG-AD2-module with DDD2-modules using the DNL method, as described in the preceding Examples. The 734-2b-2b, which comprises tetrameric IFNα2b and MAb h734 [anti-Indium-DTPA IgG$_1$], was used as a non-targeting control MAb-IFNα.

The construction of the mammalian expression vector as well as the subsequent generation of the production clones and the purification of $C_H3$-AD2-IgG-v-mab are disclosed in the preceding Examples. The expressed recombinant fusion protein has the AD2 peptide linked to the carboxyl terminus of the $C_H3$ domain of v-mab via a 15 amino acid long flexible linker peptide. Co-expression of the heavy chain-AD2 and light chain polypeptides results in the formation of an IgG structure equipped with two AD2 peptides. The expression vector was transfected into Sp/ESF cells (an engineered cell line of Sp2/0) by electroporation. The pdHL2 vector contains the gene for dihydrofolate reductase, thus allowing clonal selection, as well as gene amplification with methotrexate (MTX). Stable clones were isolated from 96-well plates selected with media containing 0.2 µM MTX. Clones were screened for $C_H3$-AD2-IgG-vmab productivity via a sandwich ELISA. The module was produced in roller bottle culture with serum-free media.

The DDD-module, IFNα2b-DDD2, was generated as discussed above by recombinant fusion of the DDD2 peptide to the carboxyl terminus of human IFNα2b via an 18 amino acid long flexible linker peptide. As is the case for all DDD-modules, the expressed fusion protein spontaneously forms a stable homodimer.

The $C_H1$-DDD2-Fab-hL243 expression vector was generated from hL243-IgG-pdHL2 vector by excising the sequence for the $C_H1$-Hinge-$C_H2$-$C_H3$ domains with SacII and EagI restriction enzymes and replacing it with a 507 bp sequence encoding $C_H1$-DDD2, which was excised from the C-DDD2-hMN-14-pdHL2 expression vector with the same enzymes. Following transfection of $C_H1$-DDD2-Fab-hL243-pdHL2 into Sp/ESF cells by electroporation, stable, MTX-resistant clones were screened for productivity via a sandwich ELISA using 96-well microtiter plates coated with mouse anti-human kappa chain to capture the fusion protein, which was detected with horseradish peroxidase-conjugated goat anti-human Fab. The module was produced in roller bottle culture.

Roller bottle cultures in serum-free H—SFM media and fed-batch bioreactor production resulted in yields comparable to other IgG-AD2 modules and cytokine-DDD2 modules generated to date. $C_H3$-AD2-IgG-v-mab and IFNα2b-DDD2 were purified from the culture broths by affinity chromatography using MABSELECT™ (GE Healthcare) and HIS-SELECT® HF Nickel Affinity Gel (Sigma), respectively, as described previously (Rossi et al., Blood 2009, 114:3864-71). The culture broth containing the $C_H1$-DDD2-Fab-hL243 module was applied directly to KAPPASE-LECT® affinity gel (GE-Healthcare), which was washed to baseline with PBS and eluted with 0.1M Glycine, pH 2.5.

The purity of the DNL modules was assessed by SDS-PAGE and SE-HPLC (not shown). Analysis under non-reducing conditions showed that, prior to the DNL reaction, IFNα2b-DDD2 and $C_H1$-DDD2-Fab-hL243 exist as disulfide-linked dimers (not shown). This phenomenon, which is always seen with DDD-modules, is beneficial, as it protects the reactive sulfhydryl groups from irreversible oxidation. In comparison, $C_H3$-AD2-IgG-v-mab (not shown) exists as both a monomer and a disulfide-linked dimer, and is reduced to monomer during the DNL reaction. SE-HPLC analyses agreed with the non-reducing SDS-PAGE results, indicating monomeric species as well as dimeric modules that were converted to monomeric forms upon reduction (not shown). The sulfhydryl groups are protected in both forms by participation in disulfide bonds between AD2 cysteine residues. Reducing SDS-PAGE demonstrated that each module was purified to near homogeneity and identified the component polypeptides comprising each module (not shown). For $C_H3$-AD2-IgG-v-mab, heavy chain-AD2 and kappa light chains were identified. hL243-Fd-DDD2 and kappa light chain polypeptides were resolved for $C_H1$-DDD2-Fab-hL243 (not shown). One major and one minor band were resolved for IFNα2b-DDD2 (not shown), which were determined to be non-glycosylated and β-glycosylated species, respectively.

Generation of 20-$C_2$-2b by DNL

Three DNL modules ($C_H3$-AD2-IgG-v-mab, $C_H1$-DDD2-Fab-hL243, and IFN-α2b-DDD2) were combined in equimolar quantities to generate the bsMAb-IFNα, 20-$C_2$-2b. Following an overnight docking step under mild reducing conditions (1 mM reduced glutathione) at room temperature, oxidized glutathione was added (2 mM) to facilitate disulfide bond formation (locking). The 20-$C_2$-2b was purified to near homogeneity using three sequential affinity chromatography steps. Initially, the DNL mixture was purified with Protein A (MABSELECT™), which binds the $C_H3$-AD2-IgG-v-MAb group and eliminates un-reacted IFNα2b-DDD2 or $C_H1$-DDD2-Fab-hL243. The Protein A-bound material was further purified by IMAC using HIS-SELECT® HF Nickel Affinity Gel, which binds specifically to the IFNα2b-DDD2 moiety and eliminates any constructs lacking this group. The final process step, using an hL243-anti-idiotype affinity gel removed any molecules lacking $C_H1$-DDD2-Fab-hL243.

The skilled artisan will realize that affinity chromatography may be used to purify DNL complexes comprising any combination of effector moieties, so long as ligands for each of the three effector moieties can be obtained and attached to the column material. The selected DNL construct is the one that binds to each of three columns containing the ligand for each of the three effector moieties and can be eluted after washing to remove unbound complexes.

The following Example is representative of several similar preparations of 20-$C_2$-2b. Equimolar amounts of $C_H3$-AD2-IgG-v-mab (15 mg), $C_H1$-DDD2-Fab-hL243 (12 mg), and IFN-α2b-DDD2 (5 mg) were combined in 30-mL reaction volume and 1 mM reduced glutathione was added to the solution. Following 16 h at room temperature, 2 mM oxidized glutathione was added to the mixture, which was held at room temperature for an additional 6 h. The reaction mixture was applied to a 5-mL Protein A affinity column, which was washed to baseline with PBS and eluted with 0.1M Glycine, pH 2.5. The eluate, which contained ~20 mg protein, was neutralized with 3 M Tris-HCl, pH 8.6 and dialyzed into HIS-SELECT® binding buffer (10 mM imidazole, 300 mM NaCl, 50 mM NaH$_2$PO$_4$, pH 8.0) prior to application to a 5-mL HIS-SELECT® IMAC column. The column was washed to baseline with binding buffer and eluted with 250 mM imidazole, 150 mM NaCl, 50 mM NaH$_2$PO$_4$, pH 8.0.

The IMAC eluate, which contained ~11.5 mg of protein, was applied directly to a WP (anti-hL243) affinity column, which was washed to baseline with PBS and eluted with 0.1M glycine, pH 2.5. The process resulted in 7 mg of highly purified 20-$C_2$-2b. This was approximately 44% of the theoretical yield of 20-$C_2$-2b, which is 50% of the total starting material (16 mg in this example) with 25% each of 20-2b-2b and 20-C2-C2 produced as side products.

Analytical Methods

Immunoreactivity was assessed by mixing excess WT, anti-IFNα, or WR2 with 20-$C_2$-2b prior to analysis of the resulting immune complex by SE-HPLC. SDS-PAGE was performed under reducing and non-reducing conditions using 12% and 4-20% gradient Tris-glycine gels (Invitrogen, Gaithersburg, Md.), respectively.

Electrospray ionization time of flight (ESI-TOF) liquid chromatography/mass spectrometry (LC/MS) was performed with a 1200-series HPLC coupled with a 6210 TOF MS (Agilent Technologies, Santa Clara, Calif.). The 20-$C_2$-2b was reduced with 10 mM Tris(2-carboxyethyl)phosphine at 60° C. for 30 min and resolved by reversed phase HPLC (RP-HPLC). For the TOF MS, the capillary and fragmentor voltages were set to 5500 and 200 V, respectively.

IFNα2b specific activities were determined using the ILITE™ Human Interferon Alpha Cell-Based Assay Kit (PBL Interferon Source, Piscataway, N.J.). Peginterferon alfa-2b (Schering Corp) was used as a positive control.

Cell Binding and Apoptosis

Cell binding and apoptosis were assessed by flow cytometry using a GUAVA® PCA and the reagents, software and suggested protocols for GUAVA® Express and GUAVA® Nexin, respectively (Millipore, Billerica, Mass.). For binding assays, live cells were incubated for 1 h at 4° C. with MAbs or MAb-IFNα diluted in 1% BSA-PBS. Cells were pelleted and washed twice with 1% BSA-PBS before incubation for 1 h at 4° C. with 2 μg/mL PE-conjugated mouse-anti human IgG-Fc (Southern Biotech, Birmingham, Ala.). After three washes, binding was measured by flow cytometry. For apoptosis assays, cells ($5\times10^5$/mL) were incubated with the indicated MAb or MAb-IFNα in 24-well plates for 48 h before quantification of the % annexin-V-positive cells.

In-Vitro Cytotoxicity

Cells were seeded in 48-well plates (300 μL/well) at predetermined optimal initial densities ($1\text{-}2.5\times10^5$ cells/mL) in the presence of increasing concentrations of the indicated agents and incubated at 37° C. until the density of untreated cells increased ≥10-fold (4-7 days). Relative viable cell densities at the end of the assay were determined using a CellTiter 96 Cell Proliferation Assay (Promega, Madison, Wis.).

Ex-Vivo Depletion of Daudi from Whole Blood

Blood specimens were collected under a protocol approved by the New England Institutional Review Board (Wellesley, Mass.). Daudi ($5\times10^4$) cells were mixed with heparinized whole blood (150 μL) from healthy volunteers and incubated with MAbs or MAb-IFNα at 1 nM for 2 days at 37° C. and 5% $CO_2$. Cells were stained with FITC-anti-CD19, FITC-anti-CD14, APC-anti-CD3 or APC-mouse $IgG_1$ isotype control MAb (BD Biosciences, San Jose, Calif.) and analyzed by flow cytometry using a FACSCALIBUR® (BD Biosciences). Daudi cells are CD19+ and in the monocyte gate. Normal B and T cells are CD19+ and CD3+ cells, respectively, in the lymphocyte gate. Monocytes are CD14+ cells in the monocyte gate.

Generation and Characterization of 20-$C_2$-2b

The bispecific MAb-IFNα was generated by combining the IgG-AD2 module, $C_H3$-AD2-IgG-v-mab, with two different dimeric DDD-modules, $C_H1$-DDD2-Fab-hL243 and IFNα2b-DDD2. Due to the random association of either DDD-module with the two AD2 groups, two side-products, 20-C2-C2 and 20-2b-2b are expected to form, in addition to 20-$C_2$-2b.

Non-reducing SDS-PAGE (not shown) resolved 20-$C_2$-2b (~305 kDa) as a cluster of bands positioned between those of 20-C2-C2 (~365 kDa) and 20-2b-2b (255 kDa). Reducing SDS-PAGE resolved the five polypeptides (v-mab HC-AD2, hL243 Fd-DDD2, IFNα2b-DDD2 and co-migrating v-mab and hL243 kappa light chains) comprising 20-$C_2$-2b (not shown). IFNα2b-DDD2 and hL243 Fd-DDD2 are absent in 20-C2-C2 and 20-2b-2b. MABSELECT™ binds to all three of the major species produced in the DNL reaction, but removes any excess IFNα2b-DDD2 and $C_H1$-DDD2-Fab-hL243. The HIS-SELECT® unbound fraction contained mostly 20-C2-C2 (not shown). The unbound fraction from WT affinity chromatography comprised 20-2b-2b (not shown). Each of the samples was subjected to SE-HPLC and immunoreactivity analyses, which corroborated the results and conclusions of the SDS-PAGE analysis.

Following reduction of 20-$C_2$-2b, its five component polypeptides were resolved by RP-HPLC and individual ESI-TOF deconvoluted mass spectra were generated for each peak (not shown). Native, but not bacterially-expressed recombinant IFNα2, is O-glycosylated at Thr-106 (Adolf et al., Biochem J 1991; 276 (Pt 2):511-8). We determined that ~15% of the polypeptides comprising the IFNα2b-DDD2 module are O-glycosylated and can be resolved from the non-glycosylated polypeptides by RP-HPLC and SDS-PAGE (not shown). LC/MS analysis of 20-C2-2b identified both the O-glycosylated and non-glycosylated species of IFNα2b-DDD2 with mass accuracies of 15 ppm and 2 ppm, respectively (not shown). The observed mass of the O-glycosylated form indicates an O-linked glycan having the structure NeuGc-NeuGc-Gal-Ga1NAc, which was also predicted (<1 ppm) for 20-2b-2b (not shown). LC/MS identified both v-mab and hL243 kappa chains as well as hL243-Fd-DDD2 (not shown) as single, unmodified species, with observed masses matching the calculated ones (<35 ppm). Two major glycoforms of v-mab HC-AD2 were identified as having masses of 53,714.73 (70%) and 53,877.33 (30%), indicating G0F and G1F N-glycans, respectively, which are typically associated with IgG (not shown). The analysis also confirmed that the amino terminus of the HC-AD2 is modified to pyroglutamate, as predicted for polypeptides having an amino terminal glutamine.

SE-HPLC analysis of 20-$C_2$-2b resolved a predominant protein peak with a retention time (6.7 min) consistent with its calculated mass and between those of the larger 20-C2-C2 (6.6 min) and smaller 20-2b-2b (6.85 min), as well as some higher molecular weight peaks that likely represent non-covalent dimers formed via self-association of IFNα2b (not shown).

Immunoreactivity assays demonstrated the homogeneity of 20-$C_2$-2b with each molecule containing the three functional groups (not shown). Incubation of 20-$C_2$-2b with an excess of antibodies to any of the three constituent modules resulted in quantitative formation of high molecular weight immune complexes and the disappearance of the 20-$C_2$-2b peak. The HIS-SELECT® and WT affinity unbound fractions were not immunoreactive with WT and anti-IFNα, respectively (not shown).

Cell Binding

The MAb-IFNα showed similar binding avidity to their parental MAbs (not shown). At sub-saturating concentrations, similar binding levels were observed for 20-$C_2$-2b and hL243γ4p. The antigen density of HLA-DR is ~6-fold greater than CD20 in these cells, allowing more binding of 20-$C_2$-2b compared to 20-2b-2b. Binding curves, which were analyzed using a one-site binding non-linear regression model, demonstrated that 20-$C_2$-2b can achieve a 4.7-fold higher $B_{max}$ compared to 20-2b-2b, with no significant difference observed between their binding affinities ($K_d$~4 nM) (not shown).

IFNα Biological Activity The specific activities for various MAb-IFNα were measured using a cell-based reporter gene assay and compared to peginterferon alfa-2b (not shown). Expectedly, the specific activity of 20-$C_2$-2b (2454 IU/pmol), which has two IFNα2b groups, was significantly lower than those of 20-2b-2b (4447 IU/pmol) or 734-2b-2b (3764 IU/pmol), yet greater than peginterferon alfa-2b (P<0.001). The difference between 20-2b-2b and 734-2b-2b was not significant. The specific activity among all agents varies minimally when normalized to IU/pmol of total IFNα. Based on these data, the specific activity of each IFNα2b group of the MAb-IFNα is approximately 30% of recombinant IFNα2b (4000 IU/pmol).

In-vitro cytotoxicity: NHL The results of in-vitro cytotoxicity assays with B-cell NHL are summarized in FIG. 18. The relative antigen densities of HLA-DR and CD20 for each cell line has been reported (Stein et al., 2010, Blood 115:5180-90). The targeting index (TI) represents the fold-increase in potency of a targeted MAb-IFNα compared to non-targeted MAb-IFNα (734-2b-2b), with the $EC_{50}$ values converted to total IFNα concentration (1-$EC_{50}$). Daudi is very sensitive to cell killing by IFNα2, as demonstrated with the non-targeting MAb-IFNα, 734-2b-2b (1-$EC_{50}$=14 pM). Targeting CD20 on Daudi with the monospecific 20-2b-2b (1-$EC_{50}$=0.4 pM) further enhanced the potency 25-fold (TI=25), consistent with previous results (Rossi et al., Blood 2009, 114:3864-71). The potency enhancement for the bispecific 20-$C_2$-2b (1-$EC_{50}$=0.08 pM; TI=125) was 5-fold greater than 20-2b-2b, which can be attributed to the added antigen density of HLA-DR and possibly its high-avidity tetravalent tumor binding. It is less likely that hL243-induced signaling contributes additional cytotoxicity at these low concentrations. The mixture of v-mab, hL243γ4p and 734-2b-2b (v-mab+hL243+734-2b) was equal to 734-2b-2b alone, supporting the conclusion that hL243-induced signaling does not contribute to the high TI of 20-$C_2$-2b.

Apoptosis was induced in Daudi with only 1 pM of any MAb-IFNα but not with 10 pM of v-mab or hL243γ4p (FIG. 19A). Treatment with 20-2b-2b or 20-$C_2$-2b resulted in significantly more apoptotic cells than 734-2b-2b or v-mab+hL243+734-2b (P<0.0005). There was no significant difference observed between 734-2b-2b and the mixture.

The 734-2b-2b had less effect on Raji (1-$EC_{50}$=32 nM) and Ramos (1-$EC_{50}$>80 nM), resulting in maximal inhibition ($I_{max}$) of only 62% and 35%, respectively. Under these conditions, hL243γ4p, but not v-mab (not shown), inhibited these Burkitt lymphoma lines. The observed enhancement in potency of 20-$C_2$-2b (TI=118) was >50-fold greater than 20-2b-2b (TI=2) for Raji, which has much greater HLA-DR antigen density than CD20. Unlike Daudi and Raji, the densities of HLA-DR and CD-20 are similar on Ramos, yet the TI for 20-$C_2$-2b was 15-fold greater than 20-2b-2b, indicating additive activities of hL243 and IFNα2b.

The v-mab+hL234+734-2b mixture was more potent than any of the single agents alone for Raji and Ramos. Targeting the IFNα2b was critical for achieving maximal potency. In each of the three Burkitt lymphoma lines, 20-$C_2$-2b was more effective than v-mab+hL234+734-2b, which comprises the same number of anti-CD20 and anti-HLA-DR Fabs and twice the amount (and activity) of IFNα2b.

The mantle cell lymphoma, Jeko-1, was considerably more responsive to hL243γ4p ($EC_{50}$=0.4 nM) and less sensitive to IFNα2b (minimal effect with 734-2b-2b). Any treatment comprising hL243 was superior to 20-2b-2b ($EC_{50}$=1 nM). The 20-$C_2$-2b exhibited two-fold enhanced potency compared to hL243γ4p or v-mab+hL243+734-2b. At 0.5 nM, hL243γ4p and 734-2b-2b induced similar levels of apoptosis and their effects are apparently additive, since treatment with v-mab+hL243+734-2b resulted in approximately twice the number of annexin-V-positive cells compared to either agent alone (FIG. 19A). Presumably, v-mab has little contribution in the mixture, since alone it had only a modest effect. Both 20-$C_2$-2b and the mixture were superior to 20-2b-2b (P<0.002), due to the action of hL243.

In-Vitro Cytotoxicity: Myeloma

Whereas the eight MM cell lines vary in HLA-DR levels (and only KMS12-BM expresses CD20) and sensitivity to IFNα2b (FIG. 20), all responded to 20-$C_2$-2b. Dose-response curves for each of the eight MM cell lines tested are shown in FIG. 21, and the results are summarized in FIG. 18. For example, five were highly responsive to IFNα2 (1-$EC_{50}$<1 nM for 734-2b-2b), but varied in HLA-DR antigen density. Of these, only CAG, which has high HLA-DR density, was inhibited by hL243γ4p (>1 nM), and showed an increased (additive) response to a mixture of hL243γ4p and 734-2b-2b (hL243+734-2b) at higher concentrations. The 20-$C_2$-2b (1-$EC_{50}$=10 pM) exhibited considerably enhanced potency (TI=55) for CAG.

Apoptosis of CAG was evident following treatment with hL243γ4p, 20-2b-2b, 734-2b-2b, or hL243+734-2b at 1 nM, but not at 0.1 or 0.01 nM (FIG. 19B). The 20-$C_2$-2b induced apoptosis even at 0.01 nM, and the level observed for 0.1 nM 20-$C_2$-2b was equal or higher than that resulting from any other treatment at 10-fold higher (1 nM) concentration.

Enhanced potency of 20-$C_2$-2b was evident, but lower, for OPM6 (TI=2), U266 (TI=7) and MM.1R (TI=10), which were each highly-IFNα-responsive but have lower HLA-DR density and were not inhibited by hL243γ4p. No increased potency was observed for 20-$C_2$-2b on NCI-H929, which was highly IFNα-responsive but is HLA-DW.

KMS12-BM has high HLA-DR and CD20 antigen densities, and surprisingly, was inhibited by 20-2b-2b (1-$EC_{50}$=31 nM) but not 734-2b-2b (1-$EC_{50}$>100 nM) or v-mab. KMS12-BM was more responsive to v-mab+hL243+734-2b ($EC_{50}$=3 nM) compared to hL243+734-2b ($EC_{50}$=0.7 nM), which in turn was superior to hL243γ4p alone ($EC_{50}$=3.5 nM). Each of these treatments resulted in strong induction of apoptosis, with the relative levels consistent with the in-vitro cytotoxicity results (FIG. 19C). Additionally, v-mab+hL243 induced more apoptosis than hL243γ4p alone, but less than v-mab+hL243+734-2b. These results suggest that for the HLA-DR$^+$/CD20$^+$ MM cells, the activity of all three components of 20-$C_2$-2b ($EC_{50}$=0.1 nM) can contribute to cytotoxicity when combined, even though two of them have virtually no effect when used alone.

Evaluation of two additional DNL constructs in KMS12-BM helped elucidate the enhanced potency of 20-$C_2$-2b. A MAb-IFNα designated $C_2$-2b-2b, which comprises hL243 IgG$_1$ and tetrameric IFNα2b (twice that of 20-$C_2$-2b) exhibited less potent cytotoxicity ($EC_{50}$=0.4 nM) and weaker apoptosis-induction compared to 20-$C_2$-2b, supporting a contribution of v-mab. More revealing was the finding that 20-C2-C2, a bispecific MAb comprising v-mab and four HLA-DR Fabs, showed high-level induction of apoptosis and >50-fold enhanced potency ($EC_{50}$=0.06 nM) compared to hL243γ4p, indicating that crosslinking of HLA-DR and CD20, which occurs with 20-$C_2$-2b, effectively induces cytotoxicity, perhaps via a unique signaling cascade. Although each construct was potent ($EC_{50}$<0.5 nM), 20-C2-C2 ($I_{max}$-67%) and $C_2$-2b-2b ($I_{max}$=70%) did not kill KMS12-BM as effectively as 20-$C_2$-2b ($I_{max}$-99%), supporting the requirement of all three components for achieving the maximal effect. That the v-mab+hL243+734-2b ($I_{max}$ 87%) mixture was the only other treatment resulting in >70% killing substantiates this hypothesis.

Together, these data demonstrate that antigen density and sensitivity to the actions of IFNα2b, as well as those of the targeting MAbs, are all important determinants of the in-vitro responsiveness of a particular cell line to the various MAb-IFNα. However, in-vivo tumor killing may be augmented by ADCC and the actions of immune effector cells, which can be stimulated by the high local concentration of IFNα2b.

Effector Functions and Stability in Human Serum

We previously reported that 20-2b-2b exhibited enhanced ADCC compared to its parent v-mab (Rossi et al., Blood 2009; 114:3864-71). By design, hL243γ4p has diminished ADCC (Stein et al., Blood 2006; 108:2736-44). However, 20-C2-C2 induced significantly (P=0.0091) greater ADCC compared to v-mab (not shown). Notably, 20-$C_2$-2b induced significantly greater ADCC than either 20-2b-2b (P=0.0040) or 20-C2-C2 (P=0.0115), indicating an enhancement of the effector function by the presence of IFNα2b. As was demonstrated previously for 20-2b-2b (Rossi et al., Blood 2009; 114:3864-71), 20-$C_2$-2b does not induce CDC in vitro (not shown).

Two different assays for stability of 20-$C_2$-2b in human serum gave very similar results, indicating a loss of ~3.5%/day with roughly 65% remaining after 11 days at 37° C. (not shown).

Ex-Vivo Depletion of NHL from Whole Human Blood

As shown in FIG. 22, Daudi cells were depleted from whole blood (ex vivo) more effectively by 20-$C_2$-2b (91%) compared to 20-2b-2b (69%), v-mab (49% depletion), hL243γ4p (46%) or 734-2b-2b (10%). Both targeted MAb-IFNα were less toxic to normal B cells compared to Daudi. Under these conditions, B cells were significantly depleted by 20-$C_2$-2b (57%) and hL243γ4p (41%), but not by v-mab, 734-2b, or 20-2b-2b. Monocytes were depleted by hL243γ4p (48%), 734-2b-2b (30%), and 20-2b-2b (21%), but not by v-mab. The 20-$C_2$-2b (98%) was highly toxic to monocytes. None of the agents had a significant effect on T cells. Statistical significance with P<0.001 was determined by Student's t-test for each of the differences in % depletion indicated above.

Discussion

We and others have reported that fusion proteins comprising CD20-targeting MAbs and IFNα are more effective against NHL compared to combinations of MAb and IFNα in xenograft and syngeneic mouse models, indicating that MAb-IFNα can overcome the toxicity and Pk limitations associated with IFNα (Rossi et al., Blood 2009; 114:3864-71; Xuan et al., Blood 2010; 115:2864-71). Although CD20 is an attractive candidate for targeted MAb-IFNα therapy of B-cell lymphoma, its expression is largely limited to malignancies of this lineage, with some individuals exhibiting low antigen density. Here we report the first bispecific immunocytokine, 20-$C_2$-2b, which specifically targets IFNα2b to both CD20 and HLA-DR, thus potentially expanding the hematopoietic tumor types amenable to this immunocytokine therapy.

Anti-HLA-DR MAbs efficiently induce apoptosis, which is mediated by direct signaling without the requirement of additional crosslinking, and are also potent inducers of ADCC and CDC (Stein et al., Blood 2006; 108:2736-44; Rech et al., Leuk Lymphoma 2006; 47:2147-54) Where ADCC may enhance therapeutic potential, CDC is largely responsible for the pathogenesis of the side effects associated with the MAb infusion (van der Kolk et al., Br J Haematol 2001; 115:807-11). The humanized anti-HLA-DR MAb, hL243γ4p, used as a control in this study was engineered for improved clinical safety by using the constant region of the human $IgG_4$ isotype, resulting in diminished ADCC and CDC. The 20-$C_2$-2b is unique among anti-HLA-DR MAbs in that it lacks CDC, similar to hL243γ4p, but has potent (enhanced) ADCC, making this agent an attractive candidate for immunotherapy.

In the ex-vivo setting, v-mab can deplete cells via signaling-induced apoptosis, ADCC, and CDC. MAb-IFNα can employ enhanced ADCC as well as both MAb- and IFNα2b-induced signaling, but not CDC; and hL243-$Y_4$p is limited to only direct signaling (Stein et al., Blood 2006; 108:2736-44). Although the full spectrum of IFNα-mediated activation of innate and adaptive immunity that might occur in vivo is not realized in this setting, it provides pharmacodynamic data. The 20-$C_2$-2b depleted lymphoma cells more effectively than normal B cells and had no effect on T cells. However, it did efficiently eliminate monocytes. Where v-mab had no effect on monocytes, depletion was observed following treatment with hL243α4p and MAb-IFNα, with 20-2b-2b and 734-2b-2b exhibiting similar toxicity. Therefore, the predictably higher potency of 20-$C_2$-2b is attributed to the combined actions of anti-HLA-DR and IFNα, which may be augmented by HLA-DR targeting. These data suggest that monocyte depletion may be a pharmacodynamic effect associated anti-HLA-DR as well as IFNα therapy; however, this side affect would likely be transient because the monocyte population should be repopulated from hematopoietic stem cells.

The four NHL and eight MM cell lines we studied encompass the naturally-occurring heterogeneity in expression and antigen density of HLA-DR and CD20, as well as responsiveness to the actions of IFNα, hL243 and v-mab, which all impact MAb-IFNα immunotherapy. Six and eight (of twelve lines) were inhibited ($I_{max}$>30%) to varying degrees by hL243γ4p and 734-2b-2b, respectively. The 20-$C_2$-2b potently inhibited ($EC_{50}$<1 nM) 11 of the 12 cell lines, with an $EC_{50}$≤0.01 nM for five. Even the least affected MM line (KMS11), which was not inhibited by 734-2b-2b, was responsive to 20-$C_2$-2b ($EC_{50}$=17 nM).

An enhancement in potency of 20-$C_2$-2b over 734-2b-2b was observed in all of the lines besides NCI-H929, which is HLA-DR$^-$/CD20$^-$. Higher levels of HLA-DR antigen density as well as responsiveness to hL243 correlated with a greater TI for 20-$C_2$-2b, demonstrating additive activities of IFNα and hL243, as well as the significance of targeting, even in vitro. The 20-C2-2b was superior to the mixture of v-mab+ hL243+734-2b in 10 of the lines, further highlighting the impact of tumor targeting, which will be considerably greater in vivo, as demonstrated previously for 20-2b-2b (Rossi et al., Blood 2009; 114:3864-71). Further, in-vivo-targeted MAb-IFNαc might elicit a potent anti-tumor immune response.

Whereas the vast majority of cells comprising primary MM specimens are non-clonogenic and have a plasma cell phenotype (CD138$^+$/CD19$^-$/CD20$^-$), putative MM cancer stem cells are CD138$^-$ and express B-cell surface antigens, including CD45, CD19, CD20, and CD22, reminiscent of memory B cells (Matsui et al., Blood 2004; 103:2332-6). Although a variety of clinical approaches have produced responses, MM remains largely incurable due to relapses thought to be mediated by cancer stem cells, which are resistant to the various therapies. The B-cell phenotype of the putative stem cells prompted clinical investigation with rituximab in MM. However, limited effects on outcome were realized (Treon et al., J Immunother 2002; 25:72-81).

The in vitro results with KMS12-BM are compelling, because it is CD20$^+$, similar to the proposed MM stem cells. The 20-$C_2$-2b exhibited potent cytotoxicity and robustly induced apoptosis of KMS12-BM. Even though non-targeted MAb-IFNα and v-mab were ineffective as single agents, they both apparently contribute to cytotoxicity when used in combination with hL243. The results also indicate that bispecific binding of CD20 and HLA-DR may induce an additional (potent) signal that further enhances toxicity to these cells and may sensitize them to IFNα.

MAb-IFNα produced by DNL exhibits comparable activity to recombinant IFNα. Recently, Xuan et al. reported that anti-CD20-IFNα fusion proteins made by traditional recombinant engineering showed a 300-fold reduction in IFNα activity (Xuan et al., Blood 2010; 115:2864-71). This is noteworthy in comparisons of similar Daudi xenograft studies, where a single 17 ng dose of 20-2b-2b significantly improved survival (Rossi et al., Blood 2009; 114:3864-71), compared to three 30 µg doses (>5000-fold more) used for recombinant anti-CD20-hIFNα (Xuan et al., Blood 2010; 115:2864-71). Studies using IFNα-secreting tumors demonstrated enhanced immune responses elicited by a localized concentration of IFNα (Ferrantini et al., Biochimie 2007; 89:884-93). Where this might also be achieved with highly active MAb-IFNα, the reduced activity of traditional recombinant MAb-IFNα may not efficiently recruit and stimulate an anti-tumor immune response, as was reported by Xuan et al. (Blood 2010; 115:2864-71)

The bispecific MAb-IFNα 20-$C_2$-2b is attractive for the treatment of NHL, because each of the three components is active against this disease. This study shows that 20-$C_2$-2b may also be useful for the therapy of MM and other hematopoietic malignancies.

The skilled artisan will realize that the approach described here to produce and use bispecific immunocytokine, or other DNL constructs comprising three different effector moieties, may be utilized with any combinations of antibodies, antibody fragments, cytokines or other effectors that may be incorporated into a DNL construct.

Example 41

DNL Vaccine Constructs for Cancer Therapy

The subject DNL constructs are of use for applications relating to vaccine formulations. In preferred embodiments, the vaccine DNL constructs comprise at least one antibody moiety, which targets the DNL complex to an antigen-presenting cell (APC), such as a dendritic cell (DC), and an antigenic protein or peptide. In certain embodiments, the antigenic protein or peptide is a xenoantigen, which is a homolog of a human antigenic protein or peptide from a non-human species. In alternative embodiments, the antigenic protein or peptide is derived from a pathogenic organism, such as a virus, bacterium, protozoan, mycoplasma, fungus or other pathogen.

Certain preferred embodiments relate to the design and generation of dendritic cell-based, in vivo antigen targeting vaccines for therapy of cancer, such as multiple myeloma. In more preferred embodiments, the effector moieties comprise a humanized anti-CD74 antibody and a tumor-associated xenoantigen, such as a CD20 xenoantigen. In most preferred embodiments, the anti-CD74 antibody is an hLL1 antibody. The DNL constructs are of use for preparation of pharmaceutical compositions, for generation of vaccines against cancers, such as multiple myeloma (MM), and for induction of an immune response against tumor antigen-expressing cells, such as CD20 positive cancer cells in patients with multiple myeloma or other CD20-expressing cancers. The skilled artisan will realize that the exemplary embodiment is not limiting and that the subject DNL vaccine constructs may comprise other xenoantigens and/or antibodies against other immune cell antigenic targets. A variety of antigens associated with dendritic cells are known in the art, including but not limited to CD209 (DC-SIGN), CD34, CD74, CD205, TLR 2 (toll-like receptor 2), TLR 4, TLR 7, TLR 9, BDCA-2, BDCA-3, BDCA-4, and HLA-DR.

Multiple myeloma (MM) is a hematological malignancy characterized by clonal proliferation of neoplastic plasma cells in the bone marrow. Although responsive to many chemotherapeutic agents, MM remains largely incurable and the majority of patients ultimately relapse, due to the existence of a minor population of MM cancer stem cells that survive standard or high-dose chemotherapy and are resistant to chemotherapeutic drugs (Reece et al., Leuk Lymphoma, 2008, 49:1470-85). This small number of MM cancer stem cells constitutes the minimal residual disease and causes relapse, eventually leading to the failure of all treatments. Thus, eradication of MM cancer stem cells may offer a long-term control or even cure of MM.

A small population of clonotypic B cells, that do not express the characteristic plasma cell surface antigen CD138 but do express the B cell antigen CD20, was identified from both MM cell lines and primary bone marrow of MM patients (Matsui et al., Blood 2004, 103:2332-6). This small population of cells is resistant to multiple clinical anti-myeloma drugs and is capable of clonogenic growth in vitro (Matsui et al., Blood 2004, 103:2332-6; Matsui et al., Cancer Res. 2008, 68:190-7) and in a 3-D culture model (Kirshner et al., Blood 2008, 112:2935-45), and is capable of differentiation into MM cells in vitro and in engrafted NOD/SCID mice during both primary and secondary transplantation (Matsui et al., Cancer Res. 2008, 68:190-7). It has been suggested that these $CD138^{neg}CD20^+$ cells represent the putative multiple myeloma cancer stem cells (Huff and Matsui, J Clin Oncol. 2008, 26:2895-900).

Like other cancer stem cells, MM cancer stem cells are refractory to multiple chemotherapeutic drugs and responsible for tumor re-growth and relapse (Huff and Matsui, J Clin Oncol. 2008, 26:2895-900; Yang and Chang, Cancer Invest. 2008, 26:741-55). Strategies and approaches that could selectively target and eradicate cancer stem cells, such as MM stem cells, are needed. Due to the multiple drug resistance in cancer stem cells, immunotherapy and vaccination may offer a potential modality to eradicate these cells, particularly after standard therapies and/or stem cell transplantation, the time when tumor load is greatly reduced.

Immunization with Xenoantigen as a Means for Breaking Immune Tolerance for Cancer Immunotherapy Many tumor-associated antigens (TAAs) represent tissue differentiation antigens which are not inherently immunogenic. T cells that recognize these TAAs/self-antigens with high avidity are either clonally deleted in the thymus or anergized in the periphery. However, immunization with xenoantigen has been shown to be capable of overcoming the immune tolerance against the homologous self-antigen. In a phase I clinical trial, 11 of 21 prostate cancer patients immunized with dendritic cells pulsed with recombinant mouse PAP developed type I T-cell proliferative responses to the homologous self-antigen, and 6 patients had clinical stabilization of their previously progressing prostate cancer (Fong et al., J. Immunol. 2001, 167(12):7150-6). These results demonstrate that xenoantigen immunization can break tolerance to a self-antigen in humans, resulting in a clinically significant antitumor effect.

CD20 as a Target for Immunotherapy and Vaccination Against MM

As stated above, CD20 is a hallmark of MM cancer stem cells. As a self-antigen which is expressed on normal B cells at most stages of differentiation, it is theoretically difficult to be targeted by vaccine strategies due to immune tolerance. However, successful vaccination has been achieved by a xenogeneic DNA vaccine against CD20 in a tumor challenge model of B-cell lymphoma. Although autoimmunity against B cells could be induced by a vaccine targeting CD20, it should not cause a large problem because the B cell pool is not a vital and critical tissue and can be replenished from its lineage progenitor. Based on these considerations, a therapeutic vaccine targeting CD20 would be effective in selective eradication of MM cancer stem cells.

Monoclonal Anti-CD20 Antibody as a Potential Modality for Eradication of MM Stem Cells The discovery of CD20+ MM progenitor cells has prompted several small clinical trials to test the efficacy of rituximab, an anti-CD20 monoclonal antibody, in MM patients. As reviewed by Kapoor et al. (*Br J. Haematol.* 2008, 141:135-48), anti-CD20 therapy with rituximab elicits a partial response in approximately 10% of CD20+ patients with multiple myeloma. In addition, there is preliminary evidence of disease stabilization in 50-57% of CD20+ patients for a period of 10-27 months (Kapoor et al., (Br J. Haematol. 2008, 141:135-48). Furthermore, a case report by Bergua et al. (Leukemia. 2008, 22:1082-3) where rituximab was used in combination with chemotherapy demonstrated no minimal residual disease found after treatment, either in immunophenotype, bone marrow aspiration or biopsy, and the CD20+ plasma cells disappeared. These results justify large scale clinical trials to establish the role of this strategy in the treatment of myeloma. The vaccine approach, due to its induction of CTL response, would be expected to supplement the monoclonal antibody therapy against CD20 MM stem cells.

In Vivo Targeting of Antigens to Dendritic Cells and Other Antigen-Presenting Cells as an Efficient Strategy for Vaccination and Breaking Immune Tolerance As the professional antigen-presenting cells, dendritic cells (DCs) play a pivotal role in orchestrating innate and adaptive immunity, and have been harnessed to create effective vaccines (Vulink et al., Adv Cancer Res. 2008, 99:363-407; O'Neill et al., Mol. Biotechnol. 2007, 36:131-41). In vivo targeting of antigens to DCs represents a promising approach for DC-based vaccination, as it can bypass the laborious and expensive ex vivo antigen loading and culturing, and facilitate large-scale application of DC-based immunotherapy (Tacken et al., Nat Rev Immunol. 2007, 7:790-802). More significantly, in vivo DC targeting vaccination is more efficient in eliciting anti-tumor immune response, and more effective in controlling tumor growth in animal models (Kretz-Rommel et al., J Immunother 2007, 30:715-726). In addition to DCs, B cells are another type of potent antigen-presenting cells capable of priming Th1/Th2 cells (Morris et al, J. Immunol. 1994, 152:3777-3785; Constant, J. Immunol. 1999, 162:5695-5703) and activating CD8 T cells via cross-presentation (Heit et al., J. Immunol. 2004, 172:1501-1507; Yan et al., Int Immunol. 2005, 17:869-773). It was recently reported that in vivo targeting of antigens to B cells breaks immune tolerance of MUC1 (Ding et al., Blood 2008, 112: 2817-25).

CD74 as a Potential Receptor for Targeting Vaccination

Some receptors expressed on DCs have been used as the targets for in vivo antigen targeting, such as the mannose receptor (He et al., J. Immunol. 2007, 178, 6259-6267; Ramakrishna et al., J. Immunol. 2004, 172, 2845-2852) CD205 (Bonifaz et al., J Exp Med. 2004, 199:815-24), DC-SIGN (Tacken et al., Blood 2005, 106:1278-85), and $LOX_1$ (Deineste et al., Immunity 2002, 17, 353-362), etc. CD74 is a type II integral membrane protein essential for proper MHC II folding and targeting of MHC 11-CD74 complex to the endosomes (Stein et al., Clin Cancer Res. 2007, 13:5556s-5563s; Matza et al., Trends Immunol. 2003, 24(5):264-8). CD74 expression is not restricted to DCs, but is found in almost all antigen-presenting cells (Freudenthal et al., Proc Natl Acad Sci USA. 1990, 87:7698-702; Clark et al., J. Immunol. 1992, 148(11):3327-35). The wide expression of CD74 in APCs may offer some advantages over sole expression in myeloid DCs, as targeting of antigens to other APCs like B cells has been reported to break immune tolerance (Ding et al., Blood 2008, 112:2817-25), and targeting to plasmacytoid DCs cross-presents antigens to naïve CD8 T cells. More importantly, CD74 is also expressed in follicular DCs (Clark et al., J. Immunol. 1992, 148(11):3327-35), a DC subset critical for antigen presentation to B cells (Tew et al., Immunol Rev. 1997, 156:39-52). This expression profile makes CD74 an excellent candidate for in vivo targeting vaccination.

Humanized Anti-CD74 Monoclonal Antibody hLL1 as a Novel Targeting Tool with Dock-and-Lock Technology Platform hLL1 is a humanized monoclonal antibody against human CD74 (Leung et al., Mol. Immunol. 1995, 32:1416-1427; Losman et al., Cancer 1997, 80:2660-2666; Stein et al., Blood 2004, 104:3705-11). hLL1, in the presence of cross-linking by a second antibody, exhibits cytotoxicity against B cell malignancies. The naked hLL1 is also capable of controlling tumor growth in a MM mouse model. However, our recent data demonstrate that hLL1, in the presence or absence of cross-linking, has no cytotoxicity against human monocyte-derived DCs. But, our preliminary data shows hLL1 could efficiently bind different subsets of blood DCs and B cells. It also could moderately induce DC maturation and polarize naïve T cell differentiation toward Th1 effector cells, suggesting it has some adjuvant activity and may be a good candidate for use as a targeting tool. This makes it feasible to construct a DNL-based tumor vaccine targeted to APCs through the DNL-carried hLL1 antibody.

Immunotherapy for Selective Elimination of Cancer Stem Cells

Cancer stem cells are capable of self-renewal, possess the ability for unlimited proliferation, and are resistant to multiple therapeutic approaches. A question is raised if cancer stem cells are sensitive to immunotherapy. In the case of leukemia, it was reported that CD8(+) minor histocompatibility antigen-specific cytotoxic T lymphocyte clones could eliminate human acute myeloid leukemia stem cells (Bonnet et al., Proc Natl Acad Sci U.S.A. 1999, 96:8639-8644). More recently, Rosinski et al. (Blood 2008, 111:4817-26) reported that DDX36-encoded H-Y epitope is expressed by leukemic stem cells and can be recognized by the DDX36-specific CTLs, which can prevent engraftment of human acute leukemia in NOD/SCID mice (Rosinski et al. Blood 2008, 111: 4817-26). Another report indicates that engraftment of mHA myeloid leukemia stem cells in NOD/SCID$\gamma c^{null}$ mice was completely inhibited by in vitro preincubation with the mHA-specific CTL clone (Kawase et al., Blood 2007, 110:1055-63). These results highlight the prospects that immunotherapy would be a potentially effective approach for selective elimination of cancer stem cells including MM stem cells, which would be required for achieving long-term control or even cure of this malignancy.

Example 42

Construction of mCD20-Anti-CD74 DNL Vaccine for MM Therapy

Generation of DDD2-mCD20(136-178) and Construction of DDD2-mCD20(136-178)-pdHL2

DDD2-mCD20(136-178)-pdHL2 is the expression vector for DDD2-mCD20(136-178), which comprises DDD2-linker-mCD20(136-178)-HHHHHH(HHHHHH disclosed as SEQ ID NO: 126). The extracellular domain of mouse CD20 (mCD20) is referred to as mCD20(136-178) (SEQ ID NO:137), comprising amino acid residues 136 to 178 of the murine CD20 sequence (SEQ ID NO:138):

```
mCD20(136-178)
                                            (SEQ ID NO: 137)
TLSHFLKMRRLELIQTSKPYVDIYDCEPSNSSEKNSPSTQYCN murine CD20
                                            (SEQ ID NO: 138)
MSGPFPAEPTKGPLAMQPAPKVNLKRTSSLVGPTQSFFMRESKALGAVQI

MNGLFHITLGGLLMIPTGVFAPICLSVWYPLWGGIMYIISGSLLAAAAEK

TSRKSLVKAKVIMSSLSLFAAISGIILSIMDILNMTLSHFLKMRRLELIQ

TSKPYVDIYDCEPSNSSEKNSPSTQYCNSIQSVFLGILSAMLISAFFQKL

VTAGIVENEWKRMCTRSKSNVVLLSAGEKNEQTIKMKEEIIELSGVSSQP

KNEEEIEIIPVQEEEEEEAEINFPAPPQEQESLPVENEIAP
```

The DNA segment comprising the nucleotide sequence of mCD20(136-178) flanked by BamHI and XhoI restriction sites is obtained by PCR using a full length murine CD20 cDNA clone as template and the two primers shown below:

```
Upstream primer: BamHI_mCD20 primer
                                            (SEQ ID NO: 139)
5'-GGATCCACACTTTCTCATTTTTTAAAAATG Downstream primer: XhoI mCD20 primer
                                            (SEQ ID NO: 140)
5'-CTCGAGGTTACAGTACTGTGTAGATGGGGA
```

The PCR amplimer (141 bp) is cloned into the PGEMT® vector. A DDD2-pdHL2 mammalian expression vector, for example, N-DDD2-hG-CSF-His-pdHL2, is prepared for ligation with the amplimer by digestion with XbaI and Bam HI restriction endonucleases. The mCD20-amplimer is excised from PGEMT® with XbaI and Bam HI and ligated into the DDD2-pdHL2 vector to generate the expression vector DDD2-mCD20(136-178)-pdHL2.

Transfection and Screening to Obtain Clones Expressing DDD2-mCD20(136-178)

The vector DDD2-mCD20(136-178) is linearized by digestion with SalI enzyme and stably transfected into SpESF myeloma cells by electroporation. A number of clones are found to have detectable levels of DDD2-mCD20(136-178) by ELISA, from which the best producing clone is selected and subsequently amplified with increasing methotrexate (MTX) concentrations from 0.1 to 0.8 µM over five weeks. At this stage, it is sub-cloned by limiting dilution and the highest producing sub-clone is expanded.

The clone is expanded to 34 roller bottles containing a total of 20 L of serum-free Hybridoma SFM with 0.8 µM MTX and allowed to reach terminal culture. The supernatant fluid is clarified by centrifugation and filtered (0.2 µM). The filtrate is diafiltered into 1× Binding buffer (10 mM imidazole, 0.5 M NaCl, 50 mM $NaH_2PO_4$, pH 7.5) and concentrated to 310 mL in preparation for purification by immobilized metal affinity chromatography (IMAC). The concentrate is loaded onto a 30-mL Ni-NTA column, which is washed with 500 mL of 0.02% Tween 20 in 1× binding buffer and then 290 mL of 30 mM imidazole, 0.02% Tween 20, 0.5 M NaCl, 50 mM $NaH_2PO_4$, pH 7.5. The product is eluted with 110 mL of 250 mM imidazole, 0.02% Tween 20, 150 mM NaCl, 50 mM $NaH_2PO_4$, pH 7.5. The purity of DDD2-mCD20(136-178) is assessed by SDS-PAGE under reducing conditions.

Generation of 74-mCD20 DNL Vaccine Comprising hLL1 IgG Linked to Four Copies of mCD20(136-178)

$C_{H3}$-AD2-IgG-hLL1 (anti-CD74) is produced as described in the Examples above. The construct comprises an AD2 moiety attached to the C-terminal end of each heavy chain of the hLL1 IgG. A DNL reaction is performed by mixing hLL1 IgG-AD2 and DDD2-mCD20(136-178) in PBS containing 1 mM reduced glutathione. On the next day oxidized glutathione is added to a final concentration of 2 mM and the reaction mixture is purified on a Protein A column 24 h later. In this embodiment, two copies of the DDD2-mCD20 are attached to each AD2 moiety, resulting in a DNL complex comprising one hLL1 IgG moiety and four mCD20 xenoantigen moieties.

In an alternative embodiment, the Fab of hLL1 is linked to DDD2 and the mCD20(136-178) to AD2. Formation of a DNL construct results in the formation of an MM vaccine, designated hLL1-F(ab)$_2$-mCD20(136-178), which comprises a single mCD20(136-178) attached to two Fab moieties of hLL1. The generation of AD2-mCD20(136-178) is described below.

Administration of 74-mCD20(136-178) or hLL1-F(ab)$_2$-mCD20(136-178) to subjects with MM induces an immune response against CD138$^{neg}$CD20$^+$ putative MM stem cells. The immune response is effective to reduce or eliminate MM disease cells in the subjects.

Generation of Recombinant AD2-mCD20(136-178)

AD2-mCD20(136-178)-pdHL2 is the expression vector for recombinant AD2-mCD20(136-178), which comprises AD2-linker-mCD20(136-178)-HHHHHH(HHHHHH disclosed as SEQ ID NO: 126). The DNA segment comprising the nucleotide sequence of mCD20(136-178) flanked by Bgl2 and Eag1 restriction sites is obtained by PCR using a full length murine CD20 cDNA clone as template and the two primers shown below:

```
Upstream primer: Bgl2_mCD20 primer
                                            (SEQ ID NO: 141)
5'-AGATCTACACTTTCTCATTTTTTAAAAATG Downstream primer: Eag1_mCD20 primer
                                            (SEQ ID NO: 142)
5'CGGCCGTCAGTGGTGGTGGTGGTGGTGGTTACAGTACTGTGTAGATGG
```

The PCR amplimer (162 bp) is cloned into the PGEMT® vector. An AD2-pdHL2 mammalian expression vector, for example, N-AD2-hTransferrin-His-pdHL2, is prepared for ligation with the amplimer by digestion with Bgl2 and Eag1 restriction endonucleases. The mCD20-amplimer is excised from PGEMT® with Bgl2 and Eag1 and ligated into the AD2-pdHL2 vector to generate the expression vector AD2-mCD20(136-178)-pdHL2. Clones expressing AD2-mCD20 (136-178) are obtained as described above and AD2-mCD20 (136-178) is purified from culture supernatants using Ni-select.

Example 43

Effects of hLL1 on DCs

Efficient Binding of hLL1 with Different Subsets of APCs

CD74 is expressed in most antigen-presenting cells including blood DCs, B cells, monocytes. To further characterize the expression profile of CD74 in APCs, we examined the expression of CD74 in different subsets of human PBMCs and in vitro monocyte-derived DCs. We found that all of the blood DC subsets, the myeloid DC1 (MDC1) and DC2 (MDC2), and plasmacytoid DC(PDC) expressed CD74, with MDC2 expressing the highest level of CD74 (not shown). CD74 was also expressed in monocyte-derived immature DCs at much higher level than in LPS-matured DCs (not shown). Consistent with the CD74 expression profiles, hLL1 bound efficiently with blood DC subsets, B cells, monocytes, and monocyte-derived immature DCs, but not LPS-matured DCs (not shown). The binding efficiency of hLL1 in these APC subsets correlates well with their CD74 expression levels. These data provide the basis for in vivo targeting of antigen to APCs using hLL1 as the targeting vehicle.

Cytotoxic Effect of hLL1 on CD74-Expressing Malignant B Cells but not on Normal DCs Since CD74 is highly expressed in immature DCs, with which hLL1 binds efficiently, we wondered if hLL1 has the same cytotoxicity in DCs, as it does a in CD74-expressing B cell lymphoma, which was shown previously (Stein et al., Blood 2004, 104:3705-11). To this end, the effects of hLL1 on the cell viability of B cell malignancy Daudi cells and human monocyte-derived DCs were side-by-side compared using an MTS assay and microscope imaging. The results demonstrated that hLL1, in the presence of GAH (goat anti-human antibody), the second antibody for hLL1 cross-linking, significantly reduced cell viability of Daudi cells but not DCs (not shown), which normally expressed high level of CD74. The microscopic imaging showed that Daudi cells treated with hLL1 crosslinked with GAH became clumped and condensed, while the DCs maintained normal morphology after the same treatment (not shown). The cytotoxicity against Daudi cells by hLL1 cross-linked with GAH was consistent with the earlier study by Stein et al. (2004) showing that hLL1 was cytotoxic to B cell malignancies in vitro and in vivo. The lack of cytotoxicity of hLL1 plus GAH on DCs was further demonstrated in apoptosis assay, which showed that the hypodiploid nuclei populations were not influenced by hLL1 cross-linked with GAH (not shown).

To further confirm the lack of cytotoxicity of hLL1 on DCs, we performed apoptosis assay using flow cytometry. The nuclei from hLL1 treated immature DCs were obtained and stained with PI for flow cytometry analysis. The PI+ particles were gated first, and the debris was excluded by gating out the SSC-low particles. The resulting gated nuclei were analyzed for apoptosis by measuring hypodiploid nuclei population. The results demonstrate that hLL1 had no influence on DC apoptosis in both donors, in the presence or absence of a second mAb (20 µg/ml) for cross-linking (GAH, F(ab')$_2$ GAH IgG Fcy-specific) (not shown). These data demonstrated that hLL1, unlike its cytotoxic effect on B cell malignancies, has little cytotoxicity against normal dendritic cells which also express CD74 surface antigen.

Moderate Enhancement of DC Constitutive Maturation by hLL1

Human IgG can interact with DCs through FcR ligation and has opposing effects on DC maturation depending on which subtype(s) of FcR is involved. hLL1, as a humanized IgG, may interact with human DCs not only through CD74 but also through FcR expressed on DCs. For this reason, we speculated that hLL1 may influence DC functions through interaction with CD74 or FcR, or both. To investigate this, we tested the effect of hLL1 on DC constitutive maturation during in vitro culture of monocytes in the presence of hGM-CSF and hIL-4.

Since DC maturation is usually reflected by its morphological change, we also examined if hLL1 treatment has any effect on DC morphology. DCs treated with hLL1, at different doses for various days, in the absence or presence of GAH cross-linking, appeared healthy and intact (not shown). The hLL1-treated DCs exhibited some minor morphological changes featured with fiber-like cells, which are similar to but less obvious than LPS-treated DCs (not shown).

As mature DCs differ from immature DCs mainly in the upregulation of antigen-presenting and costimulatory molecule expression, altered cytokine production, and enhanced T-cell stimulatory ability, we then investigated if hLL1 has any effect on the expression level of antigen-presenting molecule HLA-DR and costimulatory molecules CD54 and CD86 in DCs. The results showed that hLL1 could upregulate HLA-DR, CD54, and CD86 in a dose-dependent manner within the range of hLL1 concentrations at 0.05-5 µg/ml (not shown). However, the effect was not strong, as the expression of HLA-DR and costimulatory molecules, CD54 and CD86, were only 10% upregulated at 5 µg/ml hLL1 compared to 0 µg/ml (not shown). At the highest concentration (50 µg/ml), the expression of HLA-DR, CD54 and CD86 was not further upregulated but slightly reduced, compared to hLL1 at 5 µg/ml (not shown). These results indicate that hLL1, although not potently, could enhance the constitutive maturation of DCs.

Lack of Significant Influence on T Cell Expansion by hLL1-Treated DCs

The functional difference between immature DCs and mature DCs is that mature DCs have a stronger capacity to stimulate T cell proliferation and expansion. Since hLL1 could enhance the constitutive maturation by upregulating the expression of HLA-DR, CD54 and CD86 expression in DCs, we determined whether this DC-maturing effect could be reflected by an enhanced T cell expansion by DCs. DCs treated with hLL1 at 0.05 to 50 µg/ml did not influence the DC-mediated T cell expansion, including total T cells, CD4+ and CD4− T cells (not shown). This result suggests that hLL1-enhanced DC constitutive maturation was not strong enough to be translated into an enhanced T cell stimulatory ability.

Polarization of Naïve CD4+ T Cells Toward Th1 Effector Cells by hLL1-Treated DCs DCs have another important function: the polarization of naïve CD4 T cells to differentiate into different effector cells, Th1, Th2, Th17 and Th17-1 cells. Th1 cells are critical for cellular immunity against intracellular pathogens and cancers, whereas induction of Th2 cells is responsible for humoral immunity. The IL-17-producing Th17 and Th17-1 cells are other polarized cell populations which have multiple functions in immunity to certain pathogens and autoimmune inflammation. The polarization of these effector cells is largely mediated through DC-secreted cytokines, the so-called "signal 3", that DCs provide to T cells in the DC/T cell synapse. The CD4+ naïve T cells can differentiate into Th1, Th2 and Th0 cells which mediate different effector functions, among which the Th1 effector cells play an essential role in maintaining CTL response against cancer and infectious diseases. We have shown that hLL1 at 0.05 to 50 µg/ml could enhance DC constitutive maturation in a weak but dose-dependent manner, but DCs treated with these concentrations of hLL1 didn't influence the DC-mediated T cell expansion (not shown). We were then interested if the hLL1-treated DCs could influence the polarization of CD4+ naïve T cells. hLL1-treated DCs polarized the CD4+ naïve T cells to differentiate toward more Th1 effector cells and fewer Th2 and Tnp cells (not shown). These results indicate that DCs can be functionally modulated by hLL1. As Th1 plays a crucial

Example 44

In Vitro Properties of 74-mCD20

Induction of hCD20-Specific Immunity by
74-mCD20 in Human PBMCs

CD20 is a self antigen normally expressed on B cells, which is theoretically difficult to target by vaccine strategies due to immune tolerance. However, specific T-cell immune response to CD20 has been achieved in tumor bearing mice by vaccination with a minigene encoding the extracellular domain of human CD20 (Palomba et al., Clin Cancer Res 2005; 11:370-9), or a conjugate comprising the extracellular domain of human CD20 and a carrier protein with QS21 adjuvant (Roberts et al., Blood 2002; 99:3748-55). Several other reports have also demonstrated the feasibility of using xenoantigens to break immune tolerance, as shown for MUC 1 in animal models (Ding et al., Blood 2008; 112:2817-25; Soares et al., J Immunol 2001; 166:6555-63) as well as in patients (Ramanathan et al., Cancer Immunol Immunother 2005; 54:254-64). To test whether 74-mCD20ould successfully induce hCD20-specific immunity and overcome the immune tolerance of CD20, the following experiment is performed.

Human DCs are generated from PBMCs by culturing for 5 days in the presence of hGM-CSF and hIL-4. The immature DCs are loaded with 74-mCD20, and matured by LPS plus IFN-gamma. The mature DCs are used to stimulate autologous PBMCs for 10 days. Restimulation with the same loaded DCs is performed twice weekly. After the last restimulation, the T cells are tested for their antigen specificity by measuring cytokine response (IFN-gamma) upon stimulation by sorted CD20-positive MM cancer stem cells. The CD20-negative MM cells are used as a control. The T cells show a positive reaction to CD20-positive MM cancer stem cells but not to control CD20-negative MM cells.

Specific Binding, Internalization and Intracellular Location of 74-mCD20 in Various Antigen-Presenting Cells In Vitro Our preliminary data showed that hLL1 efficiently and specifically binds with different APCs, including myeloid DC 1 and myeloid DC2, plasmacytoid DC, B cells and monocytes. In order to confirm that 74-mCD20 has the same efficiency and specificity in binding with APCs as hLL1 alone, the following experiment is performed.

74-mCD20 and the control M1-mCD20 (comprising the anti-MUC1 antibody hPAM4 linked to four copies of mCD20) are used. Binding assays are performed as follows. Briefly, 15 μg of 74-mCD20 or M1-mCD20 are labeled with a ZENON™ ALEXA FLUOR® 488 human IgG labeling kit (INVITROGEN®) following the manufacturer's instructions. The labeled preparations are used to stain the human PBMCs as described below.

Human PBMCs isolated from buffy coat using FICOLL-PAQUE™ are treated with human FcR blocking Reagent (Miltenyi Biotec, 1:20 dilution) at 4° C. for 10 min. The washed cells are stained with specifically labeled mAbs and analyzed by flow cytometry (FACSCALIBUR®). The labeled mAbs used for the study include FITC-labeled anti-CD74 mAb ALEXA FLUOR® 488-labeled 74-mCD20; ALEXA FLUOR® 488-labeled M1-mCD20; PE-conjugated anti-CD19 mAb (for B cells); PE-conjugated anti-CD14 mAb (for monocytes); and APC-conjugated mAb to BDCA-1 (for MDC1), BDCA-2 (for PDC), or BDCA-3 (for MDC2). A gating strategy is used for identification of B cells, monocytes, MDC1, MDC2, and PDC. Data were analyzed for mean fluorescence intensity and positive cell populations expressing the surface markers.

To see if 74-mCD20 is internalized to endosomes for further processing to MHC class II presentation and MHC class I cross-presentation, the following experiment is performed. 74-mCD20 or M1-mCD20 is mixed with human PBMCs, and incubated at 4° C. for 1 hr, followed by extensive washing. The cells are then transferred to 37° C., fixed at different time points (0, 15, 30, or 45 min) and stained with ALEXA FLUOR®-labeled anti-human IgG secondary antibody with or without prior permeabilization. The mean fluorescence is determined by flow cytometry, and the amount of internalized antibody is calculated by subtracting the mean fluorescence in fixed cells (surface bound) from that recorded with fixed and permeabilized cells (internalized and surface bound) at various time points.

The results show that the 74-mCD20 DNL complex has the same efficiency and specificity in binding with APCs as hLL1 alone.

Example 45

Induction of hCD20-Specific Immune Responses by
74-mCD20 In Vivo

Intrahepatic injection of CD34+ human cord blood cells (HLA A1 healthy donor) into irradiated newborn Rag2−/−γc−/− mice is performed to generate the animal model for a reconstituted human adaptive immune system including human T, B, and DC cells, and structured primary and secondary lymphoid organs (Huff et al., J Clin Oncol. 2008, 26:2895-900; Yang and Chang, Cancer Invest. 2008, 26:741-55). These mice are called Hu-Rag2−/−γc−/− mice.

To assess the immune responses induced by 74-mCD20, human CD34+ cells reconstituted in Rag2−/−γc−/− mice are immunized weekly for three times with 74-mCD20 or M1-mCD20(50 μg per mouse), in combination with or without CpG (50 μg per mouse) for in vivo DC maturation. Five days after the last immunization, splenocytes of each animal are isolated and restimulated with HLA-matched MM cancer stem cells for cytokine (IFN-gamma) production, as assessed by intracellular cytokine staining with flow cytometry. The specific cytotoxicity against MM cancer stem cells is assessed by a calcein AM release assay with MM cancer stem cells as the target cells. The CD20+ MM cancer stem cells are isolated from the MM cell line RPMI8226 using magnetic beads. The stem cell property is verified by staining with aldehyde dehydrogenase. The results indicate that 74-mCD20 is capable of inducing an anti-hcd20 specific immune response in vivo.

Example 46

Therapeutic Potential of 74-mCD20 Against MM
Cancer Stem Cells

In Vivo Evaluation by hPBMC/NOD/SCID Mouse
Model or Adoptive Transfer

The best way for in vivo evaluation of the therapeutic effect of 74-mCD20 is to immunize an animal model that can support both the growth of MM and the development of a human adaptive immune system. Since human CD34+ cell-reconstituted Rag2−/−γc−/− mice are immune-competent, which may not support MM growth, the hPBMC/NOD/SCID mouse model is used to test the therapeutic effect of 74-mCD20 against MM stem cells. The NOD/SCID mice have been used for engraftment of clonogenic multiple myeloma stem cells by Matsui et al. (Blood 2004, 103:2332-6; Cancer Res 2008, 68:190-7).

The NOD/SCID mice are also used for evaluating the therapeutic effect by co-engraftment of tumor cells and hPBMC. By carefully adjusting the cell numbers infused, this model can support both tumor growth and hPBMC engraftment, and has been used for testing the effect of an in vivo vaccine targeting DC-SIGN.

Four to six-week-old female NOD/SCID mice (Jackson Laboratories, Barr Harbor, Me.) are irradiated with 300 cGy (84 cGy/min using a 137Cs gamma irradiator). 12-16 h later, sorted CD20+ MM cancer stem cells (2 million) are injected via dorsal tail vein. Meanwhile, a mixture of human PBMCs (3 million), immature DC (30,000) and the DNL vaccine is injected into the mice subcutaneously. At certain time points (days), mice are euthanatized and bone marrow is harvested from the long bones and the engraftment and therapeutic efficacy are determined by staining for human CD138$^+$ MM cells.

In order to further evaluate the therapeutic potential of 74-mCD20, an alternative method by adoptive transfer is used to test the vaccine-elicited cytotoxicity against MM stem cells. The human CD34+ cell-reconstituted Rag2−/−γc−/− mice are immunized with 74-mCD20 as described above. The splenocytes are harvested and injected via the tail vein into NOD/SCID mice engrafted with CD20+ MM cancer stem cells. At certain time points (days), mice are euthanatized and bone marrow is harvested from the long bones and the engraftment and therapeutic efficacy are determined by staining for human CD138+ MM cells. The results confirm that 74-mCD20 is capable of inducing an immune response against CD20$^+$ MM stem cells in vivo.

Example 47

Generation of DDD2-mPAP and DNL Vaccine Complex

A DDD2 conjugated PAP xenoantigen is generated from murine prostatic acid phosphatase. The efficacy of dendritic cell based vaccination with a PAP xenoantigen has been previously disclosed (Fong et al. J Immunol 2001, 167:7150-56). A DDD2-mPAP-pdHL2 expression vector is constructed as described above and the DDD2-mPAP xenoantigen fusion protein is expressed in cell culture. The murine prostatic acid phosphatase sequence is disclosed, for example, in the NCBI database at Accession No. AAF23171. A DDD2-mPAP-6His fusion protein ('6His' disclosed as SEQ ID NO: 126) is expressed and purified by immobilized metal affinity chromatography (IMAC).

A DNL construct comprising one copy of $C_{H3}$-AD2-IgG-hLL1 (anti-CD74) and four copies of DDD2-mPAP is prepared. The hLL1 IgG moiety comprises an AD2 sequence attached to the C-terminal end of each heavy chain of the hLL1 IgG. A DNL reaction is performed by mixing hLL1 IgG-AD2 and DDD2-mPAP in PBS containing 1 mM reduced glutathione. On the next day oxidized glutathione is added to a final concentration of 2 mM and the reaction mixture is purified on a Protein A column 24 h later. Two copies of the DDD2-mPAP are attached to each AD2 moiety, resulting in a DNL complex comprising one hLL1 IgG moiety and four mPAP xenoantigen moieties.

Administration of DNL vaccine anti-CD74-mPAP to subjects with prostate cancer induces an immune response against PAP expressing prostatic cancer stem cells. The immune response is effective to reduce or eliminate prostatic cancer cells in the subjects.

Example 48

Generation of DDD2-mEGFR and DNL Vaccine Complex

A DDD2 conjugated EGFR xenoantigen is generated from murine EGFR. The efficacy of EGFR xenoantigen at inducing a humoral immune response has been previously disclosed (Fang et al. Int J Mol Med 2009, 23:181-88). A DDD2-mEGFR-pdHL2 expression vector comprising the extracellular domain of murine EGFR is constructed and the DDD2-mEGFR xenoantigen fusion protein is expressed in cell culture. The murine EGFR sequence is disclosed, for example, in the NCBI database at Accession No. AAG43241. A DDD2-mEGFR-6H is fusion protein ('6His' disclosed as SEQ ID NO: 126) is expressed and purified by immobilized metal affinity chromatography (IMAC).

A DNL construct comprising one copy of $C_{H3}$-AD2-IgG-hLL1 (anti-CD74) and four copies of DDD2-mEGFR is prepared. The hLL1 IgG moiety comprises an AD2 sequence attached to the C-terminal end of each heavy chain of the hLL1 IgG. A DNL reaction is performed by mixing hLL1 IgG-AD2 and DDD2-mEGFR in PBS containing 1 mM reduced glutathione. On the next day oxidized glutathione is added to a final concentration of 2 mM and the reaction mixture is purified on a Protein A column 24 h later. Two copies of the DDD2-mEGFR are attached to each AD2 moiety, resulting in a DNL complex comprising one hLL1 IgG moiety and four mEGFR xenoantigen moieties.

Administration of DNL vaccine anti-CD74-mEGFR to subjects with EGFR-expressing NSCLC induces an immune response against EGFR-expressing cancer stem cells. The immune response is effective to reduce or eliminate EGFR positive cancer cells in the subjects.

The skilled artisan will realize that DNL-based vaccines incorporating xenoantigen moieties corresponding to a wide variety of tumor-associated antigens may be constructed and utilized according to the techniques described herein.

Example 49

DNL Vaccine Constructs for Poxvirus Therapy

Other embodiments relate to DNL constructs for vaccines against infectious disease pathogens, such as poxvirus, including but not limited to smallpox. Preferably, the vaccines comprise an immunoconjugate of a subunit antigenic peptide derived from one or more viral proteins. More preferably, the viral proteins are immunomodulating factors, such as the viral IL-18 binding protein (vIL18BP), although alternative viral proteins may be used, such as viral envelope proteins. In other alternative embodiments, subunit-based vaccines may comprise combinations of antigenic peptides from more than one viral protein, such as an immunomodulating factor and an envelope protein. The viral antigenic peptide is attached to an antibody or antigen-binding fragment thereof that targets the subunit to antigen-producing cells (APCs). Preferably, the subunit-based vaccine incorporates an antibody or antibody fragment against the HLA-DR antigen, such as the L243 antibody; although the skilled artisan will realize that other APC targeting antibodies are known and may be used. Optionally, the vaccine may incorporate one or more adjuvants, such as aluminum hydroxide, CpG DNA, calcium phosphate or bacterial-based adjuvant (e.g., *L. delbroeckii/bulgaricus*). Use of the immunoconjugate provides substantially increased immunogenicity and improved immune system response against viral antigens, while avoiding the possibility of infection of immunocompromised individuals exposed to live virus-based vaccines. Most preferably, the subunit-based vaccine is effective to induce immunity against and to prevent infection by smallpox and/or other poxviruses in vivo.

Background

The Orthopoxviruses, a group of complex viruses with cross-reacting antigens, includes vaccinia virus (VV), monkeypox virus, and the virus that causes smallpox (variola, VAR). Smallpox is no longer a naturally occurring infection, having been eradicated by a massive immunization program up to 1978, when routine vaccination of the world's population ceased (Minor, 2002, British Med J 62:213-224). At that time, the remaining stocks of virus were deposited in the U.S. and the former Soviet Union. The recent threat of bioterrorism, a recent outbreak of monkeypox (CDC MMWR 2003), and the deadly nature of smallpox disease, especially in a world where it is estimated that less than half the population is vaccinated, has stimulated renewed interest in development of vaccine protection against VAR, or other dangerous members of this family of viruses.

Smallpox vaccine, which employs active VV, currently represents the most effective means to immunize against smallpox (Rosenthal et al, 2001, Emerg. Infect. Dis. 7: 920-926). This vaccine produces a transient viremia which is resolved in most individuals, and which leaves long-lasting immunity. However, this vaccine also raises safety issues because of serious adverse reactions, which include systemic viremia and death (He et al, 2007, JID 196: 1026-1032; Rosenthal et al, 2001). Therefore, development of alternative vaccination strategies is required if circumstances necessitate immunization of the population.

Several approaches to alternative vaccines have been tried, or are in development. Attenuated forms of poxvirus, such as the Akhara Modified Vaccinia (MVA), with deleted or mutated genes (Grandpre et al., Vaccine 27:1549-56, 2009), may confer partial immunity to highly virulent strains of poxvirus. Immunization with inactivated virus has been investigated, but it does not confer the same degree of protection as live virus; $10^3$-$10^4$ more units of inactivated virus are required to protect mice from challenge, regardless of the inactivation method used (Turner et al. 1970, J. Hyg. Camb 68:197-210). This fact implies that the protection derived from immunization with active virus includes factors that are not produced by, or are not present in, inactive virus. Poxviruses produce a spectrum of secreted host immune response modifying factors which neutralize host cytokines and innate defense mechanisms. By weakening the host's first line of defense, the virus may be able to establish infection (e.g. in the mucosa) and begin the first phase of infectious replication in host cells. A need exists for vaccines against poxviruses, such as smallpox, that are more effective than inactivated virus but which avoid the safety issues seen with live virus vaccines.

Poxvirus Antigens and APC-Targeting Antibodies

Viral Antigens

One host immune modulating factor produced by both VV and VAR is the viral interleukin-18 binding protein (vIL18BP, vaccinia virus C12L gene). Like other viral host defense modulating factors, this gene is expressed in the early phase of infection, and it cripples host immunity by neutralizing a key pro-inflammatory cytokine, IL-18, which stimulates NK, CD8, and Th1 CD4 cells to produce interferon-gamma (IFN), which in turn activates antigen presenting cells (APCs), and other cells and which directs immune responses toward the Th1 type (Born et al, 2000, J. Immunol. 164: 3246-3254; Scott, 1991, J Immunol 147:3149-3155; Pien et al, 2002, Immunol. 169:5827-5837; Xiang and Moss, 1999, Proc. Natl. Acad. Sci. USA 96:11537-11542). In preferred embodiments, the subunit antigenic peptide is selected to mimic an epitope of vIL18BP. Other exemplary host immune modulating factors and their locus tag identifiers are provided in Table 12.

In other preferred embodiments the subunit antigenic peptide is derived from a viral immunomodulating protein. The skilled artisan will realize that various viral immunomodulating proteins are known and may be of use. Non-limiting examples include the interferon-gamma (IFN-gamma) receptor homolog (B8R gene), complement control protein homolog (B5R gene) and serine protease inhibitors (B13R, B14R, B22R genes). A wide variety of poxvirus immunomodulatory proteins have been reported, although their effect on viral immunogenicity has not been well characterized. (See, e.g., Jackson et al. J Virol 79:6554-59, 2005; B12R gene (ser/thr protein kinase); B15R gene (IL-1 and IL-6 receptor); B16R gene (IL-1 receptor), B18R gene (IFN-α receptor), B19R gene (IL-1 and IL-6 receptor, IFN inhibitor.)

TABLE 12

| Poxvirus Immunomodulating Proteins | |
|---|---|
| VACWR001 | TNF-alpha receptor-like |
| VACWR011 | apoptosis |
| VACWR012 | zinc(Zn)-finger-like |
| VACWR013 (VAC WR C12L) | IL-18 binding protein |
| VACWR025 | blocks C3b/C4b complement activation |
| VACWR028 | intracellular signal transduction inhibitor |
| VACWR033 | serine protease inhibitor |
| VACWR034 | interferon resistance |
| VACWR059 | ds RNA binder; interferon binder |
| VACWR172 | Toll-like receptor modulator |
| VACWR190 | IFN-gamma receptor-like |
| VACWR208 | Zn-finger-like |
| VACV WR 215 | TNF-alpha R |
| VACWR217 | TNF-alpha receptor-like |
| VACV COP B19R (VACWR200) | IFN-type I binder |
| VACV COP A39R | semaphoring-like |
| VACV COP A40R | type II membrane protein |
| VACV COP A41L | secreted glycoprotein |
| VACV A4L | immunodominant antigen |
| VACV A27L (VACWR150) | surface binding heparin sulfate |
| VACV D8L (VACWR113) | surface binding chondroitin sulfate |
| VACV B5R (VACWR187) | essential for membrane wrapping of IMV in trans-Golgi |

In alternative embodiments, the subunit antigenic peptide may be derived from a viral envelope protein or other viral proteins. Non-limiting examples include the protein products of the DBL, A27L, L1R and A33R genes. The skilled artisan will realize that the DNA and amino acid sequences of the various poxyiral genes and proteins are well known in the art and are publicly available (see, e.g., GenBank Accession No. AY243312 for the complete genomic sequence of Vaccinia virus WR, along with the encoded protein sequences).

Anti-APC Antibodies

As the professional antigen-presenting cells, dendritic cells (DCs) play a pivotal role in orchestrating innate and adaptive immunity, and have been harnessed to create effective vaccines (Vulink et al., Adv Cancer Res. 2008, 99:363-407; O'Neill et al., Mol. Biotechnol. 2007, 36:131-41). In vivo targeting of antigens to APCs and DCs represents a promising approach for vaccination, as it can bypass the laborious and expensive ex vivo antigen loading and culturing, and facilitate large-scale application of immunotherapy (Tacken et al., Nat Rev Immunol. 2007, 7:790-802). More significantly, in vivo APC and/or DC targeting vaccination is more efficient in eliciting anti-tumor immune response, and more effective in controlling tumor growth in animal models (Kretz-Rommel et al., J Immunother 2007, 30:715-726).

In addition to DCs, B cells are another type of potent antigen-presenting cells capable of priming Th1/Th2 cells (Morris et al, J. Immunol. 1994, 152:3777-3785; Constant, J. Immunol. 1999, 162:5695-5703) and activating CD8 T cells via cross-presentation (Heit et al., J. Immunol. 2004, 172:1501-1507; Yan et al., Int Immunol. 2005, 17:869-773). It was recently reported that in vivo targeting of antigens to B cells breaks immune tolerance of MUC1 (Ding et al., Blood 2008, 112:2817-25).

In various embodiments of the present invention, antibodies against antigens expressed by APCs in general and DCs in particular may be incorporated into immunoconjugate vaccines to target subunit antigenic peptides to immune system cells. The antibody component of the immunoconjugate directs the complex to APCs, where the antigenic peptide component is processed to invoke an immune response against poxviruses and/or infected cells expressing the target antigen. Various APC targeting antibodies are known in the art, such as antibodies that bind to an antigen selected from the group consisting of HLA-DR, CD74, CD209 (DC-SIGN), CD34, CD74, CD205, TLR 2 (toll-like receptor 2), TLR 4, TLR 7, TLR 9, BDCA-2, BDCA-3 and BDCA-4.

Two exemplary APC antigens are HLA-DR and CD74. HLA-DR is a major histocompatibility complex class II cell surface receptor which functions in antigen presentation to elicit T-cell immune responses. HLA-DR is found on a wide variety of antigen presenting cells, such as macrophages, B-cells and dendritic cells. Antibodies against HLA-DR, including the L243 antibody, are known in the art (see, e.g., U.S. Pat. Nos. 6,416,958, 6,894,149; 7,262,278, the Examples section of each of which is incorporated herein by reference). Such antibodies may be conjugated to subunit antigenic peptides for delivery to APCs.

Another APC expressed antigen is CD74, which is a type II integral membrane protein essential for proper MHC II folding and targeting of MHC 11-CD74 complex to the endosomes (Stein et al., Clin Cancer Res. 2007, 13:5556s-5563s; Matza et al., Trends Immunol. 2003, 24(5):264-8). CD74 expression is not restricted to DCs, but is found in almost all antigen-presenting cells (Freudenthal et al., Proc Natl Acad Sci USA. 1990, 87:7698-702; Clark et al., J. Immunol. 1992, 148(11):3327-35). The wide expression of CD74 in APCs may offer some advantages over sole expression in myeloid DCs, as targeting of antigens to other APCs like B cells has been reported to break immune tolerance (Ding et al., Blood 2008, 112:2817-25), and targeting to plasmacytoid DCs cross-presents antigens to naïve CD8 T cells. More importantly, CD74 is also expressed in follicular DCs (Clark et al., J. Immunol. 1992, 148(10:3327-35), a DC subset critical for antigen presentation to B cells (Tew et al., Immunol Rev. 1997, 156:39-52). This expression profile makes CD74 an excellent candidate for in vivo targeting vaccination. A variety of anti-CD74 antibodies are known in the art, such as the LL1 antibody (Leung et al., Mol. Immunol. 1995, 32:1416-1427; Losman et al., Cancer 1997, 80:2660-2666; Stein et al., Blood 2004, 104:3705-11; U.S. Pat. No. 7,312,318, the Examples section of which is incorporated herein by reference). Alternatively, other anti-CD74 antibodies or antibodies against other APC- or DC-associated antigens may be utilized (see, e.g., LifeSpan Biosciences Inc., Seattle, Wash.; BioLegend, San Diego, Calif.; Abcam, Cambridge, Mass.).

Example 50

Immune Response to Poxvirus Subunit Antigenic Peptides

Materials and Methods

Peptide design 9-mer or 15-mers peptide sequences bearing multiple potential binding sites for both HLA class I and/or HLA class II molecules were derived from poxvirus open reading frames by visual screening for HLA anchor residues at the correct spacing, or by use of web-based methods (e.g., BIMAS or SYFPEITHI [Parker et al., J Immunol 152:163-75, 1994; Rammensee et al., Immunogenetics 50:213-19, 1999]), with selection based on high potential for specific HLA-binding (Table 13). The nucleotide and amino acid sequences of vIL18BP (C12L), A4L (Boulanger et al., J Virol 72:170-79, 1998), A27L (Chung et al., J Virol 72:1577-85, 1998), or D8L (Hsaio et al., J Virol 73:8750-61) VV antigens were retrieved from NIH GenBank, Accession number: AY243312. These peptides are designated by their gene source and a number (e.g., vIL18BP105 or vD8L118).

TABLE 13

Amino acid number and HLA restriction of poxvirus vIL18BP-derived peptides, A4L229, and TT830.

| Peptide | Peptide length (amino acids) | Potential HLA binding[@] |
|---|---|---|
| TT830* | 15-mer | HLA-A02, (A03, DR04, DR15) |
| vA4L229[#] | 9-mer | HLA-A02, (A03, A11) |
| vIL18BP008 | 9-mer | HLA-A02, (A03, A11) |
| vIL18BP110 | 9-mer | HLA-A02, (A03, A11) |
| vIL18BP105 | 15-mer | HLA-A02, A03, (A11), A35, |
| vIL18BP102 | 25-mer | DR01, DR04, DR07, DR11, DR15 |
| vA27L003 | 15-mer | HLA-A01, A02, A03, (A11), DR01, DR03, DR04, DR07, DR15 |
| vD8L118 | 15-mer | HLA-A01, A02, A03, A11, DR01, (DR03), DR04, DR07, DR11, (DR15) |
| vD8L110 | 25-mer | |

*TT830, Tetanus toxoid T-cell helper peptide;
[#]A4L229, epitope from vaccinia A4L ORF; vIL18BP, poxvirus IL-18 binding protein-derived peptides (vaccinia C12L).
[@]Binding potential without parentheses ≥ 15; within parentheses, binding probability of 10-14. 15-mers may contain more than one potential HLA class I binding epitope in addition to HLA class II epitopes. Only a limited number of HLA types are shown.

Peptide amino acid sequences are shown below. Peptides were screened for similarities with the human genome, using the NIH Blast server. Peptides with homology to the human proteome were discarded. All newly designed peptides were commercially synthesized at 95% purity (Sigma-Genosys, Woodlands, Tex. USA, New England Peptide, Gardner, Mass.).

```
vIL18BP008
CVLTTLNGV                         (SEQ ID NO: 143)

vIL18BP102
KFAHYRFTCVLTTLNGVSKKNIVVLK        (SEQ ID NO: 144)

vIL18BP105
HYRFTCVLTTLNGVS                   (SEQ ID NO: 145)

vIL18BP110
CVLTTLNGV                         (SEQ ID NO: 146)
```

-continued

| | |
|---|---|
| vIL18BP117<br>GVSKKNIWL | (SEQ ID NO: 147) |
| vA4L229 (variola virus)<br>ALKDLMSSV | (SEQ ID NO: 148) |
| TT830 (Clostridium tetani)<br>QYIKANAKFIGITEL | (SEQ ID NO: 149) |
| vA27L003-027<br>GTLFPGDDDLAIPAT | (SEQ ID NO: 150) |
| vA27L003-012<br>GTLFPGDDDLAIPATEFFSTKAAKK | (SEQ ID NO: 151) |
| vA27L004-012<br>TLFPGDDDL | (SEQ ID NO: 152) |
| vD8L110-134<br>HDDGLIIISIFLQVLDHKNVYFQKI | (SEQ ID NO: 153) |
| vD8L118-132<br>SIFLQVLDHKNVYFQ | (SEQ ID NO: 154) |
| vD8L116-124<br>IISIFLQVL | (SEQ ID NO: 155) |
| vB5R001-025<br>MKTISVVTLLCVLPAVVYSTCTVPT | (SEQ ID NO: 156) |
| vB5R004-018<br>ISVVTLLCVLPAVVY | (SEQ ID NO: 157) |
| vB5R008-016<br>TLLCVLPAV | (SEQ ID NO: 158) |

Donor samples Buffy coats were obtained from the Blood Center of New Jersey (NJBB) (West Orange, N.J. USA). Other PBMC samples were obtained from local donors after approval for use of human blood by the New England Institutional Review Board (Wellesley, Mass. USA), or from Cellular Technology Limited (CTL) (Shaker Hts, Ohio USA). Table 14 summarizes the donor HLA types, age, and vaccine status. Due to limited numbers of cells in each sample, not all samples were included in every assay.

TABLE 14

Summary of blood donor vaccine status, age, and HLA type.

| Vaccine status | Average age ± SD (range) | % (HLA allele) |
|---|---|---|
| Vaccinated<br>(N = 22) | 43 ± 11<br>(18-66) | 14% (A01), 45% (A02),<br>9% (A03), 0% (A11), 11% (DR01), 16% (DR04),<br>9% (DR07), 2% (DR11),<br>9% (DR15) |
| Unvaccinated<br>(N = 14) | 30 ± 12<br>(17-49) | 7% (A01), 50% (A02),<br>0% (A03), 4% (A11), 4% (DR01), 0% (DR04),<br>14% (DR07), 14% (DR11),<br>7% (DR15) |

DNA from donor PBMCs was amplified according to HLA-Typing kit (Biotest, Dreieich, Germany) specifications. HLA type was provided for the CTL, Inc., samples. Vaccinated donors were persons who either stated that they had previously received the live smallpox vaccine, or vaccination status was presumed based on age, while unvaccinated donors were persons who stated they had not received a smallpox vaccination or were born after vaccination ceased in the U.S. Due to limited numbers of cells in most samples, not all samples was tested in all assays. When the HLA type of the donors was not determined by the supplier, PBMCs were typed for HLA by SSP-PCR using the Biotest kit (Biotest, Dreieich, Germany).

Peptide screening Transporter associated with antigen-processing protein-1 and -2 (TAP1 and 2)-deficient human B/T hybridoma cell line, T2 cells (ATCC, Manassas, Va. USA), which expresses surface HLA-A02 exclusively, and which increases its expression when stabilized by peptide in the antigen presentation groove (Nijman et al., Eur J Immunol 23:1215-19, 1993), was incubated with beta-2-microglobulin and peptides at the indicated concentrations. Due to TAP deficiency, peptides are not processed, and so must be of a length that allows binding to HLA-A02 (9-mer). Analysis of HLA was performed using FITC-labeled W6/32 (BD Pharmingen, San Diego, Calif. USA) and a FACSCALIBUR™ flow cytometer (Becton Dickinson, San Jose, Calif. USA). Binding of the peptide epitopes to human PBMCs obtained from donors was detected by incubation of PBMCs at $1\times10^6$/mL with biotinylated peptides, followed by addition of avidin-FITC conjugate to fixed cells, and flow cytometry.

T-cell proliferation and phenotype analysis For evaluation, peptides were screened in vitro against PBMCs from smallpox-vaccinated and naïve donors, using a carboxyfluorescein diacetate succinimidyl ester (Invitrogen, Carlsbad, Calif. USA) based cell proliferation assay (Younes et al., J Exp Med 198:1909-22, 2003). For comparison purposes, peptides derived from the immunodominant poxvirus protein, A4L (Boulanger et al., J Virol 72:170-79, 1998), another from Tetanus Toxoid (TT830) (Demotz et al., J Immunol 142:394-402, 1989), or the HW gag protein (HIVgag) (Kan-Mitchell et al., J Immunol 172:5249-61, 2010), were included. Briefly, $10–50\times10^6$ PBMCs were labeled with CFSE (1.5 μM). $2\times10^5$ cells (200 μL) were incubated with indicated concentrations of peptides, *Staphylococcus aureus* enterotoxin (SEA) (10 ng/mL), or phytohemagglutinin (2.5 μg/mL) (PHA, both from Sigma-Aldrich). Cells were stained with antibodies against CD8 or CD3, and for viability (7-AAD) after 5 days. 20,000 events, gated on live CD3+ lymphocytes, were collected by flow cytometry, and analyzed using Flow-Jo software (Mountain View, Calif. USA). Proliferation was evaluated based on the reduction of CFSE fluorescence. The fluorescence index (FI) of proliferating cells was calculated by dividing the number of cells losing CFSE dye in the presence of the stimulating peptide (test) by the number of cells proliferating in the absence of the peptide (control).

For phenotype analysis, PBMCs in GOLGIPLUG™ (Brefeldin A, 1 μg/mL) were incubated with 10 μg/mL of the indicated peptides, medium control (with PBS added in same volume as peptide stock), or SEA or PHA, for 14 h. Cells were then surface- or intracellularly-stained (after permeabilization) with the indicated fluorescently-labeled antibodies (IFN-γ or IL-2). Cells were also stained for CD8, CD45RA to determine prior encounter with antigen, CCR7 (lymph node homing marker) (38), or CD107a (cytolytic capacity marker) (1). The percentages of CD8+ or CD8-effector-memory ($T_{EM}$) or terminally differentiated T cells (both CD45RA−CCR7−), central-memory T cells ($T_{CM}$) (CD45RA−CCR7+), and cytokine-driven differentiated T cells ($T_{EMRA}$) (CD45RA+CCR7−) (12) in peptide-stimulated and control assays were determined. CD8-negative T cells were considered to contain the CD4+ population.

Antibody analysis A modified ELISA-based method (Makabi-Panzu et al., Vaccine 16:1504-10, 1998) was used to assess serum antibody. Briefly, ELISA plate wells were coated with 10 μg/mL of target peptide. After blocking and washing, test sera were added in 2-fold serial dilutions in PBS. Binding of antibody was detected with peroxidase-conjugated anti-human antibody. Plates were developed with o-phenylenediamine dihydrochloride peroxidase substrate (Sigma-Aldrich, St. Louis, Mo. USA) and the optical density of wells was measured at 490 nm with an ELISA reader.

Data analysis The significance of differences observed under the experimental conditions was determined by Student's t-test with Fisher's corrections for multiple comparisons or Analysis of Variance (ANOVA) as indicated. P<0.05 was considered significant.

Results

Poxvirus peptide design and screening Poxvirus vIL18BP (SEQ ID NO:159) was parsed into 9-, 15-, or 25-mer peptides based on a high score for HLA-binding potential according to the ranking system of SYFPEITHI or BIMAS, with emphasis on HLA-A02- and HLA-DR04-binding. The vIL18BP-derived peptides were tested for binding to the TAP-deficient T2 hybridoma, which increases expression of HLA-A02 when stabilized by a peptide in the antigen-presenting groove. The 9-mer peptides, vIL18BP110 (SEQ ID NO:146), vIL18BP117 (SEQ ID NO:147), and A4L (SEQ ID NO:148) all contain sequences with potential HLA-A0201 binding capability (without processing). Of these peptides, vA4L (SEQ ID NO:148), and vIL18BP110 (SEQ ID NO:146) bound HLA-A02 on T2 cells in a concentration-dependent manner (FIG. 23A). The vIL18BP117 (SEQ ID NO:147) peptide, despite moderate to high probability of binding HLA-A02, did not. Nor did the 15-mer peptides incorporating the sequence of vIL18BP110 (SEQ ID NO:146), which T2 cells cannot process (vIL18BP008, SEQ ID NO:143 and 105, SEQ ID NO:145).

```
vIL18BP sequence
                                     (SEQ ID NO: 159)
MRILFLIAFMYGCVHSYVNAVETKCPNLDIVTSSGEFYCSGCVEHMSKFS

YMYWLAKDMKSDEYTKFIEHLGDGIKEDETIRTTDGGITTLRKVLHVTDT

NKFAHYRFTCVLTTLNGVSKKNIWLK
```

The vIL18BP peptides were also predicted to bind several other HLA haplotypes (Table 13), most of which were represented in the PBMC donor population, summarized in Table 14. When peptides were tested in binding to donor cells, vIL18BP008 (SEQ ID NO:143, 15-mer) and vIL18BP110 (SEQ ID NO:146, 9-mer) demonstrated strong binding to PBMCs from Donors NJ04 (A01/03, DR04) and NJ01 (A11, DR15), and relatively weak binding to NJ07 (A01, DR16) and NJ08 (A01/02, DR16) PBMCs (FIG. 23B). Taking into account donor HLA-types, the predicted HLA target of the peptides, and the T2 results, it can be concluded that vIL18BP110 (SEQ ID NO:146), a 9-mer, does not bind HLA-A01, but binds HLA-A02, -A03, and -A11, all of which were represented by T2 cells, or the donor panel.

The 15-mer, vIL18BP105 (SEQ ID NO:145), was predicted to bind HLA class II DR04 and DR15 (NJ01 and NJ04), and all of class I HLA types represented by the donors except HLA-A01. In addition to HLA-A01, donor NJ08 is HLA-A02-positive, thus HLA-A02 may account for the measured binding. Evidence for binding of vIL18BP105 (SEQ ID NO:145) to HLA-DR16 is suggested by the strong signal from Donor NJ07, which expresses HLA-DR16 and non-binding HLA-A01. While the consensus motif for HLA-DR16 has not been well-characterized (Onion et al., J Gen Virol 88:2417-25, 2007), there is at least one report that suggests the binding motifs of HLA-DR15 and -DR16 share similarities (Zeng et al., J Virol 70:3108-17, 1996).

Immunoreactivity of peptides as antigen mimics for T cells was assessed by 5-day CFSE-based proliferation assays, where CFSE-loaded PBMCs from vaccinated or unvaccinated donors were incubated with vIL18BP105 (SEQ ID NO:145) and peptides from two other poxvirus genes, vD8L118 (SEQ ID NO:154) and vA27L003-027 (SEQ ID NO:150). The results for all the vIL18BP105 (SEQ ID NO:145) assays are summarized in Table 15. Results for concurrent assays for vIL18BP105 (SEQ ID NO:145), vD8L118 (SEQ ID NO:154), and vA27L003-027 (SEQ ID NO:150) are shown in FIG. 24A (vaccinated donors) and FIG. 24B (unvaccinated donors).

Overall, vIL18BP105 (SEQ ID NO:145) induced significant proliferation of PBMCs from vaccinated donors (Table 15) at a concentration of 10 µg/mL. Vaccinated donor cells also proliferated when incubated with vD8L118 (SEQ ID NO:154) (6 of 7) and vA27L003-027 (SEQ ID NO:150) (4 of 7, FIG. 24A). These results indicate that vIL18BP105 (SEQ ID NO:145), vD8L118 (SEQ ID NO:154), and vA27L003-027 (SEQ ID NO:150) include epitopes that are recognized by lymphocytes from smallpox-vaccinated donors. Cells from unvaccinated donors were overall unresponsive to the poxvirus peptides (FIG. 24B). When samples from vaccinated donors (12A, 416, 417) and unvaccinated donors (213, 704, 706) were assayed for markers of activation and intracellular cytokine production in separate experiments (14-h assays), an IFN-γ response was noted in both CD4+ and CD8+ cells. CD8+ cells also expressed the cytolytic capacity marker, CD107a (P<0.05 vs. medium controls, FIG. 24C).

TABLE 15

Summary table of PBMC proliferative responses to vIL18BP105

| Donor vaccine status | Fluorescence index (FI) | |
|---|---|---|
| | vIL18BP105 | PHA or SEA |
| Yes (N = 11) | 5.07 ± 3.37 | 25.27 ± 14.15 |
| No (N = 10) | 1.00 ± 0.46 | 49.68 ± 24.39 |

Concentrations of 10 µg/mL of vIL18BP105 peptide (SEQ ID NO:145), 2.5 µg/mL of PHA (P), or 10 ng/mL SEA (S) were used. Fluorescence Index (FI) is estimated by dividing the number of cells proliferating in the presence of peptide (or P or S) by the number of cells proliferating in the absence of peptide (or P or S) using the CFSE-based cell proliferation assay described in Materials and Methods. N=number of individual donors. All samples were assayed in triplicate (mean±SD). P<0.001, vaccinated vs. unvaccinated for vIL18BP105 (ANOVA).

Phenotype of proliferating cells To determine the CD4 or CD8 phenotype of the proliferating cells, CFSE-loaded PBMCs from vaccinated and unvaccinated controls incubated with either vA27L003-027 (SEQ ID NO:150) or vIL18BP105 (SEQ ID NO:145), (5 days) were probed for CD4 or CD8 expression. Both CD4+ (4/5) and CD8+ (2/5) cells proliferated in samples from vaccinated donors, with little to no proliferation of either subset of cells in the unvaccinated donor samples (0 of 3, Table 16).

Further determinations of responding cells' phenotype were performed in 14-hour intracellular cytokine staining assays. Increased IFN-γ production in the CD8+ T cell population was found in samples incubated with vD8L118 (SEQ ID NO:154) (2/5) or vIL18BP105 (SEQ ID NO:145) (2/5) (Table 17, P<0.05). Despite stimulating proliferation in the 5-day CFSE-based assay, vA27L003-027 (SEQ ID NO:150) did not stimulate IFN-γ or IL-2 increases (not shown). IFN-γ production did not significantly increase in the CD4+ T cells, but isolated samples responded. However, IL-2 production increased significantly in the CD4+ population (vD8L118, SEQ ID NO:154) and in CD8+ cells (vIL18BP105, SEQ ID NO:145) (Table 17; P<0.04).

TABLE 16

CD4+ or CD8+ phenotype of proliferating T
cells incubated with vA27L003-027 (SEQ ID NO: 150) or
vIL18BP105 (SEQ ID NO: 145) peptides (5-day assay).

|  | CD4 | | | | CD8 | | | |
| --- | --- | --- | --- | --- | --- | --- | --- | --- |
|  | Cont | PHA | vA27L | vIL18BP | Cont | PHA | vA27L | vIL18BP |
| UNVACCINATED | | | | | | | | |
| NJ01 | 7.73 | 37.44 | Nd | 1.10 | 1.31 | 20.38 | nd | 0.94 |
| E | 0.61 | 11.46 | 1.11 | nd | 0.15 | 5.91 | 0.15 | nd |
| G | 0.92 | 2.40 | 0.63 | nd | 0.21 | 0.46 | 0.00 | nd |
| VACCINATED | | | | | | | | |
| NJ04 | 1.66 | 12.57 | Nd | 6.02 | 1.01 | 6.91 | nd | 3.64 |
| D | 3.52 | 20.84 | 3.52 | nd | 1.65 | 29.22 | 1.22 | nd |
| F | 1.08 | 17.67 | 8.30 | nd | 1.12 | 19.80 | 7.85 | nd |
| H | 4.46 | 49.20 | Nd | 25.73 | 2.75 | 11.00 | nd | 15.14 |
| NJ08 | 3.10 | 26.47 | Nd | 6.25 | 3.76 | 36.29 | nd | 7.26 |

Stored human PBMCs were thawed, incubated with CFSE for 24 h, followed by incubation with either PHA-P (2.5 μg/mL) or 20 μg/mL peptide as indicated, after which they were stained for CD4 or CD8 expression. Analysis was by flow cytometry. Column headings: Cont: medium control; vA27L: vA27L003-027 (SEQ ID NO:150); vIL18BP: vIL18BP105 (SEQ ID NO:145). Values in bold-face are ≥1.5-fold vs. control.

CD8+/IFN-γ-producing T cells from the same vaccinated donors were further analyzed for markers related to memory phenotype by staining for CD45RA, a marker of naïve and a subset of effector CD8 cells ($T_{EMRA}$), and CCR7, a lymph node homing marker. This analysis differentiates between $T_{CM}$ (CCR7+CD45RA−), precursors (CCR7+CD45RA+), $T_{EMRA}$ (CCR7−CD45RA+), and $T_{EM}$ and terminally differentiated (CCR7−CD45RA−) cell populations. The cell types that developed were CCR7−CD45RA− ($T_{EM}$ or terminally-differentiated effector) (not shown). The vD8L118 (SEQ ID NO:154) antigen peptide was most active in generating these cell types (P<0.019 vs. medium controls). In addition, 2 donors in each assay also responded similarly to vIL18BP105 (SEQ ID NO:145), and vA27L003-027 (SEQ ID NO:150).

TABLE 17

IL-2 or IFN-γ production by CD4 and CD8
T cells incubated with poxvirus peptides for 14 h.

|  | Medium control | | PHA | | vD8L118 | | vIL18BP105 | |
| --- | --- | --- | --- | --- | --- | --- | --- | --- |
| IFN-γ | CD4 | CD8 | CD4 | CD8 | CD4 | CD8 | CD4 | CD8 |
| Donor: | | | | | * | | * | |
| NJ291 | 0.06 | 0.01 | 1.25 | 0.48 | 0.16 | 0.08 | 0.04 | 0.02 |
| NJ663 | 0.49 | 0.06 | 4.68 | 0.31 | 0.40 | 0.10 | 0.60 | 0.10 |
| NJ652 | 1.17 | 0.2 | 8.05 | 0.62 | 0.97 | 0.37 | 1.34 | 0.25 |
| 12B | 0.3 | 0.01 | 5.66 | 2.28 | 0.45 | 0.11 | 0.48 | 0.02 |
| 920 | 0.37 | 0.02 | 7.05 | 0.49 | 0.13 | 0.02 | 0.41 | 0.02 |
| IL-2 | | | | | * | | * | |
| NJ291 | 0.02 | 0.01 | 0.26 | 0.02 | 0.21 | 0.01 | 0.02 | 0.04 |
| NJ663 | 0.22 | 0.01 | 1.97 | 0.11 | 2.93 | 0.11 | 0.17 | 0.05 |
| NJ652 | 0.14 | 0.03 | 0.60 | 0.15 | 2.44 | 0.27 | 0.20 | 0.08 |
| 12B | 0.03 | 0 | 0.30 | 0.03 | 0.08 | 0.01 | 0.06 | 0.01 |
| 920 | 0.06 | 0.01 | 0.71 | 0.06 | 1.20 | 0.04 | 0.08 | 0.02 |

Values shown are percent positive cells for each cytokine for each donor after 14 h of incubation with the designated peptide. Cells were stained for CD8, and the CD8-negative lymphocytes were considered CD4+. CD8+ cells consisted of 10-30% of total lymphocytes. All donors were vaccinated against smallpox. Concentration of peptides: 10 μg/mL; PHA, 2.5 μg/mL. Values in bold-face are ≥1.5-fold above medium control. Response to HIV peptide and vA27L003-027 (SEQ ID NO:145) was not significantly different than medium-only controls. *P<0.05 for CD8/IFN-γ/vD8L118 (SEQ ID NO:154) and vIL18BP105 (SEQ ID NO:145) vs. medium control: P<0.04 for CD4/IL-2/vD8118 (SEQ ID NO:154) vs. medium control; P<0.013 for CD4/IL-2/vIL18BP105 (SEQ ID NO:145) vs. medium control (t-test).

The capacity of the CD8+ effector cell population to degranulate, i.e., their ability to perform effector function, was assayed by determination of the expression of CD107a (Berhanu et al., J Virol 82:3517-29, 2008) (FIG. 25). In both the CD8+IFN-γ+ and the CD8+IFN-γ− populations, CD107a expression increased 2-7-fold in 3 of 5 PBMC samples incubated with vD8L118 (SEQ ID NO:154) (P<0.04). Increased CD107a was also measured in the CD8+IL-2+ population when incubated with vIL18BP105 (SEQ ID NO:145), (P<0.01) and vD8L118 (SEQ ID NO:154), although the latter did not achieve significance.

CD8+IFN-γ+ cells from unvaccinated donors were unresponsive to the peptides in similar 14-hour intracellular cytokine staining assays (not shown).

Serum antibody titers Antibody against poxvirus is required for protection upon secondary exposure, and the presence of anti-vaccinia antibody is maintained in 90% of vaccinees for decades after vaccination (Hammarlund et al., Nat Med 9:1131-37, 2003). Therefore, serum antibody from previously vaccinated patients would be directed toward immunologically relevant B-cell epitopes. To determine if the antigen peptides' sequence included recognizable B-cell epitopes, 1:200 diluted sera from vaccinated and unvaccinated donors were tested with the peptides vA27L003-027 (SEQ ID NO:150) (15-mer), vIL18BP102 (SEQ ID NO:144), and vD8L110 (SEQ ID NO:153) (25-mers). The results (FIG. 26) show that serum antibody to the vD8L110 (SEQ ID NO:153) and vA27L003-027 (SEQ ID NO:150) peptides was higher overall, and significantly above that from unvaccinated individuals (P<0.05). Although 3 donors produced antibody that recognized vIL18BP102, the overall results did not achieve significance. The results suggest that the experimental peptides contained one or several sequences that are B-cell epitopes. The presence of anti-peptide antibodies did not differ according to age of donor or time since vaccination (not shown).

Discussion

Inclusion of antigenic peptides in an alternative poxvirus vaccine requires that they be relevant targets of human immunity. The results described above determined whether or not specific peptides derived from poxvirus antigens were able to elicit memory responses in PBMCs from vaccinated donors. The epitopes were derived from three poxvirus antigens, including an antigen (vIL18BP) that is uncharacterized in host immunity, as well as the known poxyiral envelope antigens, A27L and DBL, which are characterized for host protection, but for which specific epitopes have not previously been characterized (Chung et al., J Virol 72:1577-85, 1998; Hsaio et al., J Virol 73:8750-61, 1999). The types of responses elicited by each peptide varied.

Poxvirus IL18BP modulates host innate immunity by neutralizing NK cell IL-18 which, in turn, prevents IFN-γ production. Recognition of one set of peptides from vIL18BP, vIL18BP105 (SEQ ID NO:145), and its derivatives, by CD4+ and CD8+ cells, and serum antibody from vaccinated donors, confirms the hypothesis that this, and most likely other, transiently-expressed viral host-response modulators are targets of host immunity. Neutralization of vIL18BP may aid in protection from initial infection, and therefore, establishment of infection, as was demonstrated recently for poxvirus type I IFN-binding protein (Xu et al., J Exp Med 205:981-92, 2008).

The design of an antigen epitope-based vaccine strategy requires that the viral components interact with HLA for T-cell development. The peptides in this study were predicted to bind several defined HLA haplotypes. But, despite predictions of HLA-binding, only some epitopes bound, as was demonstrated by the peptides from the C12L sequence (vIL18BP).

Peptides from C12L (vIL18BP), as well as the antigens A27L and DSL, elicited proliferation by CD4+ and CD8+ cells from vaccinated donors, indicating that APCs take up the peptides and process them for presentation in the context of both HLA class I for CD8+, and class II for CD4+ lymphocytes.

Immunity to poxvirus is dependent on both cellular and humoral immunity (Dunne et al., Blood 100:933-40, 2002; Ferrier-Rembert et al., Viral Immunol 20:214-20, 2007; Meseda et al., Clin Vaccine Immunol 16:1261-71, 2009; Xu et al., J Immunol 172:6265-71, 2004), both of which require T-cell help for class switching and affinity maturation. The proximity of T and B epitopes within a polypeptide may impact antibody production due to differences in their presentation. However, natural B-cell epitopes are quite often proximal to HLA-binding regions (Simitsek et al., J Exp Med 181:1957-63, 1995). A number of factors may influence the formation of antibody, including HLA type (Quaratino et al., J Immunol 174:557-63, 2005).

In the studies described above, we demonstrated measurable antibody in a sub-set of ⅓ of the vaccinated donors. In addition, the peptides encompassed linear sequences, and therefore the antibody recognized linear epitopes, which can include as few as 3 amino acids (Tahtinen et al., Virology 187:156-64, 1992). In the case of vIL18BP105 (SEQ ID NO:145), further evidence of the presence of a relevant B-cell epitope is provided by mouse studies, where serum antibody against vIL18BP105 (SEQ ID NO:145) recognized full length recombinant vIL18BP(C12L) protein (not shown). Overall, these results show that the antigen peptides used in this study present T- and B-cell targets of human response.

Cytokine and marker production revealed that vIL18BP105 (SEQ ID NO:145) and vD8L118 (SEQ ID NO:154) elicited IL-2 production, which preserves the proliferation capacity of T cells, even in the absence of CD4 help (Zimmerli et al., Proc Natl Acad Sci USA 102:7239-44, 2005). This supports the proliferation data and further demonstrates the utility of vIL18BP peptides for subunit-based vaccines. IFN-γ production by peptide-stimulated CD8+ $T_{EM}$ cells has multiple effects, including induction of anti-viral effector function. Thus, when vD8L118 (SEQ ID NO:154) stimulated CD8+ T cells with effector and proliferative potential, the results were similar to that reported for cells incubated with virus (Laouar et al., Plos One 3:e4089, 2008). IFN-γ production also characterizes generation of a Th1 response, which is necessary for development of cytotoxicity against vaccinia (Meseda et al., Clin Vaccine Immunol 16:1261-71, 2009; Xu et al., J Immunol 172:6265-71, 2004). Additionally, production of IL-2 and IFN-γ by CD4+ cells implicates helper Th1-oriented T-cell participation. The A27L peptide did not stimulate increased IFN-γ or IL-2 in CD8+ or CD4+ cells, even though T cells proliferated when incubated with this peptide. The lack of activity in the A27L samples may be due to different kinetics of response, or stimulation of alternate populations of cells which produce different cytokines or interleukins, such as IL-4, for which we did not assay.

Our results with respect to CD107a, a marker of cytolytic capacity, are similar to a recent study, where a subset of CD4+ cells from revaccinated donors expressed CD107a upon stimulation by vaccinia virus (Puissant-Lubrano et al., J Clin Invest 120:1636-44, 2010). In our study, CD8+ cells from vaccinated donors demonstrated enhanced expression of this marker upon stimulation by the peptides.

In contrast to the finding of Combadiere et al. (J Exp Med 199:1585-89, 2004), we did not observe loss of ability to produce cytokines in response to vaccinia antigens when smallpox vaccination took place more than 45 years previously.

In summary, we have presented evidence that subunit antigenic peptides from 3 poxvirus antigens are capable of stimulating recall responses from vaccinated donors, including T-cell proliferation, expression of cytokines, and serum antibody recognition of B-cell epitopes. One antigenic epitope was from a heretofore uncharacterized host defense modulator produced by vaccinia, the IL18BP. The results presented here show that development of an alternative vaccine against poxvirus using select peptide epitopes could produce immunity without the hazards of vaccination with active virus. An advantage of this virus-free approach over immunization with attenuated forms of poxvirus, the virulence genes of which are often deleted or mutated, is that the immunologically-relevant portions of any poxvirus gene, as well as altered genes, can be included.

Example 51

Conjugation of APC-Targeting Antibody to Subunit Antigenic Peptides for Poxvirus Vaccines Summary The vIL18BP105 (SEQ ID NO:145) peptide was conjugated to the anti-HLA-DR antibody, L243, for better presentation to the immune system, and used to immunize HLA-DR04-expressing transgenic (tg) mice. Conjugated vIL18BP105 (CIL18BP105) was more readily taken up by human and HLA-DR transgenic mouse cells than free vIL18BP105 (SEQ ID NO:145). Splenocytes from HLA-DR04 transgenic mice immunized with CIL18BP105 proliferated in vitro when stimulated with vIL18BP105 (SEQ ID NO:145). Proliferation of CIL18BP105-inoculated mouse splenocytes involved CD3+CD4+CD45RA− cells. Proliferation was accompanied by interferon-γ production (quantitative sandwich ELISA). CIL18BP105-innoculated mice also showed early and rapidly rising titers of peptide-specific antibodies, 4 times that of vIL18BP105-injected controls at day 7 after the first boost. At a later time, both CIL18BP105 and vIL18BP105 (SEQ ID NO:145) induced IgG2a and IgG1, suggesting the initiation of both Th1 and Th2 immunity. Serum antibody from CIL18BP105-immunized mice recognized whole recombinant C12L protein. These results demonstrate that conjugation of antigenic peptides to anti-HLA-DR antibody boosts immunogenicity and enhances peptide delivery to antigen-presenting cells expressing HLA-DR.

Methods

HLA-DR antibody-conjugates Peptides that were found to stimulate proliferation of immune donor PBMCs were conjugated with L243 antibody using the heterobifunctional cross-linker, sulfosuccinimidyl-4-(N-maleimidomethyl)cyclohexane-1-carboxylate (Sulfo-SMCC), "SMCC", containing H-hydroxysuccinimide (NHS) ester and maleimide groups, following the manufacturer's protocol (Piere, Rockford, Ill., USA). SMCC interacts with primary amine of the antibody through its NHS ester groups to form amide bonds, and the maleimide groups form thioester bonds with the free sulfhydryl group of a C-terminal cysteine on the peptide. The conjugate was purified by size exclusion to remove free peptide. Before being injected into mice, conjugate preparations were filter-sterilized through a 0.22-μm PVDF filter (Millipore, Bedford, Mass.), and emulsified in incomplete Freund's adjuvant (IFA).

Immunization of mice Six-to-eight week old female C57BL/6J (B6) transgenic (tg) mice expressing HLA-DR04 (HLA-DR tg) were obtained from Taconic (Germantown, N.Y., USA). Mice were maintained in a pathogen-free area. For immunizations, groups of 3 mice were primed, and then boosted twice at two-week intervals by the subcutaneous route, with 25 μg of vIL18BP105 (SEQ ID NO:145) peptide emulsified in IFA in either free, or antibody-conjugated, form. Mice injected with IFA-emulsified PBS served as naïve controls. Blood was collected at one-week intervals from priming to sacrifice, which was 7 days after the final boost. Spleen samples were collected at sacrifice. Serum for antibody detection and isotyping by ELISA was prepared from blood after overnight coagulation at 4° C. Splenocytes used in CFSE-based T-cell proliferation assays and TCR repertoire analysis, were isolated by mechanical disruption of spleens through stainless steel mesh. A modified ELISA-based method from a previous report was used (Makabi-Panzu et al, 1998) to assess antibody production and isotype.

T-cell proliferation assay and TCRVβ repertoire analysis T-cell proliferation for either donor PBMCs or murine splenocytes was assessed using a 5-day CFSE-based cell proliferation assay as reported previously (Younes et al, 2003). Briefly, 10–50×10$^6$ PBMC or splenocytes were labeled with CFSE at a final concentration of 1.5 μM. Cells were washed twice in PBS and re-suspended in complete RPMI medium at 10$^6$ cells/ml. 2×10$^5$ cells were incubated with indicated concentrations of peptides or PHA (2.5 μg/ml) for positive control wells. Cells were stained with CD4-APC, CD8-PE with 7-AAD or CD3-perCp after 5 days of in vitro incubation at 37° C. in a 5% $CO_2$ atmosphere. A minimum of 20,000 events gated on live CD3+ lymphocytes were collected on a FACS-CALIBUR® flow cytometer, and analyzed using Flow Jo software. T-cell proliferation was evaluated based on the reduction of CFSE fluorescence of growing cells. An integrated cell proliferation Flow Jo program was used for analysis. The fluorescence index of proliferating cells was calculated by dividing the number of cells losing the CFSE dye in the presence of the stimulating peptide (test) by the number of cells proliferating in the absence of the peptide (control).

For the TCRVβ repertoire analysis, washed splenocytes from immunized or naive mice were washed again with complete RPMI-1640 medium and with staining buffer, then pre-stained for T-cell surface markers as described above, for 20 min at 4° C., before being incubated again for 15 min at 4° C. with the blocking 2.4G2 anti-FcRIII/I mAb. The cells were then stained with an appropriate fluorescently labeled anti-TCRVβ antibody without removal of the FcR-blocking mAb. Following this last incubation, the cells were washed with stain buffer and analyzed by flow cytometry.

Data analysis The significance of differences observed under the experimental conditions was determined using one way analysis of variance followed as appropriate by a t-test with Fisher's corrections for multiple comparisons. P<0.05 was considered significant.

Results

In vitro T-cell proliferation in response to vIL18BP105 (SEQ ID NO:145) peptide To test whether conjugation of a sub-unit antigen to an APC-targeting mAb would generate an enhanced immune response, the peptide vIL18BP105 (SEQ ID NO:145) was conjugated chemically to the mAb L243 (CIL18BP105) and used to immunize mice. The results were compared to mice given PBS/IFA (naive) and free vIL18BP105 (SEQ ID NO:145) in IFA. Using a 5-day CFSE-based in vitro cell proliferation assay, splenocytes from CIL18BP105-immunized mice proliferated in a concentration-dependent manner. Cells from naïve or free-peptide immunized mice were relatively unresponsive (FIG. 27). The TCRVβ repertoire of CD4-positive splenocytes from HLA-DR04 μg mice following immunization with either form of vIL18BP105 (SEQ ID NO:15) skewed toward TCRVβ 8.3 (not shown).

Antibody production in response to vIL18BP105 (SEQ ID NO:15) peptide Humoral immunity to poxvirus is essential for protection against infection. Therefore, the antibody response against CIL18BP105 versus vIL18BP105 (SEQ ID NO:145) was investigated in the immunized HLA-DR04 tg mice. The results are shown in FIG. 28. At day 7 after the first boost (day 21 after priming), CIL18BP105-injected mice displayed higher peptide-specific antibody production than mice injected with vIL18BP105 (SEQ ID NO:15) (FIG. 28). But, at 14 days after the first boost, the amounts of antibody were similar (FIG. 28). Both IgG1 and IgG2a isotypes were induced by CIL18BP105 and vIL18BP105 (SEQ ID NO:15), but CIL18BP105 caused more production of IgG1 antibodies than its free counterpart (not shown). The production of IgG1 and IgG2a suggests a mature antibody response with T-cell help. Both Th1 and Th2 helper cell participation is also suggested by this antibody response. Serum antibody from CIL18BP105-immunized mice reacted strongly with whole vIL18BP protein (C12L) (not shown), indicating that subunit antigenic peptide conjugated to anti-APC antibody is capable of inducing a systemic immune response against intact virions. Immunization with CIL18BP105 was more effective than immunization with vIL18BP105 (SEQ ID NO:145) at promoting interferon-γ production from splenocytes stimulated in vitro with vIL18BP105 (SEQ ID NO:145) peptide (Table 18).

These results show that the poxvirus sub-unit peptide, vIL18BP105 (SEQ ID NO:145), induced both cellular and humoral immune responses in HLA-DR04 μg mice when conjugated with the anti-HLA-DR antibody, L243. T-cell proliferative responses, which are indicative of cell-mediated immunity, were especially enhanced by the antigen-L243 conjugate. Antibody production rose more quickly in the CIL18BP105-immunized mice. The peptide-antibody conjugate induced higher titers of antibody earlier than the free peptide. These results show that T-cell response against a relatively small peptide antigen can be elicited successfully by conjugation to L243.

TABLE 18

Interferon-γ Production From Immunized Mice

| Treatment | #CIL18BP105-splenocyte | IL18BP105-splenocyte | Naive-splenocyte |
|---|---|---|---|
| Medium | 00.00 + 00.00 | 00.00 + 00.00 | 00.00 + 00.00 |
| vIL18BP105, 10 ug/ml | 101.03 + 11.61* | 25.78 + 11.27 | 38.32 + 11.27 |
| Con A, 5 ug/ml | 373.15 + 4.23 | 84.68 + 10.00 | 149.00 + 12.46 |
| SEA, 100 ng/ml | 363.00 + 21.44 | 148.24 + 00.00 | 66.46 + 17.55 |

Conclusions

A vaccine against poxvirus requires Th1 and Th2 immune responses, cell-mediated and humoral immunity, and a suitable pool of memory CD4 T cells (Belyakoc et al, Proc. Natl. Acad. Sci. USA 100: 9458-9463, 2003). The results presented above show that sub-unit antigens conjugated to APC-targeting antibody can enhance and induce Th1, Th2, and humoral immune responses.

Example 52

Nasal Administration of DNL Subunit Vaccine

Mice (HLA-DR04 Tg) are anesthetized and vaccine is administered (15-25 μg peptide total) intranasally (i.n.) (10 μl/nostril). Vaccine is either free peptide, or peptide-L243 conjugate. For these experiments, the adjuvant is the calcium phosphate adjuvant described by He et al. (Clin Diagnos Lab Immunol 9:1021-1024, 2002) (10 μg/dose of antigen). Controls consist of unimmunized (naïve) mice, mice immunized with the whole viral protein (i.n.), systemically immunized mice (peptide, sub-cutaneous (s.c.)), and mice immunized with carrier/adjuvant only (i.n.). Equal amounts of peptide are administered in each case. Mice are boosted twice using the same route as prime, at weeks 2 (d14) and 4 (d28) after priming. Combinations of route of immunization may be employed (e.g., s.c. prime, followed by i.n. immunization on day 14).

Five mice from each treatment group are sacrificed at day 35 after prime immunization (25 of the 75 mice). Serum is harvested before priming immunization (d0), at day 7, 28, and 56. In addition nasal lavage (NL) fluids or bronchoalveolar lavage (BAL) and splenocytes are harvested at sacrifice.

Antigen-specific antibody in the respiratory tract fluids (gathered by NL or BAL upon sacrifice), and in the serum are titred by serial dilution and application to ELISA, with immobilized whole recombinant antigen (or vaccinia proteins), peptide, non-relevant peptide control and serially diluted serum from all treatment groups, including naïve mice. Isotype of specific antibodies is determined.

Neutralizing antibodies are present in mice immunized by either nasal or subcutaneous administration. The antibodies react with both antigenic peptide and whole viral protein. Nasal administration is more efficient to promote a mucosal immune response, while subcutaneous administration is more efficient to promote a systemic immune response against poxvirus.

The following peptides are made as AD2 modules incorporating a linking sequence attaching a subunit vaccine peptide. The AD2-peptide fusion is combined with DDD2-linked IgG or Fab moieties to provide a subunit based vaccine incorporating an APC-targeting antibody or antibody fragment.

ND8L
(SEQ ID NO: 160)
SIFLQVLDHKNVYFQGGGSCGQIEYLAKQIVDNAIQQAGC

CD8L
(SEQ ID NO: 161)
CGQIEYLAKQIVDNAIQQAGCGGGSSIFLQVLDHKNVYFQ

NIL18BP
(SEQ ID NO: 162)
HYRFTCVLTTLNGVSGGGSCGQIEYLAKQIVDNAIQQAGC

CIL18BP
(SEQ ID NO: 163)
CGQIEYLAKQIVDNAIQQAGCGGGSHYRFTCVLTTLNGVS

CSCRD8L
(SEQ ID NO: 164)
CGQIEYLAKQIVDNAIQQAGCGGGSYHQFVIDQLKLSVNF

CSCRIL18BP105
(SEQ ID NO: 165)
CGQIEYLAKQIVDNAIQQAGCGGGSGNCTFVTYLRHLSTV

Example 53

Liposome Formulation for Nasal Administration of Subunit Based Vaccine

A liposome formulation of antigenic peptide conjugated to L243 antibody was prepared by standard techniques. The intranasal peptides were designed with linkers at both the C-terminal and N-terminal ends. The C-terminal linker was used for conjugation of the L243 antibody. The N-terminal linker was used to facilitate attachment to the liposome, via palmitoylation. The peptide conjugates were as indicated below. The CD8L118 peptide was not a lipoprotein and was encapsulated into liposomes.

L1R183
GVQFYMIVIGVIILAALF                 (SEQ ID NO: 166)

Conjugated L1R183
KKKKGVQFYMIVIGVIILAALFPSEC         (SEQ ID NO: 167)

Conjugated A27L3
KSGTLFPGDDDLAIPATEFFSTKAAKKPSEC    (SEQ ID NO: 168)

Conjugated IL18BP105
KSHYRFTCVLTTLNGVSPESC              (SEQ ID NO: 169)

CD8L118
HDDGLIIISIFLQVLDHKNVYFQKIGGGSC     (SEQ ID NO: 170)

FIG. 29(A) shows the results of nasal administration of a liposome formulated subunit vaccine. Peptides were prepared and conjugated to antibody as described above. The results presented in FIG. 29 show T cell proliferation in response to incubation with the designated peptide in vitro after nasal immunization of mice. The strongest effect on T cell proliferation (FIG. 29A) was observed with the L1R183 antigenic peptide (SEQ ID NO:166) derived from the L1R antigen, an immunodominant intracellular mature virion (IMV) protein that offers post-exposure prophylaxis. Immunization of mice with liposome-displayed bare peptide alone (FIG. 29B) produced little effect on T cell proliferation, regardless of the tested peptide. Immunization with free peptide in the absence of liposome or with empty liposomes also had little to no effect on T cell proliferation (data not shown). The results demonstrate that nasal administration of a subunit based poxvirus vaccine, using conjugation to an APC targeting antibody, is effective to induce an immune response.

It will be readily apparent to one skilled in the art that varying substitutions and modifications may be made to the invention disclosed herein without departing from the scope and spirit of the invention. Thus, such additional embodiments are within the scope of the present invention.

What is claimed is:

1. An isolated DNL complex comprising:
   a) a first fusion protein comprising (i) an antibody selected from the group consisting of hRS7 (anti-EGP-1), hA20 (anti-CD20), hLL2 (anti-CD22) and hL243 (anti-HLA-DR), and (ii) an AD moiety, wherein the amino acid sequence of the AD moiety is from the anchoring domain of an AKAP (A-kinase anchoring protein); and
   b) a second fusion protein comprising (iii) ranpirnase, and (iv) a DDD moiety, wherein the amino acid sequence of the DDD moiety is from the dimerization and docking domain of human protein kinase A regulatory subunit R1α, R11α or R11β;
   wherein two copies of the DDD moiety form a dimer that binds to one copy of the AD moiety to form the DNL complex.

2. The DNL complex of claim 1, wherein the DNL complex comprises one copy of the antibody and either two or four copies of the ranpirnase.

3. The DNL complex of claim 1, wherein the DNL complex is conjugated to at least one diagnostic agent or therapeutic agent.

* * * * *

UNITED STATES PATENT AND TRADEMARK OFFICE
CERTIFICATE OF CORRECTION

PATENT NO. : 8,883,160 B2
APPLICATION NO. : 13/036820
DATED : November 11, 2014
INVENTOR(S) : Chien-Hsing Chang et al.

It is certified that error appears in the above-identified patent and that said Letters Patent is hereby corrected as shown below:

On the Title page, Item (57), Abstract, should read as follows:

Disclosed herein are methods and compositions dock and lock (DNL) complexes comprising an AD moiety selected from an AKAP protein and a DDD moiety selected from a protein kinase A regulatory subunit. Also disclosed are fusion proteins comprising an AD moiety or DDD moiety attached to an effector moiety. The DDD moieties form dimers that bind to the AD moiety to form the DNL complexes. The effector moieties may be selected from a wide range of known effector moieties that produce one or more physiological effects, including but not limited to cell death. The DNL complexes may further comprise one or more diagnostic and/or therapeutic agents. The DNL complexes are of use for treating and/or diagnosing a variety of diseases or conditions.

Signed and Sealed this
Twenty-third Day of June, 2015

Michelle K. Lee
*Director of the United States Patent and Trademark Office*

```
                              SEQUENCE LISTING

<160> NUMBER OF SEQ ID NOS: 176

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 8
<211> LENGTH: 51
<212> TYPE: PRT
<213> ORGANISM: Homo sapiens
```

<400> SEQUENCE: 8

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 12

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 16

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
```

```
                               polypeptide

<400> SEQUENCE: 20

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 24
<211> LENGTH: 44
<212> TYPE: PRT
<213> ORGANISM: Artificial Sequence
<220> FEATURE:
```

<223> OTHER INFORMATION: Description of Artificial Sequence: Synthetic
    polypeptide

<400> SEQUENCE: 24

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 27

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 32
<211> LENGTH: 17
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 32

Asn Ile Glu Tyr Leu Ala Lys Gln Ile Val Asp Asn Ala Ile Gln Gln
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15

Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15

Ala

<210> SEQ ID NO 37
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ile Glu Thr Leu Ala Lys Gln Ile Val Asp Asn Ala Ile Gln Gln
1               5                   10                  15

Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
1               5                   10                  15

Ala

<210> SEQ ID NO 42
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ile Glu Tyr Leu Ala Lys Asn Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Tyr Leu Ala Lys Gln Ile Val Asp Gln Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Tyr Leu Ala Lys Gln Ile Val Asp Asn Ala Ile Asn Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Leu Ala Lys Gln Ile Val Asp Asn Ala Ile Gln Asn
1               5                   10                  15

Ala
```

```
<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Leu Ala Lys Gln Ile Val Asp Asn Ala Ile Gln Gln
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Lys Gln Ile Val Asp Asn Ala Ile Gln Gln
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Val Ala Lys Gln Ile Val Asp Tyr Ala Ile His Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15

Ala
```

```
<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr His Ala Lys Gln Ile Val Asp His Ala Ile His Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys
```

```
<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Tyr Gln Phe Ala Asp Arg Phe Ser Glu Leu Val Ile Ser Glu
1               5                   10                  15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15
```

Ala Val

<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Lys Gln Ala Ala Phe Gln Leu Ile Ser Gln Val Ile Leu Glu
1               5                   10                  15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

```
Phe Gln Gln Cys
            20

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15

Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 71

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 76
<211> LENGTH: 25
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                   10                  15
```

Ile Val Ser Asp Ile Met Gln Gln Ala
            20                  25

<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
aatgcggcgg tggtgacagt a                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aagctcagca cacagaaaga c                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
uaaaaucuuc cugcccacct t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
ggaagcuguu ggcugaaaat t                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
aagaccagcc ucuuugccca g                                              21

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
ggaccaggca gaaaacgag                                                 19

<210> SEQ ID NO 91
<211> LENGTH: 17

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cuaucaggau gacgcgg                                                    17

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
ugacacaggc aggcuugacu u                                               21

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93
ggtgaagaag ggcgtccaa                                                  19

<210> SEQ ID NO 94
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gatccgttgg agctgttggc gtagttcaag agactcgcca acagctccaa cttttggaaa     60

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
aggtggtgtt aacagcagag                                                 20

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
aaggtggagc aagcggtgga g                                               21

<210> SEQ ID NO 97
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 97
aaggagttga aggccgacaa a                                                   21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
uauggagcug cagaggaugt t                                                   21

<210> SEQ ID NO 99
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
tttgaatatc tgtgctgaga acacagttct cagcacagat attctttt                      49

<210> SEQ ID NO 100
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
aatgagaaaa gcaaaaggtg ccctgtctc                                           29

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
aaucaucauc aagaaagggc a                                                   21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
augacuguca ggauguugct t                                                   21
```

```
<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
gaacgaaucc ugaagacauc u                                             21

<210> SEQ ID NO 104
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
aagcctggct acagcaatat gcctgtctc                                     29

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
ugaccaucac cgaguuuaut t                                             21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aagtcggacg caacagagaa a                                             21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
cuaccuuucu acggacgugt t                                             21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 108
ctgcctaagg cggatttgaa t                                          21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
ttauuccuuc uucgggaagu c                                          21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
aaccttctgg aacccgccca c                                          21

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gagcatcttc gagcaagaa                                             19

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
catgtggcac cgtttgcct                                             19

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
aactaccaga aaggtatacc t                                          21

<210> SEQ ID NO 114
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
ucacaguguc cuuuauguat t                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
gcaugaaccg gaggcccaut t                                              21

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ccggacagtt ccatgtata                                                 19

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Pro Lys Ser Cys
1

<210> SEQ ID NO 118
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Gly Ser Gly Gly Gly Gly Ser Gly Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 119
```

-continued

```
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Gly Ser Gly Gly Gly Gly Ser Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 120
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
agatctgcct tttgcctcct ccttctc                                         27

<210> SEQ ID NO 121
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
tcatgagcct tcgagaatgt gagctc                                          26

<210> SEQ ID NO 122
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
tcatgagttg tggcggaagc cttcgagaat gtgagc                               36

<210> SEQ ID NO 123
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Cys(SS-tbu)
<220> FEATURE:
<223> OTHER INFORMATION: C-term amidated

<400> SEQUENCE: 123

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 124
```

```
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (21)..(21)
<223> OTHER INFORMATION: Cys(SS-tbu)
<220> FEATURE:
<223> OTHER INFORMATION: C-term EDANS

<400> SEQUENCE: 124

Cys Gly Gln Ile Glu Tyr Leu Ala Lys Gln Ile Val Asp Asn Ala Ile
1               5                   10                  15

Gln Gln Ala Gly Cys Gly
            20

<210> SEQ ID NO 125
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (1)..(1)
<223> OTHER INFORMATION: Cys-PEG3
<220> FEATURE:
<221> NAME/KEY: MOD_RES
<222> LOCATION: (2)..(2)
<223> OTHER INFORMATION: Cys(S-tbu)
<220> FEATURE:
<221> NAME/KEY: MOD_RES
<222> LOCATION: (22)..(22)
<223> OTHER INFORMATION: Cys(S-tbu)
<220> FEATURE:
<223> OTHER INFORMATION: C-term amidated

<400> SEQUENCE: 125

Cys Cys Gly Gln Ile Glu Tyr Leu Ala Lys Gln Ile Val Asp Asn Ala
1               5                   10                  15

Ile Gln Gln Ala Gly Cys Gly
            20

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 126

His His His His His His
1               5

<210> SEQ ID NO 127
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127
```

```
Lys Ser His His His His His Gly Ser Gly Gly Gly Gly Ser Gly
1               5                   10                  15

Gly Gly Cys Gly His Ile Gln Ile Pro Pro Gly Leu Thr Glu Leu Leu
            20                  25                  30

Gln Gly Tyr Thr Val Glu Val Leu Arg Gln Gln Pro Pro Asp Leu Val
        35                  40                  45

Glu Phe Ala Val Glu Tyr Phe Thr Arg Leu Arg Glu Ala Arg Ala
    50                  55                  60
```

<210> SEQ ID NO 128
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tctagacaca ggacctcatc atggccttga cctttgcttt actgg                45

<210> SEQ ID NO 129
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
ggatccatga tggtgatgat ggtgtgactt ttccttactt cttaaacttt cttgc      55

<210> SEQ ID NO 130
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys(SS-tbu)
<220> FEATURE:
<221> NAME/KEY: MOD_RES
<222> LOCATION: (21)..(21)
<223> OTHER INFORMATION: Cys(SS-tbu)
<220> FEATURE:
<223> OTHER INFORMATION: C-term amidated

<400> SEQUENCE: 130

```
Cys Gly Gln Ile Glu Tyr Leu Ala Lys Gln Ile Val Asp Asn Ala Ile
1               5                   10                  15

Gln Gln Ala Gly Cys
            20
```

<210> SEQ ID NO 131
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Arg Ser Gln Ser Arg Ser Arg Tyr Tyr Arg Gln Arg Gln Arg Ser Arg
1               5                   10                  15
```

-continued

Arg Arg Arg Arg Arg Ser
            20

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
ccggacaguu ccauguauat t                                              21

<210> SEQ ID NO 133
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Pyroglutamate

<400> SEQUENCE: 133

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
        35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys Gly Gly Gly Ser Leu Glu Cys
            100                 105                 110

Gly His Ile Gln Ile Pro Pro Gly Leu Thr Glu Leu Leu Gln Gly Tyr
        115                 120                 125

Thr Val Glu Val Leu Arg Gln Gln Pro Pro Asp Leu Val Glu Phe Ala
    130                 135                 140

Val Glu Tyr Phe Thr Arg Leu Arg Glu Ala Arg Ala Val Glu His His
145                 150                 155                 160

His His His His

<210> SEQ ID NO 134
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NOTA-ITC
<220> FEATURE:
<221> NAME/KEY: MOD_RES
<222> LOCATION: (1)..(1)

<223> OTHER INFORMATION: Benzyl-D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 134

Ala Lys Tyr Lys
1

<210> SEQ ID NO 135
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Ala
<220> FEATURE:
<221> NAME/KEY: MOD_RES
<222> LOCATION: (2)..(2)
<223> OTHER INFORMATION: D-Lys(HSG)
<220> FEATURE:
<221> NAME/KEY: MOD_RES
<222> LOCATION: (3)..(3)
<223> OTHER INFORMATION: D-Tyr
<220> FEATURE:
<221> NAME/KEY: MOD_RES
<222> LOCATION: (4)..(4)
<223> OTHER INFORMATION: D-Lys(HSG)
<220> FEATURE:
<223> OTHER INFORMATION: C-term amidated

<400> SEQUENCE: 135

Ala Lys Tyr Lys
1

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Ser Gly Gly Gly Gly Ser Gly Gly
1               5

<210> SEQ ID NO 137
<211> LENGTH: 43
<212> TYPE: PRT
<213> ORGANISM: Mus musculus

<400> SEQUENCE: 137

Thr Leu Ser His Phe Leu Lys Met Arg Arg Leu Glu Leu Ile Gln Thr
1               5                   10                  15

Ser Lys Pro Tyr Val Asp Ile Tyr Asp Cys Glu Pro Ser Asn Ser Ser

```
                20                  25                  30

Glu Lys Asn Ser Pro Ser Thr Gln Tyr Cys Asn
        35                  40

<210> SEQ ID NO 138
<211> LENGTH: 291
<212> TYPE: PRT
<213> ORGANISM: Mus musculus

<400> SEQUENCE: 138

Met Ser Gly Pro Phe Pro Ala Glu Pro Thr Lys Gly Pro Leu Ala Met
1               5                   10                  15

Gln Pro Ala Pro Lys Val Asn Leu Lys Arg Thr Ser Ser Leu Val Gly
            20                  25                  30

Pro Thr Gln Ser Phe Phe Met Arg Glu Ser Lys Ala Leu Gly Ala Val
        35                  40                  45

Gln Ile Met Asn Gly Leu Phe His Ile Thr Leu Gly Gly Leu Leu Met
    50                  55                  60

Ile Pro Thr Gly Val Phe Ala Pro Ile Cys Leu Ser Val Trp Tyr Pro
65                  70                  75                  80

Leu Trp Gly Gly Ile Met Tyr Ile Ile Ser Gly Ser Leu Leu Ala Ala
                85                  90                  95

Ala Ala Glu Lys Thr Ser Arg Lys Ser Leu Val Lys Ala Lys Val Ile
            100                 105                 110

Met Ser Ser Leu Ser Leu Phe Ala Ala Ile Ser Gly Ile Ile Leu Ser
        115                 120                 125

Ile Met Asp Ile Leu Asn Met Thr Leu Ser His Phe Leu Lys Met Arg
    130                 135                 140

Arg Leu Glu Leu Ile Gln Thr Ser Lys Pro Tyr Val Asp Ile Tyr Asp
145                 150                 155                 160

Cys Glu Pro Ser Asn Ser Ser Glu Lys Asn Ser Pro Ser Thr Gln Tyr
                165                 170                 175

Cys Asn Ser Ile Gln Ser Val Phe Leu Gly Ile Leu Ser Ala Met Leu
            180                 185                 190

Ile Ser Ala Phe Phe Gln Lys Leu Val Thr Ala Gly Ile Val Glu Asn
        195                 200                 205

Glu Trp Lys Arg Met Cys Thr Arg Ser Lys Ser Asn Val Val Leu Leu
    210                 215                 220

Ser Ala Gly Glu Lys Asn Glu Gln Thr Ile Lys Met Lys Glu Glu Ile
225                 230                 235                 240

Ile Glu Leu Ser Gly Val Ser Ser Gln Pro Lys Asn Glu Glu Glu Ile
                245                 250                 255

Glu Ile Ile Pro Val Gln Glu Glu Glu Glu Glu Ala Glu Ile Asn
            260                 265                 270

Phe Pro Ala Pro Pro Gln Glu Gln Glu Ser Leu Pro Val Glu Asn Glu
        275                 280                 285

Ile Ala Pro
    290

<210> SEQ ID NO 139
<211> LENGTH: 30
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 139
ggatccacac tttctcattt tttaaaaatg                                    30

<210> SEQ ID NO 140
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
ctcgaggtta cagtactgtg tagatgggga                                    30

<210> SEQ ID NO 141
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
agatctacac tttctcattt tttaaaaatg                                    30

<210> SEQ ID NO 142
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
cggccgtcag tggtggtggt ggtggtggtt acagtactgt gtagatgg                48

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Cys Val Leu Thr Thr Leu Asn Gly Val
1               5

<210> SEQ ID NO 144
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Lys Phe Ala His Tyr Arg Phe Thr Cys Val Leu Thr Thr Leu Asn Gly
1               5                   10                  15

Val Ser Lys Lys Asn Ile Val Val Leu Lys
            20                  25

<210> SEQ ID NO 145
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 145

His Tyr Arg Phe Thr Cys Val Leu Thr Thr Leu Asn Gly Val Ser
1               5                   10                  15

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Val Leu Thr Thr Leu Asn Gly Val
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Val Ser Lys Lys Asn Ile Trp Leu
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ala Leu Lys Asp Leu Met Ser Ser Val
1               5

<210> SEQ ID NO 149
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Tyr Ile Lys Ala Asn Ala Lys Phe Ile Gly Ile Thr Glu Leu
1               5                   10                  15

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Thr Leu Phe Pro Gly Asp Asp Asp Leu Ala Ile Pro Ala Thr
1               5                   10                  15
```

<210> SEQ ID NO 151
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Gly Thr Leu Phe Pro Gly Asp Asp Asp Leu Ala Ile Pro Ala Thr Glu
1               5                  10                  15

Phe Phe Ser Thr Lys Ala Ala Lys Lys
            20                  25

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Thr Leu Phe Pro Gly Asp Asp Asp Leu
1               5

<210> SEQ ID NO 153
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

His Asp Asp Gly Leu Ile Ile Ser Ile Phe Leu Gln Val Leu Asp
1               5                  10                  15

His Lys Asn Val Tyr Phe Gln Lys Ile
            20                  25

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ser Ile Phe Leu Gln Val Leu Asp His Lys Asn Val Tyr Phe Gln
1               5                  10                  15

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Ile Ile Ser Ile Phe Leu Gln Val Leu
1               5

<210> SEQ ID NO 156
<211> LENGTH: 25

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Met Lys Thr Ile Ser Val Val Thr Leu Leu Cys Val Leu Pro Ala Val
1               5                   10                  15

Val Tyr Ser Thr Cys Thr Val Pro Thr
            20                  25

<210> SEQ ID NO 157
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ile Ser Val Val Thr Leu Leu Cys Val Leu Pro Ala Val Val Tyr
1               5                   10                  15

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Thr Leu Leu Cys Val Leu Pro Ala Val
1               5

<210> SEQ ID NO 159
<211> LENGTH: 126
<212> TYPE: PRT
<213> ORGANISM: Unknown
<220> FEATURE:
<223> OTHER INFORMATION: Description of Unknown: Poxvirus polypeptide

<400> SEQUENCE: 159

Met Arg Ile Leu Phe Leu Ile Ala Phe Met Tyr Gly Cys Val His Ser
1               5                   10                  15

Tyr Val Asn Ala Val Glu Thr Lys Cys Pro Asn Leu Asp Ile Val Thr
            20                  25                  30

Ser Ser Gly Glu Phe Tyr Cys Ser Gly Cys Val Glu His Met Ser Lys
        35                  40                  45

Phe Ser Tyr Met Tyr Trp Leu Ala Lys Asp Met Lys Ser Asp Glu Tyr
    50                  55                  60

Thr Lys Phe Ile Glu His Leu Gly Asp Gly Ile Lys Glu Asp Glu Thr
65                  70                  75                  80

Ile Arg Thr Thr Asp Gly Gly Ile Thr Thr Leu Arg Lys Val Leu His
                85                  90                  95

Val Thr Asp Thr Asn Lys Phe Ala His Tyr Arg Phe Thr Cys Val Leu
            100                 105                 110

Thr Thr Leu Asn Gly Val Ser Lys Lys Asn Ile Trp Leu Lys
        115                 120                 125

<210> SEQ ID NO 160
<211> LENGTH: 40

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Ser Ile Phe Leu Gln Val Leu Asp His Lys Asn Val Tyr Phe Gln Gly
1               5                   10                  15

Gly Gly Ser Cys Gly Gln Ile Glu Tyr Leu Ala Lys Gln Ile Val Asp
            20                  25                  30

Asn Ala Ile Gln Gln Ala Gly Cys
        35                  40

<210> SEQ ID NO 161
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Cys Gly Gln Ile Glu Tyr Leu Ala Lys Gln Ile Val Asp Asn Ala Ile
1               5                   10                  15

Gln Gln Ala Gly Cys Gly Gly Gly Ser Ser Ile Phe Leu Gln Val Leu
            20                  25                  30

Asp His Lys Asn Val Tyr Phe Gln
        35                  40

<210> SEQ ID NO 162
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

His Tyr Arg Phe Thr Cys Val Leu Thr Thr Leu Asn Gly Val Ser Gly
1               5                   10                  15

Gly Gly Ser Cys Gly Gln Ile Glu Tyr Leu Ala Lys Gln Ile Val Asp
            20                  25                  30

Asn Ala Ile Gln Gln Ala Gly Cys
        35                  40

<210> SEQ ID NO 163
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Cys Gly Gln Ile Glu Tyr Leu Ala Lys Gln Ile Val Asp Asn Ala Ile
1               5                   10                  15

Gln Gln Ala Gly Cys Gly Gly Gly Ser His Tyr Arg Phe Thr Cys Val
            20                  25                  30

Leu Thr Thr Leu Asn Gly Val Ser
        35                  40

<210> SEQ ID NO 164
```

```
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Cys Gly Gln Ile Glu Tyr Leu Ala Lys Gln Ile Val Asp Asn Ala Ile
1               5                   10                  15

Gln Gln Ala Gly Cys Gly Gly Ser Tyr His Gln Phe Val Ile Asp
            20                  25                  30

Gln Leu Lys Leu Ser Val Asn Phe
        35                  40

<210> SEQ ID NO 165
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Cys Gly Gln Ile Glu Tyr Leu Ala Lys Gln Ile Val Asp Asn Ala Ile
1               5                   10                  15

Gln Gln Ala Gly Cys Gly Gly Gly Ser Gly Asn Cys Thr Phe Val Thr
            20                  25                  30

Tyr Leu Arg His Leu Ser Thr Val
        35                  40

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gly Val Gln Phe Tyr Met Ile Val Ile Gly Val Ile Ile Leu Ala Ala
1               5                   10                  15

Leu Phe

<210> SEQ ID NO 167
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Lys Lys Lys Lys Gly Val Gln Phe Tyr Met Ile Val Ile Gly Val Ile
1               5                   10                  15

Ile Leu Ala Ala Leu Phe Pro Ser Glu Cys
            20                  25

<210> SEQ ID NO 168
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 168

Lys Ser Gly Thr Leu Phe Pro Gly Asp Asp Leu Ala Ile Pro Ala
1               5                   10                  15

Thr Glu Phe Phe Ser Thr Lys Ala Ala Lys Lys Pro Ser Glu Cys
            20                  25                  30

<210> SEQ ID NO 169
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Lys Ser His Tyr Arg Phe Thr Cys Val Leu Thr Thr Leu Asn Gly Val
1               5                   10                  15

Ser Pro Glu Ser Cys
            20

<210> SEQ ID NO 170
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

His Asp Asp Gly Leu Ile Ile Ile Ser Ile Phe Leu Gln Val Leu Asp
1               5                   10                  15

His Lys Asn Val Tyr Phe Gln Lys Ile Gly Gly Gly Ser Cys
            20                  25                  30

<210> SEQ ID NO 171
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Lys or Arg
<220> FEATURE:
<221> NAME/KEY: MOD_RES
<222> LOCATION: (32)..(32)
<223> OTHER INFORMATION: Lys, Ile, or Val
<220> FEATURE:
<221> NAME/KEY: MOD_RES
<222> LOCATION: (42)..(42)
<223> OTHER INFORMATION: Lys, Ile, or Val
<220> FEATURE:
<221> NAME/KEY: MOD_RES
<222> LOCATION: (44)..(44)
<223> OTHER INFORMATION: Lys, Ile, or Val

<400> SEQUENCE: 171

Thr Xaa Ile Asn Ile Pro Pro Ala Leu Ser Asp Leu Leu Asn Ala Tyr
1               5                   10                  15

Ser Val Asp Val Leu Lys Asn Asn Pro Pro Glu Leu Val Asp Phe Xaa
            20                  25                  30

Val Asp Tyr Phe Ser Lys Leu Lys Asp Xaa Lys Xaa
            35                  40

```
<210> SEQ ID NO 172
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu or Val
<220> FEATURE:
<221> NAME/KEY: MOD_RES
<222> LOCATION: (4)..(4)
<223> OTHER INFORMATION: Phe, Thr, or Ser
<220> FEATURE:
<221> NAME/KEY: MOD_RES
<222> LOCATION: (5)..(5)
<223> OTHER INFORMATION: Ile or Val
<220> FEATURE:
<221> NAME/KEY: MOD_RES
<222> LOCATION: (17)..(17)
<223> OTHER INFORMATION: Leu, Ile, or Val

<400> SEQUENCE: 172

Asn Xaa Asp Xaa Xaa Ala Arg Asn Ile Val Glu Gln Ala Ile Asn Asn
1               5                   10                  15

Xaa

<210> SEQ ID NO 173
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Ile, Leu, or Ala
<220> FEATURE:
<221> NAME/KEY: MOD_RES
<222> LOCATION: (33)..(33)
<223> OTHER INFORMATION: Ile, Leu, or Ala
<220> FEATURE:
<221> NAME/KEY: MOD_RES
<222> LOCATION: (42)..(42)
<223> OTHER INFORMATION: Leu, Ile, or Val
<220> FEATURE:
<221> NAME/KEY: MOD_RES
<222> LOCATION: (44)..(44)
<223> OTHER INFORMATION: Leu, Ile, or Val

<400> SEQUENCE: 173

Thr His Ile Asn Ile Pro Pro Gly Leu Ser Glu Leu Leu Gln Gly Tyr
1               5                   10                  15

Thr Xaa Glu Val Leu Arg Asn Gln Pro Pro Asp Leu Val Glu Phe Ala
                20                  25                  30

Xaa Asp Tyr Phe Ser Lys Leu Lys Glu Xaa Arg Xaa
                35                  40

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 174

Gly Gly Gly Gly Ser Gly Gly Gly Ser Gly Gly Gly
1               5                   10

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
agatctggcg cacctgaact cctg                                          24

<210> SEQ ID NO 176
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
gaattcggat cctttacccg gagacaggga gag                                33
```